(12) United States Patent
Wilkinson

(10) Patent No.: US 11,642,141 B2
(45) Date of Patent: *May 9, 2023

(54) DEVICES AND METHODS FOR PERFORMING KNEE ARTHROPLASTY

(71) Applicant: Smith & Nephew, Inc., Memphis, TN (US)

(72) Inventor: Zachary Christopher Wilkinson, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/705,291

(22) Filed: Mar. 26, 2022

(65) Prior Publication Data

US 2022/0211395 A1    Jul. 7, 2022

Related U.S. Application Data

(60) Division of application No. 16/251,636, filed on Jan. 18, 2019, now Pat. No. 11,317,930, which is a
(Continued)

(51) Int. Cl.
*A61B 17/17* (2006.01)
*A61B 17/16* (2006.01)
(Continued)

(52) U.S. Cl.
CPC ........ *A61B 17/1764* (2013.01); *A61B 17/154* (2013.01); *A61B 17/157* (2013.01);
(Continued)

(58) Field of Classification Search
CPC . A61B 17/1764; A61B 17/154; A61B 17/157; A61B 17/16; A61B 17/1604;
(Continued)

(56) References Cited

U.S. PATENT DOCUMENTS 5,275,603 A    1/1994  Ferrante et al.
5,611,802 A    3/1997  Samuelson et al.
(Continued)

FOREIGN PATENT DOCUMENTS

EP    0556998 A1    8/1993
EP    1323386 A2    7/2003

OTHER PUBLICATIONS

International Search Report and Written Opinion of the International Searching Authority; PCT/US2012/062128, dated Jul. 18, 2013, 15 pages.

*Primary Examiner* — Marcela I. Shirsat
(74) *Attorney, Agent, or Firm* — KDW Firm PLLC

(57) ABSTRACT

Methods and devices for performing knee arthroplasty including but not limited to bicruciate retaining knee arthroplasty are provided. Methods and devices for preparing a proximal tibia for a tibial implant are also provided. These methods and devices, in at least some embodiments and uses, facilitate decreasing the complexity of knee arthroplasty procedures such as bicruciate retaining procedures while maintaining, if not improving on, the safety, accuracy and/or effectiveness of such procedures.

4 Claims, 55 Drawing Sheets

Related U.S. Application Data continuation of application No. 13/661,636, filed on Oct. 26, 2012, now Pat. No. 10,201,356.

(60) Provisional application No. 61/552,321, filed on Oct. 27, 2011.

(51) Int. Cl.
*A61F 2/46* (2006.01)
*A61B 17/15* (2006.01)
*A61F 2/38* (2006.01)

(52) U.S. Cl.
CPC .......... *A61B 17/16* (2013.01); *A61B 17/1604* (2013.01); *A61B 17/17* (2013.01); *A61F 2/4684* (2013.01); *A61B 17/1675* (2013.01); *A61F 2/389* (2013.01); *A61F 2/3859* (2013.01); *A61F 2002/4658* (2013.01); *A61F 2002/4668* (2013.01)

(58) Field of Classification Search
CPC ... A61B 17/17; A61B 17/1675; A61F 2/4684; A61F 2/389
USPC ... 606/88, 87, 86 R, 86 B, 79, 167, 184–185
See application file for complete search history.

(56) References Cited

U.S. PATENT DOCUMENTS

| | | |
|---|---|---|
| 5,830,216 A | 11/1998 | Insall et al. |
| 6,282,740 B1 | 9/2001 | Sobotka |
| 7,678,115 B2 | 3/2010 | D'Alessio, II et al. |
| 11,317,930 B2 * | 5/2022 | Wilkinson ......... A61B 17/1604 |
| 2003/0130665 A1 | 7/2003 | Pinczewski et al. |
| 2008/0015604 A1 | 1/2008 | Collazo |
| 2008/0262500 A1 | 10/2008 | Collazo |
| 2009/0264890 A1 | 10/2009 | Duggineni et al. |
| 2010/0305575 A1 * | 12/2010 | Wilkinson ........... A61B 17/157 606/88 |
| 2010/0331847 A1 | 12/2010 | Wilkinson et al. |

* cited by examiner

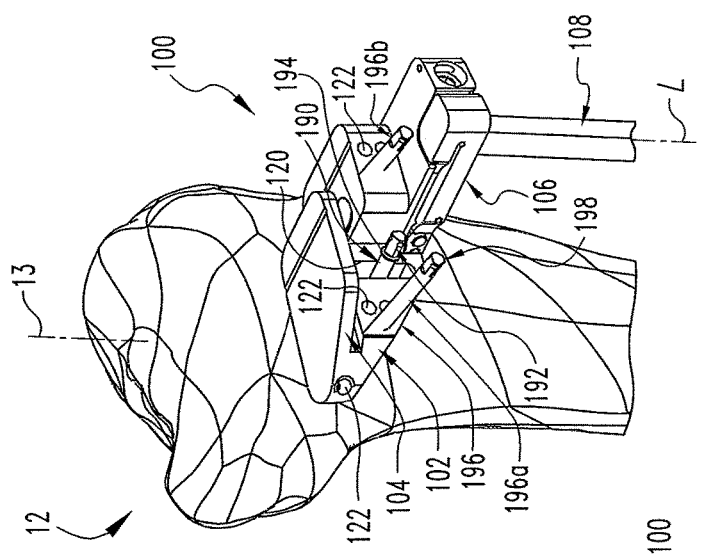
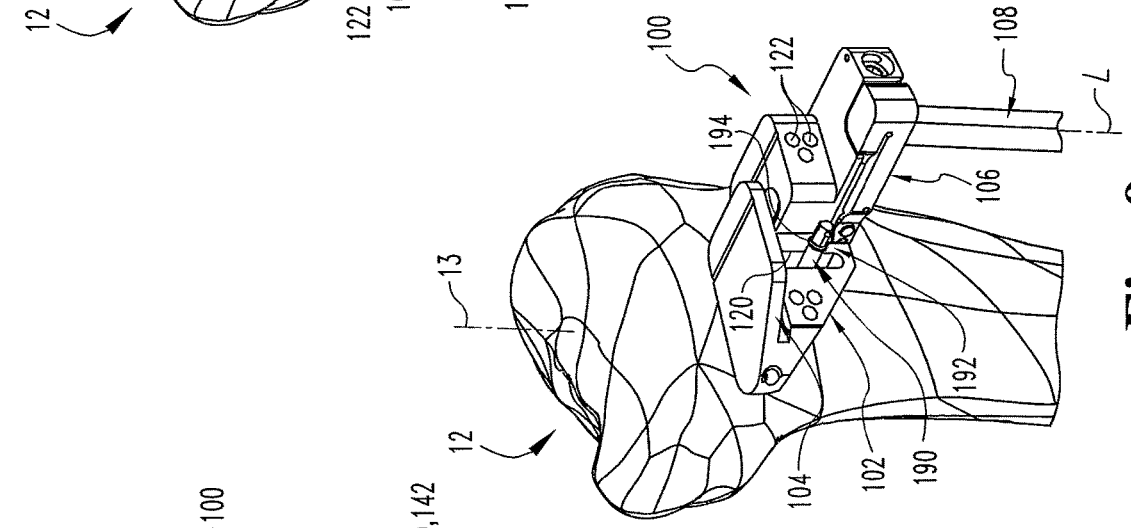
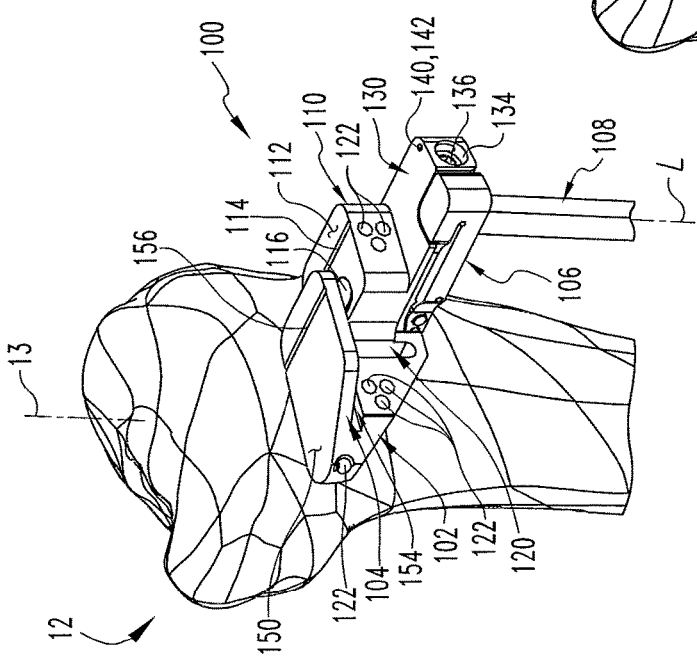

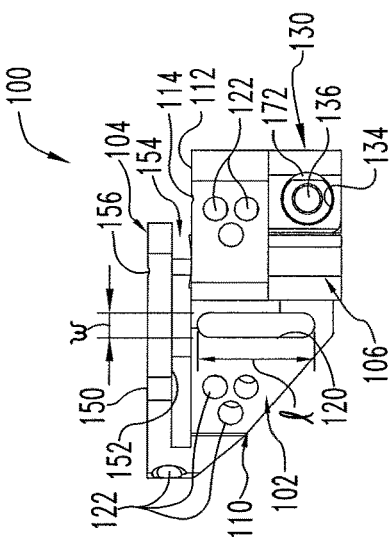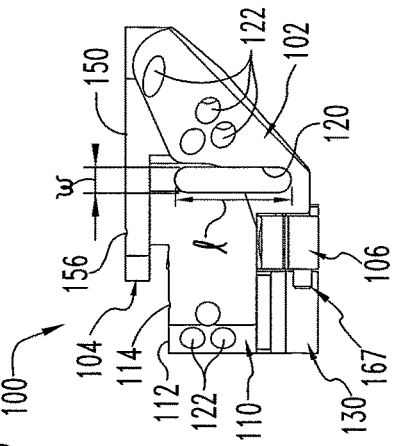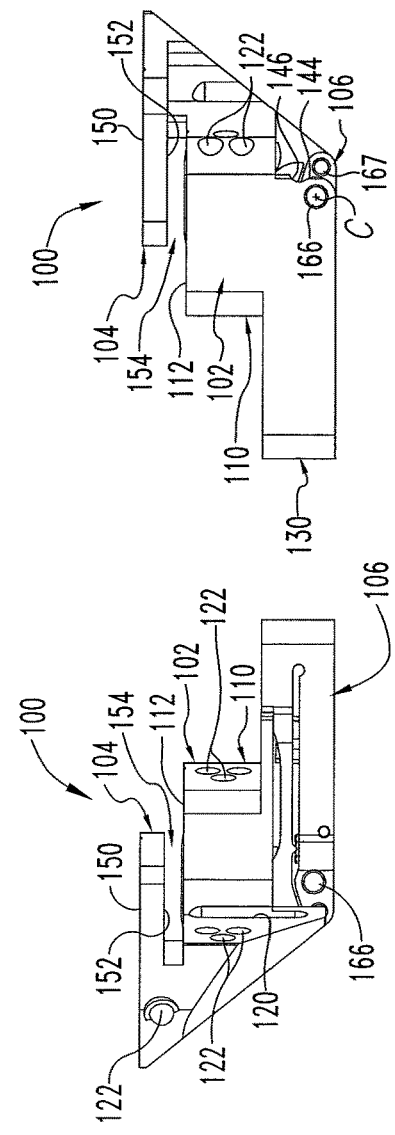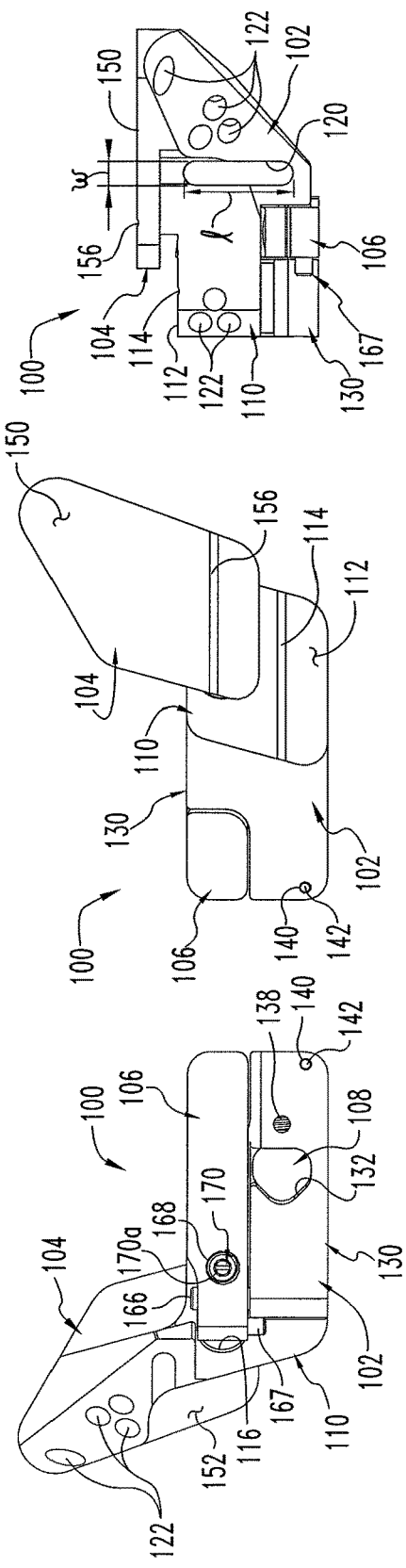

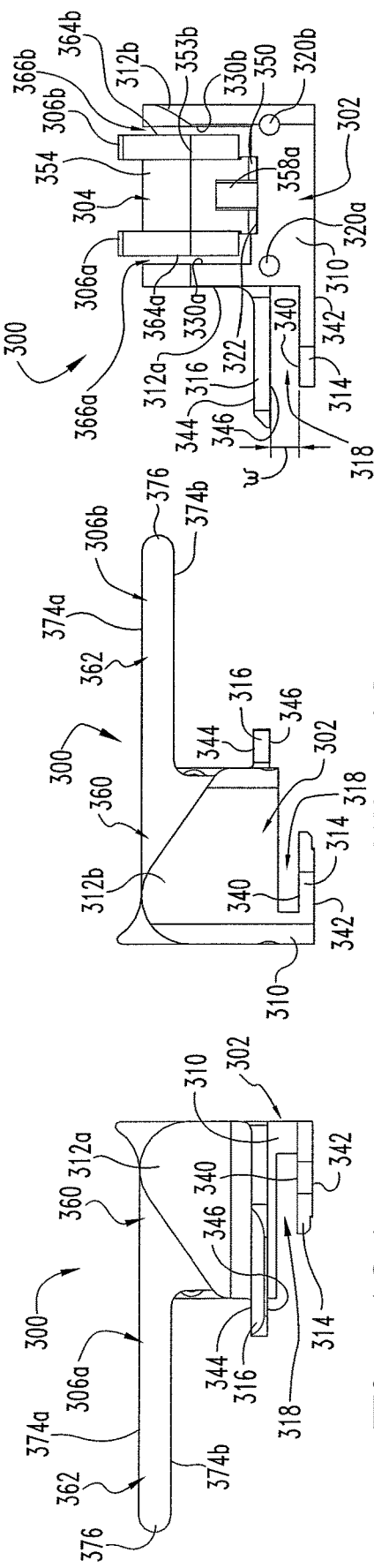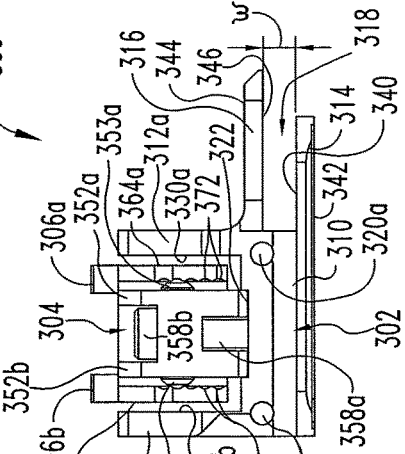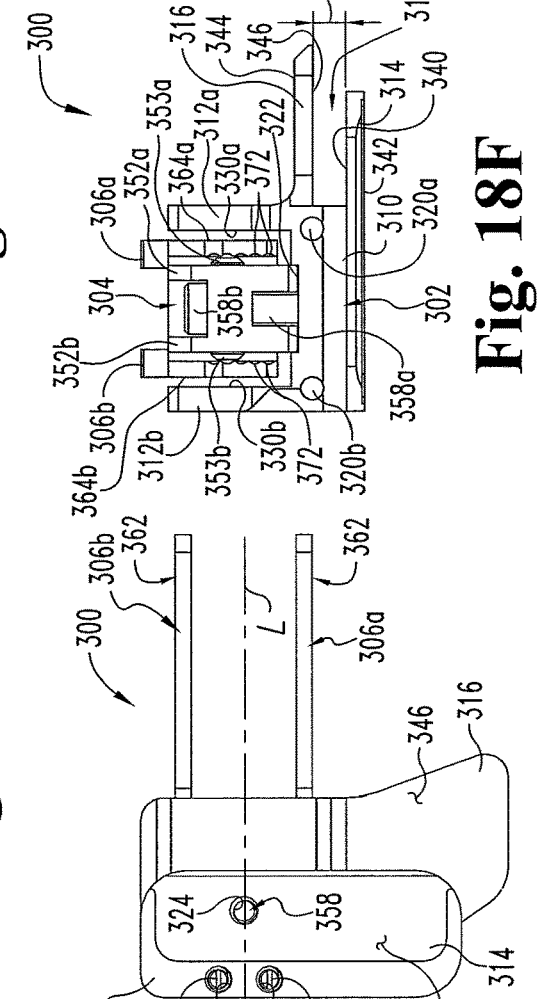

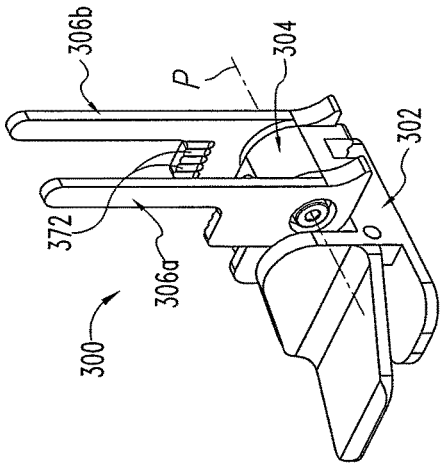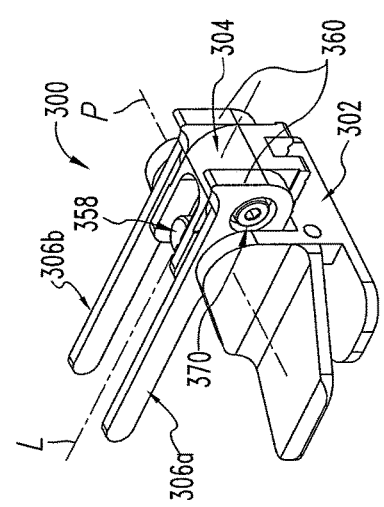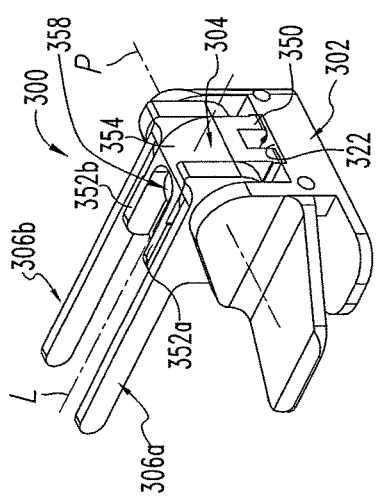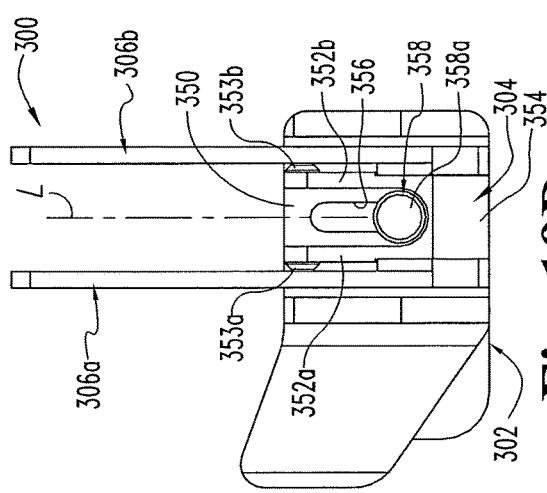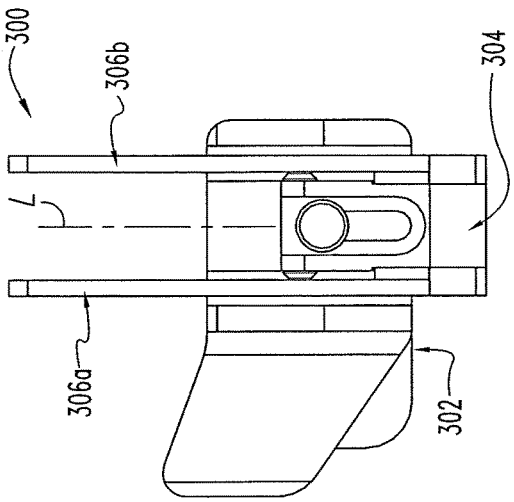

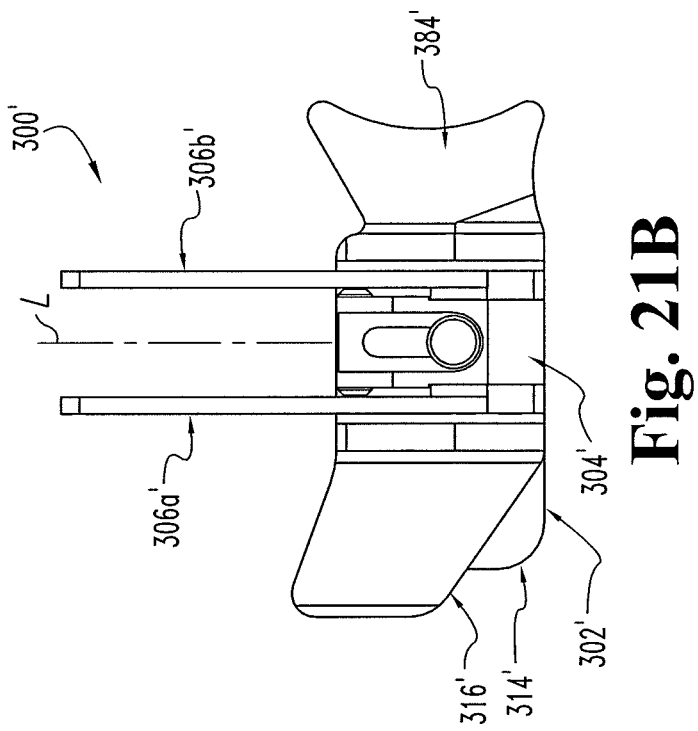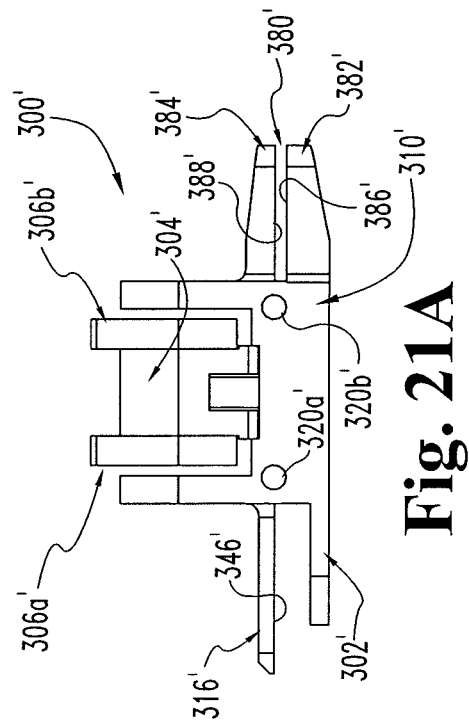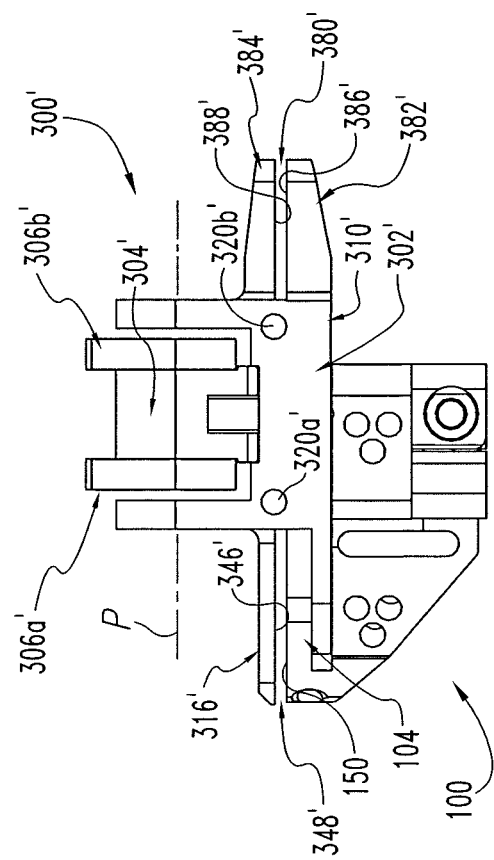

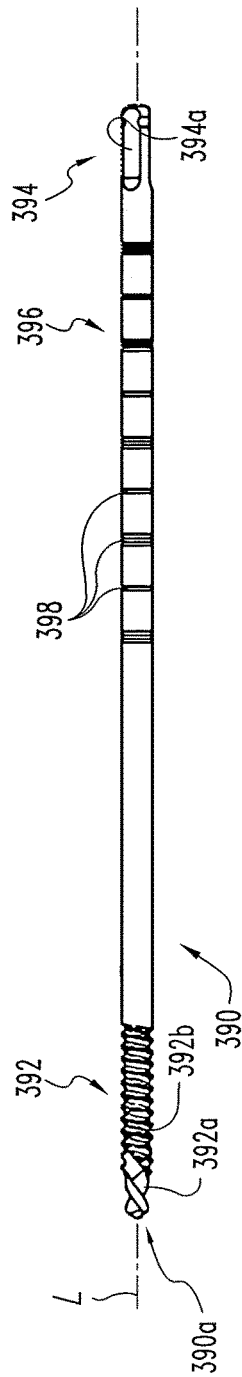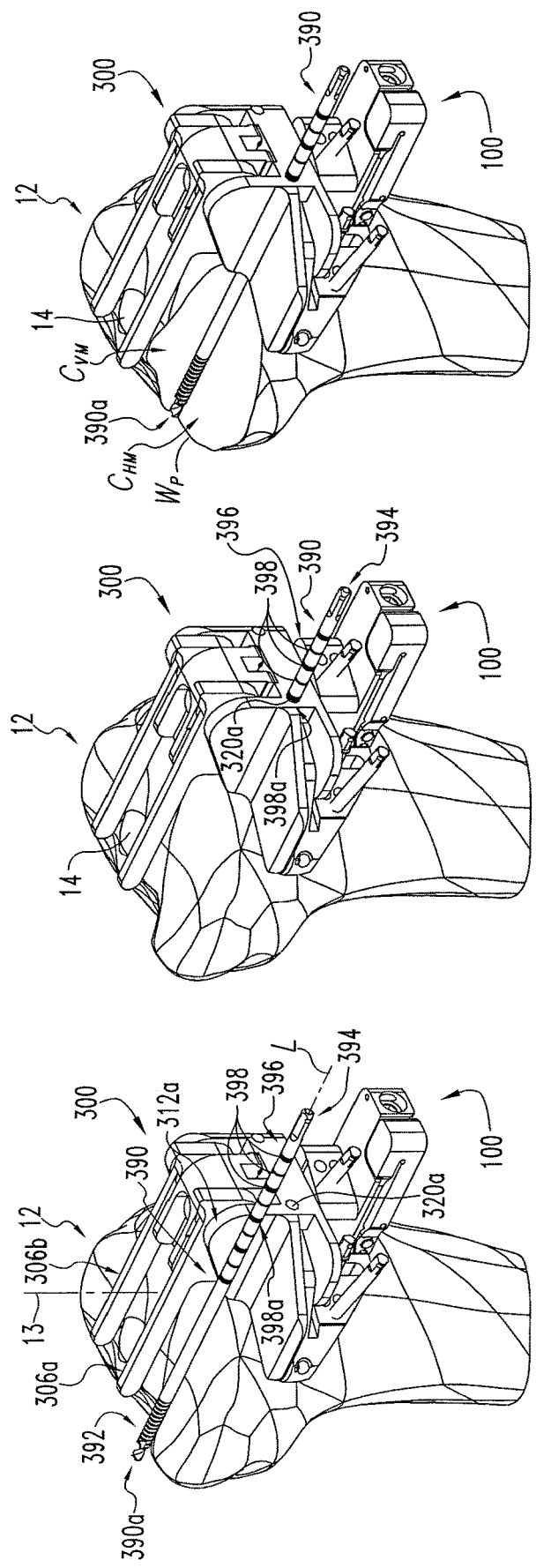

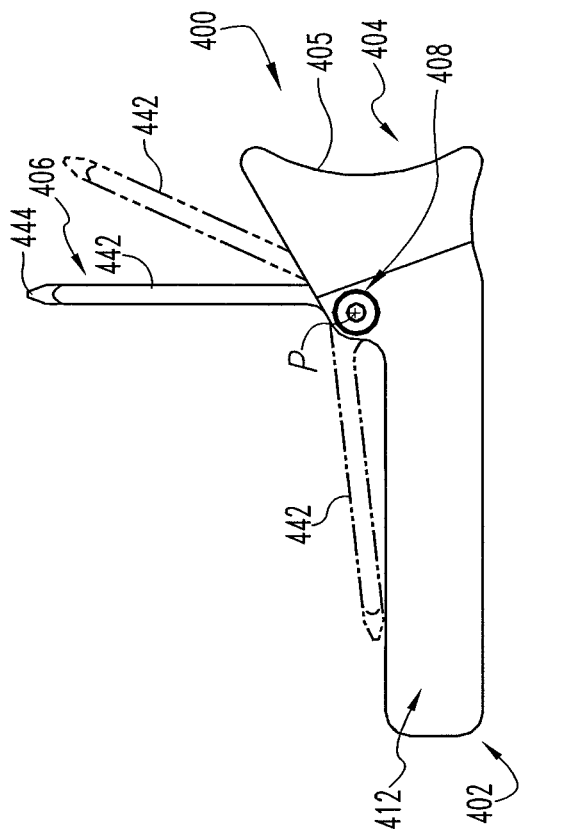
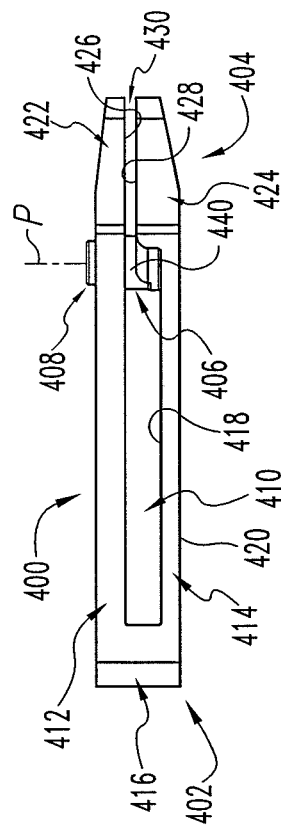
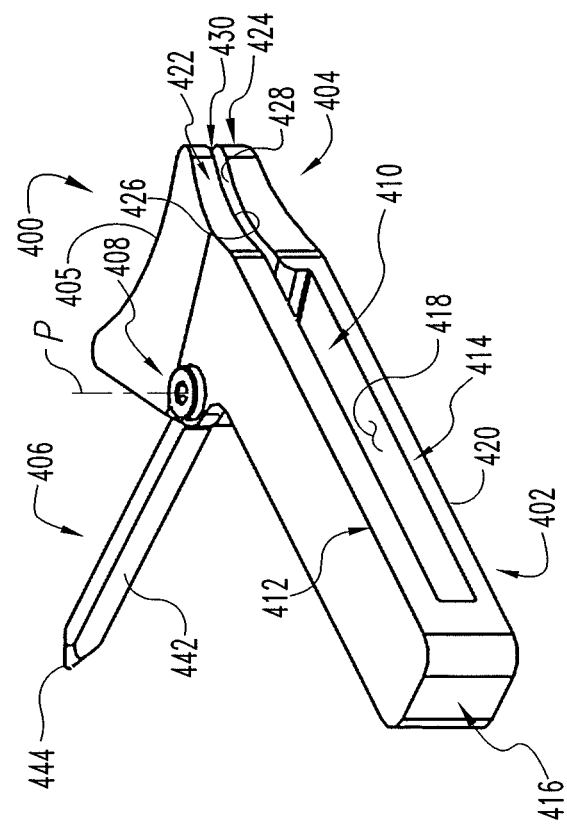

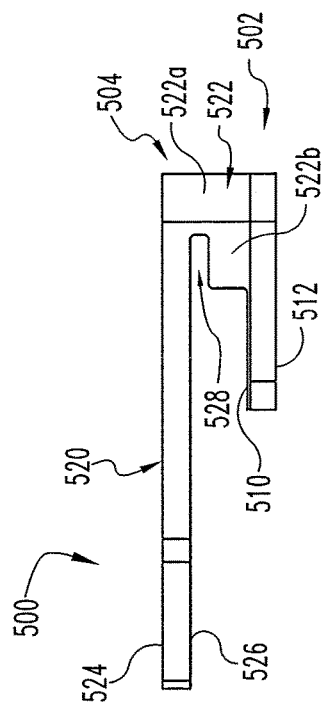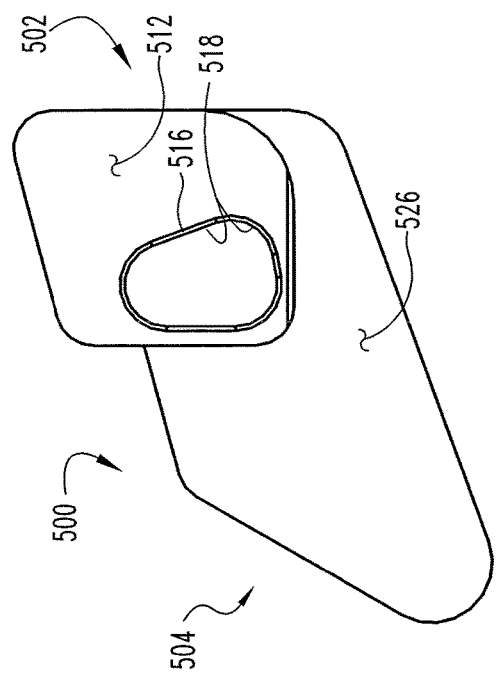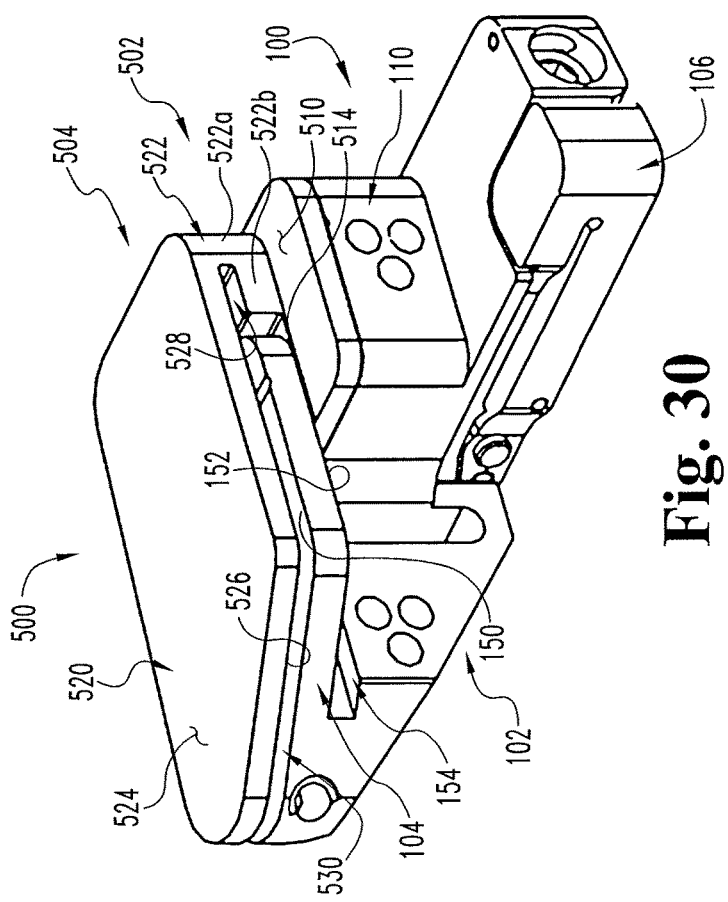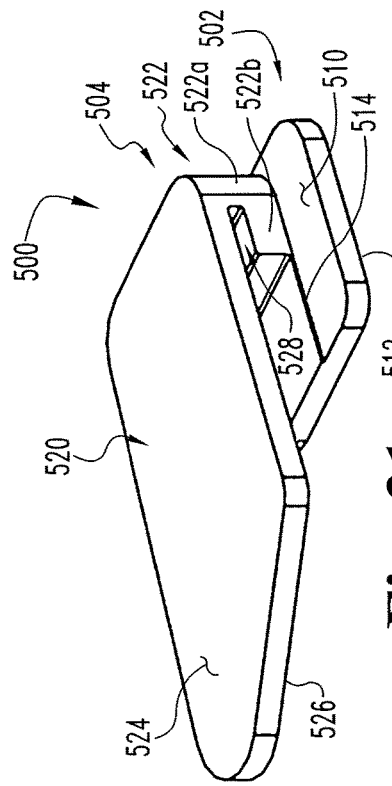

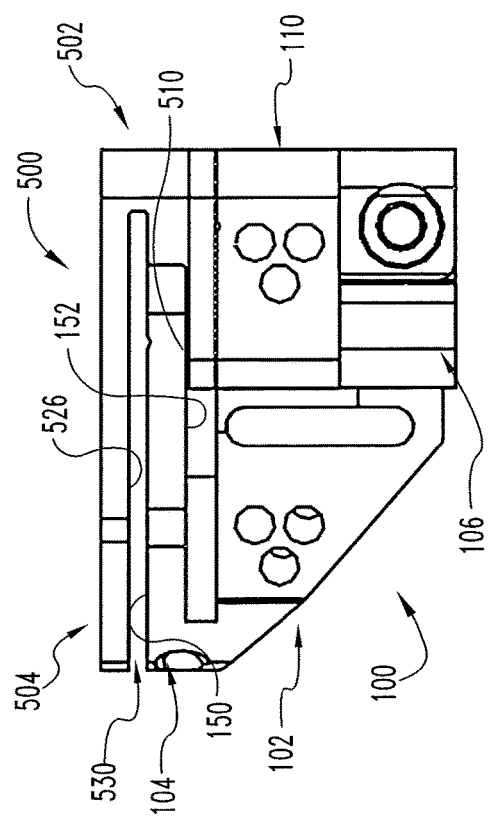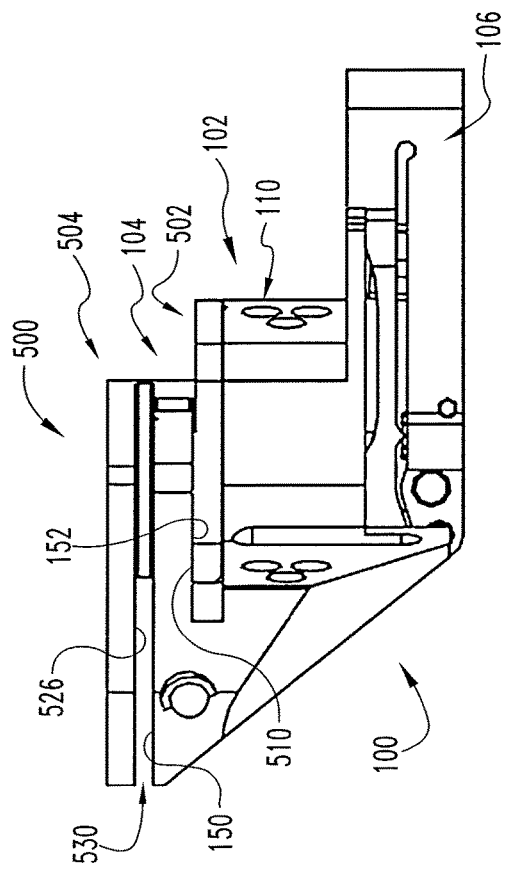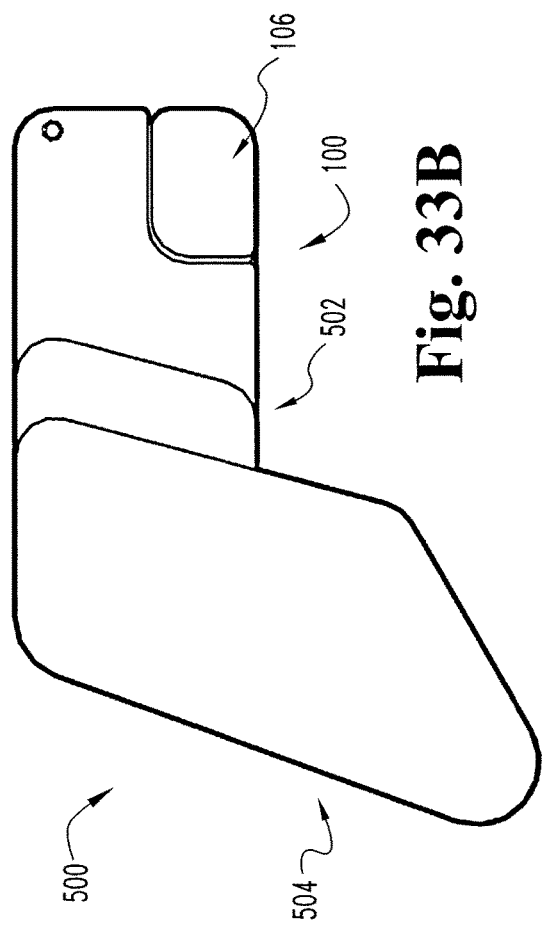

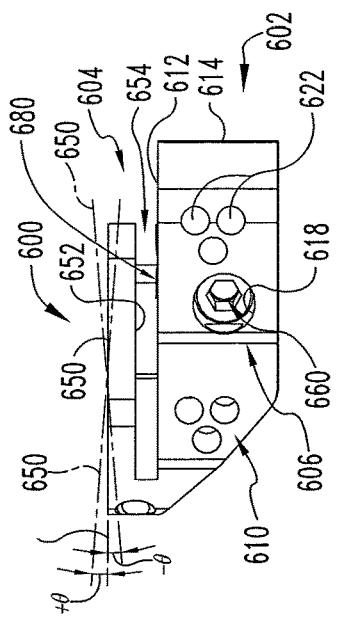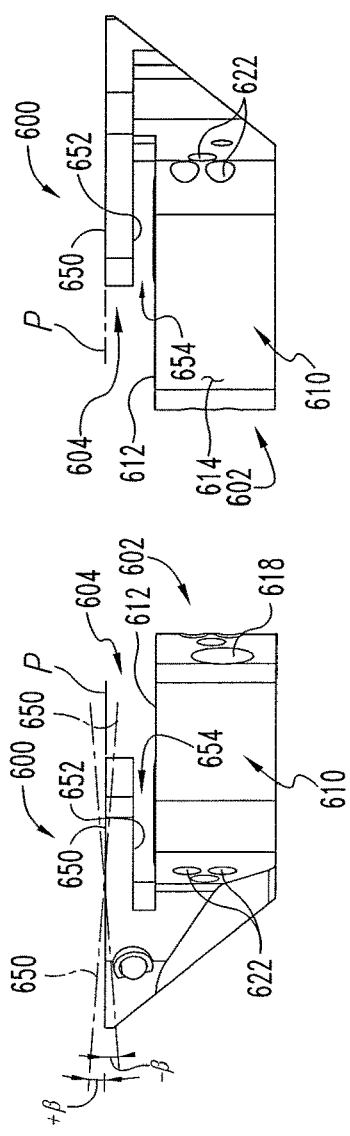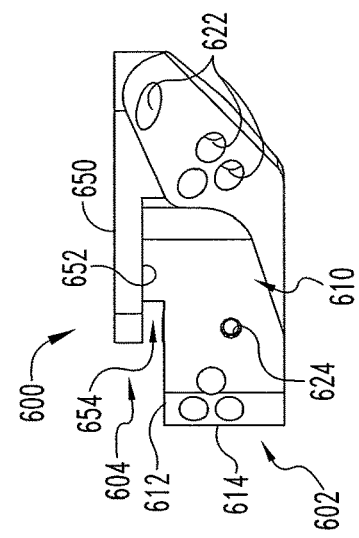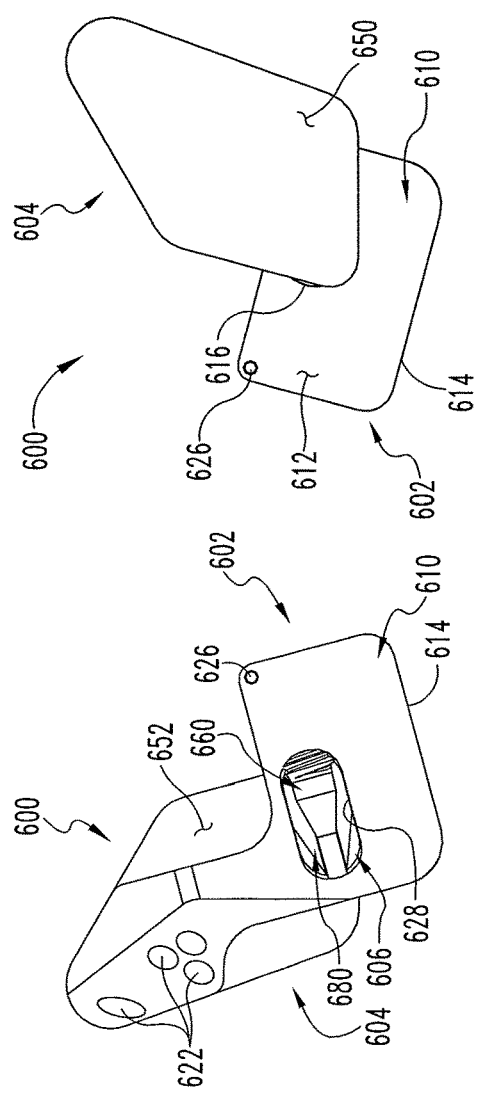
Fig. 36A Fig. 36B Fig. 36C Fig. 36D Fig. 36E Fig. 36F

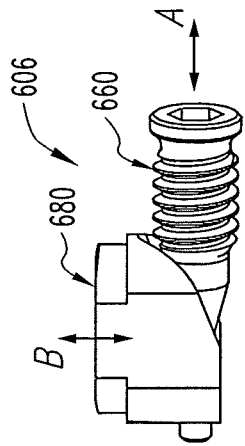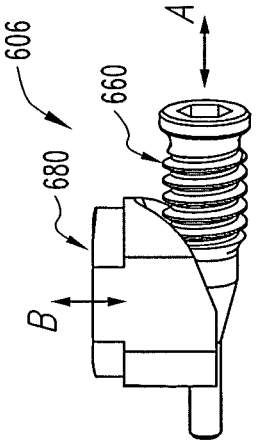
Fig. 38A      Fig. 38B
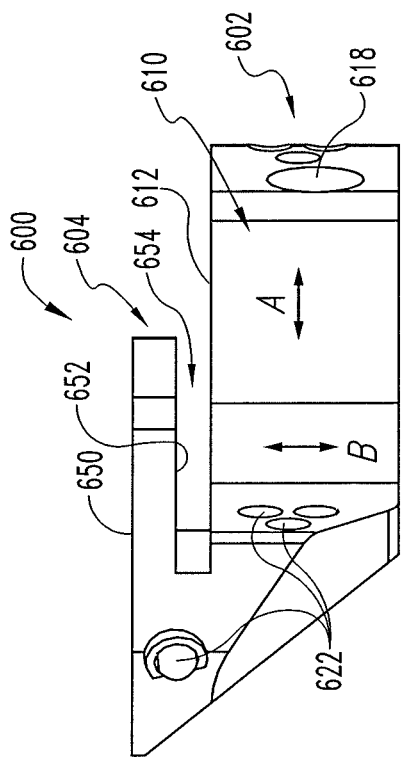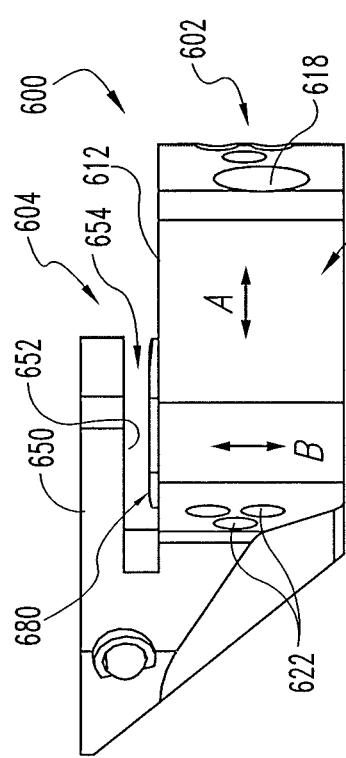
Fig. 37A      Fig. 37B

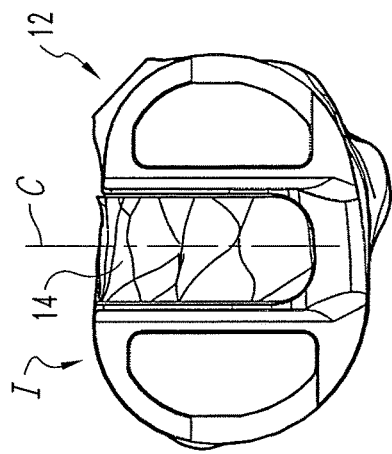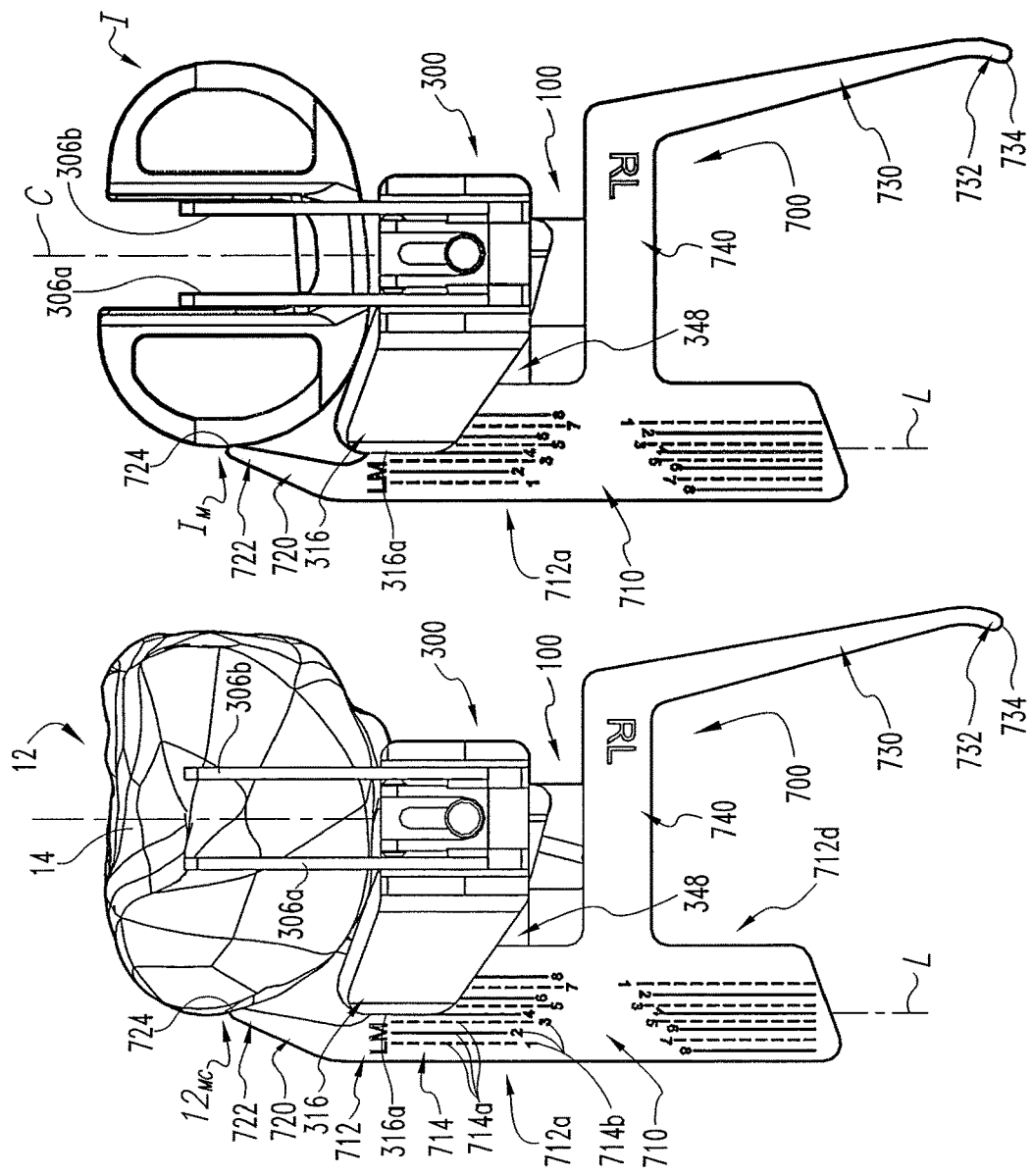
Fig. 41C
Fig. 41B
Fig. 41A

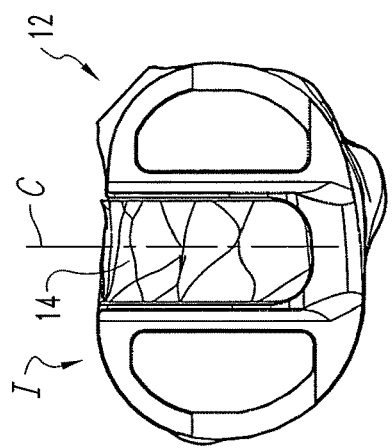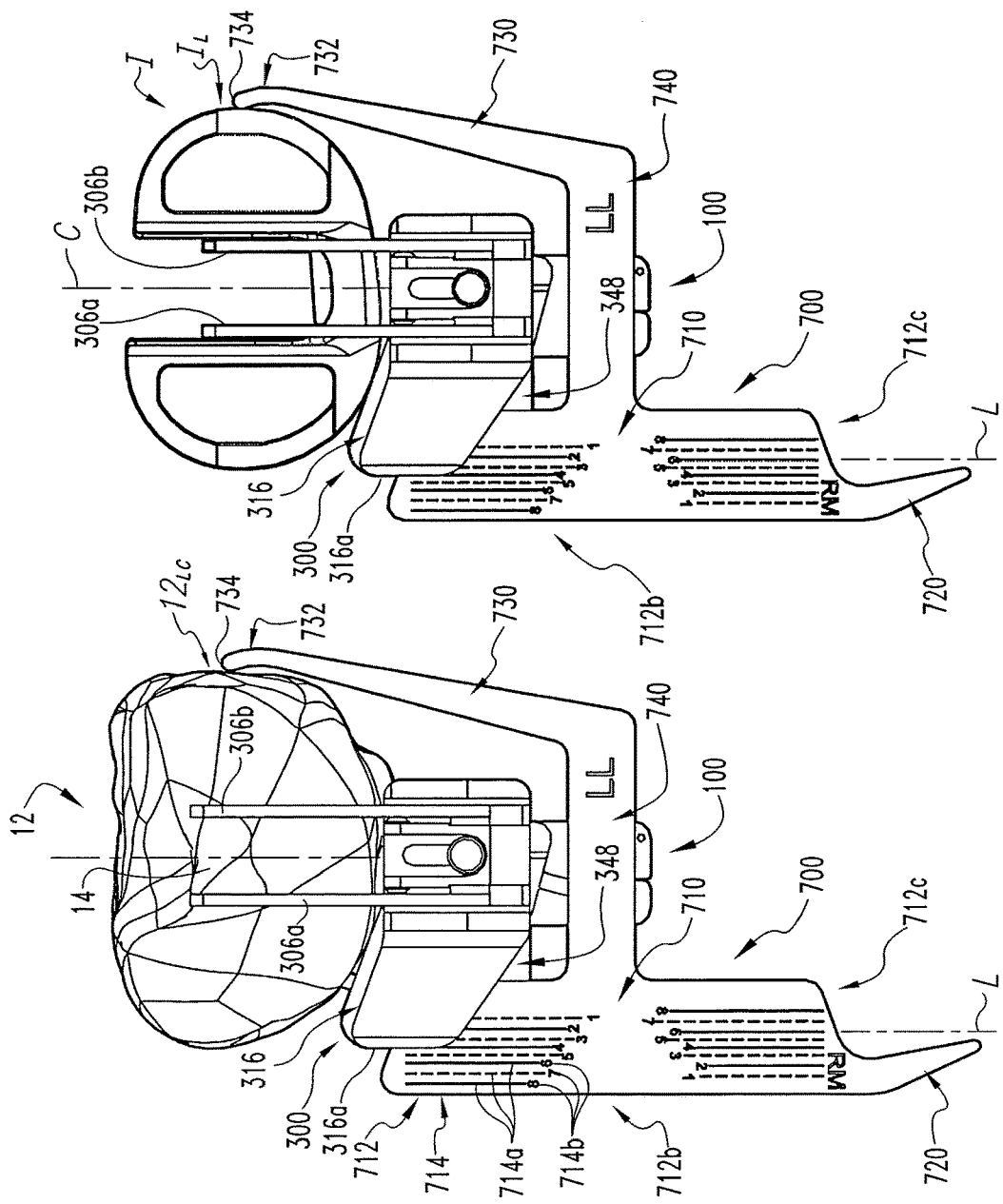
Fig. 42C
Fig. 42B
Fig. 42A

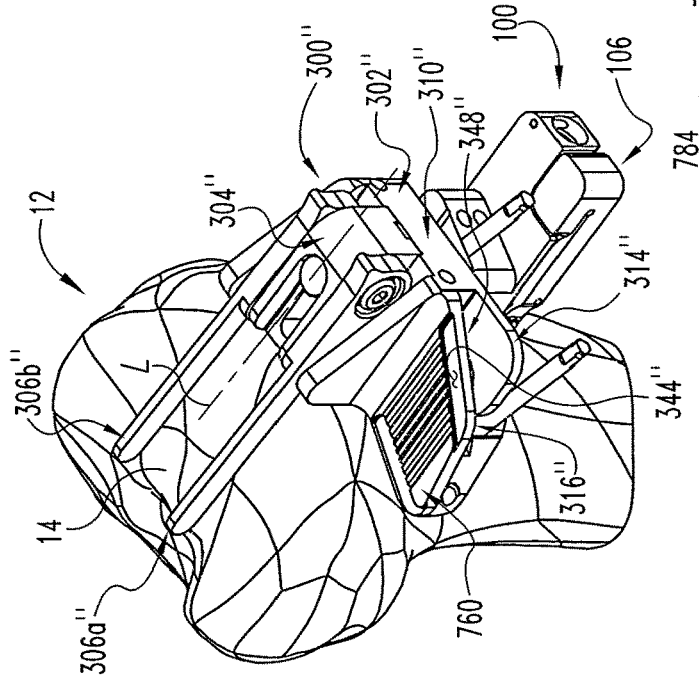
Fig. 44A
Fig. 44B
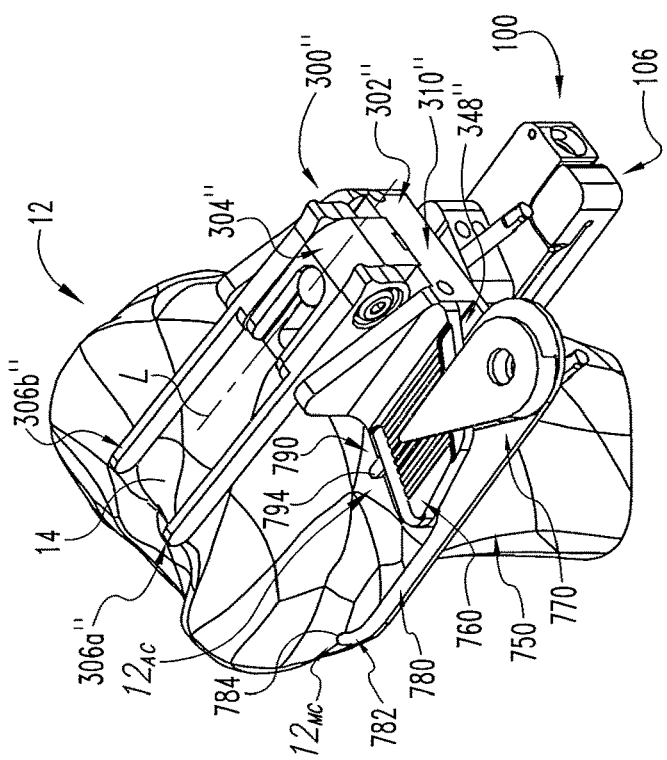
Fig. 43

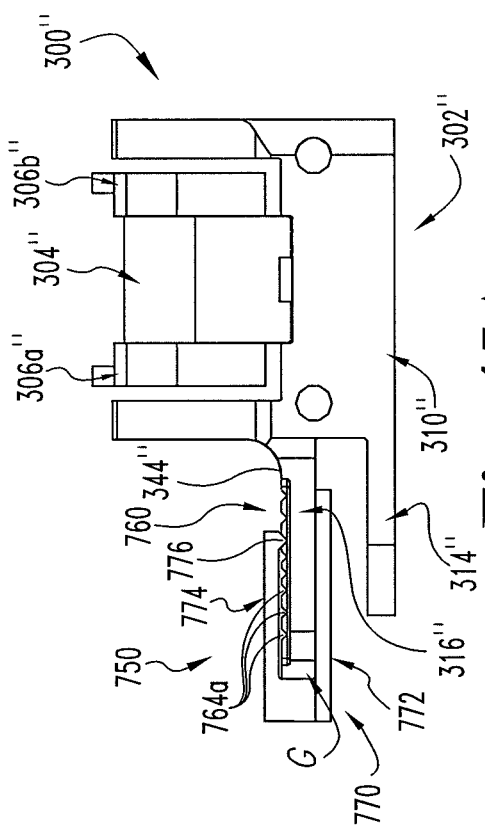
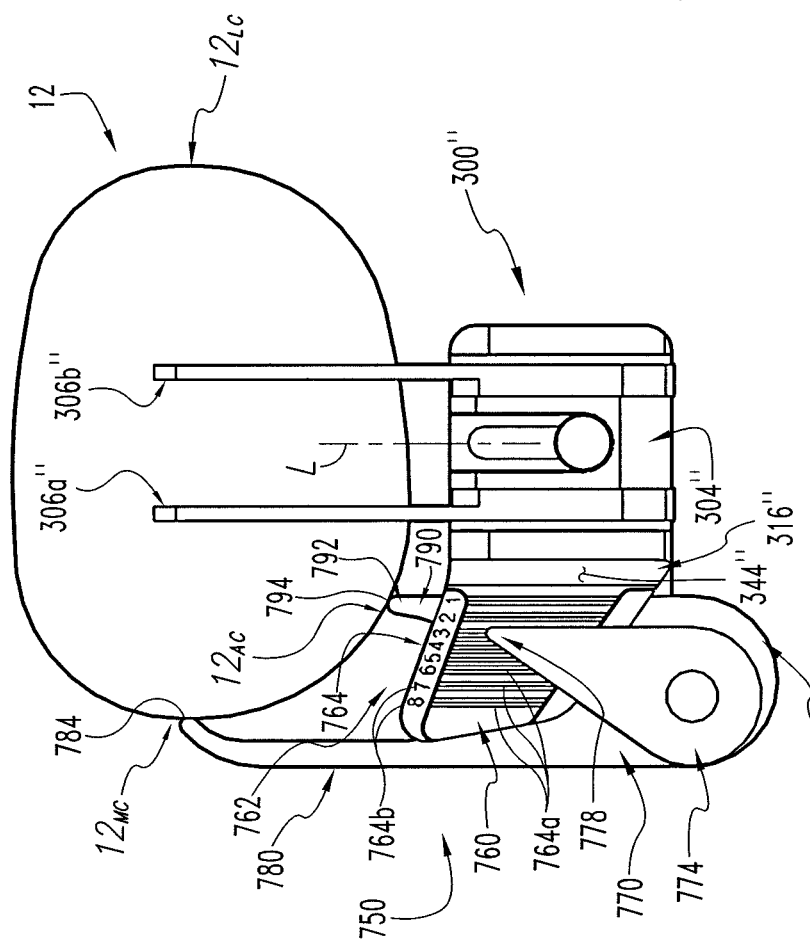

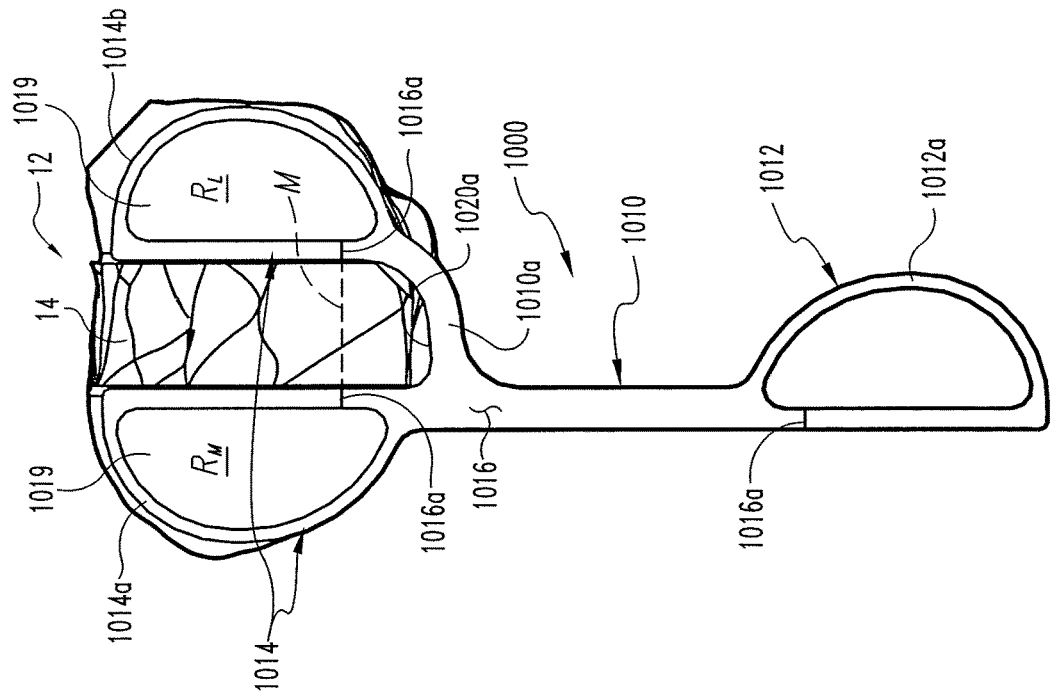
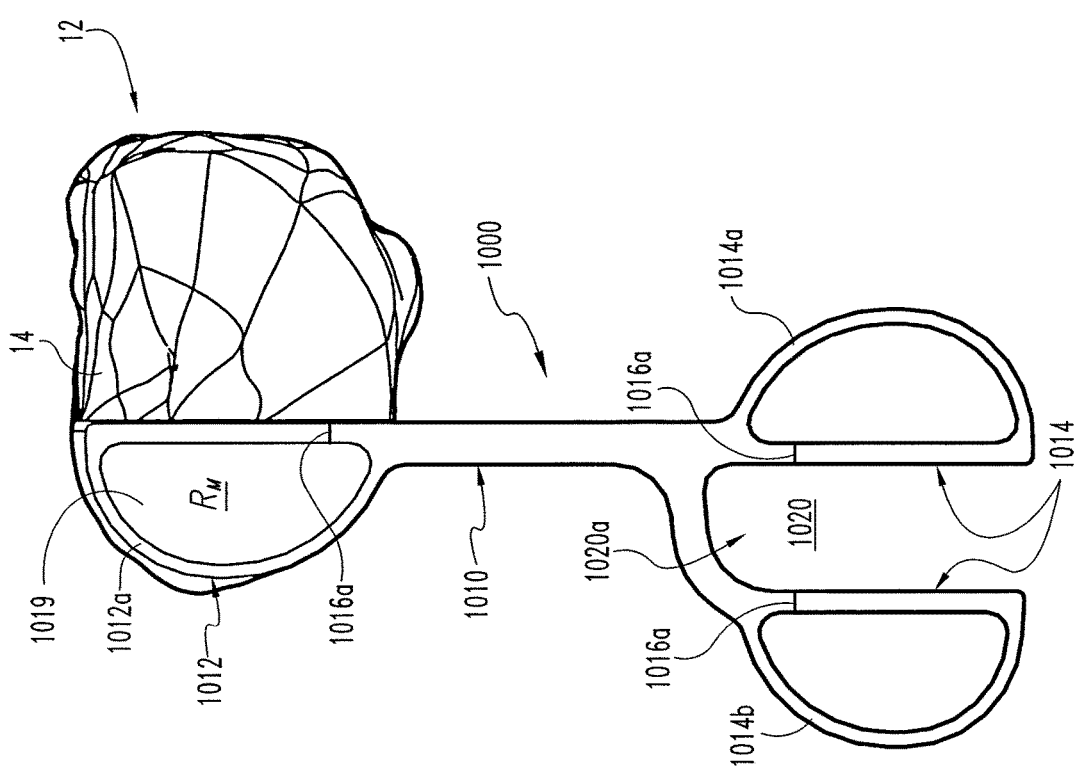
Fig. 60A
Fig. 60B

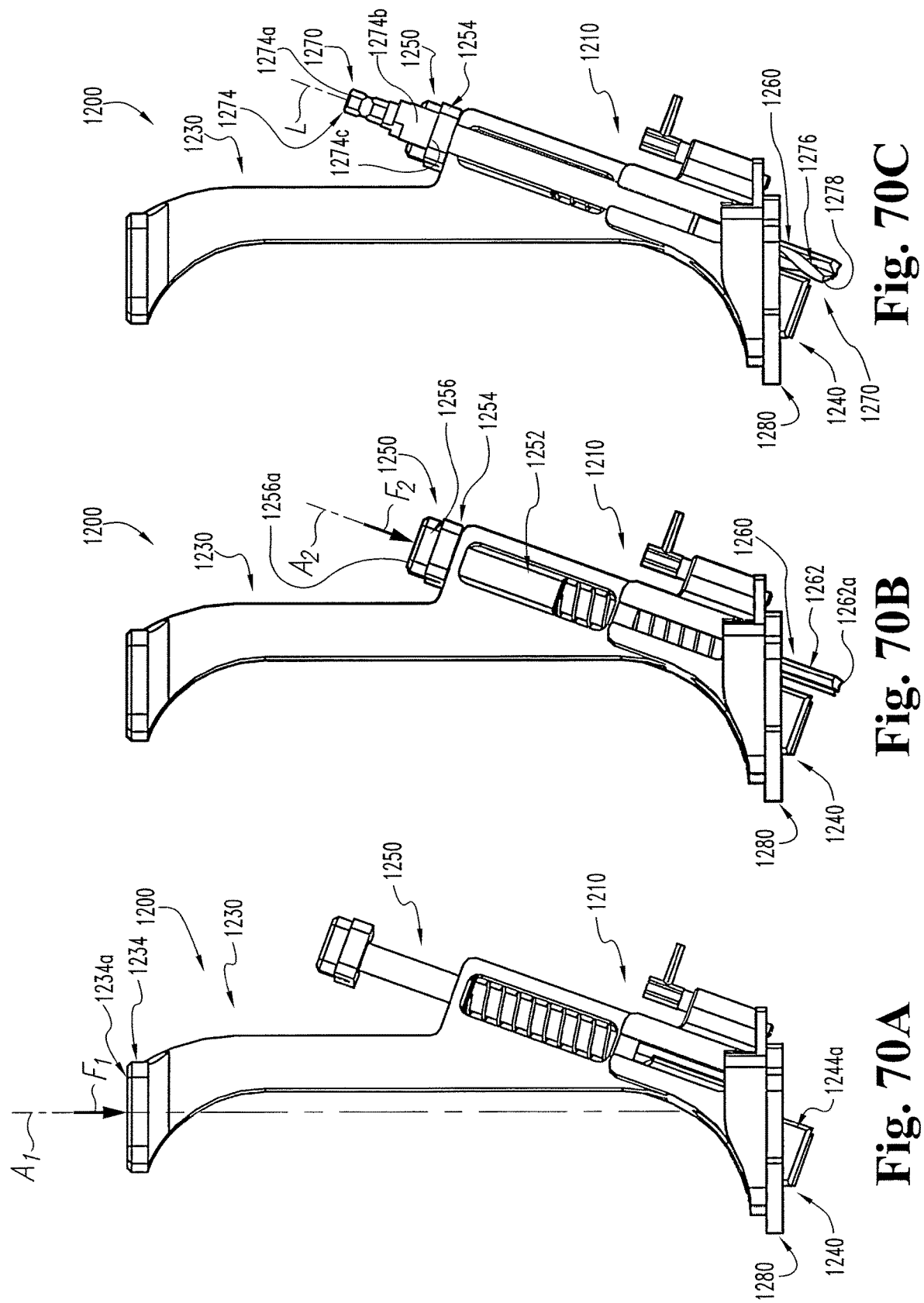

DEVICES AND METHODS FOR PERFORMING KNEE ARTHROPLASTY

CROSS-REFERENCE TO RELATED APPLICATION

The present application is a divisional of U.S. patent application Ser. No. 16/251,636, filed Jan. 18, 2019, entitled DEVICES AND METHODS FOR PERFORMING KNEE ARTHROPLASTY, which application is a continuation of U.S. patent application Ser. No. 13/661,636, filed Oct. 26, 2012, now U.S. Pat. No. 10,201,356, entitled Devices and Methods for Performing Knee Arthroplasty, which claims the benefit of U.S. Provisional Patent Application Ser. No. 61/552,321, filed Oct. 27, 2011, the contents of each application incorporated herein by reference in their entirety.

FIELD OF THE INVENTION

The present invention relates generally to surgical devices and methods, and more particularly relates to orthopaedic devices and methods for performing knee arthroplasty.

BACKGROUND

Total knee arthroplasty procedures often require the sacrifice of the anterior cruciate ligament (ACL) and/or the posterior cruciate ligament (PCL). As such, total knee prostheses often include structures and mechanisms that attempt to provide the same or similar functions provided by the ACL and PCL. However, these conventional total knee prostheses may not fully replicate the normal proprioception, kinematics, and/or biomechanical functions provided by natural ligaments. Bicruciate retaining knee replacements have been used in the past, but were associated with problems of knee stiffness and implant failure that were likely attributable to inadequate implant design, instrumentation, and/or implantation technique. Accordingly, there is a desire in some cases to preserve functioning cruciate ligaments in young and active patients who require knee joint replacement, to maintain a natural feeling, and normal biomechanical function and performance of the knee after total knee replacement. There is also a desire for more efficient and accurate devices and methods for preparing femurs and tibias for bicruciate retaining implants (i.e., ACL and PCL preserving implants), as well as other types of knee implants, since many knee procedures (especially, but not limited to, bicruciate retaining procedures) often utilize devices and methods that are less than ideal.

Thus, there remains a need to provide improved devices and methods for performing knee arthroplasty. The present invention satisfies this need and provides other benefits and advantages in a novel and unobvious manner.

SUMMARY

While the actual nature of the invention covered herein can only be determined with reference to the claims appended hereto, certain forms of the invention that are characteristic of the embodiments disclosed herein are described briefly as follows.

Devices and methods for performing knee arthroplasty procedures are provided, including device and methods used in association with total knee arthroplasty (TKA) procedures and techniques including, for example, procedures and techniques such as bicruciate retaining arthroplasty, as well as other procedures and techniques described herein.

In one form of the invention, instrumentation is provided for resection of the proximal tibia. The instrumentation includes a mounting base adapted for coupling to the proximal tibia, a cutting guide extending laterally from the mounting base and including a lateral guide channel arranged along a cutting plane and dimensioned to guide a cutting device generally along the cutting plane to form a resection cut in the proximal tibia, and an elongate pin interconnected with a mounting portion of the instrument and dimensioned for receipt within an opening in the proximal tibia, the elongate pin positioned adjacent the lateral guide channel within the cutting plane to thereby limit lateral displacement of the cutting device within the lateral guide channel along the cutting plane.

In another form of the invention, instrumentation is provided for resection of the proximal tibia. The instrumentation includes a cutting device, a mount device configured for attachment to the proximal tibia and including a generally planar reference member extending along a reference plane, a mounting base releasably lockable to the planar reference member of the mount device, a cutting guide extending laterally from the mounting base and including a lateral guide channel arranged along a cutting plane and dimensioned to guide the cutting device generally along the cutting plane to form a resection cut in the proximal tibia, and an elongate pin pivotally connected to either the mounting base or the cutting guide and configured for pivotal movement generally along the cutting plane, the elongate pin dimensioned for receipt within an opening in the proximal tibia, the elongate pin positioned adjacent the lateral guide channel within the cutting plane to thereby limit lateral displacement of the cutting device within the lateral guide channel along the cutting plane.

In another form of the invention, a method is provided for resection of the proximal tibia. The method includes the steps of providing an instrument including a cutting guide and an elongate pin, the cutting guide defining a lateral guide channel extending along a cutting plane, the elongate pin interconnected with a mounting portion of the instrument and positioned adjacent the lateral guide channel within the cutting plane, inserting the elongate pin into an opening in the proximal tibia, mounting the instrument to the proximal tibia, guiding a cutting device through the lateral guide channel generally along the cutting plane to form a resection cut in the proximal tibia, and limiting displacement of the cutting device within the lateral guide channel laterally beyond the elongate pin to control a lateral depth of the resection cut in the proximal tibia.

It is one object of the present invention to provide improved orthopaedic devices and methods for performing knee arthroplasty. Further embodiments, forms, features, aspects, benefits, objects, and advantages of the present invention will become apparent from the detailed description and figures provided herewith.

BRIEF DESCRIPTION OF THE DRAWINGS

FIG. 5 illustrates a datum block according to one form of the invention, as shown in relation to the proximal tibia.
FIG. 6A illustrates a left side view of the datum block of FIG. 5.

FIG. 6B illustrates a right side view of the datum block of FIG. 5.

FIG. 6C illustrates an anterior end view of the datum block of FIG. 5.

FIG. 6D illustrates a bottom view of the datum block of FIG. 5.

FIG. 6E illustrates a top view of the datum block of FIG. 5.

FIG. 6F illustrates a posterior end view of the datum block of FIG. 5.

FIG. 9 illustrates the datum block of FIG. 5 provisionally attached to the proximal tibia by a provisional attachment pin.

FIG. 10 illustrates the datum block of FIG. 5 terminally attached to the proximal tibia by terminal attachment pins.

FIG. 18A illustrates a left side view of the eminence stylus of FIG. 17A.

FIG. 18B illustrates a right side view of the eminence stylus of FIG. 17A.

FIG. 18C illustrates an anterior end view of the eminence stylus of FIG. 17A.

FIG. 18D illustrates a top view of the eminence stylus of FIG. 17A.

FIG. 18E illustrates a bottom view of the eminence stylus of FIG. 17A.

FIG. 18F illustrates a posterior end view of the eminence stylus of FIG. 17A.

FIG. 19A illustrates a perspective view of the eminence stylus of FIG. 17A in a first operational position.

FIG. 19B illustrates a perspective view of the eminence stylus of FIG. 17A in a second operational position.

FIG. 19C illustrates a perspective view of the eminence stylus of FIG. 17A in a third operational position.

FIG. 19D illustrates a top view of the first operational position of the eminence stylus of FIG. 19A.

FIG. 19E illustrates a top view of the second operational position of the eminence stylus of FIG. 19B.

FIG. 21A illustrates an anterior end view of an eminence stylus according to another form of the invention.

FIG. 21B illustrates a top view of the eminence stylus of FIG. 21A.

FIG. 22 illustrates the eminence stylus of FIGS. 21A and 21B locked to the datum block of FIG. 5.

FIG. 23 illustrates a graduated tibial pin according to one form of the invention.

FIG. 24A illustrates the graduated tibial pin of FIG. 23, as shown relative to the eminence stylus of FIG. 17A locked to the datum block of FIG. 5, all shown in relation to the proximal tibia.

FIG. 24B illustrates the graduated tibial pin of FIG. 23, as shown engaged with the eminence stylus and anchored in the proximal tibia.

FIG. 24C illustrates the graduated tibial pin of FIG. 23, as shown engaged with the eminence stylus and anchored in the proximal tibia in relation to the medially resected proximal tibia.

FIG. 27 illustrates a perspective view of the lateral cut guide of FIG. 26.

FIG. 28A illustrates a top view of the lateral cut guide of FIG. 27.

FIG. 28B illustrates an anterior view of the lateral cut guide of FIG. 27.

FIG. 30 illustrates a saw capture block according to one form of the invention, as shown attached to the datum block of FIG. 5.

FIG. 31 illustrates a perspective view of the saw capture block of FIG. 30.

FIG. 32A illustrates an anterior end view of the saw capture block of FIG. 31.

FIG. 32B illustrates a bottom view of the saw capture block of FIG. 31.

FIG. 33A illustrates a left side view of FIG. 30.

FIG. 33B illustrates a top view of FIG. 30.

FIG. 33C illustrates an anterior end view of FIG. 30.

FIG. 36A illustrates a left side view of the recut block of FIG. 34.

FIG. 36B illustrates a right side view of the recut block of FIG. 34.

FIG. 36C illustrates an anterior end view of the recut block of FIG. 34.

FIG. 36D illustrates a bottom view of the recut block of FIG. 34.

FIG. 36E illustrates a top view of the recut block of FIG. 34.

FIG. 36F illustrates a posterior end view of the recut block of FIG. 34.

FIG. 37A illustrates an unlocked configuration of the recut block of FIG. 34.

FIG. 37B illustrates a locked configuration of the recut block of FIG. 34.

FIG. 38A illustrates one embodiment of a locking mechanism used in association with the recut block of FIG. 37A, as shown in an unlocked configuration.

FIG. 38B illustrates the locking mechanism of FIG. 38A, as shown in a locked configuration.

FIG. 41A illustrates a first operational position of the tibia size gauge of FIG. 40, as shown in relation to the eminence stylus and the unresected medial region of the proximal tibia.

FIG. 41B illustrates the tibia size gauge of FIG. 40, as shown in relation to a medial portion of a tibial baseplate.

FIG. 41C illustrates the tibial baseplate of FIG. 41B engaged to the resected proximal tibia.

FIG. 42A illustrates a second operational position of the tibia size gauge of FIG. 40, as shown in relation to the eminence stylus and the unresected lateral region of the proximal tibia.

FIG. 42B illustrates the tibia size gauge of FIG. 40, as shown in relation to a lateral portion of a tibial baseplate.

FIG. 42C illustrates the tibial baseplate of FIG. 42B engaged to the resected proximal tibia.

FIG. 43 illustrates a tibia size gauge according to another form of the invention, including a gauge pointer engaged with another embodiment of an eminence stylus locked to the datum block of FIG. 5 in relation to the proximal tibia.

FIG. 44A illustrates a perspective view of the gauge pointer of FIG. 43.

FIG. 44B illustrates a perspective view of the eminence stylus of FIG. 43.

FIG. 45A illustrates an anterior end view of the tibia size gauge of FIG. 43.

FIG. 45B illustrates a top view of the tibia size gauge of FIG. 43, as shown in relation to the proximal tibia.

FIG. 60A illustrates a superior view of FIG. 59A.

FIG. 60B illustrates a superior view of FIG. 59B.

FIG. 65 illustrates a perspective view of a keel cavity formation instrument according to one form of the invention.

FIG. 66 illustrates an exploded view of the keel cavity formation instrument of FIG. 65.

FIG. 67 illustrates a left side view of the keel cavity formation instrument of FIG. 65.

FIG. 68 illustrates a tibial baseplate trial for use in association with the keel cavity formation instrument of FIG. 65, as shown engaged with the medially and laterally resected proximal tibia and with the superior/anterior portion of the tibial eminence removed from the proximal tibia.

FIG. 69 illustrates the keel cavity formation instrument of FIG. 65 engaged with the tibial baseplate trial of FIG. 68 in relation to the distal femur and the proximal tibia.

FIG. 70A illustrates a first operational position of the keel cavity formation instrument of FIG. 65 for forming medial and lateral keel slots in the medially and laterally resected surfaces of the proximal tibia.

FIG. 70B illustrates a second operational position of the keel cavity formation instrument of FIG. 65 for forming an anterior keel slot in the anterior resected surface of the proximal tibia.

FIG. 70C illustrates a third operational position of the keel cavity formation instrument of FIG. 65 for forming clearance openings in the proximal tibia at locations between the medial and lateral keel slots and the anterior keel slot.

FIG. 71A illustrates a superior view of the proximal tibia following formation of the medial and lateral keel slots in the medially and laterally resected surfaces of the proximal tibia.

FIG. 71B illustrates a superior view of the proximal tibia following formation of the anterior keel slot in the anterior resected surface of the proximal tibia.

FIG. 71C illustrates a superior view of the proximal tibia following formation of the clearance openings in the proximal tibia at locations between the medial and lateral keel slots and the anterior keel slot.

FIG. 72A illustrates a perspective view of an anterior tibial gauge according to one form of the invention.

Figure 72A:
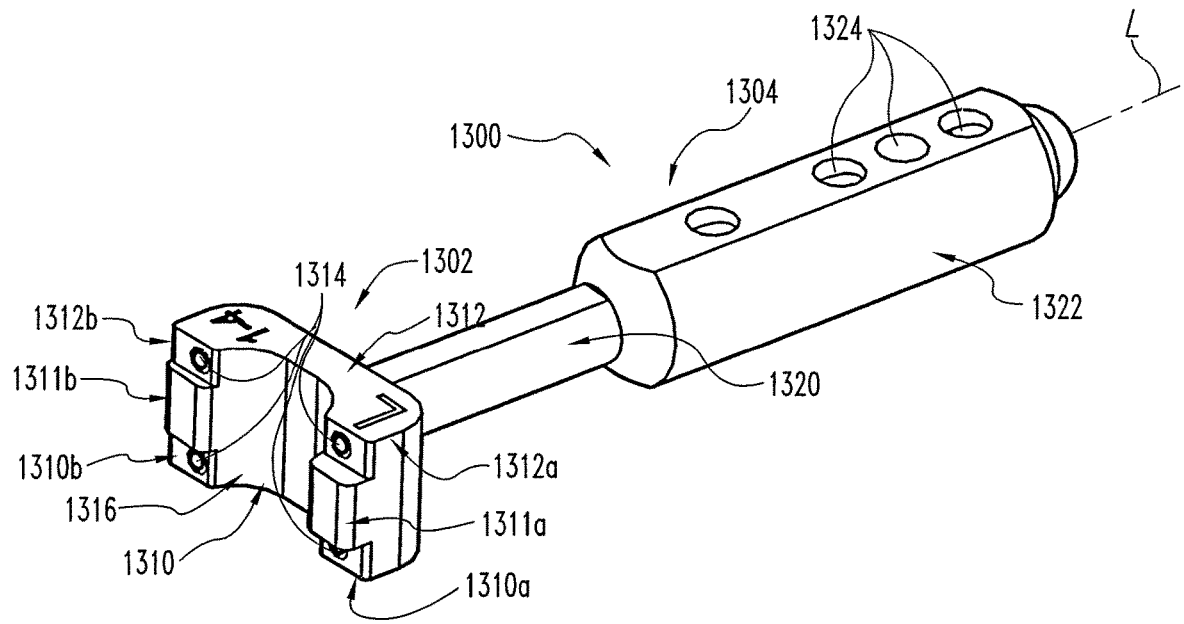
Figure 72B:
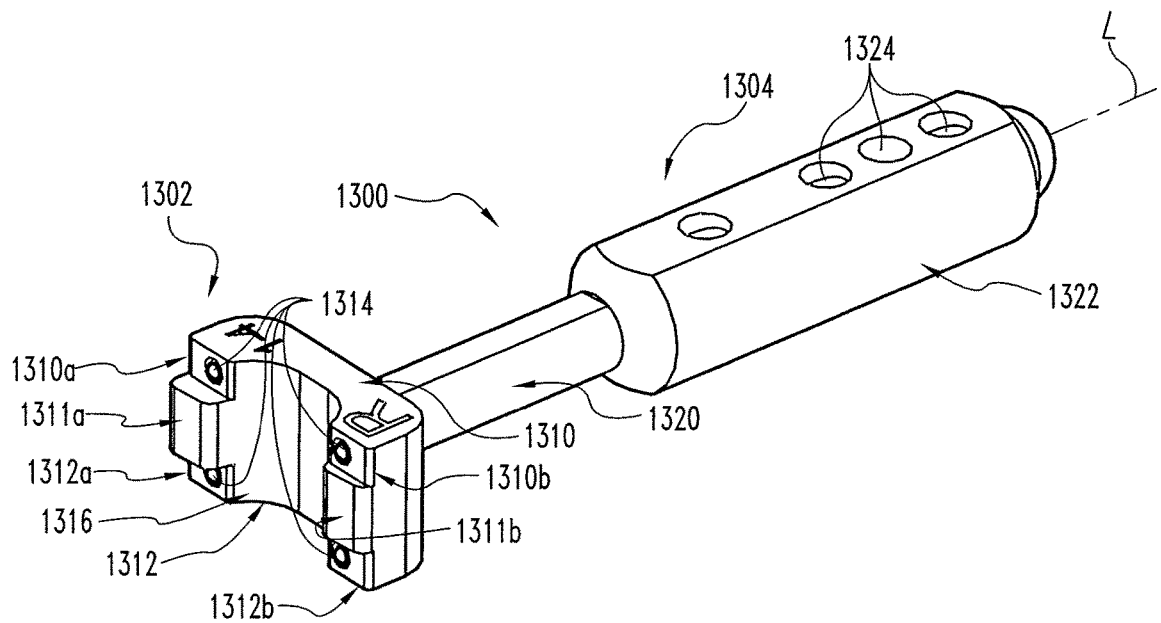

FIG. 72B illustrates another perspective view of the anterior tibial gauge of FIG. 72A.

Figure 73A:
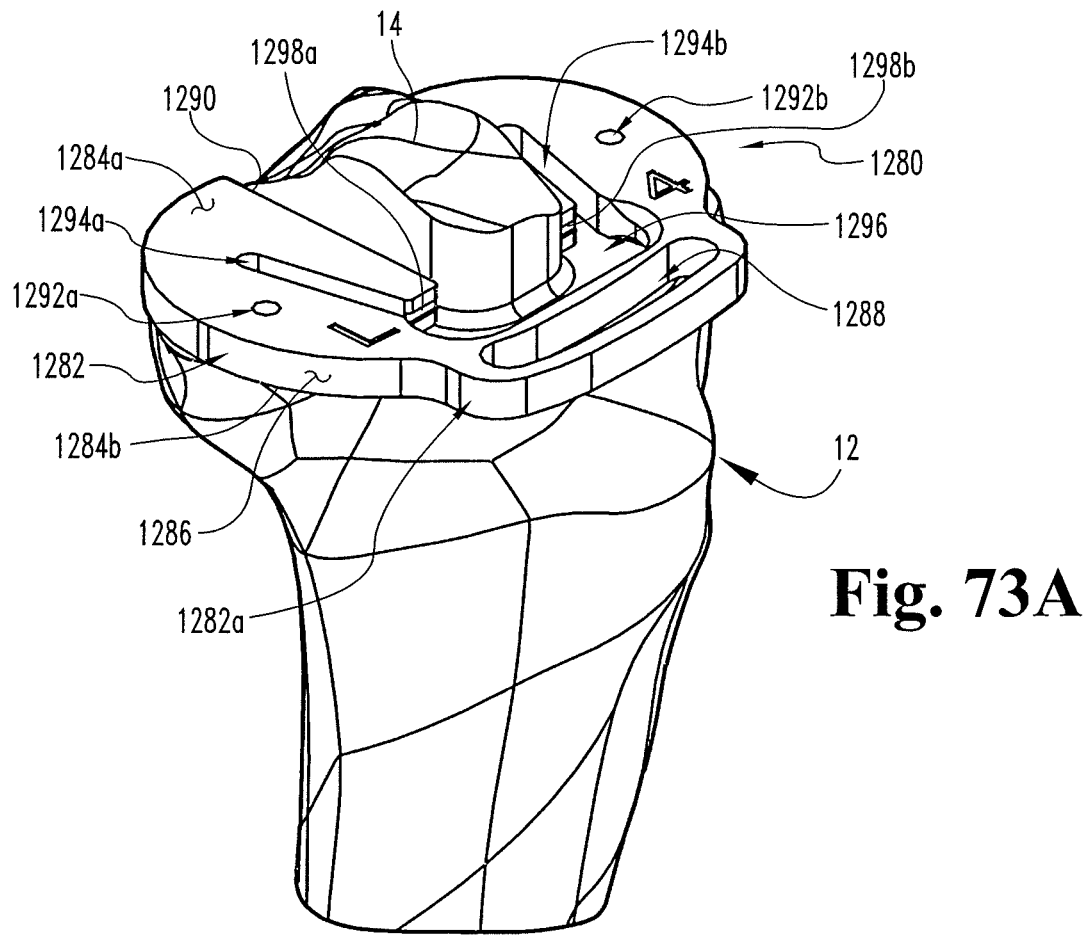

FIG. 73A illustrates a perspective view of a tibial baseplate trial according to one form of the invention engaged with the resected proximal tibia.

Figure 73B:
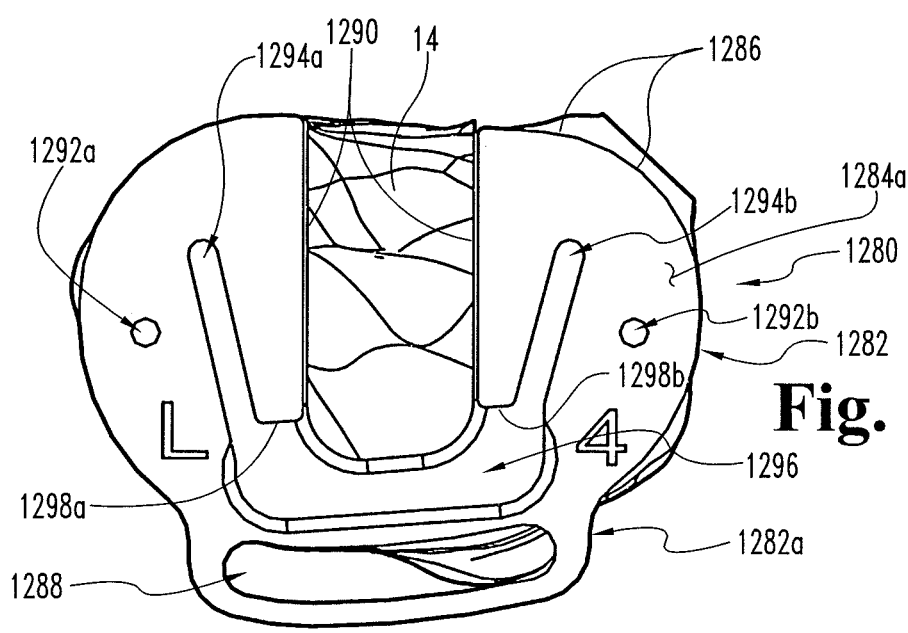

FIG. 73B is a superior view of FIG. 73A.

Figure 74A:
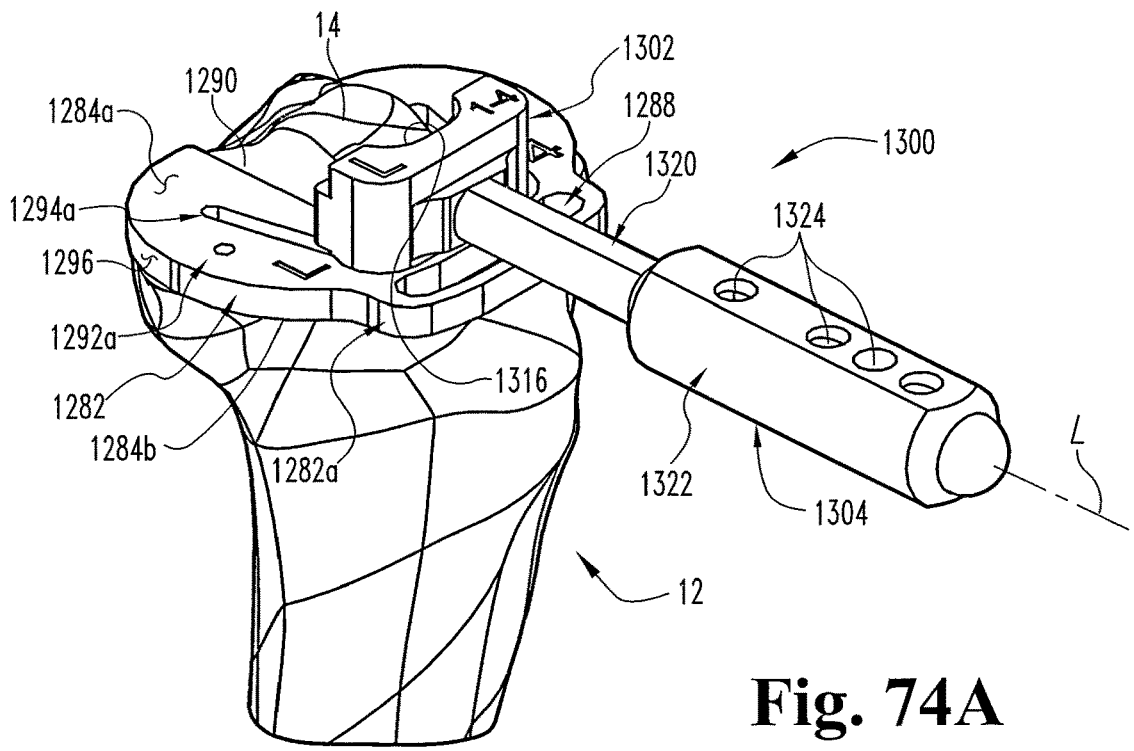

FIG. 74A illustrates a perspective view of the anterior tibial gauge of FIG. 72A engaged with the tibial baseplate trial of FIG. 73A in relation to the resected tibial eminence of the proximal tibia.

Figure 74B:
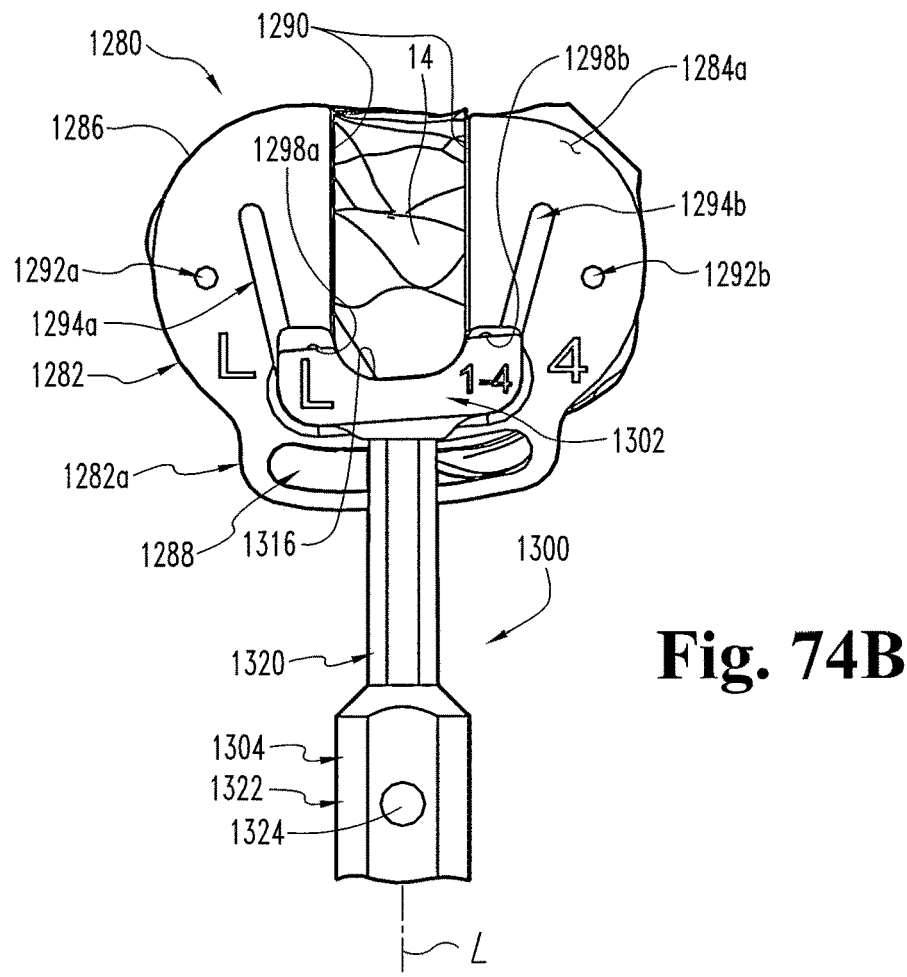

FIG. 74B is a superior view of FIG. 74A.

DESCRIPTION OF THE ILLUSTRATED EMBODIMENTS

For the purpose of promoting an understanding of the principles of the present invention, reference will now be made to the embodiments illustrated in the drawings and specific language will be used to describe the same. It will nevertheless be understood that no limitation of the scope of the invention is hereby intended. Any alterations and further modifications in the described embodiments, and any further applications of the principles of the invention as described herein are contemplated as would normally occur to one skilled in the art to which the invention relates.

The following descriptions and illustrations of non-limiting embodiments of the present invention are exemplary in nature, it being understood that the descriptions and illustrations related thereto are in no way intended to limit the inventions disclosed herein and/or their applications and uses. Certain features and details associated with other embodiments of devices and methods that may be used in association with the present invention are found in commonly owned U.S. patent application Ser. No. 12/790,137 filed on May 28, 2010, which claims the benefit of U.S. Provisional Patent Application Ser. No. 61/182,435 filed May 29, 2009 and U.S. Provisional Patent Application Ser. No. 61/299,835 filed Jan. 29, 2010, the contents of each application incorporated herein by reference in their entirety.

In total knee arthroplasty procedures, various devices and methods are used in the preparation of a distal portion of a femur for receipt of a femoral implant, and in the preparation of a proximal portion of a tibia for receipt of a tibial implant. The primary focus of this application is on devices and methods used in the preparation of the proximal tibia. However, other devices and methods used in the preparation of a distal femur which may also be used in association with the present invention are found in U.S. patent application Ser. No. 12/790,137, the contents of which have been incorporated herein by reference in their entirety.

There is a strong relationship between femoral attachment locations of soft tissues and the articulation between the tibia and the femur. As a general matter, it can be shown that for knee implant designs relying more on contrived means of kinematic control and stability rather than on the native soft tissue structures, kinematic patient outcomes are less sensitive to mismatch between, for instance, the inferior/superior position of the native femoral articular surfaces and the implanted femoral articular surfaces, although such mismatches can still be significant in some instances. However, when more native structures are preserved in order to provide kinematic control and stability (e.g., with bi-cruciate retaining implants), the preservation of the femoral joint line can sometimes become more important to patient outcome.

Currently, the common practice is to favor resection of the distal femur to the level of the trochlea, rather than by measuring a resection depth from the medial femoral condyle. However, it may be preferable in at least some cases to utilize methods and apparatus that counteract any tendency to resect the distal femur at a level other than the thickness of the distal femoral implant. For example, it may be preferable to resect an amount equivalent to the thickness of the distal femoral implant as measured from the distal medial (and/or lateral) condyle, which may better account for the mesial attachment sites on the femur of the posterior and/or anterior cruciate ligaments. It may also be preferable in at least some cases to utilize methods and apparatus that allow for early trialing and assessment of extension space and laxity.

Some methodologies associated with total knee arthroplasty procedures also reduce complications by not solving for femoral and tibial degrees of freedom simultaneously, but instead preparing the femur first and then subsequently preparing the tibia. By completing all of the femoral resections prior to the tibial resections, the surgeon is provided with a fixed set of values from which he or she can determine the remaining tibial degrees of freedom. Another benefit of preparing the femur first provided by some of the methodologies associated with total knee arthroplasty procedures is that they ensure proper kinematics. For proper kinematics, the femoral implant should generally conform to and articulate with the native anatomy well (e.g., natural soft tissues and native tibial cartilage). By separating the femoral resection steps from the tibial resection steps, the surgeon has no other input variables with which to make femoral resection decisions other than input variables provided by the native femoral anatomy. A further benefit of preparing the distal femur before the proximal tibia is that a surgeon still has the flexibility of performing a posterior stabilized, cruciate retaining surgery or a bicruciate retaining surgery with little or no time penalty or bone loss, even after the femoral side has been prepared. Many of the devices and methods described below, however, are not limited to only femur first techniques, or techniques that achieve all of the above benefits.

Figure 1:
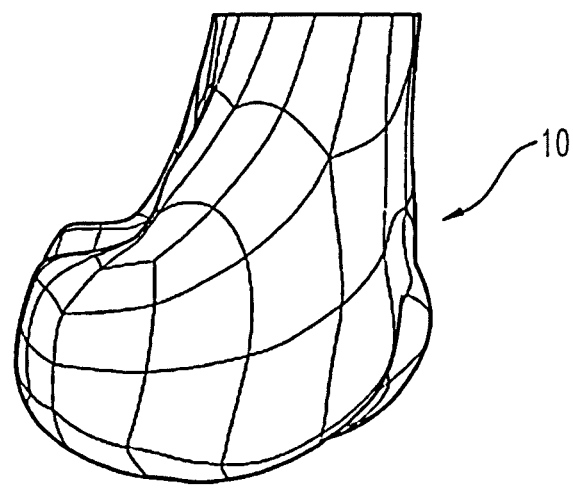
FIG. 1 illustrates a distal portion of a femur bone.
Figure 2:
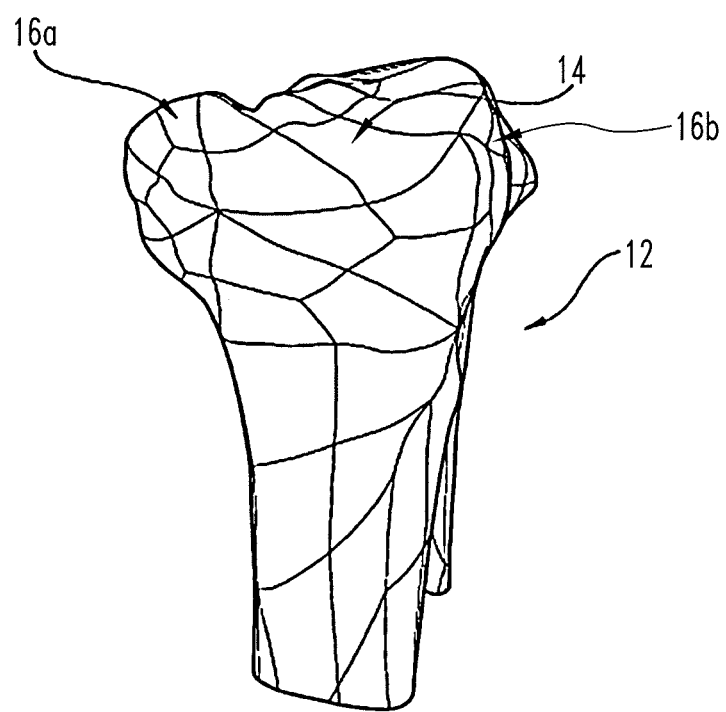
FIG. 2 illustrates a proximal portion of a tibia bone.

The following description and figures set forth a total knee arthroplasty procedure including preparation of the distal portion of the femur first, followed by subsequent preparation of the proximal portion of the tibia. By way of example, a distal portion 10 of the femur is shown in FIG. 1, and a proximal portion 12 of the tibia is shown in FIG. 2 illustrating the tibial eminence region 14, the medial tibial plateau region 16a, and the lateral tibial plateau region 16b, each shown prior to preparation for receipt of femoral and tibial implant components.

Figure 3:
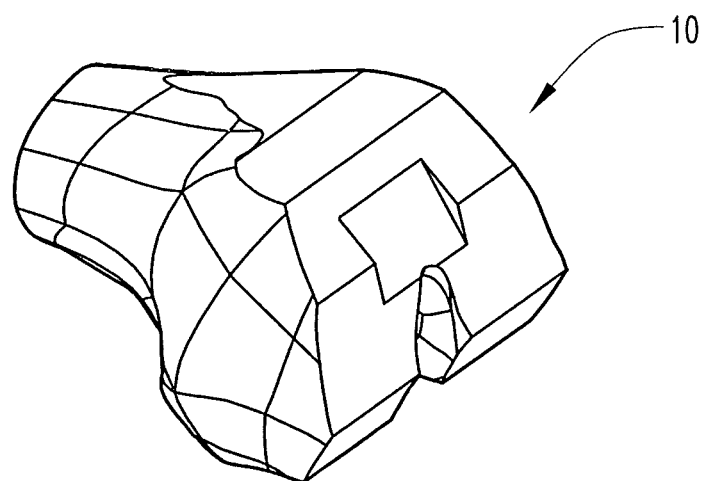
FIG. 3 illustrates a resected distal portion of a femur bone.
Figure 4:
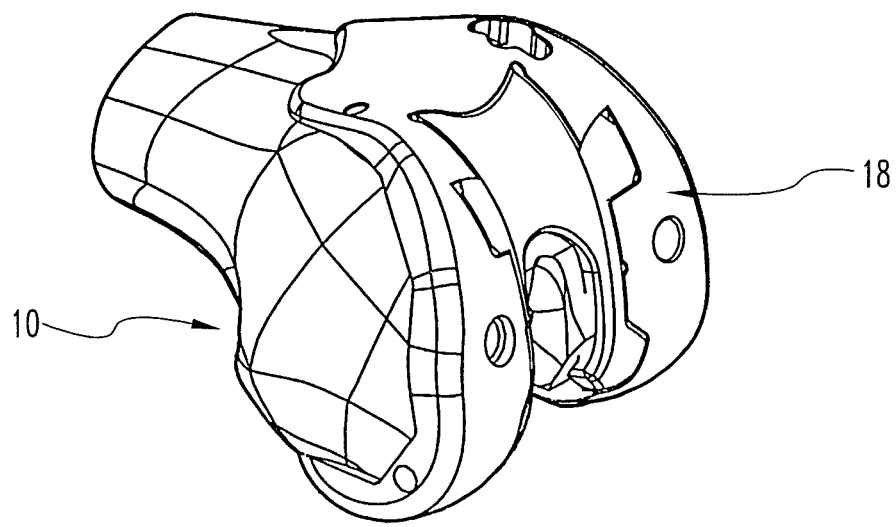
FIG. 4 illustrates a femoral trial component attached to the resected distal portion of the femur bone of FIG. 3.

As should be appreciated, the distal femur 10 may be prepared using various cutting instruments, trials, and other devices, examples of which are disclosed in U.S. patent application Ser. No. 12/790,137, the contents of which have been incorporated herein by reference in their entirety. One example of a prepared distal femur 10 is illustrated in FIG. 3. Additionally, FIG. 4 illustrates one embodiment of a femoral trial component 18 that may be attached to the prepared distal femur 10 prior to preparation of the proximal tibia 12. However, it should be understood that the shape and configuration of the prepared distal femur 10 and the femoral trial component 18 are exemplary in nature and do not limit the scope of the invention.

Following preparation of the distal femur 10, the proximal tibia 12 is prepared using the following devices and methods according to various embodiments of the present invention. However, it should be understood that the devices and methods of the present invention may be used in total knee arthroplasty procedures including simultaneous or alternating preparation of the distal femur 10 and the proximal tibia 12, or in total knee arthroplasty procedures where preparation of the proximal tibia 12 occurs first followed by preparation of the distal femur 10.

One problem faced when performing bicruciate-retaining TKA procedures that is of potential significance to at least some of the embodiments described herein is the complexity of the tibial resections. This complexity stems from at least two factors relating to the preservation of the cruciate ligaments.

A first factor is that there are more important degrees of freedom relating to bicruciate-retaining arthroplasty procedures than is apparent for typical posterior-stabilized or PCL-retaining arthroplasty procedures. For instance, in total knee arthroplasty, objects such as resection guides and other instrumentation in three-dimensional space have six degrees of freedom, including three translational degrees of freedom and three rotational degrees of freedom. At least four additional variables or "forms" may also apply in TKA procedures, including femoral implant size, tibial implant size, tibial insert thickness, and tibial insert articular shape. For a posterior-stabilized or cruciate-retaining arthroplasty procedure, only three degrees of freedom (one translational and two rotational) are usually considered important. For many, although not necessarily all, bicruciate-retaining arthroplasty procedures, there are at least three additional degrees of freedom which are considered important (i.e., one translational, one rotational, and one "form"). These three additional degrees of freedom arise due to constraints imposed by preservation of the tibial eminence to which the cruciate ligaments are attached.

A second factor of potential relevance is that bicruciate retaining knee arthroplasty requires precise surgical techniques. The trade off with a bicruciate-retaining technique is that of an increased risk of mechanical complications such as stiffness, instability, fracture or implant loosening due to the complexity of the surgery, in exchange for increased postoperative patient mobility and function. A bicruciate retaining technique therefore requires more decisions to fix additional degrees of freedom, as well as a greater degree of decision accuracy in order to mitigate the increased risks as compared to conventional posterior stabilized or posterior cruciate retaining total knee arthroplasty procedures.

Properly controlling and managing the abovementioned degrees of freedom and other factors during surgery is one of the keys to a clinically and commercially successful bicruciate retaining arthroplasty. Clinical success often depends on the ability of a surgeon to accurately and properly implant a well-designed prosthesis in order to achieve the advantages provided by the well-designed prosthesis. Commercial success often depends on the ability of the surgeon to accurately and properly implant a well-designed prosthesis with confidence, reproducibility and speed. Some, although not necessarily all, of the embodiments described herein address these concerns.

Of all knee arthroplasty procedures, the risks associated with tibial resection degrees of freedom (i.e., varus/valgus angle, posterior slope angle, and resection depth) are greater for bicruciate-retaining arthroplasty procedures than for posterior-stabilized or posterior cruciate-retaining procedures. This is because varus/valgus angle, posterior slope angle, and resection depth directly affect the operation of the cruciates in guiding proprioceptive joint motion. Moreover, the risks associated with the additional degrees of freedom specific to bicruciate retaining arthroplasty (particularly internal/external rotation angle and medial/lateral position of the tibial plateau and eminence resections) can include severe penalties for error, including but not limited to compromised structural integrity of the tibial eminence, compromised joint motion, and/or compromised cortical rim coverage. Errors associated with any of the five degrees of freedom associated with a bicruciate retaining procedure may present a surgeon with complex judgment decisions (i.e., to favor achieving the best possible cortical coverage over providing maximum preservation of the tibial eminence and its anterior and posterior cruciate ligament attachment sites). Such judgment decisions may include, for instance, whether or not to re-cut a bone to correct a perceived error, or to simply let the error remain. Re-cutting decisions contribute to an increase in both time and complexity, and may subsequently increase the likelihood of propagating further errors.

Embodiments of the bicruciate retaining total knee arthroplasty techniques and instrumentation described herein present surgeons with a truly complex surgery in a simplified format through thoughtful organization, reduction, and readily accessible information. As will be discussed herein, these embodiments may provide, at least in part, improved devices and methods for preparing a proximal tibia during total knee arthroplasty procedures. The devices and methodologies described below can be generally divided into three stages including: controlling degrees of freedom, making resections, and performing finishing steps.

As will be discussed in greater detail below, controlling degrees of freedom can include one or more of the steps of: roughly setting tibial resection depth, setting a neutral (or reference) varus/valgus angle for the medial and lateral tibial plateau resections, setting a neutral (or reference) posterior slope for the medial and lateral tibial plateau resections, fine-tuning the posterior slope angle and/or varus/valgus angle for the medial and lateral tibial plateau resections, setting medial-lateral positioning of the medial and lateral eminence bone cuts, setting an internal-external rotation angle for the medial and lateral eminence bone cuts (if desirable), determining an appropriately-sized tibial eminence width (related to implant size), and fine tuning the depth for both the medial and lateral tibial plateau resections. As will also be discussed in greater detail below, making resections can generally include one or more of the steps of making a medial tibial plateau resection, making medial and lateral tibial eminence bone cuts, performing a medial plateau balance check, performing a lateral tibial plateau resection, assessing fit of the implant to bone, and performing a trial reduction to assess range of motion, joint stability, and soft tissue tension. Additionally, finishing steps can generally include one or more of the steps of making an anterior eminence bone cut and an anterior tibial plateau resection to remove an anterior block portion of the tibial eminence, removing bone at eminence corners, assessing fit of the implant to bone, punching one or more keel cavities or openings into the cancellous bone of the proximal tibia, and implanting a tibial component. Various devices and instruments for performing these steps and procedures will now be discussed in detail below.

A. Datum Block

Referring to FIG. 5, show therein is a datum or alignment block 100 according to one form of the present invention, as shown in relation to the proximal tibia 12. The datum block 100 can be used as a fundamental instrument to provide a neutral/reference tibial foundation to which other devices or instruments may be engaged to and referenced from. The datum block 100 generally includes a main body 102 configured for attachment to the proximal tibia 12, a reference bench or table 104 extending from the main body 102 and configured for removable attachment of various devices/instruments to the datum block 100, and a locking or pinch force mechanism 106 associated with the main body 102 and configured to removably lock other devices/instruments to the datum block 100.

As shown in FIG. 5, in the illustrated embodiment, the datum block 100 is configured to engage and support an extramedullary alignment rod or "up rod" 108 having a central longitudinal axis L. In one embodiment, one end of the alignment rod 108 is removably attached to the main body 102 of the datum block 100. However, other embodiments are also contemplated wherein an end of the alignment rod 108 is removably or permanently attached to the main body 102 or other portions of the datum block 100. In still other embodiments, the opposite end of the alignment rod 108 may be removably attached to a mounting device associated with the patient's ankle to provide additional support and alignment capabilities. As should be appreciated, the alignment rod 108 may be aligned with axes and/or other features associated with the proximal tibia 12 to correspondingly align the datum block 100 (and other devices and instruments attached to the datum block 100) with such axes/features and/or other anatomic structures. For example, in some cases it may be desirable to roughly align the central longitudinal axis L of the alignment rod 108 along the anatomic and/or mechanical axis 13 of the tibia (in one or both of the sagittal and coronal planes) at the tubercle of the proximal tibia 12, while offsetting the datum block 100 from the tubercle of the proximal tibia 12. Other alignment techniques and procedures are also contemplated as falling within the scope of the present invention, many of which would occur to one having ordinary skill in the art. In the illustrated embodiment, the alignment rod 108 has a non-circular transverse cross section, and more specifically has at least one flat section for constraining rotation. However, in other embodiments, the alignment rod 108 may be provided with other suitable shapes and configurations, including a circular transverse cross section.

Referring collectively to FIGS. 6A-6F in combination with FIG. 5, shown therein are further details associated with the datum block 100. In the illustrated embodiment, the main body 102 of the datum block 100 includes a superior portion 110 and an inferior portion 130. In one embodiment, the superior and inferior portions 110, 130 are formed unitarily with one another to define a single-piece monolithic structure. However, in other embodiments, the superior and inferior portions 110, 130 may be formed separately and coupled together to define an integrated multi-piece structure.

In the illustrated embodiment, the superior portion 110 of the main body 102 of the datum block 100 defines a substantially flat/planar superior surface 112, a groove or indicia 114 extending along the planar superior surface 112 in an anterior-posterior direction, and a cavity 116 (FIGS. 5 and 6D) extending through the superior portion 110 from the planar superior surface 112 in a superior-inferior direction. In one embodiment, the groove/indicia 114 is generally aligned with the central longitudinal axis L of the alignment rod 108 and provides a visual indication or marker that may be aligned with the center of the proximal tibia 12 (i.e., alignable with the center of the tibial eminence 14) to roughly locate the datum block 100 in the appropriate position and orientation relative to the proximal tibia 12. The superior portion 110 of the main body 102 further defines an elongate pin-receiving slot 120 extending therethrough in an anterior-posterior direction and having a slot length/extending generally in a superior-inferior direction and a slot width w extending in a medial-lateral direction. The superior portion 110 also defines a plurality of pin-receiving openings 122 extending therethrough generally in an anterior-posterior direction. As will be discussed in further detail below, the elongate slot 120 is sized and configured for receipt of a provisional attachment pin or fastener 190 configured to provisionally attach the datum block 100 to the proximal tibia 12, and the openings 122 are each sized and configured for receipt of a terminal attachment pin or fastener 196 configured to terminally attach the datum block 100 to the proximal tibia 12.

In the illustrated embodiment, the inferior portion 130 of the main body 102 of the datum block 100 defines a first passage 132 extending partially therethrough from an inferior surface in an inferior-superior direction and having an inner cross section corresponding to the outer cross section of the alignment rod 108 (FIG. 6D). The inferior portion 130 of the main body 102 further defines a second passage 134 extending partially therethrough from an anterior end surface in an anterior-posterior direction and communicating with the first passage 132 (FIGS. 5 and 6C). As illustrated in FIG. 6D, the first passage 132 is sized and configured to receive an end portion of the alignment rod 108 therein. As illustrated in FIG. 6C, the second passage 134 is at least partially threaded and is configured for threaded engagement with a set screw or fastener 136 having an end portion that engages the alignment rod 108 to retain the alignment rod 108 within the first passage 132. As further illustrated in FIG. 6D, the inferior portion 130 of the main body 102 also defines a visualization opening 138 positioned adjacent the first passage 132 and communicating with the second passage 134 to provide access to the second passage 134 and visualization of the set screw 136. As also illustrated in FIG. 6D, the inferior portion 130 of the main body 102 also defines an aperture 140 positioned adjacent the anterior surface of the inferior portion 130 and sized and configured for receipt of a retention pin 142 that serves to prevent the set screw 136 from backing entirely out of the second passage 134. As illustrated in FIG. 6B, a posteriorly-facing surface of the inferior portion 130 of the main body 102 defines a radially contoured groove 144 extending along a generally uniform radius relative to a central pivot axis C and terminating at an end surface 146, the purpose of which will be discussed below.

As indicated above, the datum block 100 includes a reference bench or table 104 extending from the main body 102 and configured for removable attachment of various devices/instruments to the datum block 100. In the illustrated embodiment, the reference bench 104 is formed unitarily with the superior portion 110 of the main body 102 to define a single-piece monolithic structure. However, in other embodiments, the reference bench 104 may be formed separately from the main body 102 and coupled to the superior portion 110 to define an integrated multi-piece structure. As shown in FIG. 6B, in the illustrated embodiment, the reference bench 104 has a non-rectangular trapezoidal-shaped configuration defining a narrowing or tapered width extending away from the main body 102 in a medial-lateral direction. However, other suitable shapes and configurations of the reference bench 104 are also contemplated as falling within the scope of the present invention.

As shown in FIGS. 6A-6C, the reference bench 104 defines a substantially flat/planar superior surface 150 and a substantially flat/planar inferior surface 152, with the planar superior and inferior surfaces 150, 152 preferably arranged generally parallel with one another, although non-parallel arrangements of the planar superior and inferior surfaces 150, 152 are also contemplated. Additionally, the planar inferior surface 152 of the reference bench 104 is positioned opposite the planar superior surface 112 of the main body 102 to thereby define a space or gap 154 therebetween (FIGS. 6A-6C) sized and configured for receipt of plate-like portions of other devices and instruments to be connected with the datum block 100, details of which will be set forth below. In the illustrated embodiment, the planar inferior surface 152 of the reference bench 104 is preferably arranged generally parallel with the planar superior surface 112 of the main body 102, although non-parallel arrangements of the opposing surfaces are also contemplated. In the illustrated embodiment, the reference bench 104 also defines a groove or indicia 156 extending along the planar superior surface 150 in an anterior-posterior direction. The groove/indicia 156 is preferably arranged generally parallel with the groove/indicia 114 extending along the planar superior surface 112 of the main body 102. In one embodiment, the groove/indicia 156 provides a general visual indication or marker of the location of the vertical cut associated with the medial resection of the proximal tibia 12.

Figure 8A:
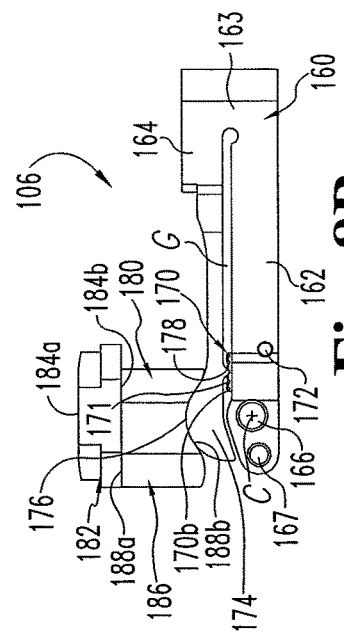
FIG. 8A illustrates one embodiment of a locking mechanism used in association with the datum block of FIG. 7A, as shown in an unlocked configuration.
Figure 8B:
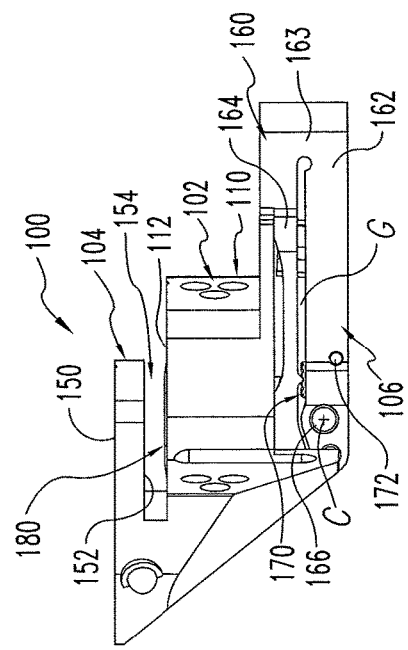
FIG. 8B illustrates the locking mechanism of FIG. 8A, as shown in a locked configuration.
Figure 7A:
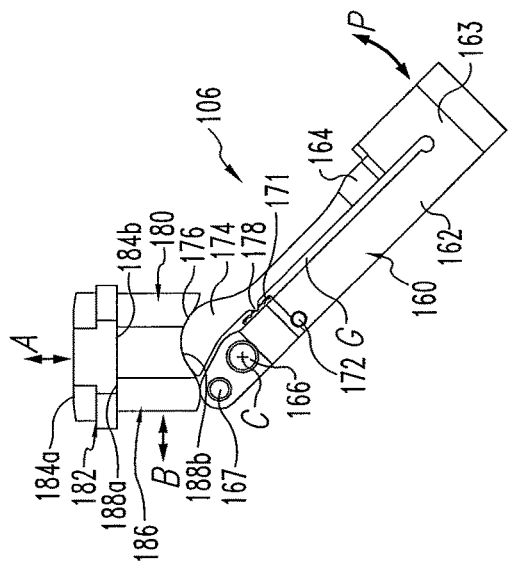
FIG. 7A illustrates an unlocked configuration of the datum block of FIG. 5.
Figure 7B:
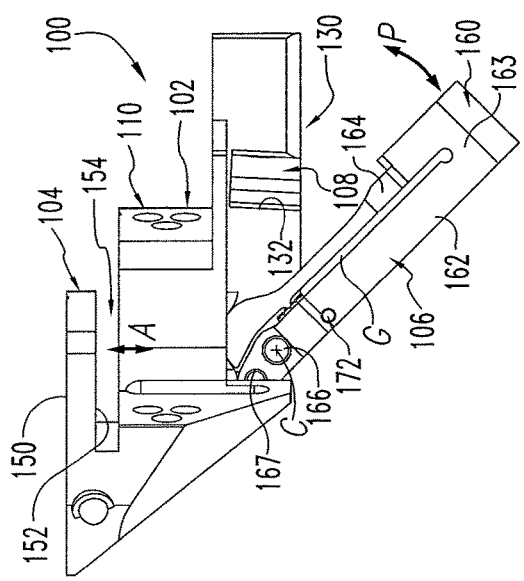
FIG. 7B illustrates a locked configuration of the datum block of FIG. 5.

As indicated above, the datum block 100 includes a locking or pinch force mechanism 106 associated with the main body 102 that is configured to removably lock various devices/instruments to the datum block 100. Referring to FIGS. 7A and 7B, illustrated therein are unlocked and locked configurations of the datum block 100, respectively. Additionally, referring to FIGS. 8A and 8B, illustrated therein are corresponding unlocked and locked configurations of the locking mechanism 106, respectively.

In the illustrated embodiment, the locking mechanism 106 generally includes a lever arm or actuator member 160 pivotally attached to the inferior portion 130 of the datum block 100, and a gripper or actuated member 180 positioned within the cavity 116 in the superior portion 110 of the datum block 100 and movably engaged with a proximal end portion of the lever arm 160. As will be discussed in further detail below, pivotal movement of the lever arm 160 in the direction of arrow P correspondingly displaces the gripper member 180 in an inferior-superior direction in the direction of arrow A to correspondingly compress the gripper member 180 against a plate-like portion of a device/instrument positioned within the space or gap 154 defined between the planar inferior surface 152 of the reference bench 104 and the planar superior surface 112 of the main body 102 of the datum block 100 to thereby capture the plate-like portion within the space 154 and retain the device/instrument in a fixed position and orientation relative to the datum block 100. The locking or pinch force mechanism 106 thereby serves to maintain the position and angular alignment/orientation of various devices/instruments with respect to the datum block 100.

In the illustrated embodiment of the locking or pinch force mechanism 106, the lever arm 160 has a generally rectangular bar-like configuration that generally includes an inferior portion 162 and a superior portion 164 that are connected to one another via a flexible hinge portion 163 which permits the superior portion 164 to be displaced toward/away from the inferior portion 162 to correspondingly vary a gap G between the inferior and superior portions 162, 164. The inferior portion 162 of the lever arm 160 is pivotally attached to the inferior portion 130 of the datum block 100 via a pivot pin 166 to thereby allow for pivotal movement of the lever arm 160 relative to the datum block 100 about a central pivot axis C. The inferior portion 162 of the lever arm 160 is also provided with a stop member or pin 167 posteriorly offset from the pivot pin 166 and configured to limit pivotal movement of the lever arm 160 away from the main body 102 of the datum block 100. As the lever arm 160 is pivoted about the pivot pin 166 away from the main body 102, the stop member 167 is displaced along the radially contoured groove 144 defined by the posteriorly-facing surface of the inferior portion 130 of the main body 102 (FIG. 6B) until the stop member 167 is engaged against the end surface 146 of the groove 144, thereby preventing further pivotal movement of the lever arm 160 away from the main body 102. Additionally, the inferior portion 162 of the lever arm 160 defines a passage 168 (FIG. 6D) anteriorly offset from the pivot pin 166 and extending through the inferior portion 162 in an inferior-superior direction. The passage 168 is at least partially threaded and is configured for threading engagement with an adjustment bolt 170 having a threaded shank portion 170a and a proximal end 170b defining a series of radially-extending notches or splined grooves 171. The inferior portion 162 of the lever arm 160 further includes a retaining pin 172 that at least partially extends into the passage 168 to prevent the adjustment bolt 170 from backing entirely out of the passage 168.

The superior portion 164 of the lever arm 160 includes a proximal end portion having a cam structure 174 that defines a superior cam surface 176 that extends along an asymmetrical curve or contour relative to the central pivot axis C. The superior portion 164 further defines a spline or V-shaped projection 178 extending from an inferior surface thereof that is sized and configured for engagement within one of the radially-extending notches or splined grooves 171 defined by the proximal end 170b of the adjustment bolt 170. As should be appreciated, tightening the adjustment bolt 170 into the passage 168 in the lever arm 160 forces the superior portion 164 of the lever arm 160 away from the inferior portion 162 to widen the gap G therebetween, which in turn displaces the superior cam surface 176 of the cam structure 174 away from the central pivot axis C. Additionally, engagement of the spline or V-shaped projection 178 of the lever arm 160 within one of the radially-extending notches or splined grooves 171 defined by the proximal end of the adjustment bolt 170 prevents the adjustment bolt 170 from loosening and backing out of the passage 168 in the lever arm 160.

Referring to FIGS. 8A and 8B, in the illustrated embodiment of the locking or pinch force mechanism 106, the gripper or actuated member 180 is provided as a two-piece component including a superior component 182 and an inferior component 186. In the illustrated embodiment, the superior component 182 is permitted to translate in an inferior-superior direction generally along the arrow A, and the inferior component 186 is also permitted to translate in an inferior-superior direction generally along the arrow A as well as in an anterior-posterior direction relative to the superior component 182 generally along arrow B. The superior component 182 may be provided with a generally circular configuration sized for displacement within the cavity 116 in the main body 102 of the datum block 100 generally along the arrow A. The superior component 182 also defines a superior gripping surface 184a that may be compressed against plate-like portions of devices/instruments positioned within the space or gap 154 defined between the reference bench 104 and the main body 102 of the datum block 100, and further defines a substantially flat/planar inferior surface 184b. The inferior component 186 may also be provided with a generally circular configuration sized for displacement within the cavity 116 in the main body 102 of the datum block 100 in the inferior-superior direction generally along arrow A and in the anterior-posterior direction generally along the arrow B. The inferior component 186 defines a substantially flat/planar superior surface 188a configured for sliding engagement with the substantially flat/planar inferior surface 184b of the superior component 182, and further defines an inferior bearing surface 188b configured for sliding engagement with the superior cam surface 176 defined by the superior portion 164 of the lever arm 160. In the illustrated embodiment, the inferior bearing surface 188b defines a curved contour extending along a generally uniform/constant radius. However, other suitable shapes and configurations of the inferior bearing surface 188b are also contemplated.

As set forth above, FIGS. 7A/7B and FIGS. 8A/8B illustrate unlocked and locked configurations of the datum block 100 and the locking or pinch force mechanism 106. In the unlocked configuration, a plate-like portion of a device/instrument may be positioned within the space or gap 154 defined between the planar inferior surface 152 of the reference bench 104 and the planar superior surface 112 defined by the main body 102 of the datum block 100. The datum block 100 and the locking mechanism 106 are then transitioned from the unlocked configuration illustrated in FIGS. 7A and 8A to the locked configuration illustrated in FIGS. 7B and 8B by pivoting the lever arm 160 about the central pivot axis C in a superior direction along arrow P. As should be appreciated, pivoting of the lever arm 160 along arrow P causes the superior cam surface 176 defined by the superior portion 164 of the lever arm 160 to slidably engage the inferior bearing surface 188b defined by the inferior component 186 of the gripper member 180, which in turn displaces the inferior component 186 generally along arrow A as well generally along arrow B. The inferior component 186 in turn forces the superior component 182 of the gripper member 180 in an inferior-superior direction generally along arrow A and compresses the superior gripping surface 184a of the superior component 182 into compressed engagement against a plate-like portion of a device/instrument positioned within the space 154 defined between the reference bench 104 and the main body 102 of the datum block 100 to thereby lock the device/instrument in a select position and orientation relative to the datum block 100.

As should be appreciated, the compression or clamping force exerted by the superior component 182 onto the plate-like portion of the device/instrument positioned within the space 154 may be adjusted or calibrated to satisfy particular clamping/locking requirements. Specifically, the compression or clamping force may be adjusted via tightening or loosening of the adjustment bolt 170. For example, tightening of the adjustment bolt 170 forces the superior portion 164 of the lever arm 160 away from the inferior portion 162 to widen the gap G therebetween, which in turn displaces the superior cam surface 176 of the cam structure 174 away from the central pivot axis C to thereby increase the compression or clamping force exerted by the superior component 182 of the gripper member 180 onto the plate-like portion of the device/instrument positioned within the space or gap 154 defined by the datum block 100. Additionally, loosening of the adjustment bolt 170 allows the superior portion 164 of the lever arm 160 to be displaced toward the inferior portion 162 to reduce the gap G therebetween, which in turn displaces the superior cam surface 176 of the cam structure 174 toward from the central pivot axis C to thereby decrease the compression or clamping force exerted by the superior component 182 of the gripper member 180 onto the plate-like portion of the device/instrument positioned within the space or gap 154 in the datum block 100.

As should be appreciated, the locking or pinch force mechanism 106 may be transitioned from the unlocked configurations illustrated in FIGS. 7A and 8A to the locked configurations illustrated in FIGS. 7B and 8B (and vice-versa) without the need for separate driver instruments or locking tools (e.g., a hex driver or a wrench). Additionally, the clamping or compression force exerted by the locking or pinch force mechanism 106 may be easily adjusted via a single adjustment mechanism (i.e., tightening or loosening of the adjustment bolt 170). Although a particular type and configuration of the locking or pinch force mechanism 106 has been illustrated and described herein for use in association with the datum block 100, it should be understood that other types and configurations of locking/pinching mechanisms or other compression structures/devices are also contemplated for use in association with the present invention in addition to or in lieu of the locking or pinch force mechanism 106.

Referring to FIG. 9, the datum block 100 is provisionally attached to the proximal tibia 12 by a provisional attachment pin or fastener 190 extending through the elongate slot 120 in the main body 102 of the datum block 100. The provisional attachment pin 190 may include a threaded distal end portion (not shown) for anchoring in bone tissue, and a proximal head portion 192 having drive features that facilitate driving of the provisional attachment pin 190 into tibial bone. In the illustrated embodiment, the drive features may include providing the proximal head portion 192 with a non-circular transverse cross section including, for example, one or more flattened regions. Additionally, the proximal head portion 192 may be provided with an enlarged annular region or ring 194 having a transverse cross section sized larger than the slot width w of the elongate slot 120. The enlarged portion 194 of the head 192 thereby serves to retain the datum block 100 on the provisional attachment pin 190 to prevent the datum block 100 from becoming disengaged from the provisional attachment pin 190. However, because of the elongate slot 120, the datum block 100 is permitted to translate along the provisional attachment pin 190 in a superior-inferior direction (i.e., to adjust resection depth), rotate about the provisional attachment pin 190 in a medial-lateral direction (i.e., to adjust the varus-valgus angle), rotate about the provisional attachment pin 190 in an anterior-posterior direction (i.e., to adjust the posterior slope angle), and translate along the provisional attachment pin 190 in an anterior-posterior direction (as limited by engagement of the enlarged head portion 194 against the anterior surface of the main body 102 of the datum block 100). As should be appreciated, placement of the provisional attachment pin 190 within the elongate slot 120 in the main body 102 of the datum block 100 provides fine-tuning capability as to adjustment of the particular position and orientation of the datum block 100 relative to the proximal tibia 12 prior to terminal/final attachment to the proximal tibia 12.

Referring to FIG. 10, once the datum block 100 is positioned in the appropriate superior/inferior position along the proximal tibia 12 and is rotated to the appropriate medial-lateral angle and anterior-posterior angle, the datum block 100 may be terminally attached to the proximal tibia 12 by a pair of terminal attachment pins or fasteners 196a, 196b extending through respective ones of the pin-receiving openings 122 in the main body 102 of the datum block 100. The terminal attachment pins 196a, 196b may include a threaded distal end portion (not shown) for anchoring in bone tissue, and a proximal head portion 198 having features that facilitate driving of the terminal attachment pins 196a, 196b into tibial bone. In the illustrated embodiment, the drive features include providing the proximal head portion 198 with a non-circular transverse cross section including, for example, one or more flattened regions. As shown in FIG. 10, the pin-receiving openings 122 and the terminal attachment pins 196a, 196b are oriented at an oblique angle relative to the elongate slot 120 and the provisional attachment pin 190. As a result, the datum block 100 is retained in position relative to the proximal tibia 12 without having to tighten the enlarged region 104 of the proximal head portion 192 of the provisional attachment pin 190 against the main body 102 of the datum block 100 and/or without having to engage a further attachment pin to the datum block 100 at an oblique angle relative to the terminal attachment pins 196a, 196b.

B. Depth Stylus

Figure 11:
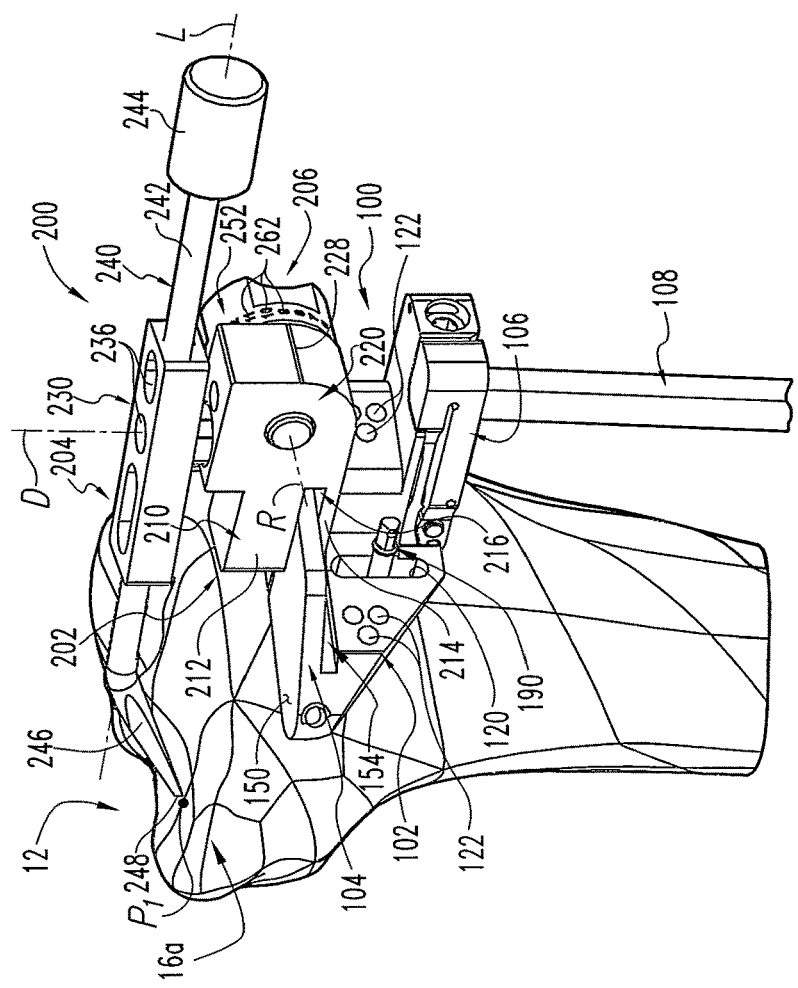
FIG. 11 illustrates a depth stylus according to one form of the invention, as shown attached to the datum block of FIG. 5 in relation to the proximal tibia.

Referring to FIG. 11, shown therein is a depth stylus 200 according to one form of the present invention, as attached to the datum block 100 in relation to the proximal tibia 12. As will be discussed in greater detail below, the depth stylus 200 can be used as a multi-functional measurement instrument to take pre-resection measurements and post-resection measurements to verify and confirm the proper depth of the medial and lateral plateau resection cuts.

The depth stylus 200 generally includes a base portion or mounting block 202 configured for attachment to the datum block 100, an articulating pointer or stylus rod 204 configured to articulate relative to the mounting block 202 and to engage a superior surface of the proximal tibia 12 for measurement relative to a reference plane, and an actuation or adjustment mechanism 206 engaged with the mounting block 202 and the stylus rod 204 to move the stylus rod 204 toward and away from the mounting block 202 in an inferior-superior direction to correspondingly adjust the vertical position of the stylus rod 204 relative to the reference plane, or vice-versa (i.e., to correspondingly adjust the position of the reference plane relative to the stylus rod 204). Further elements and features associated with the components of the depth stylus 200 will be set forth in greater detail below with particular reference to FIGS. 12-14.

In the illustrated embodiment, the mounting block 202 is a single-piece monolithic structure including a mounting portion 210 and a connector portion 220. In one embodiment, the mounting portion 210 is divided into superior and inferior portions 212, 214, respectively, that are separated from one another by a slot 216. The superior mounting portion 212 has a plate-like configuration defining substantially flat/planar superior and inferior surfaces 217a, 217b, respectively. The inferior mounting portion 214 also has a plate-like configuration defining substantially flat/planar superior and inferior surfaces 218a, 218b, respectively. The slot 216 defined between the superior and inferior mounting portions 212, 214 has a slot width w that is sized for receipt of the reference bench 104 of the datum block 100 therein. Once the depth stylus 200 is positioned in a desired position and orientation relative to the reference bench 104 of the datum block 100, the locking or pinch force mechanism 106 is actuated to lock the depth stylus 200 in a select position and orientation relative to the datum block 100. Actuation of the locking or pinch force mechanism 106 correspondingly compresses the planar superior surface 218a of the plate-like mounting portion 214 against the planar inferior surface 152 of the reference bench 104 to thereby capture/lock the plate-like mounting portion 214 within the space 154 defined between the main body 102 and the reference bench 104 of the datum block 100, which in turn retains the depth stylus 200 in a fixed position relative to the datum block 100. As should be appreciated, locking of the depth stylus 200 in a fixed inferior-superior position relative to the datum block 100 stabilizes the depth stylus 200 during measurements, which in turn removes an element of toggle/tolerance between the depth stylus 200 and the datum block 100 to thereby improve the accuracy of the measurements taken with the depth stylus 200.

Figure 13A:
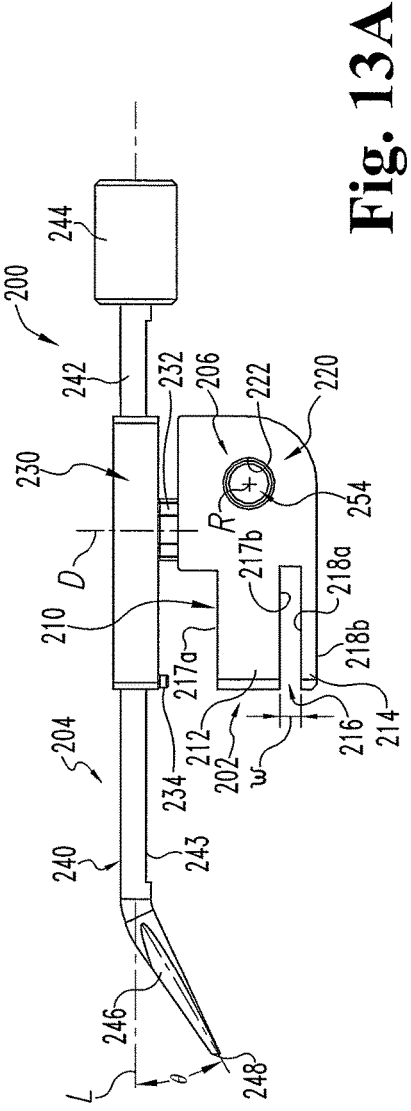
FIG. 13A illustrates a left side view of the depth stylus of FIG. 11.
Figure 13B:
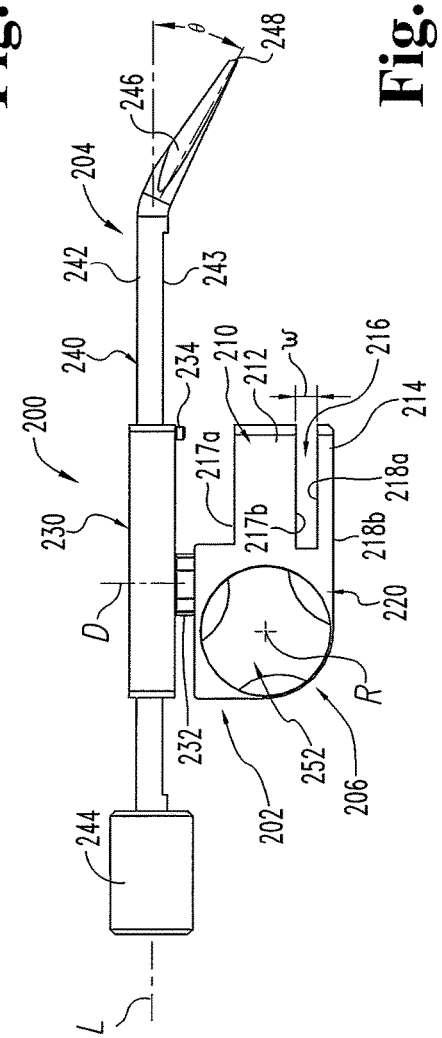
FIG. 13B illustrates a right side view of the depth stylus of FIG. 11.
Figure 13C:
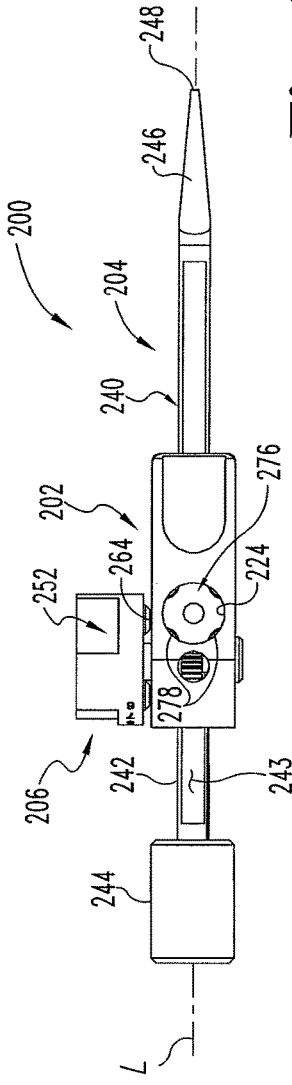
FIG. 13C illustrates a bottom view of the depth stylus of FIG. 11.
Figure 13D:
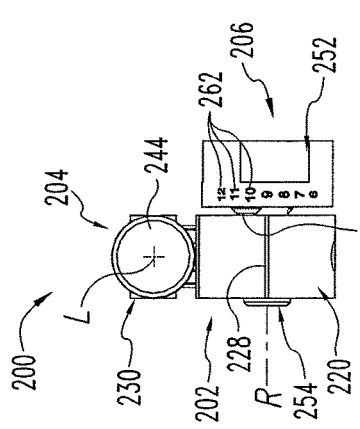
FIG. 13D illustrates an anterior end view of the depth stylus of FIG. 11.

In one embodiment, the connector portion 220 of the mounting block 202 serves to interconnect the stylus rod 204 with the adjustment mechanism 206. Specifically, the connector portion 220 defines a first passage 222 extending laterally therethrough, and a second passage 224 extending therethrough in a superior-inferior direction and arranged generally perpendicular to the first passage 222. Although the axial centerlines of the first and second passages 222, 224 are offset from one another, the passages 222, 224 are positioned in communication with one another. As will be discussed below, the passages 222, 224 are sized and configured to house components of the stylus rod 204 and the adjustment mechanism 206. The connector portion 220 further defines a third passage 226 extending therethrough in a direction generally parallel with the second passage 224 and intersecting the first transverse passage 222. The third passage 226 provides visualization of and/or access to internal components housed within the connector portion 220 of the mounting block 202. As shown in FIGS. 11 and 13D, an anterior surface of the connector portion 220 defines a reference or measurement marker 228, the purpose of which will be discussed below.

In the illustrated embodiment, the stylus rod 204 generally includes a mounting base portion 230 and a rod portion 240, each extending generally along a longitudinal axis L. In one embodiment, the base portion 230 has a generally rectangular bar-like configuration and defines an axial opening (not shown) extending therethrough generally along the longitudinal axis L for receipt of the rod portion 240. The base portion 230 also defines a spacer or stem 232 extending transversely therefrom which is sized and configured for slidable receipt within the superior-inferior passage 224 in the connector portion 220 of the mounting block 202. As shown in FIGS. 13A and 13B, a reference pin or marker 234 extends from an inferior surface of the base portion 230 in a superior-inferior direction and is positioned adjacent the distal end of the base portion 230. Additionally, the base portion 230 further defines a series of opening or slots 236 extending therethrough in a superior-inferior direction.

In the illustrated embodiment, the rod portion 240 of the stylus rod 204 generally includes an elongate rod portion 242, a handle or grip portion 244 attached to the proximal end of the elongate rod portion 242, and a pointer or reference bar 246 extending from a distal end of the elongate rod portion 242. In the illustrated embodiment, the elongate rod portion 242 and the proximal handle portion 244 each have a generally circular outer cross section, and one side of the elongate rod portion 242 is provided with a flattened or truncated surface 243 which serves to stabilize the rotational position of the elongate rod portion 242 relative to the mounting base portion 230. However, it should be understood that other shapes and configurations of the elongate rod portion 242 and the proximal handle portion 244 are also contemplated. In one embodiment, the distal pointer 246 extends from the elongate rod portion 242 at an angle θ relative to the longitudinal axis L. In one specific embodiment, the angle θ is approximately 35°. However, other angles θ are also contemplated. Additionally, the thickness of the distal pointer 246 inwardly tapers along its length to a reduced cross section adjacent its distal end to thereby define a relatively pointed distal end surface 248 to improve the accuracy of the depth stylus 200.

Figures 12, 14:
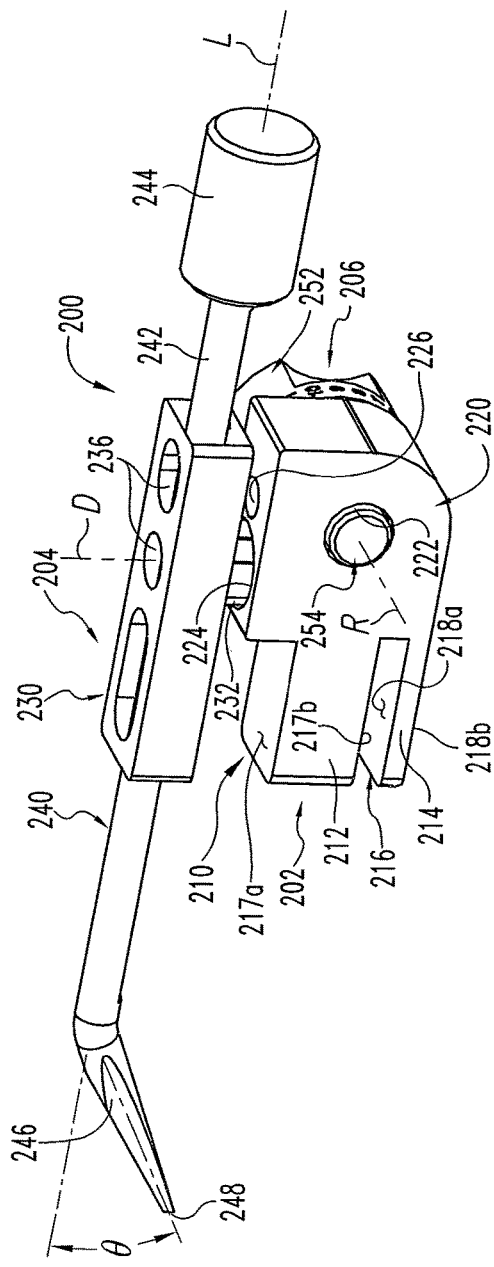
FIG. 12 illustrates a perspective view of the depth stylus of FIG. 11.
FIG. 14 illustrates one embodiment of an adjustment mechanism used in association with the depth stylus of FIG. 11.

Referring to FIG. 14, shown therein is one embodiment of the adjustment mechanism 206 which, as indicated above, serves to displace the stylus rod 204 toward and away from the mounting block 202 in an inferior-superior direction to correspondingly adjust the position of the stylus rod 204 relative to a reference plane, or vice-versa. In the illustrated embodiment, the adjustment mechanism 206 generally includes a rotational actuator or drive member 250 and a linear actuator or plunger member 270. The rotational actuator 250 includes a thumb wheel or knob grip 252, a stem or shaft 254 extending axially from the thumb wheel 252 and arranged along a rotational axis R, and a pinion gear 256 coupled to the shaft 254 and defining a series of gear teeth 258. The thumb wheel 252 includes a number of scalloped or recessed regions 260 that facilitate manual rotation of the thumb wheel 252 about the rotational axis R by a user. The thumb wheel 252 also includes numerals or other indicia/markings 262 positioned uniformly about an outer circumferential surface of the thumb wheel 252, the purpose of which will be discussed below. As should be appreciated, the shaft 254 is rotationally mounted within the transverse passage 222 extending through the connector portion 220 of the mounting block 202 to allow rotational movement of the shaft 254 and the pinion gear 256 about the rotational axis R upon exertion of a rotational force or torque onto the thumb wheel 252. The thumb wheel 252 may also be provided with one or more projections or detents 264 extending laterally from an inner side surface of the thumb wheel 252 which are positionable within recesses or grooves (not shown) formed in an adjacent side surface of the mounting block 202 to provide a certain degree of resistance to rotational movement of the drive member 250 to allow incremental rotational movement of the drive member 250 relative to the mounting block 202.

In the illustrated embodiment, the plunger member 270 of the adjustment mechanism 206 includes an actuated shaft or rack 272 extending generally along a displacement axis D and defining a series of notches or gear teeth 274 positioned along its length. The plunger member 270 further defines an enlarged head or guiding portion 276 positioned adjacent an inferior end of the rack 272 which is sized and configured for slidable displacement within the inferior portion of the passage 224 in the connector portion 220 of the mounting block 202. In one embodiment, the enlarged head 276 has a generally circular outer cross section corresponding to the circular inner cross section of the inferior portion of the passage 224, and also defines a series of scallops or recesses 278 formed along the outer circumferential surface of the enlarged head 276 to promote sliding engagement of the enlarged head 276 along the inferior portion of the passage 224. As should be appreciated, exertion of a rotational force or torque onto the thumb wheel 252 rotates the shaft 254 and the pinion gear 256 about the rotational axis R, which in turn intermeshes the gear teeth 258 of the pinion gear 256 with the notches/teeth 274 on the rack 272 to correspondingly displace the plunger member 270 along a displacement axis D, which thereby results in displacement of the stylus rod 204 toward and away from the mounting block 202 (or vice-versa) to correspondingly adjust the inferior-superior position of the stylus rod 204 relative to a reference plane.

Referring once again to FIG. 11, once the depth stylus 200 is locked in position relative to the datum block 100, the stylus rod 204 can be rotationally displaced relative to the mounting block 202 about the displacement axis D, and the rod portion 240 of the stylus rod 204 can be axially displaced along the longitudinal axis L relative to the base portion 230 to correspondingly position the distal end surface 248 of the pointer 246 at an infinite number of positions along the outer surface of the proximal tibia 12. Additionally, the inferior-superior position of the stylus rod 204 along the displacement axis D can also be adjusted relative to the mounting block 202 by turning the thumb wheel 252 in a clock-wise or counter clock-wise direction. As should be appreciated, the position of the distal end surface 248 of the pointer 246 can therefore be adjusted in three dimensions for positioning at any point along the outer surface of the proximal tibia 12.

Once the distal end surface 248 of the pointer 246 is positioned in abutment against a selected point $P_1$ along the outer surface of the proximal tibia 12 (e.g., along the medial tibial plateau 16a), the user can determine/measure the distance of the selected point $P_1$ relative to a reference plane in an inferior-superior direction. In one embodiment, the reference plane comprises the plane formed by the superior surface 150 of the reference bench 104 of the datum block 100. However, it should be understood that the depth stylus 200 may be configured to determine/measure the distance of selected points along the proximal tibia 12 in an inferior-superior direction relative to other reference planes. As will be discussed in further detail below, the plane defined by the superior surface 150 of the reference bench 104 defines the cutting plane along which horizontal medial and lateral resection cuts $C_{HM}$, $C_{VM}$ (FIGS. 20B and 20C) will be formed during resection of the medial and lateral tibial plateau regions 16a, 16b. Additionally, as shown in FIG. 11 and as set forth above, the datum block 100 may be provisionally attached to the proximal tibia 12 by the provisional attachment pin 190 extending through the elongate slot 120 in the main body 102 of the datum block 100. Because the datum block 100 is not yet terminally attached to the proximal tibia 12 (i.e., is not securely attached to the proximal tibia by the terminal attachment pins 196), the datum block 100 is permitted to translate in a superior-inferior direction via sliding engagement of the provisional attachment pin 190 along the length of the elongate slot 120, which in turn correspondingly adjusts the plane defined by the superior surface 150 of the reference bench 104 and the proposed/intended resection depth of the horizontal medial and lateral resection cuts $C_{HM}$, $C_{VM}$.

As should be appreciated, with the distal end surface 248 of the pointer 246 positioned in abutment against the selected point $P_1$ along the outer surface of the proximal tibia 12, the superior-inferior position of the datum block 100 may be adjusted via rotating the thumb wheel 252 in a clockwise or counter-clockwise direction, which in turn adjusts the superior-inferior position of the reference/cutting plane defined by the reference bench 104 on the datum block 100 to a desired resection depth (i.e., to a desired position for subsequent formation of the horizontal medial and lateral resection cuts $C_{HM}$, $C_{VM}$). As shown in FIG. 11, the inferior-superior distance from the selected point $P_1$ in contact with the distal end surface 248 of the pointer 246 relative to the reference/cutting plane (i.e., the proposed/intended resection depth) is determined by observing which of the reference numerals 262 on the thumb wheel 252 is aligned with the reference marker 228 on the anterior surface of the mounting block 202 (i.e., reference numeral "9" in the illustrated embodiment). As should be appreciated, further adjustment or fine-tuning of the position of the reference/cutting plane defined by the datum block 100 (i.e., the proposed/intended resection depth) can be made by incrementally turning the thumb wheel 252 until a desired position of the reference/cutting plane (i.e., the resection depth) is achieved. At this point, the superior-inferior position of the datum block 100 (and the desired resection depth) may be fixed by driving one or more of the terminal attachment pins 196 through corresponding pin-receiving openings 122 in the datum block 100.

In one embodiment, the distal end surface 248 of the pointer 246 may initially be positioned and held in abutment against the selected point $P_1$ along the outer surface of the proximal tibia 12, followed by rotation of the thumb wheel 252 to correspondingly adjust the superior-inferior position of the datum block 100 and the reference/cutting plane defined by the reference bench 104 until a desired resection level has been achieved (as indicated by the reference numerals 262 on the thumb wheel 252 aligned with the reference marker 228 on the mounting block 202). However, in another embodiment, the resection depth may be initially set by aligning the appropriate reference numeral 262 on the thumb wheel 252 with the reference marker 228, followed by adjustment of the superior-inferior position of the datum block 100 until the distal end surface 248 of the pointer 246 is positioned in abutment against the selected point $P_1$ along the outer surface of the proximal tibia 12.

In addition to using the depth stylus 200 to position the datum block 100 at a desired superior-inferior position and the reference/cutting plane at a desired resection depth, it should be understood that the depth stylus 200 may be used at any time in a knee arthroplasty procedure to measure and check/verify the superior/inferior position of the reference/cutting plane relative to any reference point on the proximal tibia 12 by positioning the distal end surface 248 of the pointer 246 in abutment against the reference point (i.e., via rotational/translational positional adjustment of the stylus rod 204 and inferior-superior positional adjustment via rotation of the thumb wheel 252) and observing which of the reference numerals 262 on the thumb wheel 252 is aligned with the reference marker 228 on the mounting block 202.

Figure 15:
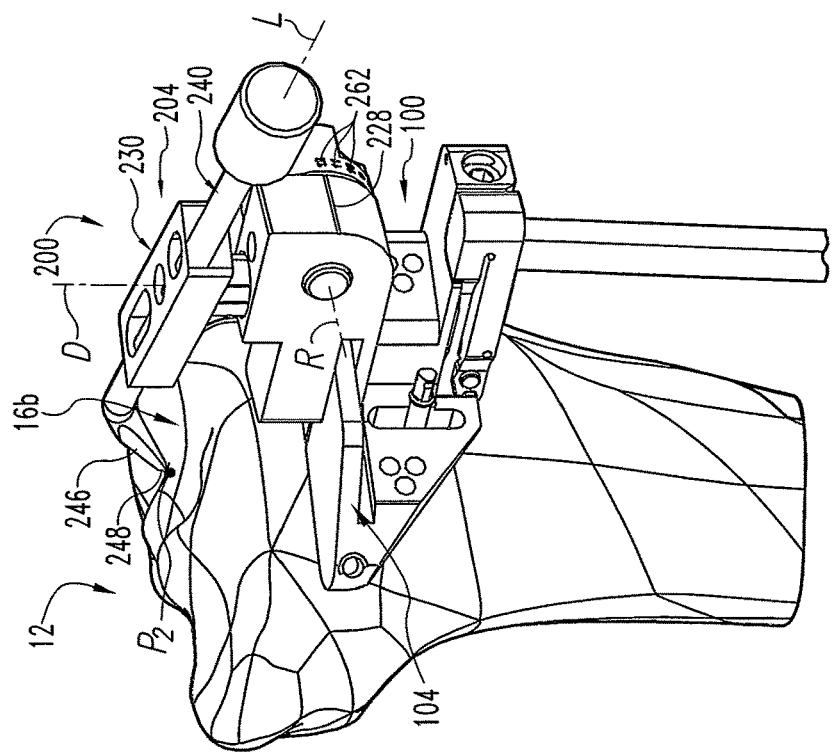
FIG. 15 illustrates a second operational position of the depth stylus of FIG. 11.

Referring to FIG. 15, shown therein is another operational position of the stylus rod 204 wherein the distal end surface 248 of the pointer 246 is positioned in contact with another selected point $P_2$ along the proximal tibia 12 (e.g., along the lateral tibial plateau 16b) to determine the distance of the selected point $P_2$ from the reference plane in an inferior-superior direction. Once again, the inferior-superior distance of the selected point $P_2$ in contact with the distal end surface 248 of the pointer 246 relative to the reference plane (i.e., the plane formed by the superior surface 150 of the reference bench 104 of the datum block 100) may be determined by observing which of the reference numerals 262 is aligned with the reference marker 228 (i.e., reference numeral "12" in the illustrated embodiment).

Figure 16A:
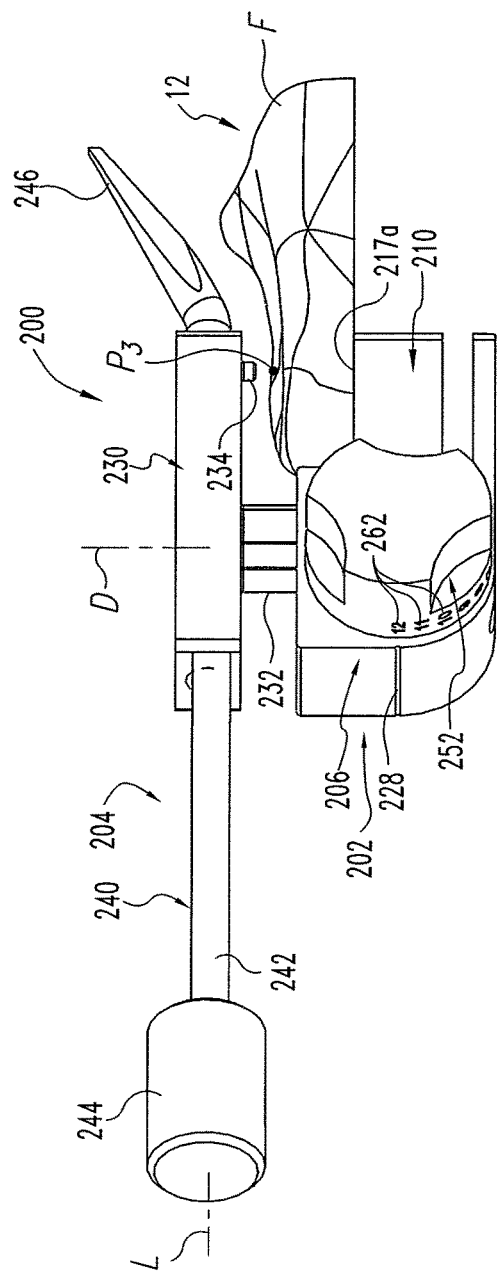
FIG. 16A illustrates an alternative operational configuration of the depth stylus of FIG. 11, as shown in a first operational position in relation to the proximal tibia.
Figure 16B:
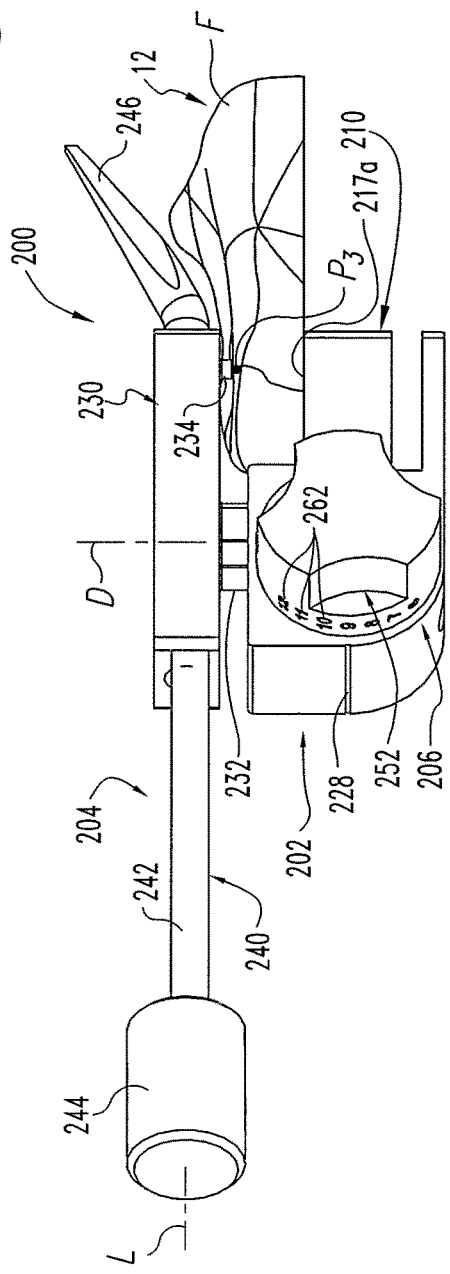
FIG. 16B illustrates an alternative operational configuration of the depth stylus of FIG. 11, as shown in a second operational position in relation to the proximal tibia.

Referring now to FIGS. 16A and 16B, shown therein is an alternative operational configuration of the depth stylus 200. In this alternative operational configuration, the depth stylus 200 may be removed/detached from the datum block 100 (via de-actuation of the pinch force mechanism 106) and used as a hand-held caliper-type instrument. This alternative operational configuration of the depth stylus 200 may be particularly useful, for example, in providing measurements of a resected bone fragment F removed/resected from proximal tibia 12. However, it should be understood that in this alternative operational configuration, the depth stylus 200 may be used to provide measurements of other structures as well including, for example, attached bone portions of the distal femur 10 or the proximal tibia 12 (i.e., the tibial eminence following resection), femoral or tibial bone implant components, or other structures of devices that require measurement.

As shown in FIG. 16A, in the alternative operational configuration of the depth stylus 200, the rod portion 240 of the stylus rod 204 may be retracted into the base portion 130 and rotated 180° about the longitudinal axis L relative to the base portion 230 to position the distal pointer 246 in a refracted position and in an upwardly extending orientation to avoid interference with the bone fragment F (or another structure or device) being measured. The bone fragment F may be inserted into the open space between the planar superior surface 217a of the mounting block 202 and the reference pin 234, with the reference pin 234 positioned directly above a selected point $P_3$ along the bone fragment F to be measured. As shown in FIG. 16B, the inferior-superior position of the stylus rod 204 may then be adjusted relative to the mounting block 202 along the displacement axis D by turning the thumb wheel 252 until the distal end surface of the reference pin 234 is positioned in contact with the selected point $P_3$ along the bone fragment F, and the opposite surface of the bone fragment F (i.e., the planar surface of the bone fragment F) is slightly compressed into contact with the planar superior surface 217a of the mounting block 202. The measured distance between the selected point $P_3$ and the opposite surface of the bone fragment F (i.e., the thickness of the bone fragment F) is determined by observing which of the reference numerals 262 on the thumb wheel 252 is aligned with the reference marker 228 on the anterior surface of the mounting block 202 (i.e., reference numeral "9" in the illustrated embodiment).

C. Eminence Stylus

Figure 17A:
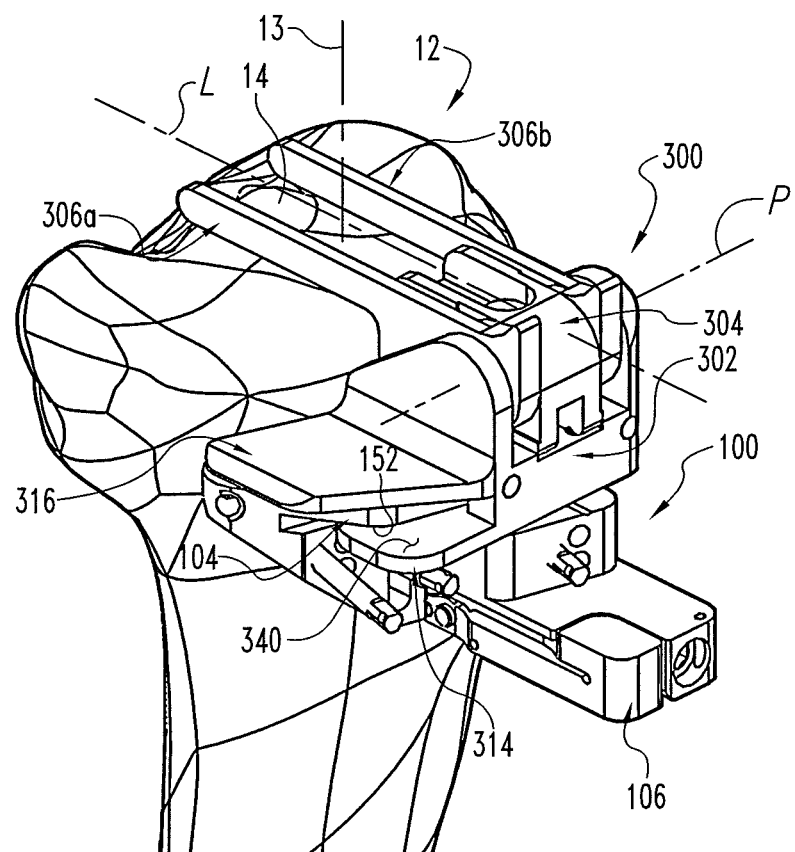
FIG. 17A illustrates an eminence stylus according to one form of the invention, as shown attached to the datum block of FIG. 5 in relation to the proximal tibia.

Referring to FIG. 17A, shown therein is an eminence stylus 300 according to one form of the present invention, as attached to the datum block 100 in relation to the proximal tibia 12. As will be discussed in greater detail below, the eminence stylus 300 includes alignment features that serve to align the eminence stylus 300 relative to anatomic features of the proximal tibia 12 and/or the distal femur 10, and also includes guide or capture features that serve to guide an oscillating or reciprocating saw or another type of cutting instrument along various cutting planes to form multiple resection cuts in the proximal tibia 12.

The eminence stylus 300 generally includes a base portion or body 302 configured for attachment to the datum block 100, a carriage 304 movably attached to the base portion 302 and configured for linear displacement along a longitudinal displacement axis L arranged in a generally anterior-posterior direction, and a pair of articulating arms or indicator members 306a, 306b pivotally attached to the carriage 304 and configured for pivotal displacement about a pivot axis P arranged generally perpendicular to the longitudinal displacement axis L. Further elements and features associated with the eminence stylus 300 will be set forth in greater detail below.

Figure 17B:
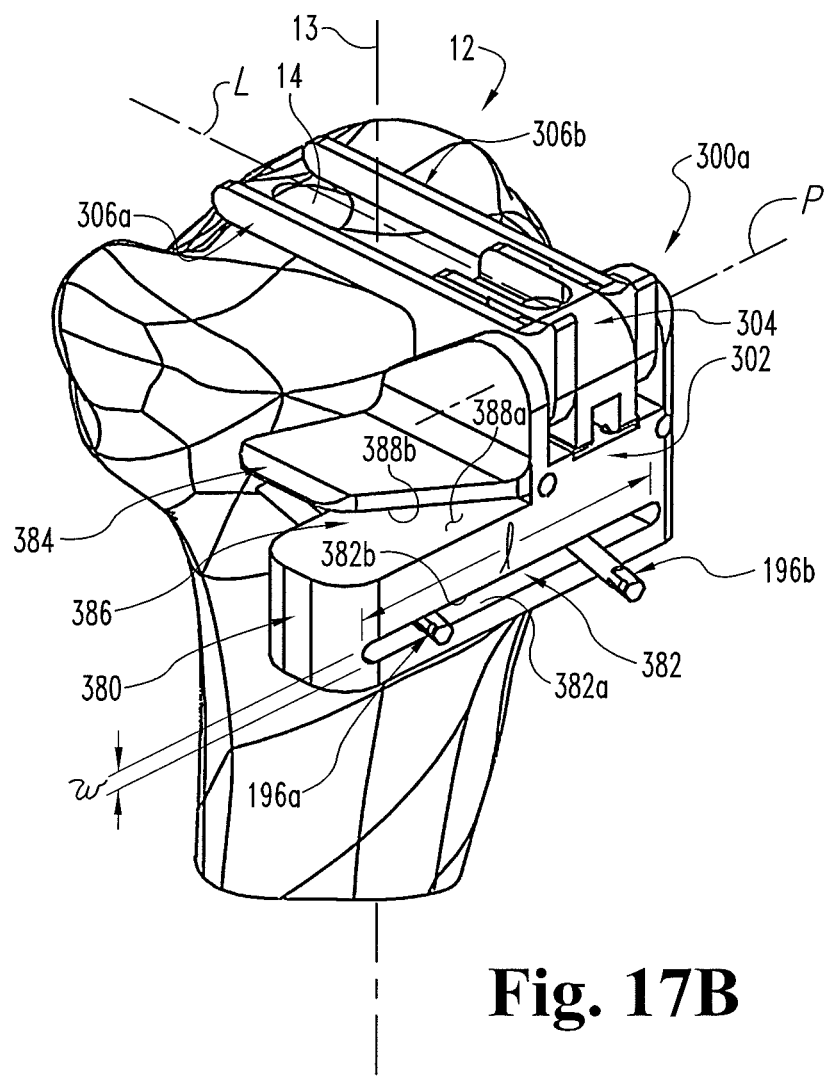
FIG. 17B illustrates an eminence stylus according to another form of the invention, as shown attached to the proximal tibia.

Referring to FIG. 17B, shown therein is an eminence stylus 300a according to another form of the present invention, as attached to the proximal tibia 12. In many respects, the eminence stylus 300a is configured similar to the eminence stylus 300 illustrated and described above. However, the eminence stylus 300a includes other elements, features and operational characteristics not found in the eminence stylus 300, the details of which will be described below.

It should be understood that like elements and features associated with the eminence stylus 300 and the eminence stylus 300a are referred to using the same reference numbers. Similar to the eminence stylus 300, the eminence stylus 300a generally includes a base portion or body 302, a carriage 304 movably attached to the base portion 302 and configured for linear displacement along a longitudinal displacement axis L arranged in a generally anterior-posterior direction, and a pair of articulating arms or indicator members 306a, 306b pivotally attached to the carriage 304 and configured for pivotal displacement about a pivot axis P arranged generally perpendicular to the longitudinal displacement axis L and the anatomic axis 13 of the tibia. Further details associated with the elements and features of the base portion 302, the carriage 304 and the indicator members 306a, 306b of the eminence stylus 300a need not be discussed herein, it being understood that these elements and features may be configured identical to like components of the eminence stylus 300. However, in other embodiments, the base portion 302, the carriage 304 and/or the indicator members 306a, 306b of the eminence stylus 300a may be configured different from those of the eminence stylus 300. Unlike the eminence stylus 300 which is configured for releasable attachment to the datum block 100 or a similar instrument or device, the eminence stylus 300a is configured for attachment directly to the proximal tibia 12. Specifically, in the illustrated embodiment, the eminence stylus 300a includes a mounting block 380 defining at least one pin-receiving opening 382 extending therethrough in an anterior-posterior direction, and with one or more attachment pins 196a, 196b positioned within and extending through the opening 382 to operatively attach the eminence stylus 300a to the proximal tibia 12. Further elements and features associated with the eminence stylus 300a will be set forth in greater detail below.

Referring collectively to 18A-18F, in the illustrated embodiment of the eminence stylus 300 shown in FIG. 17A, the base portion 302 is a single-piece monolithic structure and generally includes a base plate 310, a pair of medial and lateral cutting guide flanges 312a, 312b extending from the base plate 310 in an inferior-superior direction and spaced apart to define an open inner region or yoke therebetween, an inferior mounting flange 314 extending from the base plate 310 in a medial-lateral direction, and a superior cutting guide flange 316 extending from the base plate 310 in a medial-lateral direction and superiorly offset from the inferior mounting flange 314 so as to define a slot 318 therebetween. Although the base portion 302 has been illustrated and described as being formed as a single-piece monolithic structure, in other embodiments, various pieces/elements of the base portion 302 may be formed separately from one another and integrated into a multi-piece assembly.

In one embodiment, the base plate 310 has a generally planar configuration and a generally rectangular shape. However, other shapes and configurations are also contemplated. The base plate 310 defines a pair of circular pin receiving openings 320a, 320b extending entirely through the base plate 310 and aligned generally along the longitudinal axis L in an anterior-posterior direction, and with the openings 320a, 320b arranged symmetrical on opposite sides of the longitudinal axis L. Additionally, the base plate 310 includes a rectangular-shaped guide notch or channel 322 (FIGS. 18C and 18F) formed in the superior surface of the base plate 310 and aligned generally along the longitudinal axis L in an anterior-posterior direction. The guide channel 322 is sized and configured to receive an inferior portion of the carriage 304 therein so as to aid in guidably displacing the carriage 304 linearly along the longitudinal axis L (FIGS. 19A and 19B). The base plate 310 also defines a threaded aperture 324 (FIG. 18E) extending through the base plate 310 in an inferior-superior direction and aligned generally with the longitudinal axis L, and further defines a pair of threaded apertures 326a, 326b extending at least partially through the base plate 310 in an inferior-superior direction and arranged symmetrically on opposite sides of the longitudinal axis L. The threaded apertures 326a, 326b are configured to threadingly receive a pair of fasteners or set screws 328a, 328b.

As indicated above, the medial and lateral cutting guide flanges 312a, 312b extend from the base plate 310 in an inferior-superior direction and are spaced apart to define an open inner region or yoke therebetween. In the illustrated embodiment, the medial and lateral cutting guide flanges 312a, 312b each have a triangular-shaped configuration. However, other shapes and configurations of the medial and lateral cutting guide flanges 312a, 312b are also contemplated. Additionally, the medial and lateral cutting guide flanges 312a, 312b define substantially flat/planar inner surfaces 330a, 330b, respectively, arranged generally parallel with one another and facing the open inner region. The planar inner surfaces 330a, 330b are preferably generally aligned with the central axes of the pin receiving openings 320a, 320b, respectively. As will be discussed in further detail below, the substantially flat/planar inner surfaces 330a, 330b of the medial and lateral cutting guide flanges 312a, 312b cooperate with adjacent surfaces of the indicator members 306a, 306b to form medial and lateral cutting guides or channels configured to guide an oscillating or reciprocating saw (or another type of cutting instrument) to form vertical cuts associated with the medial and lateral resection of the proximal tibia 12.

As also indicated above, the inferior mounting flange 314 and the superior cutting guide flange 316 each extend from the base plate 310 in a medial-lateral direction and are offset from one another in an inferior-superior direction to define a slot 318 therebetween. In one embodiment, the inferior mounting flange 314 has a generally rectangular configuration and the superior cutting guide flange 316 has a generally trapezoidal-shaped configuration. However, other suitable shapes and configurations are also contemplated. In the illustrated embodiment, the inferior mounting flange 314 has a plate-like configuration defining substantially flat/planar superior and inferior surfaces 340, 342, respectively. Similarly, the superior cutting guide flange 316 likewise defines substantially flat/planar superior and inferior surfaces 344, 346, respectively. The slot 318 defined between the inferior mounting flange 314 and the superior cutting guide flange 316 has a slot width w that is sized for receipt of the reference bench 104 of the datum block 100 therein. As illustrated in FIG. 17A, once the eminence stylus 300 is positioned in a desired position and orientation relative to the reference bench 104 of the datum block 100, the locking or pinch force mechanism 106 of the datum block 100 is actuated to compress the superior surface 340 of the inferior mounting flange 314 against the inferior surface 152 of the reference bench 104 to thereby lock the eminence stylus 300 in a select position and orientation relative to the datum block 100.

Figures 20A, 20B, 20C:
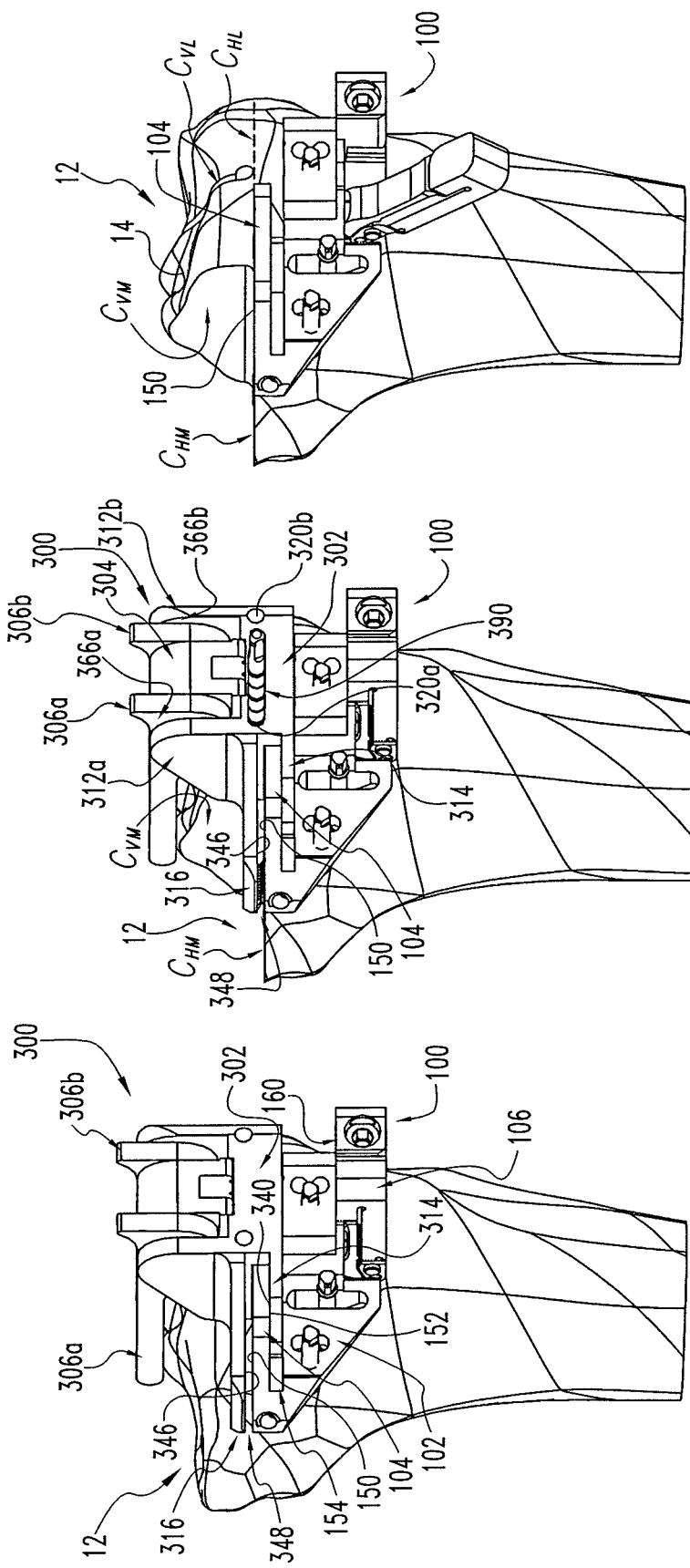
FIG. 20A illustrates the eminence stylus of FIG. 17A in relation to the datum block of FIG. 5 in preparation for medial resection of the proximal tibia.
FIG. 20B illustrates the eminence stylus of FIG. 17A locked to the datum block of FIG. 5 and pinned to the proximal tibia in relation to the medially resected proximal tibia.
FIG. 20C illustrates the datum block of FIG. 5 in relation to the medially resected proximal tibia with the eminence stylus of FIG. 17A removed from the datum block.

As will be set forth in detail below, the substantially flat/planar inferior surface 346 defined by the superior cutting guide flange 316 of the eminence stylus 300 forms a superior boundary of a cutting guide. In one embodiment, the substantially flat/planar inferior surface 346 is preferably generally aligned with the central axis of the pin receiving opening 320a (FIG. 18C). As illustrated in FIG. 20A, the substantially flat/planar inferior surface 346 of the superior cutting guide flange 316 is aligned substantially parallel with and offset from the substantially flat/planar superior surface 150 of the reference bench 104 of the datum block 100 to thereby form a medial cutting guide or channel 348 defined between the adjacent inferior and superior surfaces 346, 150. In one embodiment, the planar superior surface 150 defined by the reference bench 104 is aligned generally tangent with the diameter of the medial pin receiving opening 320a. As should be appreciated, the medial cutting guide 348 preferably defines a channel width sized in relatively close tolerance with the cutting blade thickness of an oscillating or reciprocating saw (or another cutting device) to form a smooth and accurate medial resection cut in the proximal tibia 12, further details of which will be set forth below.

In the illustrated embodiment, the carriage 304 has a generally U-shaped configuration including a base wall 350 defining a substantially flat/planar superior surface, and a pair of side walls 352a, 352b extending from the base wall 350 in an inferior-superior direction and defining substantially flat/planar inner side surfaces and substantially flat/planar outer side surfaces. The carriage 304 may also be provided with an end wall 354 to provide further structural support and rigidity to the carriage 304. Additionally, the carriage 304 may be provided with a pair of projections or detents 353a, 353b extending laterally outward from outer surfaces of the side walls 352a, 352b, respectively, the purpose of which will be discussed below. The carriage 304 also defines an elongate slot 356 having a length extending generally along the longitudinal axis L. The carriage 304 further includes a pin or fastener 358 (FIGS. 18D and 18F) including a threaded shank portion 358a and an enlarged head portion 358b. The threaded shank portion 358a extends through the elongate slot 356 and is threaded into the threaded aperture 324 in the base plate 310 (FIG. 18E). In one embodiment, the enlarged head portion 358b has a generally circular outer cross section that is positioned in relatively close tolerance and sliding engagement with the substantially flat/planar inner side surfaces of the side walls 352a, 352b of the carriage 304 (FIGS. 18D and 18F). As should be appreciated, the fastener 358 serves to retain the carriage 304 on the base portion 302 to prevent unintended or inadvertent removal of the carriage 304. However, as will be discussed in greater detail below, the carriage 304 may be axially displaced relative to the base portion 302 along the longitudinal axis L to provide a degree of adjustability to the eminence stylus 300. Additionally, as shown in FIG. 18C, an inferior region of the base wall 350 and/or the side walls 352a, 352b is recessed into the guide channel 322 formed along the superior surface of the base plate 310 to facilitate guiding displacement of the carriage 304 along the longitudinal axis L.

In the illustrated embodiment, the articulating arms or indicator members 306a, 306b each include a mounting plate portion 360 and an elongate blade portion 362. As should be appreciated, the mounting plate portion 360 and the blade portion 362 of the indicator members 306a, 306b cooperate to define substantially flat/planar outer side surface 364a, 364b, respectively. As shown in FIGS. 18C and 18D, the flat/planar outer side surface 364a, 364b of the indicator members 306a, 306b are aligned substantially parallel with and offset from the respective flat/planar inner side surfaces 330a, 330b of the medial and lateral cutting guide flanges 312a, 312b to thereby form a medial cutting guide or channel 366a defined between the adjacent side surfaces 330a, 364a, and a lateral cutting guide or channel 366b defined between the adjacent side surfaces 330b, 364b. As should be appreciated, the medial and lateral cutting guides 366a, 366b preferably define a channel width sized in relatively close tolerance with the cutting blade thickness of an oscillating or reciprocating saw (or another cutting device) to form smooth and accurate resection cuts in the proximal tibia 12, further details of which will be set forth below.

The mounting plate portions 360 of the indicator members 306a, 306b are pivotally attached to the side walls 352a, 352b of the carriage 304 via one or more pivot pins 370 (FIG. 19B) to allow for pivotal movement of the indicator members 306a, 306b about the pivot axis P from a substantially horizontal orientation (FIG. 19B) to a substantially vertical orientation (FIG. 19C). The ends or heads of the pivot pins 370 are flush with or recessed slightly below the flat/planar outer side surface 364a, 364b of the indicator members 306a, 306b to provide a substantially smooth and uninterrupted cutting guide surface. The inner surfaces of the mounting portions 360 of the indicator members 306a, 306b each define a series of recesses or grooves 372 (18F and 19C) that are sized to receive the detents 353a, 353b to thereby provide a certain degree of resistance to pivotal movement of the indicator members 306a, 306b about the pivot axis P to allow for incremental pivotal movement of the indicator members 306a, 306b relative to the carriage 304. The indicator members 306a, 306b may therefore be provisionally maintained in a select pivotal position via positioning of the detents 353a, 353b in select ones of the recesses/grooves 366. In one embodiment, the portion of the mounting plate 360 positioned adjacent the pivot axis P has a somewhat greater thickness compared to the elongate blade portion 362 to provide the indicator members 306a, 306b with greater rigidity and structural integrity. Additionally, each of the elongate blade portions 362 preferably defines substantially flat/planar upper and lower edges 374a, 374b and a rounded distal end surface 376.

Although a particular shape and configuration of the indicator members 306a, 306b has been illustrated and described herein, it should be understood that other suitable shapes and configurations are also contemplated. Additionally, although the indicator members 306a, 306b have been illustrated as pivoting simultaneously with one another about the pivot axis P relative to the carriage 304, it should be understood that the indicator members 306a, 306b may pivot independent from one another about the pivot axis P (i.e., the indicator members 306a, 306b may be positioned at different angular orientations relative to one another). Furthermore, in the illustrated embodiment of the eminence stylus 300, the indicator members 306a, 306b pivot about the pivot axis P along travel planes that are substantially parallel to one another. However, in other embodiments, the eminence stylus 300 may be configured such that the indicator members 306a, 306b pivot about the pivot axis P along travel planes that are not parallel to one another (i.e., are arranged oblique to one another).

Referring now to FIGS. 19A-19E, the carriage 304 may be axially displaced relative to the base portion 302 along the longitudinal axis L between a first fully extended posterior-most position (FIGS. 19A and 19D) and a second fully retracted anterior-most position (19B and 19E). The eminence stylus 300 is therefore capable of translating the carriage 304 (and the indicator members 306a, 306b attached to the carriage 304) toward and away from the proximal tibia 12 (or distal femur 10) in an anterior-posterior direction along the longitudinal axis L (FIG. 17A). As should be appreciated, axial displacement of the carriage 304 relative to the base portion 302 is limited by abutment of the threaded shank portion 358a of the fastener 358 against the end surfaces of the elongate slot 356 (i.e., axial displacement of the carriage 304 is limited by the length of the elongate slot 356). Additionally, it should also be appreciated that the ability to translate the carriage 304 (and the indicator members 306a, 306b attached to the carriage 304) along the longitudinal axis L may more easily accommodate for different sizes of knees (e.g., varying sizes of the distal femur 10 and the proximal tibia 12). Furthermore, the ability to translate the carriage 304 along the longitudinal axis L to the fully retracted anterior-most position (FIGS. 19B and 19E) allows the indicator members 306a, 306b to clear the distal femur 10 for pivotal displacement about the pivot axis P to their vertical orientation (FIG. 19C) which may be used to check alignment with the anterior region of the distal femur 10. As should be further appreciated, sliding displacement of the enlarged head portion 358b along the inner guide surfaces of the side walls 352a, 352b and/or sliding displacement of the inferior region of the base wall 350 along the guide channel 322 formed in the base plate 310 facilitate smooth and uninhibited guiding displacement of the carriage 304 generally along the longitudinal axis L as the carriage 304 is moved axially relative to the base portion 302.

Referring to FIGS. 20A-20C, some of the operational characteristics associated with the eminence stylus 300 according to embodiments of the invention will now be discussed. The eminence stylus 300 is initially provisionally attached to the datum block 100 by positioning the inferior mounting flange 314 of the eminence stylus 300 into the slot or channel 154 defined between the reference bench 104 and the main body 102 of the datum block 100. In this provisional attachment arrangement, the position and orientation of the eminence stylus 300 may be adjusted relative to the datum block 100 and various anatomic features associated with the proximal tibia 12 and the distal femur 10. In some embodiments, the indicator members 306a, 306b may be used to provide visual indicators to aid in adjusting the eminence stylus 300 to the desired position and orientation. For example, the longitudinal axis L and the space between the indicator members 306a, 306b might be centrally positioned and generally aligned with the anatomic axis 13 of the tibia, and the central plane extending between the space between the indicator members 306a, 306b might be arranged generally coplanar with the central plane of the tibia 12. Other alignment techniques and procedures used by those of skill in the art are generally known and need not be discussed in detail herein.

As illustrated in FIG. 20A, after the eminence stylus 300 is positioned in a desired position and orientation relative to the proximal tibia 12, the locking or pinch force mechanism 106 of the datum block 100 is actuated to compress the superior surface 340 of the inferior mounting flange 314 against the inferior surface 152 of the reference bench 104 to thereby lock the eminence stylus 300 in the selected position and orientation. However, as should be appreciated, if further adjustment to the position/orientation of the eminence stylus 300 becomes necessary or is desired, the locking or pinch force mechanism 106 of the datum block 100 can simply be deactuated/unlocked to provide further adjustment opportunity (i.e., by pivoting the lever arm 160 of the locking mechanism 106 in a downward direction).

Referring to FIG. 20B, once the eminence stylus 300 is locked in position relative to the datum block 100, a graduated tibial pin 390 according to one form of the invention is inserted into the medial pin receiving opening 320a in the eminence stylus 300 and anchored to the proximal tibia 12. A second graduated tibial pin 390 may likewise be inserted into the lateral pin receiving opening 320b and anchored to the proximal tibia 12. Further details regarding the graduated tibial pin 390 and a technique for installation/use of the graduated tibial pin 390 according to one form of the invention will be set forth in detail below. As should be appreciated, the graduated tibial pin 390 provides further stabilization and support to the eminence stylus 300 to prevent unintended/unintentional movement of the eminence stylus 300 relative to the proximal tibia 12 (and the datum block 100) during formation of the resection cuts. Additionally, the graduated tibial pin 390 also serves as a guard or stop during formation of the tibial resection cuts to control the depth of the cuts and to prevent overcutting or notching which might otherwise compromise the strength and integrity of the tibial eminence 14.

Once the graduated tibial pin 390 is inserted into the medial pin receiving opening 320a and anchored to the proximal tibia 12, an oscillating or reciprocating saw (or another cutting device) is inserted into and displaced along the medial cutting guide 348 defined between the inferior surface 346 of the superior cutting guide flange 316 (on the eminence stylus 300) and the superior surface 150 of the reference bench 104 (on the datum block 100) to form a horizontal medial resection cut $C_{HM}$. As indicated above, the graduated tibial pin 390 serves as a guard or stop to control the depth of the horizontal resection cut and to prevent overcutting or notching of the tibial eminence 14. After formation of the horizontal medial resection cut $C_{HM}$, the oscillating or reciprocating saw (or another cutting device) is inserted into and displaced along the medial cutting guide 366a defined between the adjacent flat/planar side surfaces defined by the medial cutting guide flange 312a and the medial indicator member 306a to form the vertical medial resection cut $C_{VM}$ to complete the medial resection of the proximal tibia 12. Once again, the graduated tibial pin 390 serves as a guard or stop to control the depth of the vertical resection cut and to prevent overcutting.

Following completion of the medial tibial resection, the graduated tibial pin 390 can be removed from the medial pin receiving opening 320a and inserted into the lateral pin receiving opening 320b of the eminence stylus 300 and anchored to the proximal tibia 12. Alternatively, a second graduated tibial pin (not shown) may be inserted into the lateral pin receiving opening 320b and anchored to the proximal tibia 12. The oscillating or reciprocating saw (or another cutting device) is then inserted into and displaced along the medial cutting guide 366b defined between the adjacent flat/planar side surfaces defined by the lateral cutting guide flange 312b and the lateral indicator member 306b to form a vertical lateral resection cut $C_{VL}$ in the proximal tibia 12. Once again, the graduated tibial pin 390 serves as a guard or stop to control the depth of the vertical resection cut and to prevent overcutting or notching. In one embodiment, a single-blade saw (or another type of cutting device) is used to form the vertical medial resection cut $C_{VM}$ and vertical lateral resection cut $C_{VL}$. However, in other embodiment, a dual-blade saw (or another type of cutting device) may be used to form the vertical medial resection cut $C_{VM}$ and vertical lateral resection cut $C_{VL}$ simultaneously. Examples of dual-blade saws suitable for use in association with the present invention are disclosed in U.S. patent application Ser. No. 12/790,137, the contents of which have been incorporated herein by reference in their entirety.

It should be appreciated that while the medial and lateral cutting guides 366a, 366b defined between the adjacent flat/planar side surfaces of the cutting guide flanges 312a, 312b and the mounting plate portions 360 of the medial and lateral indicator members 306a, 306b serve as the primary guide structures (a complete saw blade capture extending along both sides of the saw blade) for guiding the saw blade along a particular cutting plane (i.e., a vertical cutting plane), the elongate blade portions 362 of the indicator members 306a, 306b also serve as additional guide structures along regions of the proximal tibia 12 posterior to the cutting guides 366a, 366b during a cutting operation. In this manner, the elongate blade portions 362 of the indicator members 306a, 306b serve as an extension of the cutting guides 366a, 366b to guide/control the tip and distal portion of the saw blade and to control the path of the saw blade in locations posterior to the cutting guides 366a, 366b, particularly when forming posterior portions of the vertical eminence resection cuts. Additionally, the elongate blade portions 362 of the indicator members 306a, 306b also serve as positive inner boundaries or stops to protect the bone intended for preservation (i.e., the unresected bone). It should also be appreciated that although the indicator members 306a, 306b are illustrated and described as being positioned medially or inwardly offset from the medial and lateral cutting guide flanges 312a, 312b to form inner boundaries or stops to control/guide the position of the saw blade, in other embodiments, the indicator members 306a, 306b may be positioned outward from the medial and lateral cutting guide flanges 312a, 312b to form outer boundaries or stops to control/guide the position of the saw blade.

As shown in FIG. 20C, following the formation of the horizontal medial resection cut $C_{HM}$, the vertical medial resection cut $C_{VM}$, and the vertical lateral resection cut $C_{VL}$, the eminence stylus 300 may be removed from the datum block 100 to provide access to the medially resected tibia for inspection, trialing and/or measuring using the depth stylus 200 or other measuring instruments. If re-cutting of one or more of the resection cuts is required or desired, the eminence stylus 300 may be re-engaged with the datum block 100, re-positioned/re-aligned with respect to the proximal tibia 12, and re-locked to the datum block 100. Alternatively, other devices/instruments may be used to recut or perform other cutting operations on the proximal tibia 12, the details of which will be set forth below. As shown in FIG. 20C, due to the design and configuration of the datum block 100, one potential benefit or advantage provided by the present invention is that the planar superior surface 150 of the datum block 100 is arranged co-planar with the horizontal medial resection cut $C_{HM}$. Accordingly, the planar superior surface 150 of the datum block 100 and the horizontal medial resection cut $C_{HM}$ extend along a single reference plane, which may be beneficial when engaging other devices or instruments to the datum block 100 and/or when performing other procedures or techniques on the proximal tibia 12.

Although the formation of the horizontal and vertical resection cuts on the proximal tibia 12 have been illustrated and described as occurring in a particular order, it should be understood that other cutting sequences are also contemplated. Additionally, although formation of the vertical lateral resection cuts $C_{VL}$ has been illustrated and described as occurring immediately after completion of the medial tibial resection, it should be understood that the eminence stylus 300 may be removed from the datum block 100 after completion of the medial tibial resection to provide access to the medially resected tibia for inspection, trialing and/or measuring to verify the accuracy of the medial resection cuts (i.e., position, depth, posterior slope angle, varus/valgus angle, etc.). In this manner, if the medial resection is found to be inaccurate and/or requires re-cutting, appropriate corrections/adjustments can be made prior to forming the lateral resection cuts. The eminence stylus 300 (or other devices or instruments) may be engaged with the datum block 100 and positioned/aligned with respect to the proximal tibia 12 prior to being locked to the datum block 100, followed by re-cutting of the medial resections and/or formation of the vertical lateral resection cuts $C_{VL}$.

Referring once again to FIG. 17B, shown therein is the eminence stylus 300a attached to the proximal tibia 12 by the attachment pins 196a, 196b. In many respects, the eminence stylus 300a is configured similar to the eminence stylus 300, generally including a base portion 302, a carriage 304 movably attached to the base portion 302 and configured for linear displacement along the longitudinal displacement axis L, and a pair of indicator members 306a, 306b pivotally attached to the carriage 304 and configured for pivotal displacement about the pivot axis P. However, unlike the eminence stylus 300 which is configured for indirect coupling to the proximal tibia 12 by way of the datum block 100, the eminence stylus 300a is configured for direct attachment to the proximal tibia 12.

In the illustrated embodiment, the eminence stylus 300a includes a mounting block 380 defining at least one pin-receiving opening 382 extending therethrough in an anterior-posterior direction, and with one or more attachment pins 196a, 196b positioned within and extending through the pin-receiving opening 382 and anchored to tibial bone to operatively attach the eminence stylus 300a to the proximal tibia 12. In one embodiment, the base portion 302 and the mounting block 380 are formed unitarily with one another to define a single-piece monolithic structure. However, in other embodiments, the base portion 302 and the mounting block 380 may be formed separately and coupled/interconnected together to define an integrated multi-piece structure. In one embodiment, the pin-receiving opening 382 is configured as an elongate slot having a slot length/extending generally in a medial-lateral direction and including inferior and superior surfaces 382a, 382b that are spaced apart to define a slot width w. The slot length/preferably extends across substantially an entire width of the mounting block 380, and the slot width w is preferably sized in relatively close tolerance with the outer diameter of the attachment pins 196a, 196b to provide secure and stable engagement between the mounting block 380 of the eminence stylus 300a and the attachment pins 196a, 196b. Although the pin-receiving opening 382 is illustrated and described as an elongate slot, it should be understood that other configurations of the pin-receiving opening 382 are also contemplated including, for example, a circular configuration. Additionally, although both of the attachment pins 196a, 196b are illustrated as extending through a single pin-receiving openings 382, it should be understood that the mounting block 380 may be provided with any number of the pin-receiving openings 382, including two or more pin-receiving opening 382 sized and configured for individual receipt of respective ones of the attachment pins 196a, 196b.

In the illustrated embodiment, the eminence stylus 300a includes a superior cutting guide flange 384 configured similar to the superior cutting guide flange 316 of the eminence stylus 300. The superior cutting guide flange 384 extends from the base portion 302 in a medial-lateral direction and is offset from a medial portion of the mounting block 380 in an inferior-superior direction to thereby define a cutting guide channel 386 therebetween. In one embodiment, the mounting block 380 has a generally rectangular transverse cross-section and the superior cutting guide flange 384 has a generally trapezoidal-shaped transverse cross-section. However, other suitable shapes and configurations are also contemplated. Additionally, in the illustrated embodiment, the mounting block 380 defines a substantially flat/planar superior surface 388a and the superior cutting guide flange 384 defines substantially flat/planar inferior surface 388b, with the planar superior and inferior surfaces 388a, 388b offset from one another in an inferior-superior direction to define the cutting guide channel 386 therebetween. The cutting guide channel 386 is sized for receipt of a cutting device therein and is configured to guide the cutting device generally along a cutting plane in a medial-lateral direction to form a medial resection cut in the proximal tibia 12. In this manner, the mounting block 380 and the cutting guide flange 384 cooperate to define a cutting guide that is sized in relatively close tolerance with the thickness of the cutting device (e.g., a cutting blade of an oscillating or reciprocating saw, or another type of cutting device) to form a smooth and accurate medial resection cut in the proximal tibia 12 generally along the cutting plane of the cutting guide channel 386, further details of which have been set forth above with regard to the eminence stylus 300.

Having described the structural features associated with the eminence stylus 300a, reference will now be made to attachment of the eminence stylus 300a to the proximal tibia 12 according to one embodiment of the present invention. As discussed above in association with FIG. 10, once the datum block 100 is positioned in the appropriate superior/inferior position along the proximal tibia 12 and is rotated to the appropriate medial-lateral angle and anterior-posterior angle, the datum block 100 may be terminally attached to the proximal tibia 12 by a pair of terminal attachment pins 196a, 196b extending through respective ones of the pin-receiving openings 122 in the main body 102 of the datum block 100.

In some instances, it may be desirable to interchange the datum block 100 with the eminence stylus 300a or another instrument or device. More specifically, it may be desirable to remove the datum block 100 from the attachment pins 196a, 196b and replace the datum block 100 with the eminence stylus 300a or other instruments or devices. Since the attachment pins 196a, 196b are preferably arranged generally parallel with one another, the datum block 100 can be easily detached from the proximal tibia 12 by simply sliding the datum block 100 off of the attachment pins 196a, 196b in an anterior direction. Once the datum block 100 is removed from the attachment pins 196a, 196b, the eminence stylus 300a can be attached to the proximal tibia 12 using the same attachment pins 196a, 196b previously used to attach the datum block 100 to the proximal tibia 12 (FIG. 10). Specifically, the proximal end portions of the attachment pins 196a, 196b extending from the proximal tibia 12 may be inserted into the elongate slot 382 in the mounting block 380, and the eminence stylus 300a may be slid along the proximal end portions of the attachment pins 196a, 196b in an anterior-posterior direction and rotated about the pins 196a, 196b in a medial-lateral direction until the eminence stylus 300a is properly positioned and oriented relative to the proximal tibia 12. In one embodiment, the eminence stylus 300a is slid along the proximal portions of the attachment pins 196a, 196b in an anterior-posterior direction until the eminence stylus 300a abuts an anterior aspect of the proximal tibia 12.

As should be appreciated, since the eminence stylus 300a is attached to the proximal tibia 12 using the same attachment pins 196a, 196b that were used to attach the datum block 100 to the proximal tibia 12 (i.e., the attachment pins 196a, 196b remain anchored to the proximal tibia 12 after removal of the datum block 100), the position and orientation of the eminence stylus 300a relative to the proximal tibia 12 is advantageously based on the same points of reference used to set the position and orientation of the datum block 100. Notably, removal of the attachment pins 196a, 196b from the proximal tibia 12 is not required to detach the datum block 100 from the proximal tibia 12 or to attach the eminence stylus 300a to the proximal tibia 12.

Additionally, it should be appreciated that the elongate pin-receiving slot 382 in the mounting block 380 of the eminence stylus 300a has the same relative position and orientation as corresponding pairs of the pin-receiving openings 122 in the datum block 100. Therefore, the eminence stylus 300a may be interchanged with the datum block 100 using the same attachment pins 196a, 196b previously used to attach the datum block 100 to the proximal tibia 12, and the eminence stylus 300a may take on the same position and orientation relative to the proximal tibia 12 as the datum block 100.

In one embodiment, the eminence stylus 300a is arranged at a position and orientation on the proximal tibia 12 that corresponds to the prior position and orientation on the datum block 100. In one specific embodiment, the planar superior surface 388a of the mounting block 380 of the eminence stylus 300a is arranged substantially parallel with the previously-positioned planar superior surface 150 of the reference bench 104 of the datum block 100. In another specific embodiment, the planar superior surface 388a of the eminence stylus 300a is arranged substantially co-planar with the previously-positioned planar superior surface 150 of the datum block 100. However, other embodiments are also contemplated wherein the planar superior surface 388a of the eminence stylus 300a may be arranged non-parallel with and/or non-coplanar with the previously-positioned planar superior surface 150 of the datum block 100. As should be appreciated, the attachment pins 196a, 196b provide two reference points that define a datum plane or substantially planar datum joint that serves to attach the datum block 100 to the proximal tibia 12 in a select position and orientation corresponding to the previous position and orientation of the datum block 100.

Additionally, in other embodiments of the invention, the eminence stylus 300a may include other structures/features that provide a neutral/reference tibial foundation to which other devices or instruments may be engaged to and referenced from. For example, in some embodiments, the eminence stylus 300a may be provided with a reference table configured similar to the reference bench 104 illustrated and described above with regard to the datum block 100 to provide a structure to which other instruments or devices may be lockingly engaged. Additionally, in some embodiments, the eminence stylus 300a may be provided with a lock mechanism similar to that of the locking mechanism 106 of the datum block 100 to selectively and releasably lock other instruments or devices to a reference bench of the eminence stylus 300a.

Referring to FIGS. 21A and 21B, shown therein is an eminence stylus 300' according to another form of the present invention. Referring to FIG. 22, shown therein is the eminence stylus 300' attached to the datum block 100 (which may in turn be anchored to the proximal tibia 12). The eminence stylus 300' is configured identical to the eminence stylus 300 illustrated and described above with the exception of the additional elements and features described below. Like the eminence stylus 300, the eminence stylus 300' generally including a base portion or body 302' configured for attachment to the datum block 100, a carriage 304' movably attached to the base portion 302' and configured for linear displacement along a longitudinal displacement axis L, and a pair of articulating arms or indicator members 306a', 306b' pivotally attached to the carriage 304' and configured for pivotal movement relative to the carriage 304'. The elements and features associated with these components need not be discussed herein, it being understood that the elements and features associated with the base portion 302', the carriage 304' and the indicator members 306a', 306b' are configured identical to like elements and features associated with the base portion 302, the carriage 304 and the indicator members 306a, 306b of the eminence stylus 300.

Unlike the eminence stylus 300 which cooperates with the datum block 100 to provide a single horizontal medial cutting guide 348 (as defined between the superior cutting guide flange 316 and the reference bench 104), as illustrated in FIG. 22, the eminence stylus 300' provides both a horizontal medial cutting guide 348' and a horizontal lateral cutting guide 380'. Specifically, like the horizontal medial cutting guide 348 associated with the eminence stylus 300, the horizontal medial cutting guide 348' is likewise defined between the inferior surface 346' of the superior cutting guide flange 316' and the superior surface 150 of the reference bench 104 (FIG. 22). Additionally, the horizontal lateral cutting guide 380' is defined between an inferior cutting guide flange 382' and a superior cutting guide flange 384', each extending laterally from the right hand side of the base plate 310' in a medial-lateral direction. In one embodiment, the inferior and superior cutting guide flanges 382', 384' are formed unitarily with the base plate 310' so as to define a single-piece monolithic structure. However, in other embodiments, one or both of the inferior and superior cutting guide flanges 382', 384' may be formed separately from the base plate 310' and integrated with the base plate 310' to define a multi-piece assembly. In the illustrated embodiment, the inferior and superior cutting guide flanges 382', 384' each have an irregular shape. However, other suitable shapes and configurations are also contemplated including, for example, rectangular or trapezoidal shapes.

In the illustrated embodiment, the inferior cutting guide flange 382' defines a substantially flat/planar superior surface 386', and the superior cutting guide flange 384' similarly defines a substantially flat/planar inferior surface 388'. In one embodiment, the planar superior surface 386' defined by the inferior cutting guide flange 382' is generally tangent with the diameter of the lateral pin receiving opening 320b', and is also arranged substantially co-planar with the superior surface 150' defined by the reference bench 104 of the datum block 100 (FIG. 22). The planar inferior surface 388' of the superior cutting guide flange 384' is arranged substantially co-planar with the inferior surface 346 defined by the superior cutting guide flange 316' extending medially from the base plate 310'. Additionally, the planar superior surface 386' of the inferior cutting guide flange 382' is aligned substantially parallel with and offset from the planar inferior surface 388' of the superior cutting guide flange 384' to thereby form the lateral cutting guide or channel 380'. As should be appreciated, the lateral cutting guide 380' preferably defines a channel width equal to the channel width of the medial cutting guide 348', each being sized in relatively close tolerance with the cutting blade thickness of an oscillating or reciprocating saw (or another cutting device) to form smooth and accurate horizontal resection cuts in the proximal tibia 12.

As should be appreciated, the eminence stylus 300' may be used in the same manner as described above with regard to the eminence stylus 300 to form the horizontal medial resection cut $C_{HM}$, the vertical medial resection cut $C_{VM}$, and the vertical lateral resection cut $C_{VL}$ (FIGS. 20A-20C). However, the eminence stylus 300' may also be used to form a horizontal lateral resection cut $C_{HL}$ (shown as a dashed line in FIG. 20C) to complete the lateral resection of the proximal tibia 12. Specifically, with the graduated tibial pin 390 inserted into the lateral pin receiving opening 320b' and anchored to the proximal tibia 12, an oscillating or reciprocating saw (or another cutting device) may be inserted into and displaced along the horizontal lateral cutting guide 380' defined between the inferior cutting guide flange 382' and the superior cutting guide flange 384' to thereby form the horizontal lateral resection cut $C_{HL}$. As indicated above, the graduated tibial pin 390 serves as a guard or stop to control the depth of the horizontal resection cut and to prevent overcutting or notching of the tibial eminence 14 which might otherwise compromise the strength and integrity of the tibial eminence 14. After formation of the final resection cut, the eminences stylus 300' may be removed from the datum block 100. As should be appreciated, the design of the eminence stylus 300' allows for the formation of all necessary resection cuts to complete medial and lateral resection of the proximal tibia 12.

D. Graduated Tibial Pin

Referring to FIG. 23, shown therein is a graduated tibial pin 390 according to one form of the present invention for use in association with the eminence stylus 300 or the eminence stylus 300'. As indicated above, the graduated tibial pin 390 provides further stabilization and support to the eminence stylus 300, 300' to prevent unintended/unintentional movement of the eminence stylus 300 relative to the proximal tibia 12 (and the datum block 100), and also serves as a guard or stop during formation of the tibial resection cuts to control the depth of the cuts and to prevent overcutting or notching which might otherwise compromise the strength and integrity of the tibial eminence 14. In the illustrated embodiment, the graduated tibial pin 390 is configured as an elongate rod extending along a longitudinal axis L and generally including a distal-most end 390a, a distal bone engaging/anchoring portion 392, a proximal head portion 394, and a marked portion 396 including a series of markers or indicia 398 positioned generally along the proximal region of the pin 390.

In one embodiment, the pin 390 has a substantially circular outer cross section. However, other embodiments are also contemplated wherein the graduated tibial pin 390 is provided with other cross-sectional shapes. In another embodiment, the distal bone engaging/anchoring portion 392 includes a drill flute 392a or another type of cutting feature to provide the pin 390 with self-drilling/self-cutting capabilities, and a thread cutting tap 392b or another type of thread forming feature to provide the pin 390 with self-tapping capabilities. The threads of the tap 392b also serve to anchor the pin 390 in bone tissue to prevent the pin 390 from pulling out of the bone. However, it should be understood that in other embodiments, the pin 390 may be provided with other types of anchor elements to retain the pin 390 in bone tissue, and need not necessarily include self-drilling/self-cutting/self-cutting capabilities. In the illustrated embodiment, the proximal head portion 394 is configured for coupling with a driver or another tool/instrument capable of exerting a rotational force or torque onto the pin 390 to drive the pin 390 into bone tissue. In one embodiment, the proximal head portion 394 is provided with one or more flattened or truncated regions 394a to facilitate the application of a rotational force or torque onto the proximal head 394. However, other configurations are also contemplated including, for example, providing the proximal head 394 with a hexagonal configuration for mating engagement with a hex-driver. In one embodiment, the series of markers or indicia 398 along the marked portion 396 comprise a series of bands or lines having varying widths and/or a varying number of lines per band. However, other embodiments are also contemplated wherein the markers or indicia 398 may comprise numbers, letters, symbols, colors, or other readily identifiable indicia.

Figure 25C:
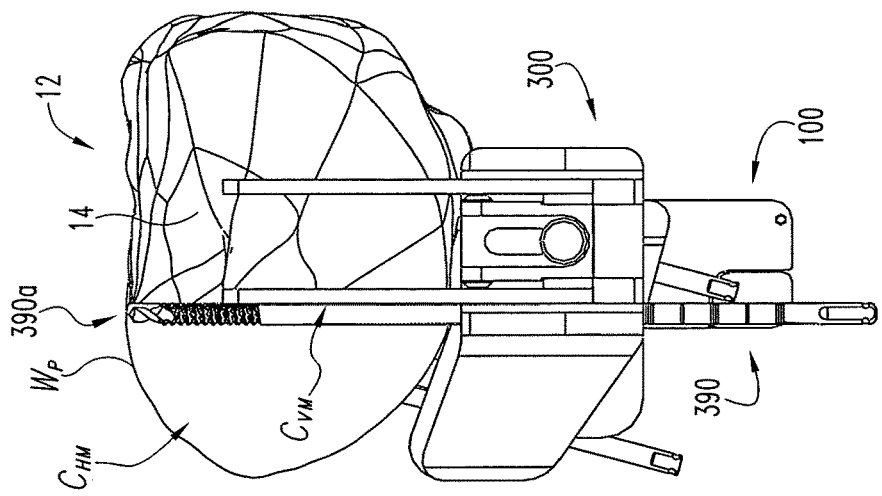
FIG. 25C illustrates a superior view of FIG. 24C.
Figure 25B:
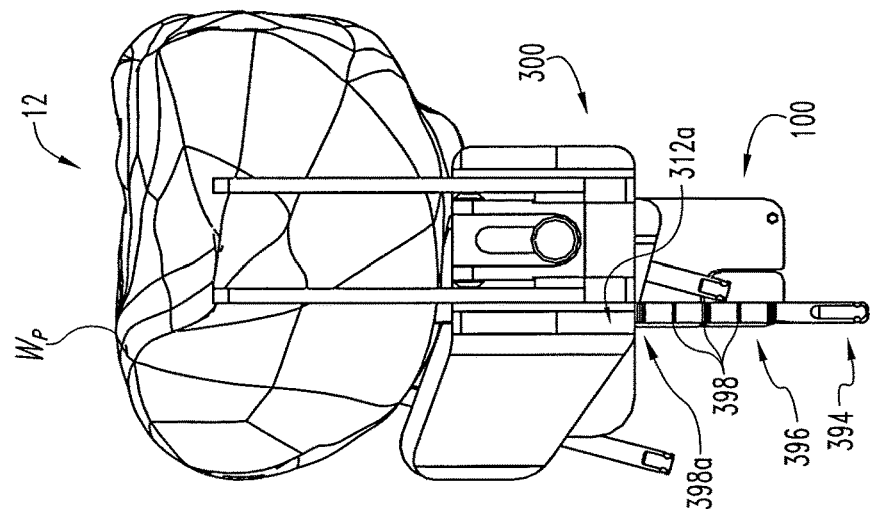
FIG. 25B illustrates a superior view of FIG. 24B.
Figure 25A:
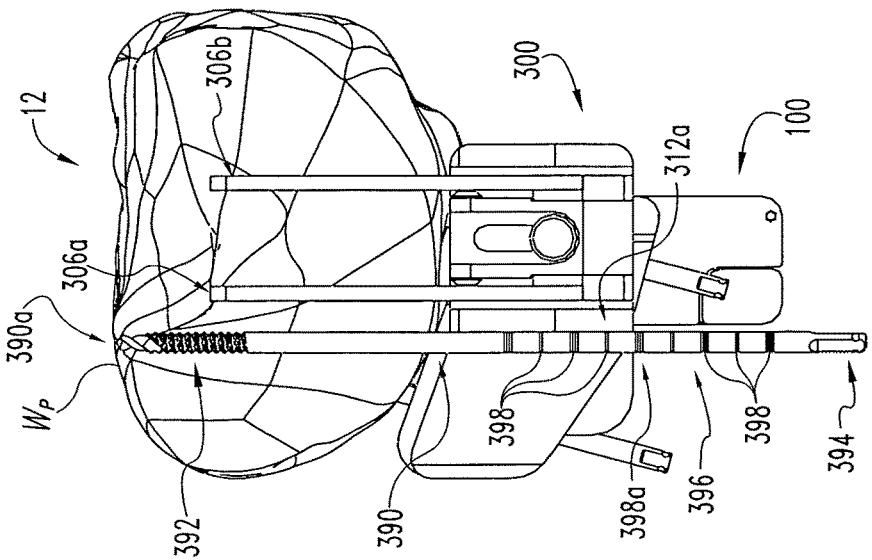
FIG. 25A illustrates a superior view of FIG. 24A.

Referring now to FIGS. 24A-24C and 25A-25C, shown therein is the graduated tibial pin 390 in relation to the proximal tibia 12 and the eminence stylus 300. As shown in FIGS. 24A and 25A, once the eminence stylus 300 is adjusted to a desired position and orientation relative to the proximal tibia 12 and locked to the datum block 100, the graduated tibial pin 390 is positioned atop the proximal tibia 12 and adjacent the medial flange 312a of the eminence stylus 300, with the longitudinal axis L of the pin 300 in general alignment with the indicator members 306a, 306b and substantially perpendicular or normal to the mechanical axis 13 of the tibia. The anterior-posterior position of the graduated tibial pin 390 is then adjusted until the distal-most end 390a of the pin 390 is positioned slightly anterior to the posterior surface of the proximal tibia 12. The position of the distal-most end 390a of the pin 390 relative to the posterior surface of the proximal tibia 12 can be determined visually or manually by tactile touch. In this position/orientation of the pin 90, an observation/notation is made as to which of the markers or indicia 398 along the marked portion 396 of the pin 390 is aligned with a particular reference location, which in the illustrated embodiment comprises the anterior end surface or edge defined by the medial flange 312a on the eminence stylus 300. However, other reference locations are also contemplated. As shown in FIGS. 24A and 25A, the indicia 398a is generally aligned with the anterior end surface of the medial flange 312a.

Referring to FIGS. 24B and 25B, the graduated tibial pin 390 is then inserted into the pin-receiving opening 320a in the eminence stylus 300 and is driven into the proximal tibia 12 until the noted indicia 398a is generally aligned with the anterior end surface of the medial flange 312a. In this position, the graduated tibial pin 390 will be fully engaged/anchored within the proximal tibia 12 with the distal-most end 390a of the pin positioned slightly anterior to the posterior surface of the proximal tibia 12. As should be appreciated, in this position, the graduated tibial pin 390 provides maximum protection against overcutting of the horizontal and vertical resection cuts, particularly along the posterior region of the proximal tibia, the likes of which might otherwise result in weakening of the remaining portion of the tibial eminence 14 and/or tibial condyles and potential fracturing of the same. However, the above-discussed procedure for inserting the graduated tibial pin 390 into the proximal tibia 12 ensures that the distal-most end 390a of the pin does not penetrate or puncture through the posterior surface of the proximal tibia 12, thereby avoiding potential damage or trauma to soft tissue structures residing behind the posterior cortex which might otherwise be damaged by the distal-most end 390a of the pin 390 protruding through the posterior cortical wall. Accordingly, by controlling the insertion depth of the pin 390 into the proximal tibia 12, the position of the distal-most end 390a of the pin 390 relative to the posterior cortical wall can be correspondingly controlled, thereby minimizing the risks associated with over-insertion of the pin 30 (i.e., puncturing the posterior cortical wall and potentially damaging adjacent soft tissue structures) and under-insertion of the pin 30 (i.e., leaving the posterior region of the proximal tibia 12 unprotected against overcutting of the horizontal and vertical resection cuts and potentially compromising the structural integrity of the unresected bone via posterior tibial notching).

Referring to FIGS. 24C and 25C, illustrated therein is the proximal tibia 12 subsequent to formation of the horizontal and vertical medial resection cuts $C_{HM}$, $C_{VM}$ and removal of the medially resected bone fragment. As discussed above and as shown in FIGS. 24C and 25C, the above-discussed procedure for inserting the graduated tibial pin 390 into the proximal tibia 12 ensures that the distal-most end 390a of the pin 390 is positioned proximately adjacent the posterior cortical wall $W_P$ but does not penetrate or puncture through the posterior cortical wall $W_P$, while at the same time providing maximum protection against overcutting of the horizontal and vertical medial resection cuts $C_{HM}$, $C_{VM}$. Although the above-discussed procedure for controlling the insertion depth of the graduated tibial pin 390 has been illustrated and described in association with medial resection of the proximal tibia 12, it should be understood that the insertion procedure can likewise be used in association with lateral resection of the proximal tibia 12.

E. Lateral Cut Guide

Figure 26:
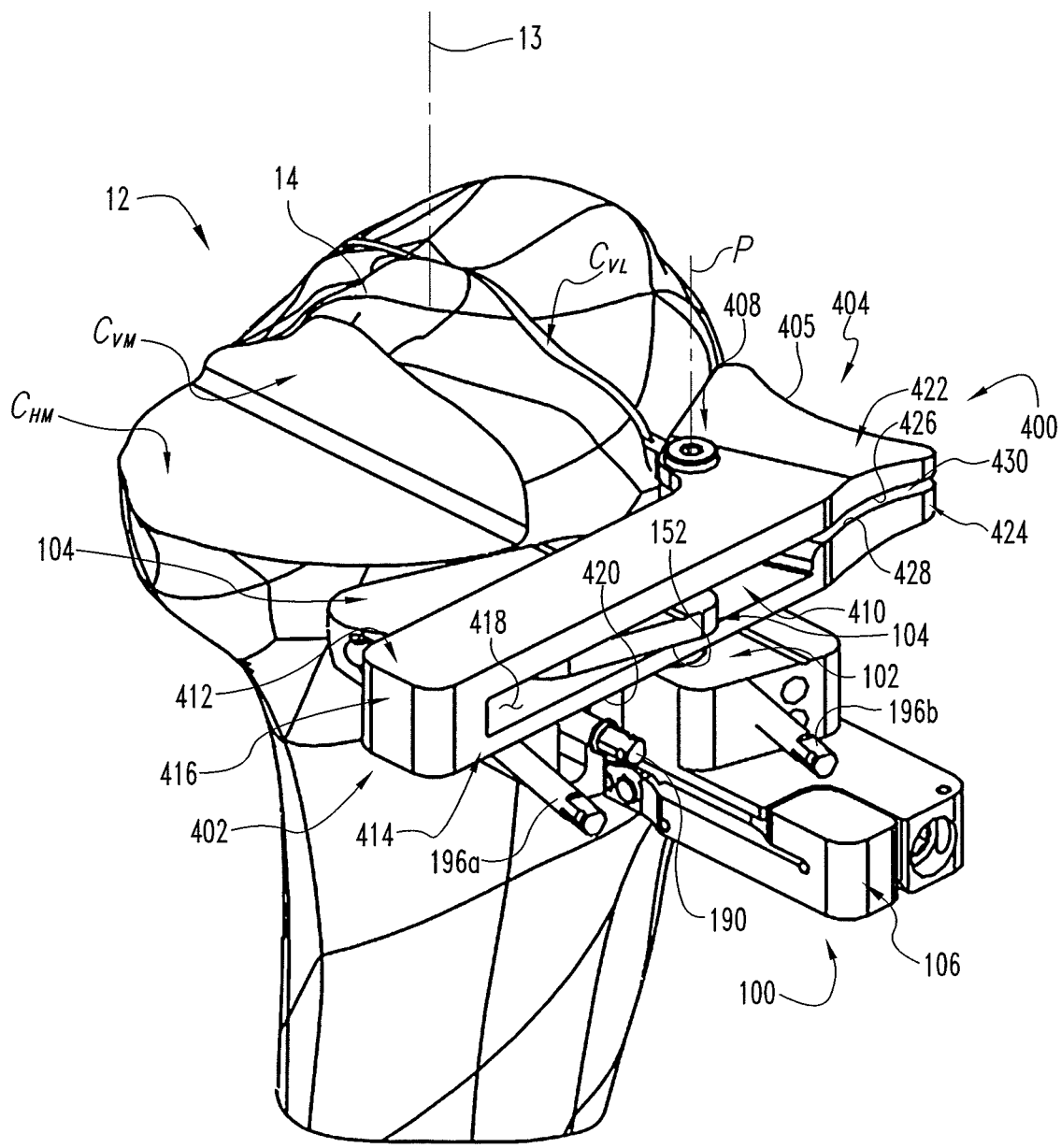
FIG. 26 illustrates a lateral cut guide according to one form of the invention, as shown attached to the datum block of FIG. 5.

Referring to FIG. 26, shown therein is a lateral cut guide 400 according to one form of the present invention, as attached to the datum block 100 in relation to the proximal tibia 12. As should be appreciated, the lateral cut guide 400 is attached to the datum block 100 via the locking or pinch force mechanism 106 of the datum block 100, details of which have been set forth above. Although the lateral cut guide 400 is shown attached to and used in association with the datum block 100, it should be understood that the lateral cut guide 400 may also be attached to and used in association with the recut block 600 (discussed below) or other devices or instruments.

Figure 29A:
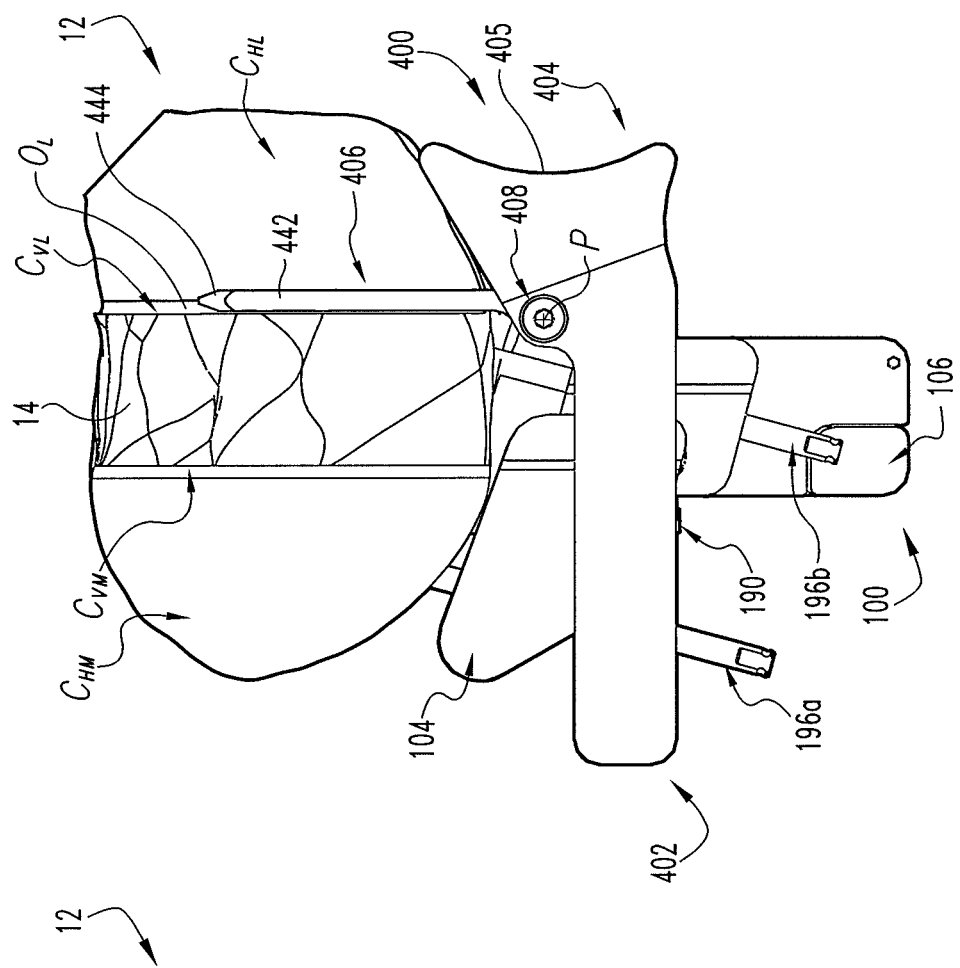
FIG. 29A illustrates a superior view of FIG. 26.

As will be discussed in greater detail below, the lateral cut guide 400 includes guide or capture features that serve to guide an oscillating or reciprocating saw (or another type of cutting instrument) along a cutting plane to form a horizontal lateral resection cut $C_{HL}$ (FIG. 29B) in the proximal tibia 12. As discussed above, the eminence stylus 300 may be used to form a horizontal medial resection cut $C_{HM}$, a vertical medial resection cut $C_{VM}$, and a vertical lateral resection cut $C_{VL}$ (FIGS. 26 and 29A). Upon removal of the eminence stylus 300 from the datum block 100 and attachment of the lateral cut guide 400 to the datum block 100, the lateral cut guide 400 may be used to form the horizontal lateral resection cut $C_{HL}$ (FIG. 29B) to complete the lateral resection of the proximal tibia 12. As also discussed above, the embodiment of the eminence stylus 300' may alternatively be used to form each of the resection cuts to perform complete medial and lateral resection of the proximal tibia 12 via a single instrument (the eminence stylus 300') attached to the datum block 100.

Referring collectively to FIGS. 27, 28A and 28B, in the illustrated embodiment, the lateral cut guide 400 generally includes a medial mounting portion 402, a lateral guide portion 404, and a tibial pin 406 attached to the mounting portion 402. In one embodiment, the mounting portion 402 and the guide portion 404 are formed unitarily with one another to define a single-piece monolithic structure. However, in other embodiments, the mounting portion 402 and the guide portion 404 may be formed separately from one another and integrated together to form a multi-piece assembly. Additionally, in the illustrated embodiment, the tibial pin 406 is pivotally attached to the mounting portion 402 via a pivot pin or hinge 408 to allow articulating pivotal movement of the tibia pin 406 relative to the mounting portion 402 about the pivot axis P (FIG. 28A). However, other embodiments are also contemplated wherein the tibial pin 406 is fixedly attached to the mounting portion 402, or fixedly, pivotally and/or translatably attached to other portions of the lateral cut guide 400.

In one embodiment, medial mounting portion 402 has a plate-like configuration and defines an elongate slot or channel 410 extending therethrough in an anterior-posterior direction to thereby define a superior mounting plate portion 412 and an inferior mount plate portion 414, each having a substantially flat/planar configuration and a generally rectangular shape. The superior and inferior mounting plates 412, 414 are connected to one another via a medial wall 416. The inferior mounting plate 412 defines substantially flat/planar superior and inferior surfaces 418, 420, respectively. Additionally, the superior mounting plate 414 may also define substantially flat/planar superior and inferior surfaces. In one embodiment, the lateral guiding portion 404 includes superior and inferior guide plate portions or wings 422, 424 that extend from the superior and inferior mounting plates 412, 414, respectively. The superior guide plate 422 defines a substantially flat/planar inferior surface 426, and the inferior guide plate 422 defines a substantially flat/planar superior surface 428. The planar inferior surface 426 of the superior guide plate 422 is aligned substantially parallel with and offset from the planar superior surface 428 of the inferior guide plate 422 to thereby form a lateral cutting guide or channel 430 defined between the adjacent inferior and superior planar surfaces 426, 428. As should be appreciated, the lateral cutting guide channel 430 preferably defines a channel width sized in relatively close tolerance with the cutting blade thickness of an oscillating or reciprocating saw (or another cutting device) to form a smooth and accurate horizontal lateral resection cut along the proximal tibia 12. The superior surface of the superior guide plate 422 and the inferior surface of the inferior guide plate 424 are tapered in a medial-lateral direction to provide increased visualization of the proximal tibia 12 during a cutting operation, but may alternatively be provided as flat/planar surfaces. Additionally, the lateral end portion of the cutting guide portion 404 preferably defines a concave region 405 that may serve as a soft tissue retractor to facilitate creation of space for entry of the sawblade into the lateral cutting guide channel 430 to avoid damage or trauma to the soft tissue.

The tibial pin 406 includes a base or mounting ring portion 440 (FIG. 28B) configured for pivotal attachment to the mounting portion 402 (via passing the pivot pin 408 through an opening in the mounting ring 440), and also includes an elongate pin portion 442 extending from the mounting ring portion 440. Since the tibial pin 406 is positively connected to the mounting portion 402, the risk of losing, misplacing or dropping the tibial pin 406 is removed. In one embodiment, the elongate pin portion 442 has a generally circular or square-shaped outer cross section that is sized substantially equal to the outer cross section of the graduated tibial pin 390. As will be discussed below, the elongate pin portion 442 is positionable in the lateral pin opening $O_L$ (FIG. 29A) previously formed in the proximal tibia 12 by the graduated tibial pin 390 that was inserted into the lateral pin-receiving opening 320b in the eminence stylus 300 and driven into the proximal tibia 12 prior to formation of the vertical lateral resection cut $C_{VL}$ (FIG. 20C). The elongate pin portion 442 is also provided with a tapered distal end 444 to facilitate insertion into the previously-formed lateral pin opening $O_L$.

Figure 29B:
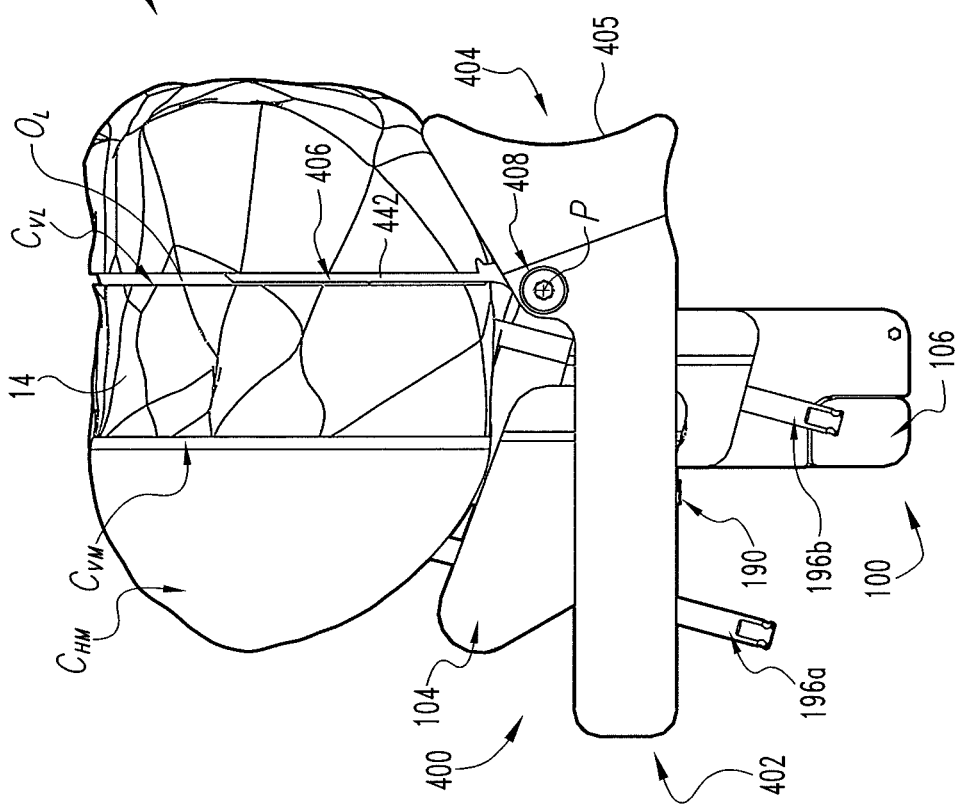
FIG. 29B illustrates a superior view of FIG. 26 following lateral resection of the proximal tibia and removal of the lateral bone fragment.

Referring collectively to FIGS. 26, 29A and 29B, shown therein is the lateral cut guide 400 attached to the datum block 100 in relation to the proximal tibia 12. Having described the structural features associated with the lateral cut guide 400, some of the operational characteristics associated with the lateral cut guide 400 according to various embodiments of the present invention will now be discussed.

The lateral cut guide 400 is initially engaged to the datum block 100 by inserting the elongate pin portion 442 of the tibial pin 406 into the previously-formed lateral pin opening $O_L$, and by positioning the inferior mounting plate 414 into the slot 154 defined between the reference bench 104 and the main body 102 of the datum block 100. In this initial engagement arrangement, since the tibial pin 406 is pivotally attached to the medial mounting portion 402 and since the elongate pin portion 42 is able to slide along the lateral pin opening $O_L$, the position and orientation of the lateral cut guide 400 may be easily adjusted relative to the datum block 100. Additionally, pivotal attachment of the tibial pin 406 to the mounting portion 402 allows the pin 406 to be adjustably maneuvered to conform to varying pin opening orientations and/or tibial bone shapes. However, it should be noted that the particular position and orientation of the lateral cut guide 400 (other than the inferior-superior position) on the datum block is not critical to the success/accuracy of the cutting operation. Additionally, as shown in FIGS. 29A and 29B, the shape/contour of the posterior region of the lateral guiding portion 404 is preferably configured to abut the anterior outer surface of the proximal tibia 12 when the lateral cut guide 400 is engaged to the datum block 100 to provide additional stabilization and support to the lateral cut guide 400 during a cutting operation to provide increased cutting accuracy. Additionally, as indicated above, the concave region 405 of the lateral guiding portion 404 is intended to serve as a soft tissue retractor to facilitate creation of space for entry of the sawblade into the lateral cutting guide channel 430 to avoid damage or trauma to the soft tissue.

Once the lateral cut guide 400 is positioned and oriented relative to the datum block 100, the pinch force mechanism 106 may be actuated to lock the lateral cut guide 400 in a position relative to the datum block 100. Actuation of the pinch force mechanism 106 correspondingly compresses the planar superior surface 418 of the inferior mounting plate 414 against the planar inferior surface 152 of the reference bench 104 to thereby capture/lock the lateral cut guide 400 to the datum block 100, which in turn retains the lateral cut guide 400 in a fixed position and orientation relative to the datum block 100. As should be appreciated, locking of the lateral cut guide 400 maintains the lateral cutting guide 430 in a fixed inferior-superior position relative to the datum block 100, which in turn provides increased cutting accuracy.

After the lateral cut guide 400 is properly aligned and positioned relate to the datum block 100 and engaged with the datum block 100 via actuation of the pinch force mechanism 106, an oscillating or reciprocating saw (or another cutting device) is inserted into and displaced along the lateral cutting guide 430 to form the horizontal lateral resection cut $C_{HL}$ in the proximal tibia 12 (FIG. 29B) to complete the lateral resection of the proximal tibia 12. As should be appreciated, positioning of the elongate pin portion 442 of the tibial pin 406 into the previously-formed lateral pin opening $O_L$ serves as a guard or stop to control the depth of the horizontal lateral resection cut $C_{HL}$ and to prevent overcutting or notching of the tibial eminence 14 which might otherwise compromise the strength and integrity of the tibial eminence 14. In addition to serving as a protective guard or stop, the tibial pin 406 also provides additional stabilization and support to the lateral cut guide 400 during the cutting operation to provide increased cutting accuracy. Although the illustrated embodiment of the elongate pin portion 442 does not extend across the entire anterior-posterior dimension of the proximal tibia 12, it should be understood that other lengths of the elongate pin portion 442 may be used that extend across substantially the entire anterior-posterior dimension of the proximal tibia 12.

As should be appreciated, the combined use of the eminence stylus 300 (described above) and the lateral cut guide 400 allows for the formation of all necessary resection cuts to complete medial and lateral resection of the proximal tibia 12. As should also be appreciated, since the eminence stylus 300 and the lateral cut guide 400 are both locked to the datum block 100 in the same manner using a constant reference plane (i.e., by compressing a planar mounting plate against the inferior surface 152 of the reference bench 104), it is possible to ensure that the horizontal medial resection cut $C_{HM}$ (formed via use of the eminence stylus 300) and the horizontal lateral resection cut $C_{HL}$ (formed via use of the lateral cut guide 400) are co-planar to one another.

F. Saw Capture Block

Referring to FIG. 30, shown therein is a saw capture block 500 according to one form of the present invention, as attached to the datum block 100. However, it should be understood that the saw capture block 500 may also be attached to and used in association with the recut block 600 (discussed below) or other devices or instruments. In the illustrated embodiment, the saw capture block 500 is attached to the datum block 100 via the locking or pinch force mechanism 106 of the datum block 100, details of which have been set forth above. Additionally, although not illustrated in FIG. 30, it should be understood that the datum block 100 is initially attached to the proximal tibia 12 via the provisional attachment pin 190 and/or the terminal attachment pins 196 (FIG. 10) prior to attachment of the saw capture block 500 to the datum block 100.

The saw capture block 500 includes features that cooperate with features of the datum block 100 (or the recut block 600) to provide a saw capture or cutting guide channel that guides an oscillating or reciprocating saw (or another type of cutting instrument) along a cutting plane to form a horizontal resection cut in the proximal tibia 12. In one embodiment, the saw capture block 500 may be used in association with the datum block 100 (or the recut block 600) to perform a total or full resection of the proximal tibia 12 (i.e., the complete removal of a proximal region of the proximal tibia 12 to form a planar resection cut extending entirely across the proximal tibia 12). For example, the saw capture block 500 may be particularly beneficial for use in association with CR (cruciate retaining) and PS (posteriorly stabilized) arthroplasty procedures, although use of the saw capture block 500 in association with other knee arthroplasty procedures is also contemplated.

Referring collectively to FIGS. 31, 32A and 32B, in the illustrated embodiment, the saw capture block 500 is a single-piece monolithic structure including an inferior mounting portion 502 and a superior guide portion 504. In one embodiment, the inferior mounting portion 502 and the superior guide portion 504 are formed as a single piece to provide the saw capture block 500 as a single-piece monolithic structure. However, in other embodiments, the inferior mounting portion 502 and the superior guide portion 504 may be formed separately from one another and integrated together to form a multi-piece saw capture block assembly.

In one embodiment, the inferior mounting portion 502 has a plate-like configuration defining substantially flat/planar superior and inferior surfaces 510, 512, respectively. Additionally, in a further embodiment, the inferior mounting plate 502 has a trapezoidal shape and defines an outer perimeter sized and configured for general alignment with an outer perimeter of the superior portion 110 of the main body 102 of the datum block 100 (FIG. 6E). As should be appreciated, alignment of the anterior region of the inferior mounting plate 502 with the anterior region of the superior portion 110 aids in proper alignment and positioning of the saw capture block 500 relative to the datum block 100 (FIG. 30). However, other shapes and configurations of the inferior mounting plate 502 are also contemplated. Additionally, an alignment mark or line indicia 514 extending in a medial-lateral direction is defined along the superior surface 510 of the inferior mounting plate 502 (FIG. 31) which may be aligned with the anterior edge of the reference bench 104 of the datum block 100 to further aid in alignment and positioning of the saw capture block 500 relative to the datum block 100 (FIG. 30).

The inferior surface 512 of the inferior mounting plate 502 may be provided with a recess or indentation 516 (FIG. 32B) that is generally alignable with the gripper member 180 associated with the pinch force mechanism 106 of the datum block 100 when the saw capture block 500 is positioned in general alignment on the datum block 100. As should be appreciated, the recess 514 has an inner cross section that is sized somewhat larger than the outer cross section of the gripper member 180 such that when the pinch force mechanism 106 is partially actuated (i.e., positioning of the lever arm 160 at a pivotal location between the fully locked and fully unlocked positions), the gripper member 180 is partially received within the recess 516, but is not compressed tightly against the mounting plate portion 502. In this operational configuration the saw capture block 500 is provisionally retained on the datum block 100, but is not securely locked to the datum block 100. The saw capture block 500 is therefore permitted to rotate relative to the datum block 100 and translate relative to the datum block 100 within the confines of the recess 516 (i.e., translation is limited by abutment of the gripper member 180 against the inner parametrical surfaces 518 of the recess 516). Use of this provisionally retained configuration may be particularly beneficial during a cutting operation to allow a wider range of motion of the cutting instrument relative to the proximal tibia 12, while still maintaining engagement of the saw capture block 500 with the datum block 100. However, at any point in the cutting operation, the saw capture block 500 may be locked in position on the datum block 100 by fully actuating the pinch force mechanism 106 to lock the saw capture block 500 in position.

Additionally, it should be understood that in other embodiments, engagement between the saw capture block 500 and the datum block 100 is fully constrained and does not allow any relative movement between the saw capture block 500 and the datum block 100. As should be appreciated, compressed engagement of the gripper member 180 against the mounting plate portion 502 via full actuation of the pinch force mechanism 106, in combination with engagement between three mating surface pairs defined between the saw capture block 500 and the datum block 100, fully and securely constrains the saw capture block 500 in position relative to the datum block 100. As shown in FIG. 33C, in the illustrated embodiment, the three mating surface pairs between the saw capture block 500 and the datum block 100 include mating engagement of the inferior planar surface defined by mounting plate 502 of the saw capture block 500 with the superior planar surface defined by the superior portion 110 of the datum block 100, mating engagement of the superior planar surface defined by the mounting plate 502 of the saw capture block 500 with the inferior planar surface defined by the reference table 104 of the datum block 100, and mating engagement of the medially-facing edge of the mounting leg 522 (FIG. 32A) of the saw capture block 500 with the laterally-facing edge defined by the reference table 104 of the datum block 100. However, other mating surface pairs defined between the saw capture block 500 and the datum block 100 are also contemplated.

In one embodiment, the superior capture or guide portion 504 has a guide plate portion 520 and a mounting leg portion 522 extending between and interconnecting the guide plate portion 520 and the inferior mounting plate 502. The guide plate portion 520 defines substantially flat/planar superior and inferior surfaces 524, 526, respectively, and has a generally trapezoidal shape defining an outer perimeter sized and configured for general alignment with an outer perimeter of the reference bench 104 of the datum block 100 (FIG. 6E). Alignment of the outer perimeter of the guide plate 520 with the outer perimeter of the reference bench 104 may further aid in proper alignment and positioning of the saw capture block 500 relative to the datum block 100 (FIG. 30). However, other shapes and configurations of the guide plate 520 are also contemplated. The mounting leg 522 includes a spacer portion 522*a* attached to the inferior surface 526 of the guide plate 520, and a base portion 522*b* that is attached to the superior surface 510 of the inferior mounting plate 502. A guide slot 528 is defined between the inferior surface 526 of the guide plate 520 and a superior surface of the mounting leg base portion 522*b*.

Referring collectively to FIGS. 30 and 33A-33C, shown therein is the saw capture block 500 attached to the datum block 100. Having described the structural features associated with the saw capture block 500, some of the operational characteristics associated with the saw capture block 500 according to various embodiments of the present invention will now be discussed.

The saw capture block 500 is initially engaged to the datum block 100 by positioning the inferior mounting plate 502 into the slot or channel 154 defined between the reference bench 104 and the main body 102 of the datum block 100. In this initial engagement arrangement, the position and orientation of the saw capture block 500 may be adjusted relative to the datum block 100. As indicated above, various features associated with the saw capture block 500 may be used to properly position and orient the saw capture block 500 relative to the datum block 100. For example, alignment of the mark or line indicia 514 defined along the superior surface 510 of the inferior mounting plate 502 with the anterior edge of the bench 104 may aid in properly positioning and orienting the saw capture block 500 relative to the datum block 100. Additionally, alignment of the anterior perimeter of the inferior mounting plate 502 with the anterior region of the superior portion 110 of the datum block 100, as well as alignment of the outer perimeter of the guide plate 520 with the outer perimeter of the reference bench 104, may further aid in properly positioning and orienting the saw capture block 500 relative to the datum block 100. Once the saw capture block 500 is properly positioned and oriented relative to the datum block 100, the pinch force mechanism 106 may be actuated to lock the saw capture block 500 in a position relative to the datum block 100. Actuation of the pinch force mechanism 106 correspondingly compresses the planar superior surface 510 of the inferior mounting plate 502 against the planar inferior surface 152 of the reference bench 104 to thereby capture/lock the saw capture block 500 to the datum block 100, which in turn retains the saw capture block 500 in a fixed position and orientation relative to the datum block 100. As should be appreciated, locking of the saw capture block 500 in a fixed inferior-superior position relative to the datum block 100 provides a fixed saw capture guide between the saw capture block 500 and the datum block 100.

As shown most clearly in FIGS. 30 and 33C, when the saw capture block 500 is engaged with the datum block 100, the planar inferior surface 526 of the guide plate 520 is aligned substantially parallel with and offset from the planar superior surface 150 of the reference bench 104 to thereby form a medial-lateral cutting guide or channel 530 defined between the adjacent inferior and superior planar surfaces 526, 150. As should be appreciated, the medial-lateral cutting guide 530 preferably defines a channel width sized in relatively close tolerance with the cutting blade thickness of an oscillating or reciprocating saw (or another cutting device) to form a smooth and accurate resection cut along the proximal tibia 12. Additionally, the width of the guide slot 528 defined between the inferior surface 526 of the guide plate 520 and the superior surface of the mounting leg base portion 522b (FIG. 32A) is equal to the distance separating the inferior and superior planar surfaces 526, 150 to thereby provide the medial-lateral cutting guide 530 with a uniform channel width entirely along the medial-lateral dimension of the saw capture block 500.

After the saw capture block 500 is properly aligned and positioned relate to the datum block 100 and engaged with the datum block 100 via actuation of the pinch force mechanism 106, an oscillating or reciprocating saw (or another cutting device) is inserted into and displaced along the medial-lateral cutting guide 530 to fully resect the proximal tibia 12. As shown in FIG. 33C, the cutting guide 530 is open and unrestricted along the anterior and posterior sides and along the medial side of the cutting guide 530. Additionally, as shown in FIG. 33A, the cutting guide 530 is open and unrestricted along the posterior region along the lateral side of the cutting guide 530, with the anterior region along the lateral side being blocked by the mounting leg 522 of the saw capture block 500. However, the open posterior region along the lateral side of the cutting guide 530 provides a pathway for the saw to fully resect the proximal tibia 12. However, as indicated above, if additional access to the proximal tibia 12 is required, the pinch force mechanism 106 may be positioned in a partially actuated position wherein the saw capture block 500 is provisionally retained on the datum block 100, but is permitted to rotate and translate (within a confined range) relative to the datum block 100 to allow for a wider range of motion of the saw or cutting instrument. Following resection of the proximal tibia 12, the saw capture block 500 may be removed from the datum block 100 to allow for engagement of other devices and instruments to the datum block 100.

G. Recut Block

Figure 35:
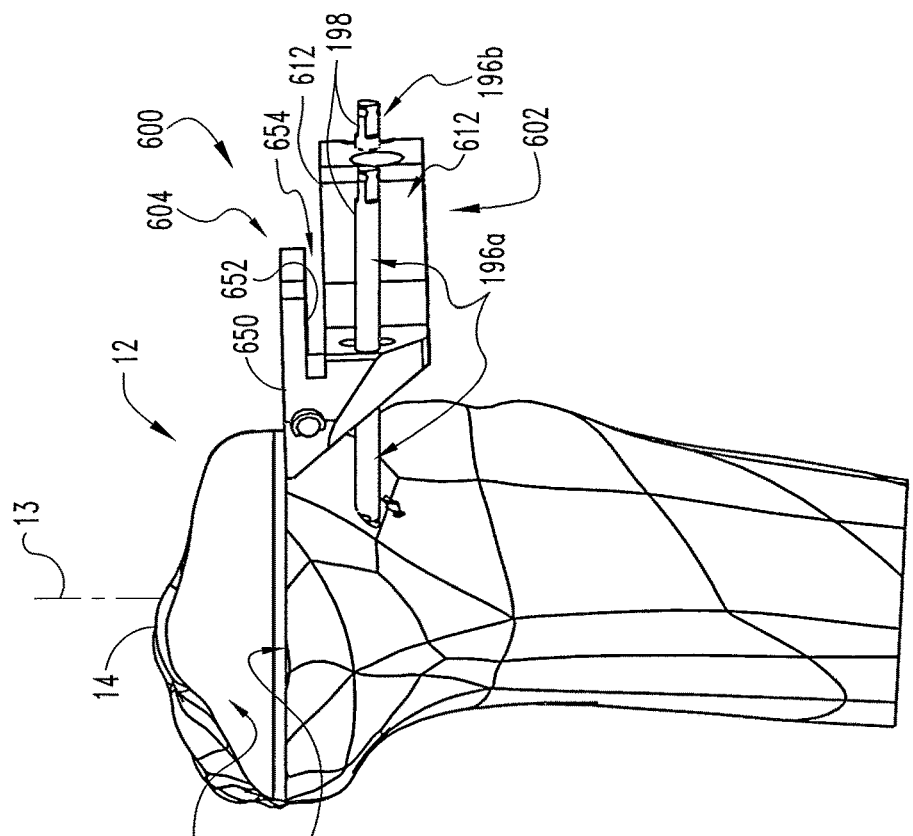
FIG. 35 illustrates a side view of FIG. 34.
Figure 34:
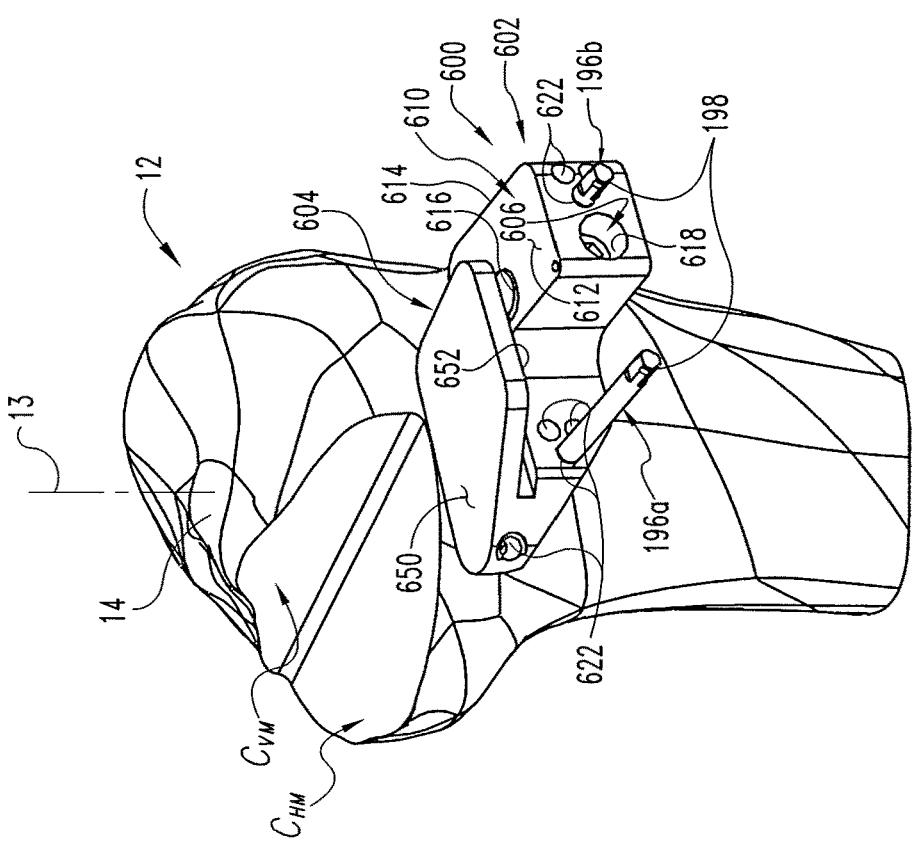
FIG. 34 illustrates a recut block according to one form of the invention, as shown terminally attached to the proximal tibia by terminal attachment pins in relation to the medially resected proximal tibia.
Figure 39A:
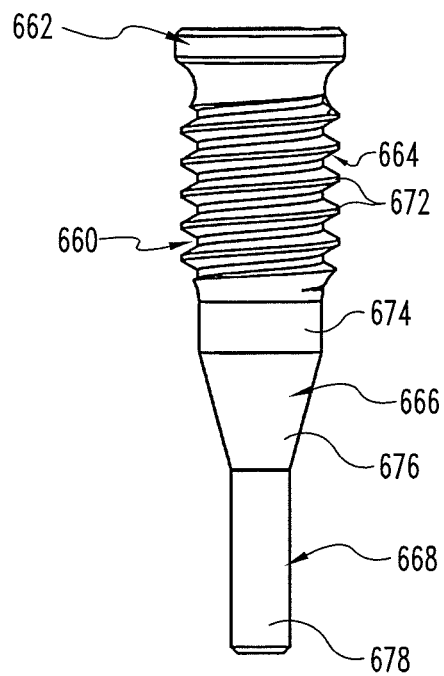
FIG. 39A illustrates one embodiment of a threaded member used in association with the locking mechanism of FIGS. 38A and 38B.
Figure 39C:
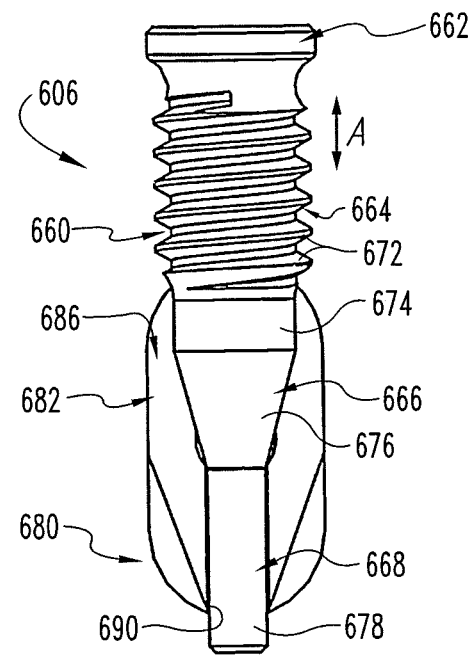
FIG. 39C illustrates a bottom view the locking mechanism of FIGS. 38A and 38B.
Figure 39B:
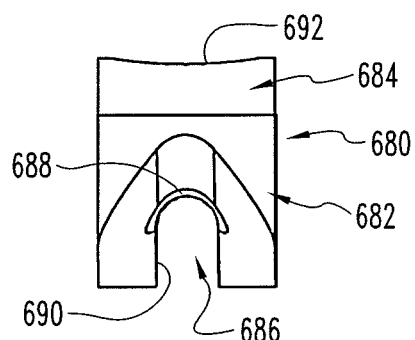
FIG. 39B illustrates one embodiment of a gripper member used in association with the locking mechanism of FIGS. 38A and 38B.
Figure 39D:
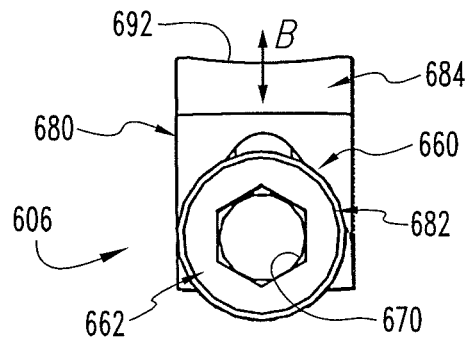
FIG. 39D illustrates an end view the locking mechanism of FIGS. 38A and 38B.

Referring to FIGS. 34 and 35, shown therein is a recut block 600 according to one form of the present invention, as shown in relation to the proximal tibia 12. In the illustrated embodiment, the recut block 600 is attached to the proximal tibia 12 using the terminal attachment pins 196a, 196b previously used to attach the datum block 100 to the proximal tibia 12 (FIG. 10), the details of which will be set forth below. Accordingly, the position and orientation of the recut block 600 relative to the proximal tibia 12 is advantageously based on the same points of reference used to set the position and orientation of the datum block 100. However, other techniques and devices for attaching the recut block 600 to the proximal tibia 12 are also contemplated.

As will also be set forth in greater detail below, the reference/resection plane (i.e., the planar superior surface of the reference bench) defined by the recut block 600 may be varied/angled relative to the horizontal reference/resection plane defined by the datum block 100. Accordingly, should a change to the horizontal medial resection cut $C_{HM}$ and/or the horizontal lateral resection cut $C_{HL}$ be desired (i.e., a different posterior slope angle, varus-valgus angle, or both), the datum block 100 can be removed from the terminal attachment pins 196a, 196b and replaced with a recut block 600 defining the appropriate reference/resection plane to recut one or both of the horizontal resection cuts to the desired angle. As should be appreciated, a kit or set containing multiple recut blocks 600 defining different reference/resection planes (i.e., different posterior slope angles, varus-valgus angles, or both) can be provided to accommodate intra-operative changes/alterations to the horizontal medial resection cut $C_{HM}$ and/or the horizontal lateral resection cut $C_{HL}$.

Similar to the datum block 100, the recut block 600 is used as a fundamental instrument to provide a neutral/reference tibial foundation to which other devices or instruments may be engaged to and referenced from. Additionally, the recut block 600 is designed to be substantially interchangeable with the datum block 100. Accordingly, any device or instrument that is used in association with the datum block 100 may also be used in association with the recut block 600. Therefore, if the datum block 100 is replaced with the recut block 600 to recut one or both of the horizontal resection cuts at a different angle, subsequent steps and techniques associated with the knee arthroplasty procedure which utilize other devices and instruments can be performed using the recut block 600.

As indicated above, the recut block 600 is attached to the proximal tibia 12 using the terminal attachment pins 196a, 196b previously used to attach the datum block 100 to the proximal tibia 12 (FIGS. 34 and 35). Notably, it is not necessary to remove the terminal attachment pins 196a, 196b from the proximal tibia 12 to detach the datum block 100 from the proximal tibia 12 or to attach the recut block 600 to the proximal tibia 12. Instead, referring back to FIG. 10, the provisional attachment pin 190 is removed from the proximal tibia 12 and the datum block 100 is simply slipped off of the terminal attachment pins 196a, 196b. Since the recut block 600 is interchangeable with the datum block 100, the recut block 600 is slipped over the proximal heads 198 of the terminal attachment pins 196a, 196b (via the same pin-receiving openings that were used to attach the datum block 100 to the proximal tibia 12) and displaced along the pins 196a, 196b until positioned adjacent the proximal tibia 12. Since the recut block 600 is attached to the proximal tibia 12 using the identical points of reference (the pins 196a, 196b) used to attach the datum block 100 to the proximal tibia 12, the position and orientation of the recut block 600 relative to the proximal tibia 12 can be set to match that of the datum block 100 (with the exception of defining a different horizontal reference/resection plane). If desired, a third terminal attachment pin may be inserted into another of the pin-receiving openings and driven into the proximal tibia at an oblique angle relative to the pins 196a, 196b to retain the recut block 600 in position adjacent the proximal tibia 12. Alternatively, a third terminal attachment pin having an enlarged head (like the provisional attachment pin 190) may be inserted into another of the pin-receiving openings and driven into the proximal tibia 12 until the enlarged head is compressed against the recut block 600 to retain the recut block 600 in position adjacent the proximal tibia 12.

Referring collectively to FIGS. 36A-36F, shown therein are further details associated with the recut block 600. The recut block 600 generally includes a main body 602 configured for attachment to the proximal tibia 12, a reference bench or table 604 extending from the main body 602 and configured for removable attachment of various devices/instruments to the recut block 600, and a locking mechanism 606 associated with the main body 602 and configured to removably lock the other devices/instruments to the recut block 600. In the illustrated embodiment, the recut block 600 is not configured to engage and support an extramedullary alignment rod (such as the alignment rod 108 associated with the datum block 100). However, in other embodiments, the recut block 600 may be configured to engage and support an extramedullary alignment rod or other types of alignment devices.

In the illustrated embodiment, the main body 602 of the recut block 600 is configured as a single-piece monolithic connection block 610 defining a substantially flat/planar superior surface 612, a laterally facing surface 614, a cavity 616 (FIG. 34) extending through the connection block 610 from the planar superior surface 612 in a superior-inferior direction, and a passage 618 (FIG. 36C) extending through the connection block 610 in an anterior-posterior direction and transversely intersecting and positioned in communication with the cavity 616. As will be discussed in greater detail below, the cavity 616 and the passage 618 serve to house components of the locking mechanism 606. The connection block 610 has a generally rectangular shape configured similar to that of the superior portion 110 of the datum block 100. However, other shapes and configuration are also contemplated.

The connection block 610 further defines a plurality of pin-receiving openings 622 extending therethrough generally in an anterior-posterior direction that are sized and configured for receipt of the terminal attachment pins 196a, 196b anchored to the proximal tibia 12 or for receipt of additional attachment pins. As should be appreciated, the pin-receiving openings 622 defined in the recut block 600 have the same relative position and orientation as the pin-receiving openings 122 defined in the datum block 100 such the recut block 600 may be interchanged with the datum block 100 using the same terminal attachment pins 196a, 196b previously used to attach the datum block 100 to the proximal tibia 12.

As indicated above, the recut block 600 includes a reference bench or table 604 extending from the main body 602 and configured for removable attachment of various devices/instruments to the recut block 600. In the illustrated embodiment, the reference bench 604 is formed unitarily with the main body 602 to define a single-piece monolithic structure. However, in other embodiments, the reference bench 604 may be formed separately from the main body 602 and coupled thereto to define an integrated multi-piece structure. As shown in FIG. 36E, the reference bench 604 has a non-rectangular trapezoidal shape configured similar to that of the reference bench 104 of the datum block 100, defining a narrowing or tapered width extending away from the main body 602 in a medial-lateral direction. However, other suitable shapes and configurations of the reference bench 604 are also contemplated as falling within the scope of the present invention.

As shown in FIGS. 36A-36C, the reference bench 604 defines a substantially flat/planar superior surface 650 and a substantially flat/planar inferior surface 652, with the planar superior and inferior surfaces 650, 652 preferably arranged generally parallel with one another, although non-parallel arrangements of the planar superior and inferior surfaces 650, 652 are also contemplated. Additionally, the planar inferior surface 652 of the reference bench 604 is positioned opposite the planar superior surface 612 of the connection block 610 to thereby define a space or gap 654 therebetween sized and configured for receipt of plate-like portions of other devices and instruments to be connected with the recut block 600, details of which will be set forth below. In the illustrated embodiment, the planar inferior surface 652 of the reference bench 604 is preferably arranged generally parallel with the planar superior surface 612 of the connection block 610, although non-parallel arrangements of the opposing superior and inferior surfaces are also contemplated. Additionally, although not specifically illustrated in the drawing figures, the reference bench 604 may be provided with a groove or indicia extending along the planar superior surface 650 in an anterior-posterior direction to provide a visual indication or marker corresponding to the location of the vertical medial resection $C_{VM}$ of the proximal tibia 12 (i.e., similar to the groove/indicia 156 defined along the reference table 104 of the datum block 100).

As discussed above and as illustrated in FIG. 36A-36C, the recut block 600 defines a reference/resection plane P extending along the planar superior surface 650 of the reference bench 604. As also discussed above, the reference/resection plane P of the recut block 600 may be varied/angled relative to the horizontal reference/resection plane of the datum block 100 (as defined along the planar superior surface 150 of the reference bench 104). Accordingly, should a change to the previously cut horizontal medial resection cut $C_{HM}$ and/or the horizontal lateral resection cut $C_{HL}$ (formed using the datum block 100) be desired (i.e., having a different posterior slope angle, varus-valgus angle, or both), the datum block 100 can be replaced with a recut block 600 defining the appropriate reference/resection plane P to recut one or both of the horizontal resection cuts to the desired angle. For example, as illustrated in FIG. 36A, the planar superior surface 650 of the recut block 600 may be provided with a reference/resection plane P having a posterior slope angle β that varies from the horizontal reference/resection plane of the datum block 100 within the range of +β to −β. Additionally, as illustrated in FIG. 36B, the planar superior surface 650 of the recut block 600 may be provided with a reference/resection plane P having a varus-valgus angle θ that varies from the horizontal reference/resection plane of the datum block 100 within the range of +θ to −θ. In other embodiments, the planar superior surface 650 of the recut block 600 may be provided with a reference/resection plane P having a varus-valgus angle θ and a posterior slope angle β that both vary from the horizontal reference/resection plane of the datum block 100.

As also discussed above, a kit or set containing multiple recut blocks 600 defining varying reference/resection planes can be provided to accommodate intra-operative changes/alterations to the horizontal medial resection cut $C_{HM}$ and/or the horizontal lateral resection cut $C_{HL}$. For example, the kit may include multiple recut blocks 600 defining reference/resection planes P having a posterior slope angle β of +2°, +4°, +6°, −2°, −4°, −6°, etc., or any other posterior slope angle β that may be used in a knee arthroplasty procedure to form a horizontal medial resection cut $C_{HM}$ and/or the horizontal lateral resection cut CH having a desired posterior slope angle. The kit may also include multiple recut blocks 600 defining reference/resection planes P having a varus-valgus angle θ of +2°, +4°, +6°, −2°, −4°, −6°, etc., or any other varus-valgus angle θ that may be used in a knee arthroplasty procedure to form a horizontal medial resection cut $C_{HM}$ and/or the horizontal lateral resection cut CH having a desired varus-valgus angle. Additionally, providing the kit with further recut blocks 600 defining reference/resection planes P exhibiting other desired features and characteristics is also contemplated as falling within the scope of the present invention.

As indicated above, the recut block 600 includes a locking mechanism 606 associated with the main body 602 that is configured to removably lock various devices/instruments to the reference bench 604. Referring to FIGS. 37A and 37B, illustrated therein are unlocked and locked configurations of the recut block 600, respectively. Additionally, referring to FIGS. 38A and 38B, illustrated therein are corresponding unlocked and locked configurations of the locking mechanism 606, respectively.

In the illustrated embodiment, the locking mechanism 606 generally includes a threaded member or bolt-type actuator member 660 threadedly engaged within the anterior-posterior passage 618 in the connection block 610 of the recut block 600, and a gripper member or actuated member 680 positioned within the inferior-superior cavity 616 in the connection block 610 and movably engaged with the threaded member 660, the details of which will be set forth below. The main body 602 of the recut block 600 includes additional elements and features associated with the locking mechanism 606. For example, the connection block 610 defines a circular opening 624 (FIG. 36F) extending through a posterior wall of the connection block 610 in communication and general alignment with the anterior-posterior passage 618 that is sized to receive a distal end portion of the threaded member 660 therein to thereby act as a bearing surface to provide additional support and stability to the locking mechanism 606. Additionally, a retaining pin 626 (FIGS. 36D and 36E) at least partially extends into the anterior-posterior passage 618 to prevent the threaded member 660 from backing entirely out of the passage 618. A visualization slot or window 628 (FIG. 36D) also extends through the inferior surface of the connection block 610 in communication with the passage 618 to provide direct visualization of and access to the components of the locking mechanism 606.

Referring specifically to FIGS. 37A/37B and 38A/38B, illustrated therein are unlocked and locked configurations of the recut block 600 and the locking mechanism 606. In the unlocked configuration shown in FIGS. 37A/38A, a plate-like portion of a device/instrument may be positioned within the space or gap 654 defined between the planar inferior surface 652 of the reference bench 604 and the planar superior surface 612 of the connection block 610. The recut block 600 and the locking mechanism may then be transitioned from the unlocked configuration illustrated in FIGS. 37A/38A to the locked configuration illustrated in FIGS. 37B/38B via actuation of the locking mechanism 606. Actuation of the locking mechanism 606 is accomplished by rotating the threaded member 660 to threadingly displace the threaded member 660 along the anterior-posterior passage 618 in the direction of arrow A, which in turn displaces the gripper member 680 in an inferior-superior direction along the cavity 616 in the direction of arrow B, and correspondingly engages the gripper member 680 against the plate-like portion of the device/instrument positioned within the gap 654 and compresses the plate-like portion against the planar inferior surface 652 of the reference bench 604 to thereby retain the device/instrument in a fixed position and orientation relative to the recut block 600.

Referring to FIGS. 39A-39D, shown therein are further details regarding the locking mechanism 606 including the threaded member 660 and the gripper member 680. In the illustrated embodiment, the threaded member 660 generally includes a proximal head portion 662, a threaded portion 664, a tapered portion 666 and a distal stem portion 668. The proximal head portion 662 includes one or more drive features 670 that facilitates receipt of a rotational force or torque onto the threaded member 660. In one embodiment, the drive feature 670 comprises a hexagonal-shaped recess formed in the proximal head portion 662. However, other types and configurations of suitable drive features are also contemplated. The threaded portion 664 includes external threads 672 that are configured for threading engagement with internal threads (not shown) formed along the anterior-posterior passage 618 in the connection block 610. Additionally, the threaded portion 664 may be provided with an unthreaded portion 674 adjacent the location where the threaded member 660 engages the gripper member 680 to avoid interference between the external threads 672 and the gripper member 680. The tapered portion 666 defines a tapered outer surface 676 that is inwardly tapered in a proximal-distal direction. The distal stem portion 668 includes a substantially smooth cylindrical-shaped shaft that extends through a guide channel formed in the gripper member 680 and which is positioned within the circular opening 624 (FIG. 36F) extending through the posterior wall of the connection block 610 to thereby act as a bearing to provide additional support and stability to the locking mechanism 606, and particularly to the threaded member 660. Although a particular configuration of the threaded member 660 has been illustrated and described herein, other configurations of actuator members, including non-threaded actuator members, are also contemplated for use in association with the locking mechanism 606.

In the illustrated embodiment, the gripper member 680 generally includes an inferior bearing portion 682 and a superior gripping portion 684. The inferior bearing portion 682 includes a channel 686 extending therethrough in an anterior-posterior direction and which is sized to receive the tapered portion 666 and the distal stem portion 668 of the threaded member therein. The channel 686 is partially bound by one or more bearing surfaces 688 configured for sliding engagement with the tapered surface 676 of the threaded member 660. The bearing surfaces 688 may be angled to define an inward taper extending in an anterior-to-posterior direction. However, non-tapered bearing surfaces 688 are also contemplated. Additionally the channel 686 narrows adjacent the posterior end of the gripper member 680 to define a guide slot 690 sized to received the distal stem portion 668 of the threaded member 660 therein to stabilize engagement between the gripper member 680 and the threaded member 660 and to allow the threaded member 660 to be linearly displaced along the channel 686. The superior gripping portion 684 of the gripper member may be provided with a generally circular outer cross section sized for guiding displacement within the inferior-superior cavity 616 in the connection block 610 generally along the arrow B. The gripping portion 684 also includes a superior gripping surface 692 configured for compressed engagement against plate-like portions of devices/instruments positioned within the gap 654 defined between the reference bench 604 and the connection block 610 of the recut block 600.

As indicated above, the recut block 600 and the locking mechanism are transitioned from the unlocked configuration illustrated in FIGS. 37A/38A to the locked configuration illustrated in FIGS. 37B/38B via actuation of the locking mechanism 606 which is accomplished by rotating the threaded member 660 using a hex driver or another type of driver instrument to threadingly displace the threaded member 600 along a threaded portion of the passage 618 in the connection block 610 in the direction of arrow A. Displacement of the threaded member 660 in the direction of arrow B slidably displaces the tapered surface 676 of the threaded member 660 along the bearing surfaces 688 of the gripper member 680, which in turn displaces the gripper member 680 along the cavity 616 in the connection block 610 in the direction of arrow B. As should be appreciated, the sliding interaction between the tapered surface 676 and the bearing surfaces 688 converts linear displacement of the threaded member 660 in the direction of arrow A into liner displacement of the gripper member 680 in the direction of arrow B. Liner displacement of the gripper member 680 in the direction of arrow B in turn compresses a plate-like portion of device/instruments positioned within the gap 654 defined between the reference bench 604 and the connection block 610 against the planar inferior surface 652 of the reference bench 604 to thereby lock/retain the device/instrument in a fixed position and orientation relative to the recut block 600.

As should be appreciated, the compression or clamping force exerted by the gripper member 680 onto the plate-like portion of the device/instrument positioned within the space 654 is controlled by incremental threading insertion or retraction of the threaded member 660 into and out of the passage 618 in the connection block 610. Although the illustrated embodiment of the locking mechanism 606 uses a hex driver (not shown) to drive the threaded member 660 into and out of the passage 618. However, other embodiments are also contemplated wherein the threaded member 660 may be rotated via a thumb wheel or a T-shaped handle that may be incorporated into the bolt-type actuator 660 to avoid the need for a separate driver instrument. Although a particular type and configuration of the locking mechanism 606 has been illustrated and described herein for use in association with the recut block 600, it should be understood that other types and configurations of locking mechanisms or other compression structures/devices are also contemplated for use in association with the present invention in addition to or in lieu of the locking mechanism 606 including, for example, the pinch force mechanism 106 illustrated and described above with regard to the datum block 100.

H. Tibia Size Gauge

Figure 40:
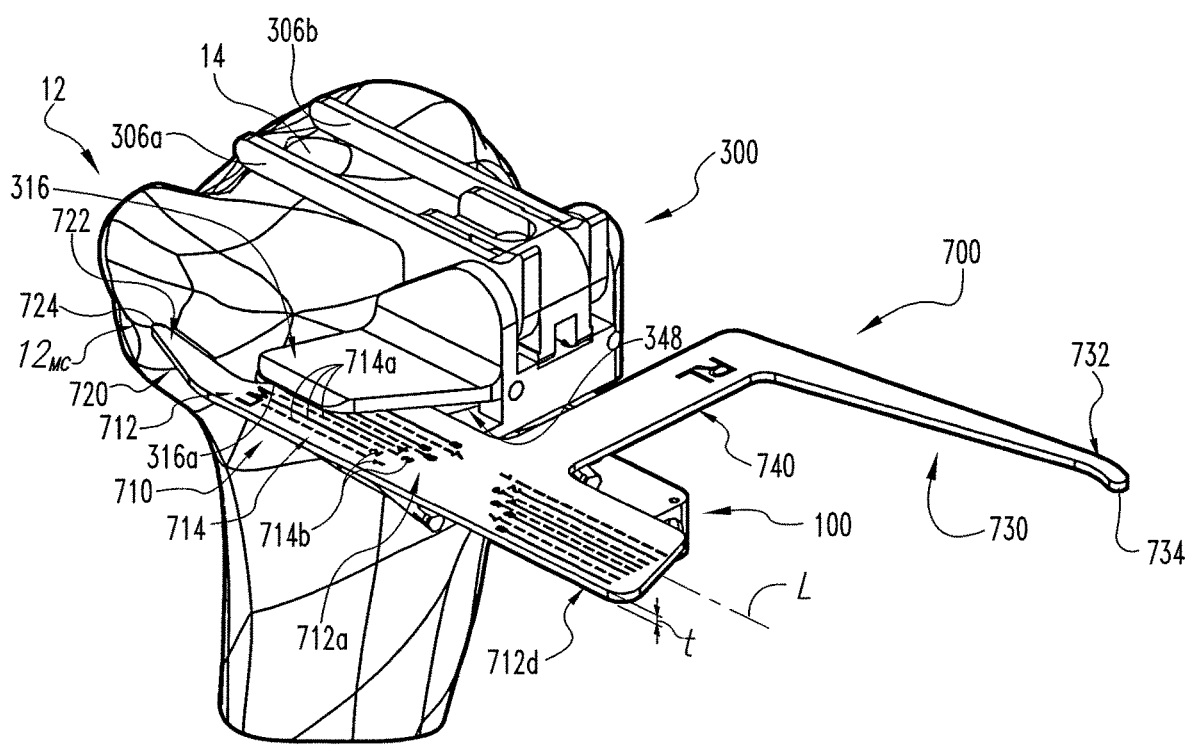
FIG. 40 illustrates a tibia size gauge according to one form of the invention, as shown relative to the datum block of FIG. 5 and the eminence stylus of FIG. 17A, all shown in relation to the proximal tibia.

Referring to FIG. 40, shown therein is a tibia size gauge 700 according to one form of the present invention. As will be discussed in greater detail below, the tibia size gauge 700 may be used to reference/measure medial and/or lateral aspects of the proximal tibia 12 along the tibial cortex (e.g., at the medial tibial cortex 12$_{MC}$ and/or at the lateral tibial cortex 12$_{LC}$) at the proposed/intended level of the horizontal resection cuts. In this manner, the tibial baseplate implant I may be appropriately sized, and the resulting position of the tibial baseplate implant I (FIGS. 41C and 42C) may be appropriately centered on the resected proximal tibia 12 in a medial-lateral direction to minimize underhang/overhang of the baseplate implant I relative to the outer periphery of the resected proximal tibia 12, which in turn results in a stronger and more secure and stable engagement of the tibial implant on the proximal tibia.

As shown in FIG. 40, the tibia size gauge 700 is used in association with the eminence stylus 300 attached to the datum block 100, with the datum block 100 in turn pinned to the proximal tibia 12, the details of which have been illustrated and described above. However, it should be appreciated that the tibia size gauge 700 may also be used in association other devices and instruments, including but not limited to the eminence stylus 300' illustrated and described above.

The tibia size gauge 700 generally includes a scaled reference or datum plate 710 having a length extending generally along a longitudinal axis L, a first reference arm 720 extending axially from the scaled datum plate 710 and including a distal pointer 722 defining a distal end surface 724 configured for engagement with an outer surface of the proximal tibia 12, and a second reference arm 730 transversely offset from the scaled plate 710 by a transversely extending spacer arm 740 and including a distal pointer 732 defining a distal end surface 734 configured for engagement with an outer surface of the proximal tibia 12. In the illustrated embodiment, the tibia size gauge 700 is provided as a single-piece, substantially flat/planar plate having a generally uniform and relatively thin plate thickness t (FIG. 40). However, other embodiments are also contemplated wherein the tibia size gauge 700 may take on other configurations and/or may be provided as multiple pieces or elements that are interconnected with one another to form the tibia size gauge 700. Additionally, in the illustrated embodiment, the first and second reference arms 720, 730 are oriented at an oblique angle relative to the longitudinal axis L of the scaled datum plate 710. However, in other embodiments, the first and second reference arms 720, 730 may be arranged generally parallel with the longitudinal axis L. Further, in the illustrated embodiment, the distal end surfaces 724, 734 of the distal pointers 722, 732 are curved or rounded to provide secure and stable engagement with an outer surface of the proximal tibia 12. However, in other embodiments, the distal end surfaces 724, 734 may be provided with a pointed configuration or a blunt configuration.

In the illustrated embodiment, the scaled datum plate 710 is configured for positioning within the medial cutting guide 348 which, as discussed above in association with FIGS. 20A-20C, is used to form the medial horizontal resection cut $C_{HM}$ in the proximal tibia 12. As also discussed above, the medial cutting guide 348 is formed between the planar inferior surface 346 defined by the cutting guide flange 316 on the eminence stylus 300 and the planar superior surface 150 defined by the reference bench 104 on the datum block 100. As should be appreciated, the superior-inferior location of the medial cutting guide 348 (which is dictated by the inferior-superior location of the datum block 100 on the proximal tibia 12) determines the level/location of the horizontal medial and lateral resection cuts $C_{HM}$, $C_{HL}$, and the internal-external angular orientation of the eminence stylus 300 dictates the internal-external angular orientation of the medial cutting guide 348 and the resulting orientation of the vertical medial and lateral resection cuts $C_{VM}$, $C_{VL}$. The thickness t (FIG. 40) of the scaled datum plate 710 is preferably sized in relatively close tolerance with the width of the medial cutting guide 348 to maintain the scaled datum plate 710 in a substantially co-planar relationship with the cutting plane defined by the medial cutting guide 348 (i.e., the plane along which the horizontal medial resection cut $C_{HM}$ is formed).

As shown in FIG. 40, the scaled datum plate 710 includes one or more measurement scales 712 that each include scaled measurement indicia 714 which serve to provide a visual indication as to the distances being measured by the tibia size gauge 700. In the illustrated embodiment, the scaled measurement indicia 714 include a series of parallel lines 714*a* and a series of numbers 714*b* corresponding to the parallel lines 714*a*. In one embodiment, the parallel lines 714*a* alternate between solid lines and dashed lines to aid in identifying/distinguishing which of the parallel lines 714*a* is aligned with a predetermined measurement reference feature, which is the present embodiment is the straight/planar medial edge 316a defined by the cutting guide flange 316 of the eminence stylus 300. However, it should be understood that other measurement reference features are also contemplated. In a further embodiment, adjacent pairs of the numbers 714b are offset from one another in an axial direction (along the longitudinal axis) to aid in identifying/distinguishing which of the numbers 714b is associated with the line that is aligned with the predetermined reference feature. Although one particular embodiment of the scaled measurement indicia 714 has been illustrated and described herein, it should be understood that other suitable types and configurations of measurement indicia are also contemplated for use in association with the tibia size gauge 700.

Additionally, in the illustrated embodiment, the tibia size gauge 700 is configured to provide measurements of medial and lateral aspects of the proximal tibia 12 (e.g., the medial tibial cortex $12_{MC}$ and the lateral tibial cortex $12_{LC}$; FIGS. 40/41A/42A). Additionally, the tibia size gauge 700 is configured to provide measurements associated with both the left knee and the right knee (i.e., the tibia size gauge 700 is configured to be ambidextrous). Accordingly, the illustrated embodiment of the scaled datum plate 710 is provided with four measurement scales 712a, 712b, 712c and 712d (FIGS. 41A/42A), with the measurement scale 712a associated with measurements of medial aspects of the left knee ("LM"), the measurement scale 712b associated with measurements of lateral aspects of the left knee ("LL"), the measurement scale 712c associated with measurements of medial aspects of the right knee ("RM"), and the measurement scale 712d associated with measurements of lateral aspects of the right knee ("RL"). However, it should be understood that the tibia size gauge 700 may be provided with any number of measurement scales 712 including, for example, a single measurement scale.

Referring now to FIGS. 41A-41C, shown there is a technique according to one form of the invention for using the tibia size gauge 700 to reference/measure medial aspects of the proximal tibia 12 along the tibial cortex (e.g., at the medial tibial cortex $12_{MC}$) at the proposed/intended level of the horizontal resection cuts to determine the appropriate size of the tibial baseplate implant I to be installed on the proximal tibia 12 subsequent to resection. As indicated above, the datum block 100 is initially pinned to the proximal tibia 12, and the eminence stylus 300 is provisionally engaged to the datum block 100 and centered/aligned in relation to the proximal tibia 12 or other anatomic structures using the indicator members 306a, 306b, the alignment rod 18 and/or other alignment structures or alignment techniques. Once the eminence stylus 300 is centered/aligned in relation to the proximal tibia 12, the eminence stylus 300 is locked in position on the datum block 100 via the pinch lock mechanism 106. As indicated above, the proposed/intended level of the horizontal resection cuts corresponds to the cutting plane defined by the medial cutting guide 348.

The scaled datum plate 710 of the tibia size gauge 700 is positioned within the medial cutting guide 348, with the measurement scale 712a associated with measurements of medial aspects of the left knee (i.e., "LM") positioned adjacent the straight/planar medial edge 316a of the cutting guide flange 316. The distal end surface 724 of the pointer 722 is then positioned in contact with the medial tibial cortex $12_{MC}$ on the medial side of the proximal tibia 12. While maintaining contact between the distal end surface 724 of the pointer 722 and the medial tibial cortex $12_{MC}$, the user observes which of the parallel lines 714a on the measurement scale 712 is aligned with the straight/planar medial edge 316a of the cutting guide flange 316. The tibia size gauge 700 may require a certain degree of internal-external rotation within the medial cutting guide 348 to obtain alignment between the appropriate line 714a and the straight/planar medial edge 316a. In the illustrated embodiment, the number 714b corresponding to the line 714a aligned with the medial edge 316a relates to the size of the tibial baseplate implant I (FIGS. 41B and 41C) that would properly fit on the proximal tibia 12 subsequent to resection. As shown in FIG. 41A, the indicated size measurement is "4", which corresponds to a size 4 tibial baseplate implant I to be installed on the proximal tibia 12 (FIG. 41B). As shown in FIG. 41C, subsequent to resection and finishing of the proximal tibia 12, the appropriately sized baseplate implant I is installed on the resected proximal tibia 12 wherein underhang/overhang of the baseplate implant I on the resected proximal tibia 12 is minimized relative to the peripheral outer boundary of the proximal tibia 12 due to the above-described implant sizing technique.

As discussed above, in the illustrated embodiment, the numbers 714b on the measurement scale 712 relate to the size of the tibial baseplate implant I. However, in other embodiments, the numbers 714b on the measurement scale 712 may relate to the actual linear distance between the medial tibial cortex $12_{MC}$ in contact with the distal end surface 724 of the pointer 722 and the centerline of the eminence stylus 300 (i.e., the centerline between the indicator members 306a, 306b), which preferably corresponds to the anatomic medial-lateral center of the proximal tibia 12 at the proposed/intended level of resection.

In the measurement technique illustrated in FIGS. 41A-41C and described above, the appropriate size of the tibial baseplate implant I to be installed on the proximal tibia 12 is determined by referencing/measuring medial aspects of the proximal tibia 12 along the tibial cortex (e.g., at medial tibial cortex $12_{MC}$) at the proposed/intended level of resection. However, referring to FIGS. 42A-42C, it should be understood that the appropriate size of the tibial baseplate implant I may also be determined by referencing/measuring lateral aspects of the proximal tibia 12 along the tibial cortex (e.g., at the lateral tibial cortex $12_{LC}$) at the proposed/intended level of resection. Specifically, once the eminence stylus 300 is centered/aligned in relation to the proximal tibia 12, the scaled datum plate 710 of the tibia size gauge 700 is initially positioned within the medial cutting guide 348 with the second reference arm 730 extending along the lateral side of the proximal tibia 12 and with the distal end surface 734 of the pointer 732 positioned in contact with the lateral tibial cortex $12_{LC}$. Additionally, the measurement scale 712b associated with measurements of lateral aspects of the left knee (i.e, "LL") is positioned adjacent the straight/planar medial edge 316a of the cutting guide flange 316. While maintaining contact between the distal end surface 734 of the pointer 732 and the lateral tibial cortex $12_{LC}$, the user observes which of the parallel lines 714a on the measurement scale 712 is aligned with the straight/planar medial edge 316a of the cutting guide flange 316. As shown in FIG. 42A, the indicated size measurement is once again indicated as "4", which corresponds to the size of the tibial baseplate implant I to be installed on the proximal tibia 12 (FIGS. 42B/42C) following resection to minimize underhang/overhang of the baseplate implant I relative to the peripheral outer boundary of the proximal tibia 12 at the level of resection.

As indicated above, the tibia size gauge 700 is configured to be ambidextrous, meaning the tibia size gauge 700 may also be used to reference/measure medial and lateral aspects of the proximal tibia 12 associated with both the left knee and the right knee. As should be appreciated, when referencing/measuring medial and lateral aspects of the proximal tibia 12 associated with the left knee, the measurement scales 712a, 712b associated with measurements of medial aspects of the left knee (i.e, "LM") and lateral aspects of the left knee (i.e., "LL") are used. However, when referencing/measuring medial and lateral aspects of the proximal tibia 12 associated the right knee, the measurement scales 712c, 712d associated with measurements of medial aspects of the right knee (i.e., "RM") and lateral aspects of the right knee (i.e., "RL") are used.

Referring collectively to FIGS. 41A-41C and FIGS. 42A-42C, a technique according to a further form of the invention may be used to ensure that the appropriately sized tibial baseplate implant I is centered on the resected proximal tibia 12 (i.e., the centerline C of the implant I is aligned with the true anatomic center of the proximal tibia 12 at the proposed/intended level of the horizontal resection cuts). Notably, determining the true anatomic center of the proximal tibia 12 at the proposed/intended level of resection may be used to ensure the correct position of the horizontal resection cuts (i.e., that the resection cuts are centered relative to the true anatomic center of the proximal tibia 12), which in turn dictates the ultimate position of the baseplate implant I on the proximal tibia 12. The disclosed centering technique references/measures both medial and lateral aspects of the proximal tibia 12 along the tibial cortex (e.g., at the medial tibial cortex $12_{MC}$ and at the lateral tibial cortex $12_{LC}$) at the proposed/intended level of resection, and uses the resulting measurements to determine the true anatomic center of the proximal tibia 12 at the proposed/intended level of resection, the details of which will be discussed below.

As discussed above and as shown in FIG. 41A, the tibia size gauge 700 is initially used to reference/measure the medial tibial cortex $12_{MC}$ at the proposed/intended level of resection by observing which of the parallel lines 714a on the measurement scale 712a is aligned with the straight/planar medial edge 316a of the cutting guide flange 316. As also discussed above and as shown in FIG. 42A, the tibia size gauge 700 may then be used to reference/measure the lateral tibial cortex $12_{LC}$ at the proposed/intended level of resection by observing which of the parallel lines 714a on the measurement scale 712b is aligned with the straight/planar medial edge 316a of the cutting guide flange 316. If the observed measurement associated with the referencing/measuring of the medial tibial cortex $12_{MC}$ is equal to the observed measurement associated with the referencing/measuring of the lateral tibial cortex $12_{LC}$, then the eminence stylus 300 is appropriately centered along the true anatomic center of the proximal tibia 12 at the proposed/intended level of resection, and the vertical resection cuts can then be made for receipt of the tibial baseplate implant I at the appropriately centered position on the resected proximal tibia 12.

However, if the observed medial and lateral measurements are not equal to one another, then the medial-lateral position and/or the orientation of the eminence stylus 300 can be correspondingly adjusted based on the observed medial and lateral measurements to more closely align the eminence stylus 300 with the true anatomic center of the proximal tibia 12 at the proposed/intended level of resection. For example, if the observed medial measurement is "3" and the observed lateral measurement is "5", then the eminence stylus 300 may be unlocked from the datum block 100 and the position of the eminence stylus 300 shifted in a lateral direction to more closely align the centerline of the eminence stylus 300 with the true anatomic center of the proximal tibia 12 at the proposed/intended level of resection. After the adjustment to the position of the eminence stylus 300 is made, further medial and lateral measurements are once again taken and compared with one another to determine if further adjustment to the position of the eminence stylus 300 is required, or whether the true anatomic center has been reached.

As should be appreciated, this iterative measurement process using the tibia size gauge 700 to reference/measure both medial and lateral aspects of the proximal tibia 12 along the tibial cortex at the proposed/intended level of resection results in more accurate centering of the eminence stylus 300 with the true anatomic center of the proximal tibia 12. As should be further appreciated, centering of the eminence stylus 300 with the true anatomic center of the proximal tibia 12 results in the formation of correctly centered/positioned resection cuts, which in turn ensures that the centerline C of the implant I is properly aligned with the anatomic center of the proximal tibia 12 at the resection level to thereby minimize underhang/overhang of the implant I relative to the peripheral outer boundary of the proximal tibia 12 (FIGS. 41C/42C).

Referring to FIGS. 43-45, shown therein is a tibia size gauge 750 according to another form of the present invention. Similar to the tibia size gauge 700 illustrated and described above, the tibia size gauge 750 may be used to reference/measure medial aspects of the proximal tibia 12 along the tibial cortex (e.g., at the medial tibial cortex $12_{MC}$) at the proposed/intended level of the horizontal resection cuts to determine the appropriate size of the tibial baseplate implant I to be installed on the resected proximal tibia 12. Additionally, the tibia size gauge 750 also includes features that serve to appropriately align/orient the resection cuts on the proximal tibia 12, which in turn results in proper alignment of the baseplate implant I on the resected proximal tibia 12 to thereby minimize underhang/overhang of the baseplate implant I on the resected proximal tibia 12. As should be appreciated, minimizing underhang/overhang of the baseplate implant I on the resected proximal tibia 12 tends to provide a stronger and more secure and stable engagement of the tibial implant on the proximal tibia 12.

As shown in FIG. 43, the tibia size gauge 750 is used in association with an eminence stylus 300" (which is a modified version of the eminence stylus 300) attached to the datum block 100, with the datum block 100 in turn pinned to the proximal tibia 12, the details of which have been illustrated and described above. In the illustrated embodiment, the tibia size gauge 750 generally includes the eminence stylus 300" which defines a scaled datum plate 760, and an indicator member 770 removably attached to the scaled datum plate 760. The indicator member 770 includes structures and features that reference/engage medial and anterior aspects of the proximal tibia 12 and, in cooperation with the scaled datum plate 760, provide a visual measurement indication as to the estimated/appropriate size of the tibial baseplate implant I to be installed on the proximal tibia 12 subsequent to resection.

As indicated above, the eminence stylus 300" is a modified version of the eminence stylus 300 illustrated and described above, and is configured virtually identical to the eminence stylus 300 with the exception of defining a scaled datum plate 760. More specifically, the eminence stylus 300" generally includes a base portion or body 302" configured for attachment to the datum block 100, a carriage 304" movably attached to the base portion 302" and configured for linear displacement along a longitudinal displacement axis L arranged in a generally anterior-posterior direction, and a pair of articulating arms or indicator members 306a'', 306b'' pivotally attached to the carriage 304'' and configured for pivotal displacement relative to the carriage 304''. Additionally, the base portion 302'' generally includes a base plate 310'', an inferior mounting flange 314'' extending from the base plate 310'' in a medial-lateral direction, and a superior cutting guide flange 316'' extending from the base plate 310'' in a medial-lateral direction and superiorly offset from the inferior mounting flange 314''. The mounting flange 314'' may be compressed against an inferior surface of the reference bench 104 via actuation of the pinch force mechanism 106 to lock the eminence stylus 300'' in a select position and orientation relative to the datum block 100. Additionally, a substantially flat/planar inferior surface defined by the cutting guide flange 316'' cooperates with a substantially flat/planar superior surface defined by the reference table 104 of the datum block 100 to thereby form a medial cutting guide or channel 348'' therebetween. It should be understood that the eminence stylus 300'' is configured substantially identical to the eminence stylus 300 and operates in a manner substantially identical to that of the eminence stylus 300, with the exception of incorporation of the features associated with the scaled datum plate 760 onto the superior surface 344'' of the cutting guide flange 316''.

As illustrated most clearly in FIGS. 45A and 45B, the scaled datum plate 760 includes a measurement scale 762 that includes scaled measurement indicia 764 which serve to provide a visual indication as to the distances being measured by the tibia size gauge 750. In the illustrated embodiment, the scaled measurement indicia 764 include a series of parallel grooves 764a cut into the superior surface 344'' of the cutting guide flange 316'' and extending in an anterior-posterior direction, and numbers 764b corresponding to the grooves 764a. In one embodiment, the grooves 764a are V-shaped and extend across the superior surface 344'' in an anterior-posterior direction. Although one particular embodiment of the scaled measurement indicia 764 has been illustrated and described herein, it should be understood that other suitable types and configurations of measurement indicia are also contemplated for use in association with the tibia size gauge 750.

In the illustrated embodiment, the indicator member 770 extends along a longitudinal axis L and generally includes an inferior flat/planar plate 772 having a generally uniform and relatively thin plate thickness t (FIG. 44A), and a superior flat/planar plate 774 offset from the inferior plate 772 to define a gap G therebetween. The superior plate 774 includes a tooth or projection 776 (FIG. 45A) extending into the gap G toward the inferior plate 772 and configured for sliding engagement within and along individual ones of the parallel grooves 764a cut into the superior surface 344'' of the cutting guide flange 316''. In the illustrated embodiment, the tooth 776 has a V-shaped profile and is sized and shaped for sliding displacement along individual ones of the parallel V-shaped grooves 764a (FIG. 45A). However, other suitable shapes and configurations of the tooth 776 and the grooves 764a are also contemplated. Additionally, the superior plate 774 is provided with a generally triangular-shaped outer profile defining an apex or arrowhead 778 at a distal end thereof. However, other suitable shapes and configurations of the superior plate 774 are also contemplated. The indicator member 770 further includes a first reference arm 780 extending axially from the inferior plate 772 and including a distal pointer 782 defining a distal end surface 784 configured for engagement with a medial aspect of the proximal tibia 12, and a second reference arm 790 which also extends axially from the inferior plate 772 and including a distal pointer 792 defining a distal end surface 794 configured for engagement with an anterior aspect of the proximal tibia 12. In the illustrated embodiment, the distal end surfaces 784, 794 of the distal pointers 782, 792 are curved or rounded to provide secure and stable engagement with the medial and anterior outer surfaces of the proximal tibia 12. However, in other embodiments, the distal end surfaces 784, 794 may be provided with a pointed configuration or a blunt configuration.

As shown in FIG. 43, the indictor member 770 is attached to the scaled datum plate 760 (which corresponds to the cutting guide flange 316'' of the datum block 300'') by positioning the inferior plate 772 into the medial cutting guide 348'' (formed between the cutting guide flange 316'' and the reference bench 104 of the datum block 100), and by positioning the V-shaped tooth 776 defined by the superior plate 774 into one of the V-shaped grooves 764a defined along the scaled datum plate 760. As should be appreciated, the superior-inferior location of the medial cutting guide 348'' determines the level/location of the resection cuts, and the inward-outward angular orientation of the eminence stylus 300'' dictates the inward-outward angular orientation of the medial cutting guide 348'' and the resulting orientation of the vertical eminence resection cut.

Referring now to FIGS. 45A and 45B, shown there is a technique according to one form of the invention for using the tibia size gauge 750 to reference medial aspects of the proximal tibia 12 along the tibial cortex (e.g., at the medial tibial cortex $12_{MC}$) at the proposed/intended level of the horizontal resection cuts to determine the appropriate position and orientation (i.e., angular alignment) of the resection cuts to be formed in the proximal tibia 12 to receive the tibial baseplate implant I. As indicated above, the datum block 100 is initially pinned to the proximal tibia 12. Based on an initial estimation of the size of the tibial baseplate implant I to be installed on the proximal tibia 12, the indictor member 770 is attached to the scaled datum plate 760 by sliding the V-shaped tooth 776 of the indicator member 770 into the appropriate V-shaped groove 764a on the scaled datum plate 760, and with the distal apex or arrowhead 778 of the indicator member 770 pointing to the estimated size of the tibial baseplate implant I. As shown in the exemplary embodiment illustrated in FIG. 45B, the estimated size of the tibial baseplate implant I to be installed on the proximal tibia 12 is set to a size of "3".

With the indictor member 770 fully engaged/assembly on the scaled datum plate 760 of the eminence stylus 300'', the eminence stylus 300'' (with the indicator member 770 attached to the scaled datum plate 760 at the scale location corresponding to the estimated size of the implant I) is engaged to the reference bench 104 of the datum block 100 and is displaced in an anterior-posterior direction until the distal end surface 784 of the pointer 782 is positioned in contact with the medial tibial cortex $12_{MC}$, and the distal end surface 794 of the pointer 792 associated with the second reference arm 790 is positioned in contact with the anterior tibial cortex $12_{AC}$ of the proximal tibia 12. Notably, these two points of contact between the indicator member 770 and the proximal tibia 12 at the level of resection serve to effectively center and align the eminence stylus 300'' relative to the proximal tibia 12 or other anatomic structures (e.g. cruciate ligaments). Proper centering/alignment of the eminence stylus 300'' may be checked/verified by observing the position/orientation of the indicator members 306a'', 306b'' relative to the proximal tibia 12 or other anatomic structures (e.g. cruciate ligaments). Although the illustrated embodiment establishes two points of contact between the tibia size gauge 750 and the proximal tibia 12, it should be understood that three or more points of contact between the tibia size gauge 750 and the proximal tibia 12 may alternatively be established.

Once the eminence stylus 300" (with the indictor member 770 attached thereto and positioned in contact with the medial and anterior aspects of the proximal tibia 12) is appropriately centered/aligned in relation to the proximal tibia 12, the eminence stylus 300" may be locked in position on the datum block 100 via actuation of the pinch lock mechanism 106. At this point, the indictor member 770 may be removed from the eminence stylus 300". Because proper centering/alignment of the eminence stylus 300" relative to the proximal tibia 12 using the above-described centering/alignment technique results in formation of the resection cuts at the appropriate position and orientation, the tibial baseplate implant I will also be properly positioned/oriented on the resected proximal tibia 12, whereby underhang/overhang of the baseplate implant I is thereby minimized relative to the peripheral outer boundary of the proximal tibia 12.

As should be appreciated, the above-described technique for centering/aligning the eminence stylus 300" relative to the proximal tibia 12 utilizes an initial estimation of the size of the tibial implant I to set the indictor member 770 at the appropriate location/position on the scaled datum plate 760, and then displaces the eminence stylus 300" (with the indictor member 770 engaged thereto) in an anterior-posterior direction to establish at least two points of contact with the proximal tibia 12 at the level of proposed/intended resection to center/align the eminence stylus 300" relative to the proximal tibia 12, the accuracy of which can be confirmed/verified via the indicator members 306a", 306b". However, other techniques for centering/aligning the eminence stylus 300" relative to the proximal tibia 12 using the tibia size gauge 750, as well as other uses of the tibia size gauge 750, are also contemplated.

For example, in another form of the invention, the datum block 100 is initially pinned to the proximal tibia 12, and the eminence stylus 300" is provisionally engaged to the datum block 100 and generally centered/aligned in relation to the proximal tibia 12 or other anatomic structures using the indicator members 306a", 306b", the alignment rod 18 and/or other alignment structures or alignment techniques. Once the eminence stylus 300" is generally centered/aligned in relation to the proximal tibia 12, the eminence stylus 300" may be provisionally locked in position on the datum block 100 via partial actuation of the pinch lock mechanism 106 (i.e., movement of the eminence stylus 300" is resisted but not prevented). The distal end surface 784 of the pointer 782 is then be generally aligned with the medial tibial cortex $12_{MC}$ on the medial side of the proximal tibia 12, and the V-shaped tooth 776 defined by the superior plate 774 of the indicator member 770 is positioned in the appropriate V-shaped groove 764a defined along the scaled datum plate 760. The V-shaped tooth 776 is then displaced along the V-shaped groove 764a by correspondingly displacing the indicator member 770 in an anterior-posterior direction until the distal end surface 784 of the pointer 782 is positioned in contact with the medial tibial cortex $12_{MC}$, and the distal end surface 794 of the pointer 792 associated with the second reference arm 790 is positioned in contact with the anterior tibial cortex $12_{AC}$ of the proximal tibia 12. If the distal end surface 784 of the pointer 782 does not contact the medial tibial cortex $12_{MC}$, the indicator member 770 is disengaged from the scaled datum plate 760 and repositioned on the scaled datum plate 760 with the V-shaped tooth 776 positioned in a different V-shaped groove 764a that provides contact of the distal end surface 784 of the pointer 782 with the medial tibial cortex $12_{MC}$, and contact of the distal end surface 794 of the pointer 792 with the anterior tibial cortex $12_{AC}$. Notably, these two (or more) points of contact between the indicator member 770 and the proximal tibia 12 further centers/aligns the eminence stylus 300" to the appropriate position/orientation relative to the proximal tibia 12. At this point, the eminence stylus 300" may be fully locked in position on the datum block 100 via full actuation of the pinch lock mechanism 106, followed by resection of the proximal tibia 12 using the techniques illustrated and described above.

Additionally, as shown in FIG. 45B, the user may observe which of the numbers 764b on the measurement scale 762 is aligned with the distal apex or arrowhead 778 defined by the indicator member 770. In the illustrated embodiment, the number 764b aligned with the distal apex or arrowhead 778 relates to the size of the tibial baseplate implant I that would properly fit on the proximal tibia 12 subsequent to resection. As shown in FIG. 45B, the indicated size measurement is "3", which corresponds to the appropriate size of the tibial baseplate implant I to be installed on the proximal tibia 12. Subsequent to resection and finishing of the proximal tibia 12, the appropriately sized baseplate implant I is installed on the resected proximal tibia 12 wherein underhang/overhang of the baseplate implant I on the resected proximal tibia 12 is minimized relative to the peripheral outer boundary of the proximal tibia 12 due to the above-described implant sizing and alignment techniques.

I. Tibia Rotation Gauge

Figure 46:
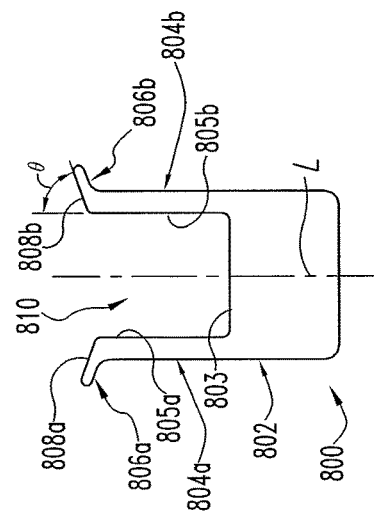
FIG. 46 illustrates a tibia rotation gauge according to one form of the invention.

Referring to FIG. 46, shown therein is a tibia rotation gauge 800 according to one form of the present invention. The tibia rotation gauge 800 may be used to align/orient the eminence stylus 300 to the appropriate angular orientation relative to the proximal tibia 12, which in turn aligns/orients the resection cuts on the proximal tibia 12 to ensure proper alignment of the baseplate implant I on the resected proximal tibia 12 to thereby minimize underhang/overhang of the baseplate implant I on the resected proximal tibia 12. As should be appreciated, minimizing underhang/overhang of the baseplate implant I on the resected proximal tibia 12 tends to provide a stronger and more secure and stable engagement of the tibial implant on the proximal tibia 12. As will be discussed in greater detail below, the tibia rotation gauge 800 is engaged with the eminence stylus 300 and includes alignment features that engage anterior aspects of the proximal tibia 12 to adjust the angular position of the eminence stylus 300 to the appropriate orientation relative to the proximal tibia 12.

Figure 47A:
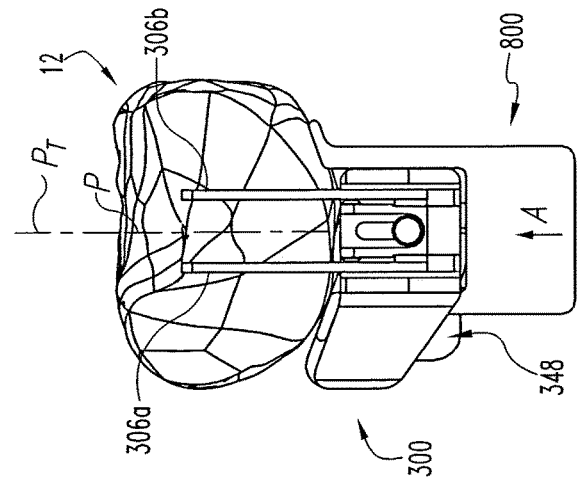
FIG. 47A illustrates the eminence stylus of FIG. 17A attached to the datum block of FIG. 5, as shown in a first misaligned rotational orientation relative to the proximal tibia.
Figure 47B:
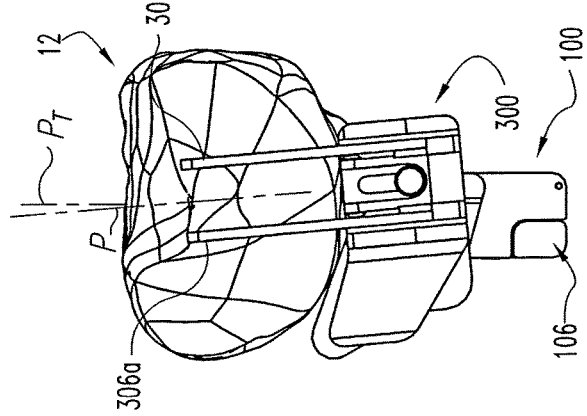
FIG. 47B illustrates the eminence stylus of FIG. 17A attached to the datum block of FIG. 5, as shown in a second misaligned rotational orientation relative to the proximal tibia.
Figure 48:
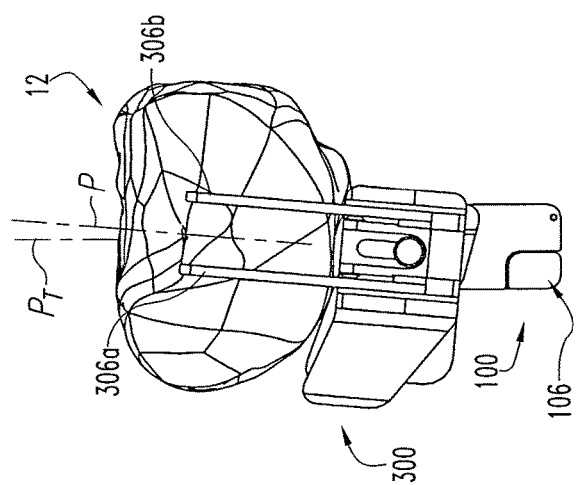
FIG. 48 illustrates the tibia rotation gauge of FIG. 46 engaged with the eminence stylus and the anterior surface of the proximal tibia to correct the misaligned rotational orientations shown in FIGS. 47A and 47B.

As shown in FIGS. 47A, 47B and 48, the tibia rotation gauge 800 may be used in association with the eminence stylus 300 attached to the datum block 100, with the datum block 100 in turn pinned to the proximal tibia 12, the details of which have been illustrated and described above. However, it should be understood that the tibia rotation gauge 800 may also be used in association other devices and instruments, including but not limited to the eminence stylus 300', the recut block 600, the tibia size gauge 700, and the tibia size gauge 750. The tibia rotation gauge 800 may be particularly useful when used in association with the tibia size gauge 700 and/or the tibia size gauge 750 to align/orient the eminence stylus 300 to the appropriate orientation relative to the proximal tibia 12 prior to performing the sizing/centering techniques associated with the tibia size gauge 700 and the sizing/alignment techniques associated with the tibia size gauge 750.

Referring once again to FIG. 46, in the illustrated embodiment, the tibia rotation gauge 800 extends along a longitudinal axis L and generally includes a base plate or handle portion 802, a medial alignment leg 804a extending axially from the base plate 802 and including a distal alignment foot or flange 806a defining a distal end bone-contacting surface or edge 808a configured for engagement with the anterior outer surface of the proximal tibia 12, and a lateral alignment leg 804b extending axially from the base plate 802 and including a distal alignment foot or flange 806b defining a distal end bone-contacting surface or edge 808b configured for engagement with the anterior outer surface of the proximal tibia 12. The distal end bone-contacting surfaces or edges 808a, 808b are outwardly tapered at a taper angle θ relative to the longitudinal axis L. The taper angle θ is preferably set to generally match or conform to the contour or outer profile of the anterior outer surface of the proximal tibia 12, and more specifically the anterior tibial cortex $12_{AC}$, at the level of the horizontal resection cuts. In one embodiment, the taper angle θ falls within a range of about 30° to 90°. In another embodiment, the taper angle θ falls within a range of about 45° to 75°. In a further embodiment, the taper angle θ is set at approximately 60°. However, other taper angles θ are also contemplated. Additionally, in the illustrated embodiment, the distal end surfaces or edges 808a, 808b are substantially flat/planar. However, in other embodiments, the distal end surfaces or edges 808a, 808b may be curved or partially curved in a concave or convex configuration.

The tibia rotation gauge 800 further defines a slot or open inner region 810 arranged generally along the longitudinal axis L and extending from an open end adjacent the distal end surfaces or edges 808a, 808b toward the base plate 802. The open ended slot 810 has a generally rectangular configuration and is bound/defined by the distal end surfaces or edges 808a, 808b, substantially flat/planar inner side surfaces or edges 805a, 805b defined by the medial and lateral alignment legs 804a, 804 and arranged generally parallel with the longitudinal axis L, and a substantially flat/planar inner end surface 803 defined by the base plate 802 and arranged generally perpendicular to the longitudinal axis L. As will be discussed below, the open ended slot 810 is sized to receive the base plate 310 defined by the main body 302 of the eminence stylus 300 (FIGS. 17-20) therein such that the planar inner side surfaces or edges 805a, 805b of the medial and lateral alignment legs 804a, 804b are engaged in relatively close tolerance with the substantially flat/planar outer side surface of the base plate 310.

Additionally, in the illustrated embodiment, the tibia rotation gauge 800 is provided as a single-piece, substantially flat/planar plate having a generally uniform and relatively thin plate thickness that is preferably sized in relatively close tolerance with the width of the medial cutting guide 348 defined between the datum block 100 and the eminence stylus 300. However, other embodiments are also contemplated wherein the tibia rotation gauge 800 may take on other configurations and/or may be provided as multiple pieces or elements that are interconnected with one another to form the tibia rotation gauge 800.

Figure 49:
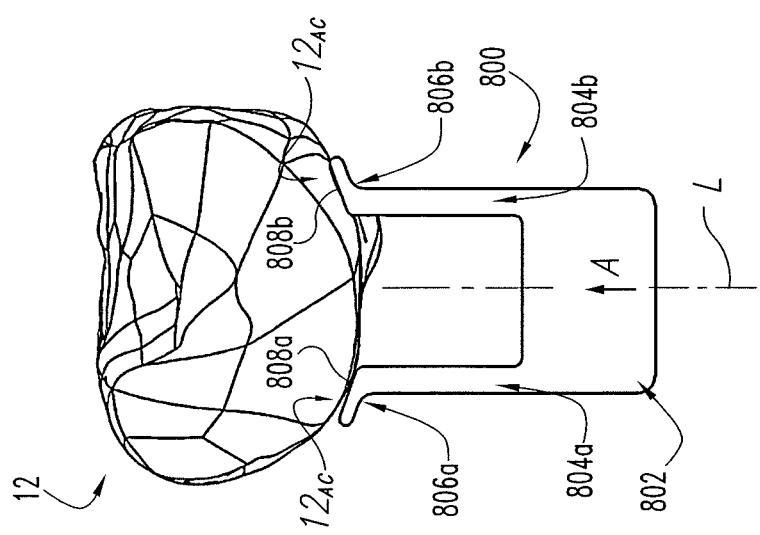
FIG. 49 illustrates the tibia rotation gauge of FIG. 46 engaged with the anterior surface of the proximal tibia to correct the misaligned rotational orientations shown in FIGS. 47A and 47B.

Referring now to FIGS. 47-49, shown there is a technique according to one form of the invention for using the tibia rotation gauge 800 to align/orient the eminence stylus 300 to the appropriate angular orientation relative to the proximal tibia 12, which in turn aligns/orients the resection cuts on the proximal tibia 12 to ensure proper alignment of the baseplate implant I on the resected proximal tibia 12 to minimize underhang/overhang of the baseplate implant I on the resected proximal tibia 12.

Referring to FIGS. 47A and 47B, the datum block 100 is initially pinned to the proximal tibia 12, and the eminence stylus 300 is engaged to the datum block 100 and generally centered/aligned in relation to the proximal tibia 12 or other anatomic structures using the indicator members 306a, 306b, the alignment rod 18 and/or other alignment structures or alignment techniques. Once the eminence stylus 300 is centered/aligned in relation to the proximal tibia 12, the eminence stylus 300 may be locked in position on the datum block 100 via actuation of the pinch lock mechanism 106. However, as shown in FIGS. 47A and 47B, in some instances, the eminence stylus 300 may remain in a misaligned angular orientation relative to the proximal tibia 12. In other words, the central plane P of the eminence stylus 300 (defined between the flat/planar indicator members 306a, 306b) may not be properly aligned with the central anatomic plane $P_T$ of the tibia (i.e., the central plane P of the eminence stylus 300 is inwardly/outwardly rotational offset from the central anatomic plane $P_T$ of the tibia).

Referring to FIGS. 48 and 49, the misaligned condition of the eminence stylus 300 (FIGS. 47A and 47B) may be corrected via use of the tibia rotation gauge 800. First, the eminence stylus 300 is unlocked from the datum block 100 via de-actuation of the pinch lock mechanism 106 such that the eminence stylus 300 is free to internally/externally rotate relative to the datum block 100. The tibia rotation gauge 800 is then engaged to the eminence stylus 300 by aligning the open ended slot 810 of the tibia rotation gauge 800 with the base plate 310 of the eminence stylus 300 and inserting the medial alignment leg 804a into the medial cutting guide 348 (defined between the cutting guide flange 316 on the eminence stylus 300 and the reference bench 104 on the datum block 100). As discussed above in association with FIGS. 20A-20C, the medial cutting guide 348 is used to form the medial horizontal resection cut $C_{HM}$ in the proximal tibia 12, and the cutting plane defined along the medial cutting guide 348 is therefore positioned at the level of resection. The thickness of at least the medial alignment leg 804a is preferably sized in relatively close tolerance with the width of the medial cutting guide 348 to maintain the tibia rotation gauge 800 in a substantially co-planar relationship with the cutting plane defined by the medial cutting guide 348.

As should be appreciated, the planar inner side surfaces or edges 805a, 805b defined by the medial and lateral alignment legs 804a, 804b of the tibia rotation gauge 800 are engaged in relatively close tolerance with the substantially flat/planar outer side surface of the base plate 310 of the eminence stylus 300. Accordingly, angular rotation of the tibia rotation gauge 800 will result in corresponding angular rotation of the eminence stylus 300. As the tibia rotation gauge 800 is displaced along the base plate 310 of the eminence stylus 300 in an anterior-posterior direction (in the direction of arrow A), the distal feet 806a, 806b of the medial and lateral alignment legs 804a, 804b will engage the anterior surface of the proximal tibia 12 at the level of resection (i.e., at the level where the horizontal resection cuts will be formed). More specifically, the distal bone-contacting surfaces or edges 808a, 808b defined by the distal feet 806a, 806b will engage the anterior tibial cortex $12_{AC}$ to define at least two points or locations of contact between the tibia rotation gauge 800 and the anterior surface of the proximal tibia 12 at the level of resection. As indicated above, the distal bone-contacting surfaces or edges 808a, 808b are configured to generally match or conform to the profile of the anterior outer surface of the proximal tibia 12 at the level of resection. Accordingly, as the tibia rotation gauge 800 is displaced in the direction of arrow A and into compressed engagement with the proximal tibia 12, engagement of the distal bone-contacting surfaces or edges 808a, 808b against the anterior tibial cortex $12_{AC}$ along two established points or locations of contact will draw the tibia rotation gauge 800 into proper alignment with the proximal tibia 12, which will in turn rotate the eminence stylus 300 into a properly aligned orientation relative to the proximal tibia 12 with the central plane P of the eminence stylus 300 generally aligned with the central anatomic plane $P_T$ of the tibia. At this point, the eminence stylus 300 may once again be locked in position on the datum block 100 via actuation of the pinch lock mechanism 106, and the tibia rotation gauge 800 can be removed from the eminence stylus 300.

As should be appreciated, use of the tibia rotation gauge 800 to properly align the eminence stylus 300 to the correct angular orientation relative to the proximal tibia 12 will result in formation of the resection cuts at the proper alignment and orientation relative to the proximal tibia 12, which will in turn ensure proper alignment of the baseplate implant I on the resected proximal tibia 12 to minimize underhang/overhang of the baseplate implant I relative to the outer periphery of the resected proximal tibia 12. As should also be appreciated, minimizing underhang/overhang of the baseplate implant I on the resected proximal tibia 12 tends to provide a stronger and more secure and stable engagement of the tibial implant on the proximal tibia 12. Additionally, it should be further appreciated that the tibia rotation guide 800 is ambidextrous, meaning that the tibia rotation guide 800 can be used to perform knee arthroplasty procedures on both the right knee and the left knee.

Figure 51:
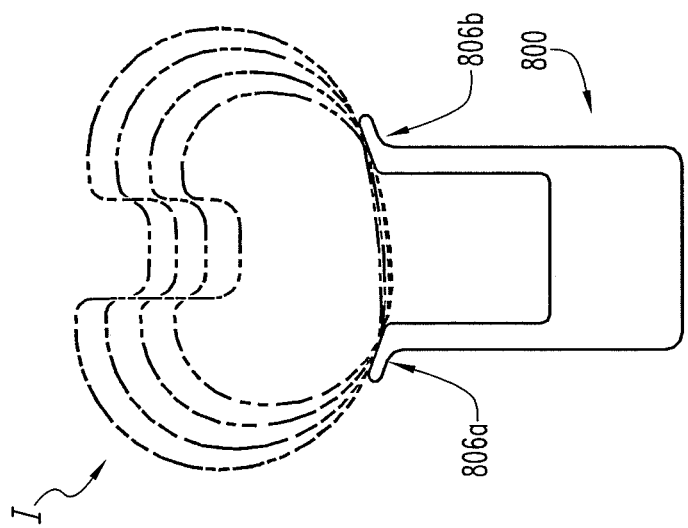
FIG. 51 illustrates a schematic illustration of the tibia rotation gauge of FIG. 46 engaged with an anterior surface of a set of tibial baseplates having varying sizes.
Figure 50:
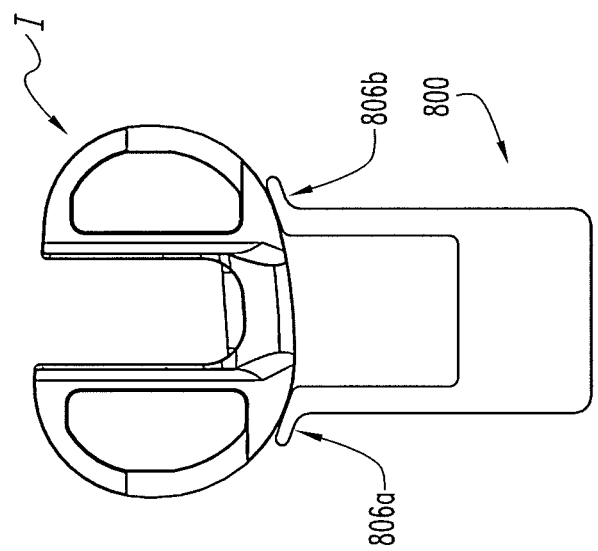
FIG. 50 illustrates the tibia rotation gauge of FIG. 46 engaged with an anterior surface of a tibial baseplate.

Referring to FIG. 50, the points of contact between the tibia rotation guide 800 and the baseplate implant I are substantially similar to the points of contact between the tibia rotation guide 800 and the anterior surface of the proximal tibia 12 at the level of resection. Accordingly, use of the tibia rotation gauge 800 to properly align the eminence stylus 300 relative to the proximal tibia 12 prior to forming the resection cuts will ensure a properly aligned fit of the baseplate implant I on the resected proximal tibia 12. As shown in FIG. 51, since the shape and configuration of the distal feet 806a, 806b of the tibia rotation gauge 800 are compatible with multiple sizes of the baseplate implant I (shown in phantom), the same tibia rotation gauge 800 may be used universally across the multiple sizes of the baseplate implants I (i.e., a different tibia rotation gauge 800 is not required to accommodate various sizes of the baseplate implant I).

J. Tibia Insert Trial

Figure 52:
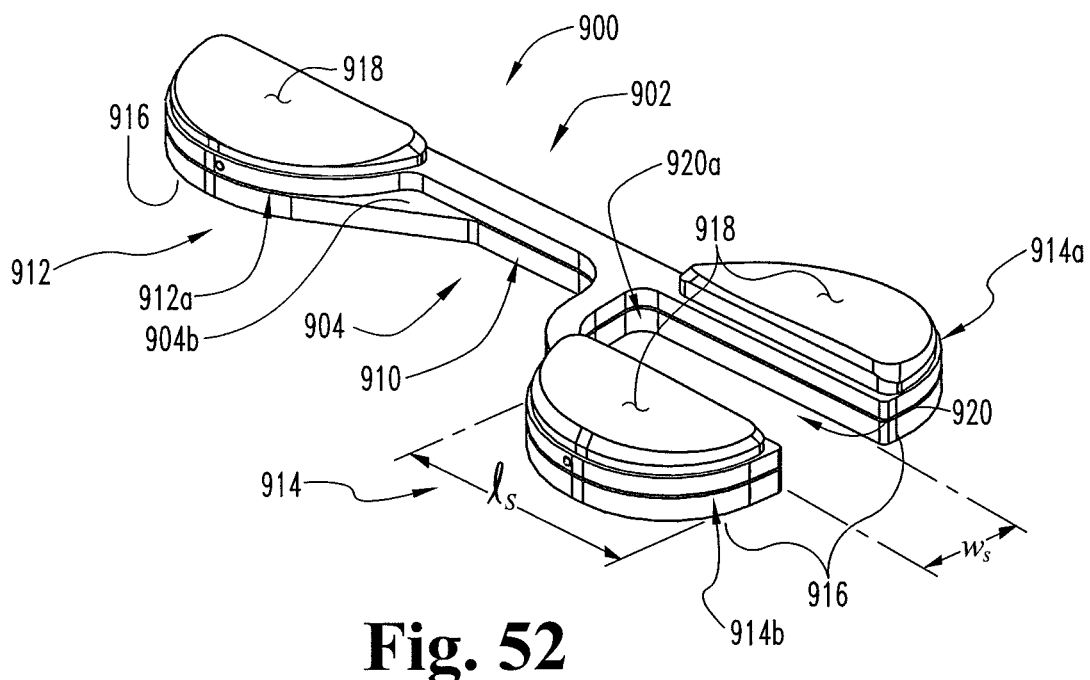
FIG. 52 illustrates a perspective view of a tibia insert trial according to one form of the invention.
Figure 55B:
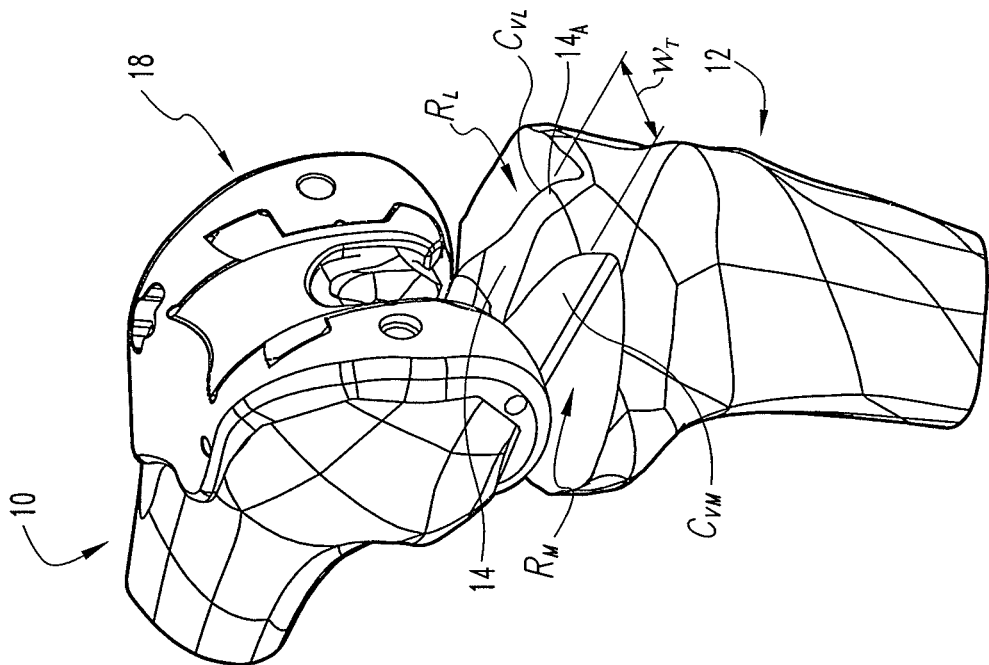
FIG. 55B illustrates a femoral trial component attached to the resected distal femur in relation to the medially and laterally resected proximal tibia.
Figure 55A:
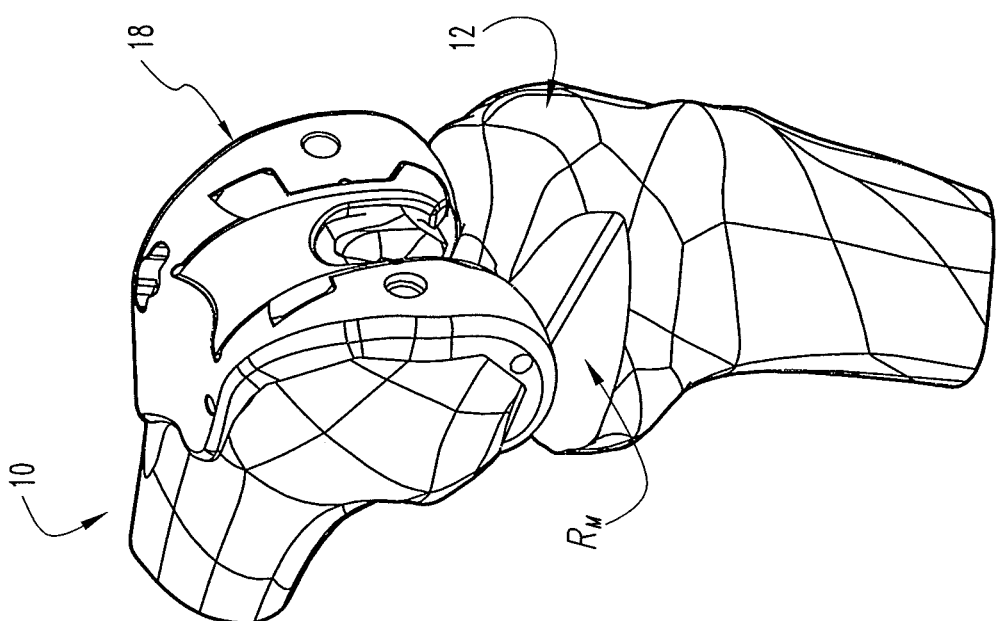
FIG. 55A illustrates a femoral trial component attached to the resected distal femur in relation to the medially resected proximal tibia.

Referring to FIG. 52, shown therein is a tibia insert trial 900 according to one form of the present invention. As will be discussed in greater detail below, the tibia insert trial 900 is used in the evaluation of the medial tibial resection $R_M$ (FIGS. 55A and 56A) to check/verify the size, shape, depth, position and/or orientation of the cuts associated with the medial tibial resection $R_M$ and their relation to the femoral trial 18 attached to the distal femur 10, and/or in the simultaneous evaluation of the medial and lateral tibial resections $R_M$, $R_L$ (FIGS. 55B and 56B) to check/verify the size, shape, depth, position and/or orientation of the cuts associated with the medial and lateral tibial resection $R_M$, $R_L$ and their relation to the femoral trial 18 attached to the distal femur 10.

Evaluations using the tibia insert trial 900 can take the form of a variety of different checks on the suitability of the size, shape, depth, position and/or orientation of the medial resection $R_M$ or the medial and lateral resections $R_M$, $R_L$, or the potential need to re-cut or redo the resection cuts at a different depth or orientation (e.g., at a different posterior slope angle, at a different varus-valgus angle, and/or at an inward-outward rotation angle). In some embodiments, evaluations using the tibia insert trial 900 can take the form of articulating a femoral trial (FIG. 56A) on a medial lobe of the tibia insert trial 900, which may allow the surgeon to check the balance, tightness, and/or laxity of the knee joint in flexion and extension. In other embodiments, evaluations using the tibia insert trial 900 can take the form of simultaneously articulating a femoral trial (FIG. 56B) on medial and lateral lobes of the tibia insert trial 900, which may also allow the surgeon to check the balance, tightness, and/or laxity of the knee joint in flexion and extension. In still other embodiments, evaluations using the tibia insert trial 900 can involve the selection of one or more shim components (selected from a kit or set of shim components) that are removably attachable to a main trial component to provide various configurations of trial lobes (i.e., varying thicknesses, posterior slope angles, varus-valgus angles, etc.) to evaluate the relationship between the medial/lateral resections of the proximal tibia and a femoral trial attached to the distal femur 10. In still further embodiments, the tibia insert trial 900 may also be used to simulate the effect of a re-cut of the medial/lateral resections or the use of a different tibial implant articulation on the balance of the knee joint which may, in some embodiments, reduce the risk associated with having to re-cut the resection.

Figure 53:
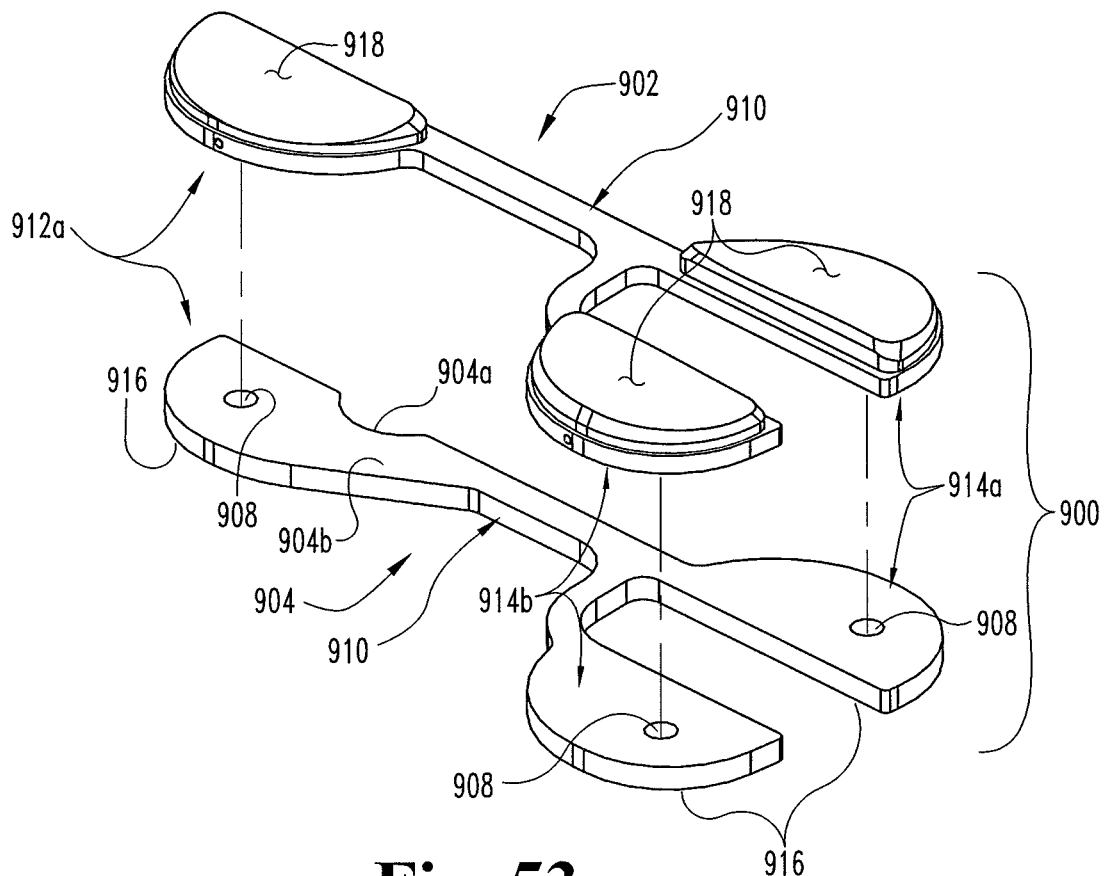
FIG. 53 illustrates an exploded view of the tibia insert trial of FIG. 52.
Figure 54:
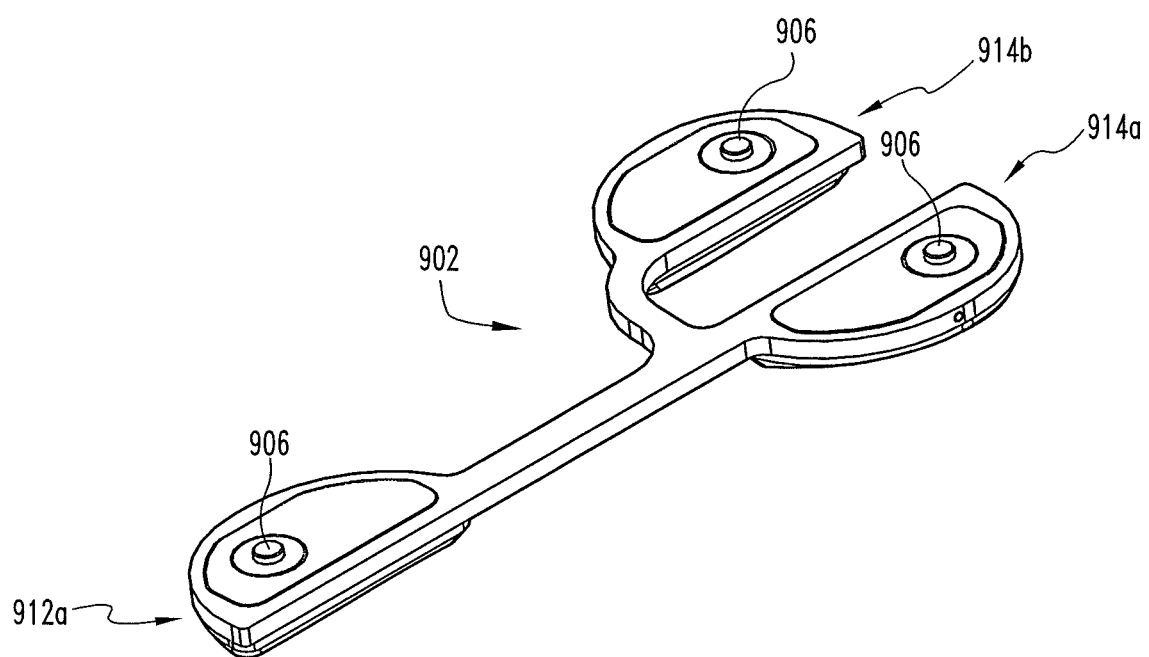
FIG. 54 illustrates a bottom view of the main body component of the tibia insert trial of FIG. 52.

Referring collectively to FIGS. 52 and 53, in the illustrated embodiment, the tibia insert trial 900 is configured as a two-piece assembly including a main trial component 902 and a shim component 904 that are removably attachable to one another to form the tibia insert trial 900. In one embodiment, the main trial component 902 and the shim component 904 each have substantially identical outer cross-sectional shapes/profiles that substantially match up with another when assembled together. In another embodiment, the shim component 904 is removably attachable to the main trial component 902 by way of one or more magnetic attraction forces. As shown in FIG. 54, the inferior side of the main trial component 902 is provided with a series of magnets 906 projecting therefrom that are received in corresponding openings 908 formed in the shim component 904 (FIG. 53). As should be appreciated, at least the portion of the shim component 904 surrounding the openings 908 may be formed of a ferrous material to generate a magnetic attraction force with the magnets 906 to maintain a connection between the main trial component 902 and the shim component 904. Positioning of the magnets 906 within the openings 908 not only serves to draw the main trial component 902 and the shim component 904 into connection with one another via magnetic attraction forces, but also serves as a positive interconnection or catch that prevents the components from sliding off of one another. Although the shim component 904 has been illustrated and described as being removably attachable to the main body component 902 by way of one or more magnetic attraction forces, other structures and techniques may alternatively be used to removably attach the shim component 904 to the main body component 902 including, for example, a friction fit, a clamp fit, a tongue-and-groove arrangement, one or more fasteners, or by other suitable structures or techniques for removable attachment of the shim component 904 to the main body component 902.

In the illustrated embodiment, the magnets 906 and the openings 908 have been illustrated as having a circular configuration. However, other suitable shapes and configurations of the magnets 906 and the openings 908 are also contemplated. Additionally, although the magnets 906 have been illustrated as being associated with the main trial component 902 and the openings 908 have been illustrated as being associated with the shim component 904, it should be understood that a reverse configuration is also contemplated. Further, in the illustrated embodiment, the magnets 906 project from a surface of the main trial component 902 for receipt within corresponding openings 908 in the shim component 904. However, in other embodiments, the magnets 906 may be embedded within portions of either the main trial component 902 or the shim component 904. Moreover, although the magnets 906 have been illustrated as extending from each of the three lobed regions of the main trial component 902 and the openings 908 have been illustrated as being defined in each of the three lobed regions of the shim component 904, it should be understood that the magnets 906 and the openings 908 can alternatively be associated with other portions/regions of the main trial component 902 and the shim component 904 such as, for example, the interconnecting handle 910. Additionally, although the main trial component 902 has been illustrated as including three magnets, it should also be understood that any number of the magnets 906 positionable within a corresponding number of openings 908 may be used to removably attach the shim component 904 to the main trial component 902.

As discussed above, in the illustrated embodiment, the main trial component 902 and the shim component 904 each have substantially identical outer cross-sectional shapes/profiles that substantially match up with another when assembled together. However, the main trial component 902 and the shim component 904 may be provided with one or more outer profile regions that do not correspond to one another to facilitate separation of the components. For example, in one embodiment, the shim component 904 is provided with a cut-out or recessed region 904a (FIGS. 53 and 56B) that is not found in the corresponding area of the main trial component 902, thereby allowing the user to more easily grasp and manipulate the main trial component 902 relative to the shim component 904 to facilitate separation of the components. Additionally, the shim component 904 may be provided with a projecting region or flange 904b (FIGS. 53 and 56A) that is not found in the corresponding area of the main trial component 902, thereby allowing the user to more easily grasp and manipulate the shim component 904 relative to the main trial component 902 to facilitate separation of the components. It should be understood that other features associated with the main trial component 902 and/or the shim component 904 may be provided that facilitate separation of the components from one another. Additionally, in still other embodiments, multiple shim components may be provided that are removably attached to just the lobed regions of the main body component 902, or multiple trial components may be provided that are removably attached to just the lobed regions of the shim component. Moreover, although the tibia insert trial 900 has been illustrated and described as a two-piece assembly including a main trial component 902 removably attached to a shim component 904, other embodiments are also contemplated wherein the tibia insert trial 900 comprises a unitary, single-piece structure.

Referring collectively to FIGS. 52-54, in the illustrated embodiment, the tibia insert trial 900 includes an elongate connector portion or handle 910, a single-lobe trial portion 912 located at a first end of the handle 910 and including a medial tibia trial lobe 912a, and a dual-lobe trial portion 914 located at an opposite second end of the handle 910 and including both a medial tibia trial lobe 914a and a lateral tibia trial lobe 914b. The medial tibia trial lobes 912a, 914a each have a hemi-elliptical or hemi-ovular configuration sized and shaped to generally match the size and shape of the corresponding medial portion of the tibia implant to be installed on the proximal tibia 12. Similarly, the lateral tibia trial lobe 914b has a hemi-elliptical or hemi-ovular configuration sized and shaped to generally match the size and shape of the corresponding lateral portion of the tibia implant to be installed on the proximal tibia 12. Accordingly, the tibia insert trial 900 can be used to evaluate/check the suitability of the size and shape of the medial resection $R_M$ or the medial and lateral resections $R_M$, $R_L$ and whether the resections will accommodate the tibial implant to be installed on the proximal tibia 12. Additionally, each of the tibia trial lobes 912a, 914a and 914b includes a substantially flat/planar inferior surface 916 (defined by the shim component 904) that is configured to rest against/abut the superior horizontal surfaces of the medial and lateral resections $R_M$, $R_L$ of the proximal tibia 12. Each of the tibia trial lobes 912a, 914a and 914b also includes a superior articulation surface 918 (defined by the main trial component 902) that is curved/contoured to match a particular implant and to mate with the corresponding curved/contoured inferior surface defined by the femoral trial 18 attached to the distal femur 10.

Figure 56B:
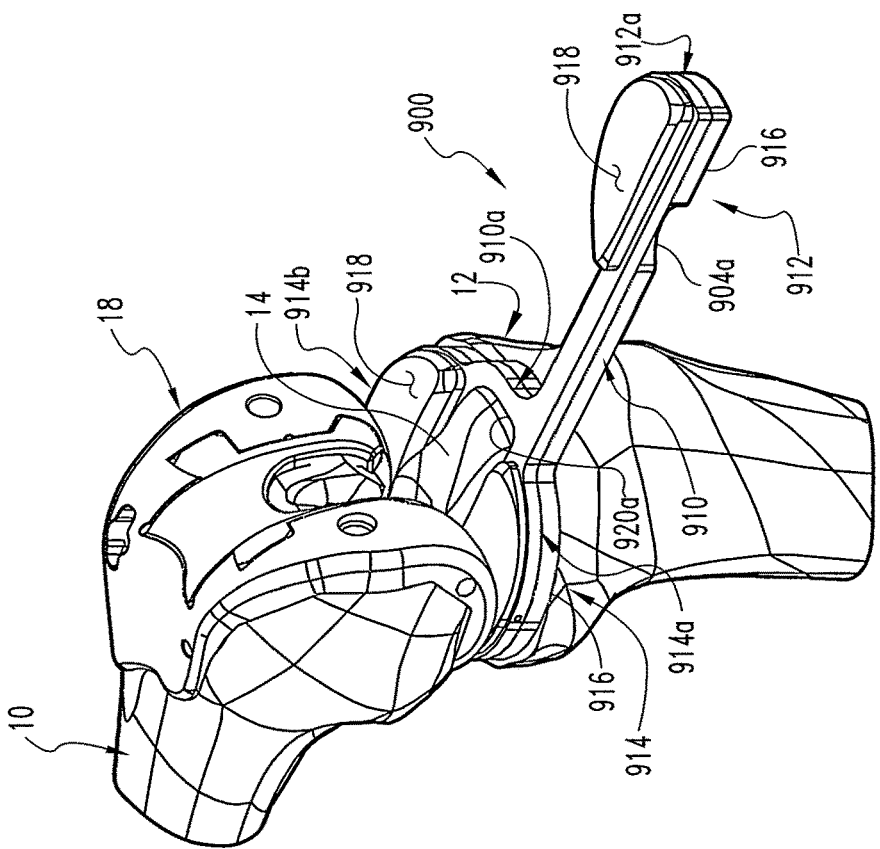
FIG. 56B illustrates a second operational position of the tibia insert trial of FIG. 52 inserted between the femoral trial component and the medially and laterally resected proximal tibia of FIG. 55B.
Figure 56A:
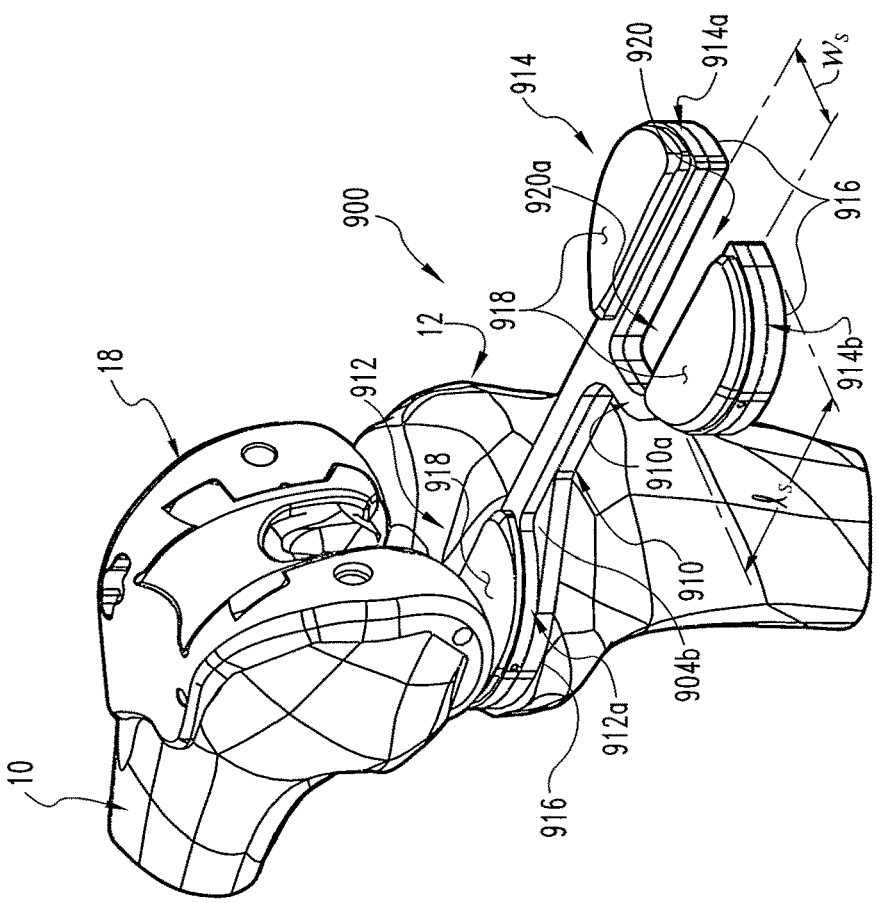
FIG. 56A illustrates a first operational position of the tibia insert trial of FIG. 52 inserted between the femoral trial component and the medially resected proximal tibia of FIG. 55A.
Figure 57:
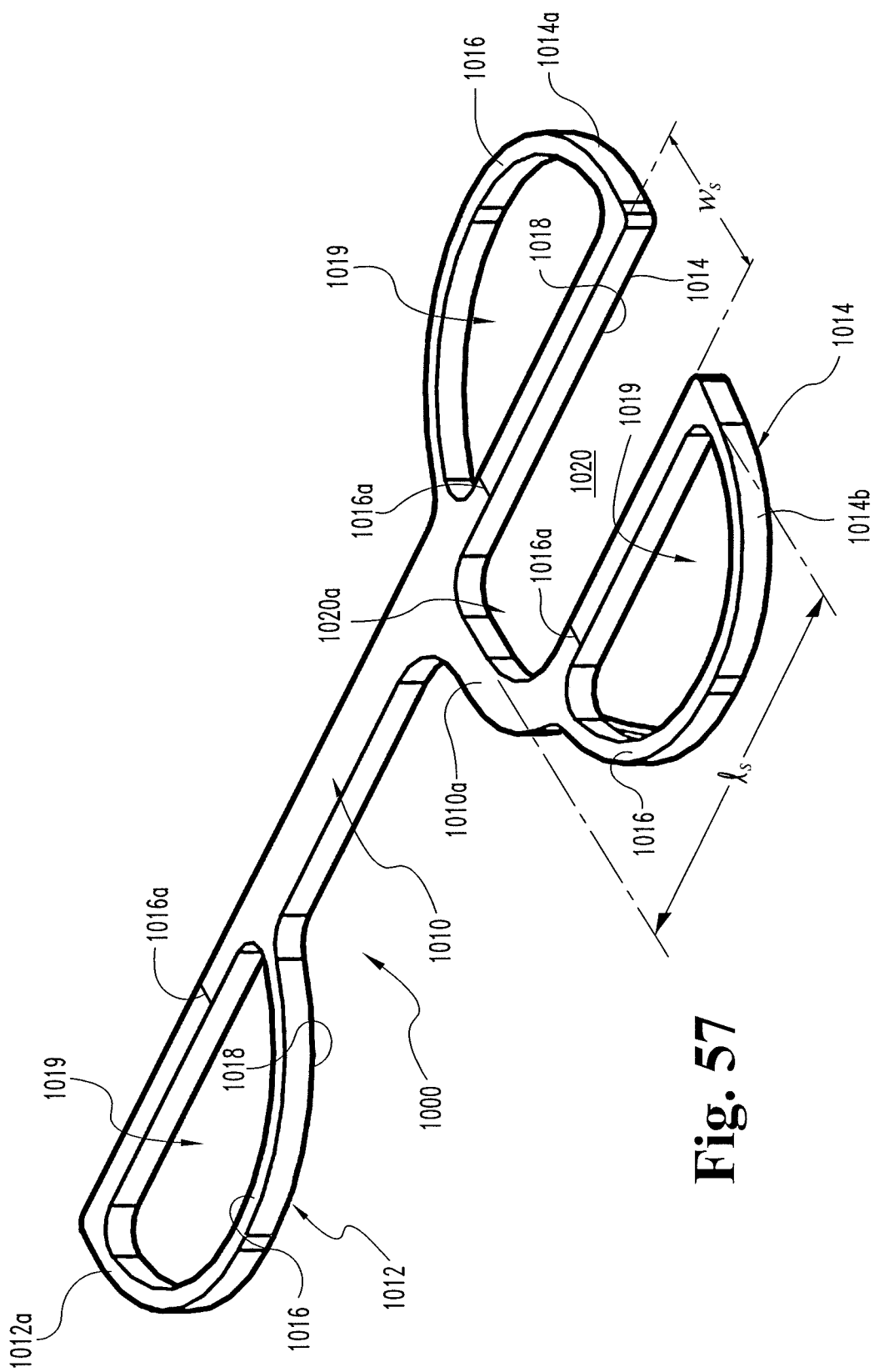
FIG. 57 illustrates a perspective view of a tibia size template according to one form of the invention.
Figure 58A:
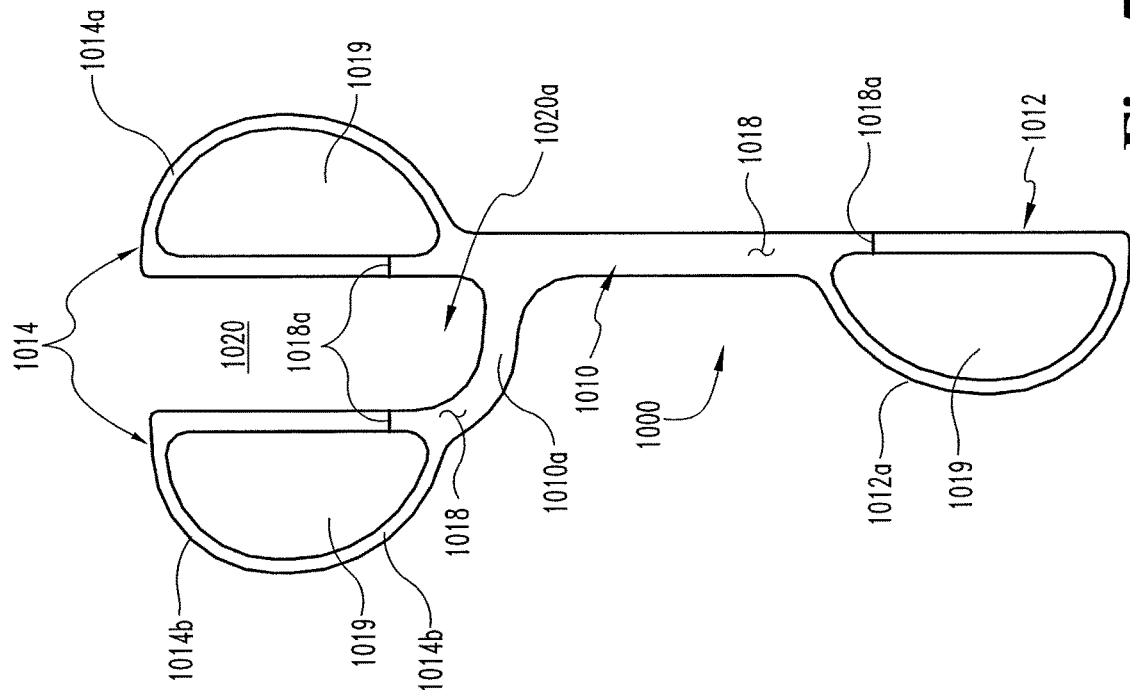
FIG. 58A illustrates a superior view of the tibia size template of FIG. 57.
Figure 58B:
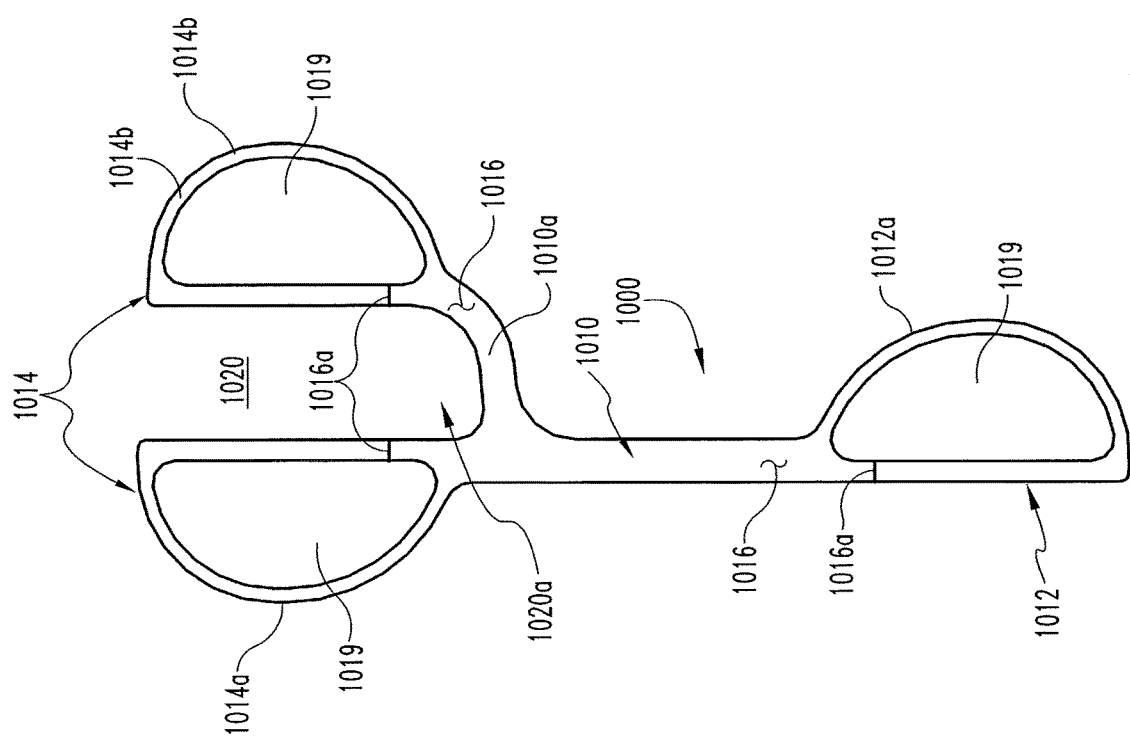
FIG. 58B illustrates an inferior view of the tibia size template of FIG. 57.

In the illustrated embodiment, the dual-lobe trial portion 914 includes an open ended slot or spacing 920 which separates the medial and lateral tibia trial lobes 914a, 914b and which has a width $w_S$ slightly larger greater than the width $w_T$ of the tibial eminence 14 (FIG. 55B) so as to allow the medial and lateral tibia trial lobes 914a, 914b to be simultaneous positioned on the medial and lateral resections $R_M$, $R_L$, and with the tibial eminence 14 positioned within the open ended slot 920 (FIG. 56B). Additionally, in some embodiments, the dual-lobe trial portion 914 is used to evaluate the medial and lateral resection $R_M$, $R_L$ prior to resection of the anterior tibial eminence $14_A$ (discussed below). Thus, the overall length is of the slot 920 must be sized to accommodate the full anterior-posterior length of the tibial eminence 14 prior to anterior resection of the tibial eminence 14. Accordingly, the slot 920 is provided with an extended portion 920a that extends beyond the anterior ends of the medial and lateral tibia trial lobes 914a, 914b adjacent the handle portion 910 for receipt of the unresected anterior tibial eminence $14_A$. Stated another way, the handle portion 910 includes a notched bridge region 910a that interconnects the medial and lateral tibia trial lobes 914a, 914b and which is sized to receive the unresected anterior tibial eminence $14_A$ therein.

As should be appreciated, the medial tibia trial lobe 912a of the single-lobe trial portion 912 is configured for positioning on the medial resection $R_M$ (FIGS. 55A and 56A) for evaluation of the size, shape, depth, position and/or orientation of the medial resection $R_M$ and their relation to the femoral trial 18 attached to the distal femur 10. As should also be appreciated, the medial and lateral tibia trial lobe 914a, 914b of the dual-lobe trial portion 914 are configured for simultaneous positioning on the medial and lateral resections $R_M$, $R_L$ (FIGS. 55B and 56B) for simultaneous evaluation of the size, shape, depth, position and/or orientation of the medial and lateral tibial resections $R_M$, $R_L$ and their relation to the femoral trial 18 attached to the distal femur 10. As should be further appreciated, due to the unique configuration of the tibia insert trial 900, each of these evaluations can be performed using a single instrument as opposed to two separate instruments. Additionally, although not specifically illustrated in FIGS. 52-54, it should be understood that in an alternative embodiment, another single-lobe trial portion may extend from a central portion of the handle 910 which includes a single lateral tibia trial lobe configured for positioning on the lateral resection $R_L$ for evaluation of the size, shape, depth, position and/or orientation of the lateral resection $R_L$ and their relation to the femoral trial 18.

In another form of the present invention, the tibia insert trial 900 may be provided in a kit or set including multiple main trial components 902 and multiple shim components 904. The main trial components 902 may be provided in various sizes/articulation configurations that correspond to the various sizes/articulation configurations associated with the tibial implants that may be installed on the proximal tibia 12. The shim components 904 may be provided in various sizes that correspond to the sizes of the main trial components 902, and in various incremental thicknesses (i.e., +1, +2, +3, etc.) that serve to vary the overall thickness of the tibia trial lobes 912a, 914a and 914b to simulate the thickness of the tibial implant to be installed on the proximal tibia 12, and to check/verify whether the depth of the medial resection $R_M$ or the medial and lateral resections $R_M$, $R_L$ are correct/appropriate or if a re-cut is necessary. Additionally, a shim component 904 having a particular thicknesses may be selected and attached to the main trial component 902 to simulate the effect of a re-cut (i.e., a "re-cut simulation" to simulate a different resection cut depth) to check/verify whether the proposed re-cut is desired prior to actually making the re-cut. In this way, the surgeon may investigate options for compensating for laxity or tightness in flexion/extension without actually performing the proposed re-cut. As should be appreciated, the number of potential re-cuts is therefore minimized.

In addition to providing the shim components 904 in various incremental thicknesses, the insert trial kit/set may also be provided with shim components 904 having various incremental posterior slope angles (i.e., −2, −1, 0, +1, +2, etc.) that serve to vary the posterior slope angle associated with the tibia trial lobes 912a, 914a and 914b to simulate the posterior slope angle of the tibial implant to be installed onto the proximal tibia 12, and to check/verify whether the medial resection $R_M$ or the medial and lateral resections $R_M$, $R_L$ are correct/appropriate or whether a re-cut is necessary. Additionally, the insert trial kit/set may also be provided with shim components 904 having various incremental varus/valgus angles (i.e., −2, −1, 0, +1, +2, etc.) that serve to vary the varus/valgus angles associated with the tibia trial lobes 912a, 914a and 914b to simulate the varus/valgus angle of the tibial implant to be installed onto the proximal tibia 12, and to check/verify whether the medial resection $R_M$ or the medial and lateral resections $R_M$, $R_L$ are correct/appropriate or whether a re-cut is necessary. Accordingly, a shim component 904 having a particular posterior slope angle and/or a particular varus/valgus angle may be selected and attached to the main trial component 902 to simulate the effect of a re-cut (i.e., a "re-cut simulation" to simulate a different posterior slope angle and/or a different varus/valgus angle) to check/verify whether the proposed re-cut is desired prior to actually making the re-cut.

In other embodiments, multiple shim components 904 may be attached to the main trial component 902 to vary both the overall thickness of the tibia trial lobes 912a, 914a and 914b, and to vary the posterior slope angle and/or the varus/valgus angle. For example, a first shim component 904a having a particular thicknesses may be selected and attached to the main trial component 902, and a second shim component 904b having a particular posterior slope angle and/or varus/valgus angle may be selected and attached to the first shim component 904b. As should be appreciated, this additional degree of modularity may reduce the number of shim components 904 included in the kit/set associated with the tibia insert trial 900 (i.e., eliminating the need for shim components 904 having varying posterior slope angles and/or varus/valgus angles in multiple thickness levels). As should also be appreciated, each of the shim components 904 is ambidextrous, meaning that the shim component 904 can be flipped over and used in association with the other knee. Accordingly, individual shim components 940 can be used to perform knee arthroplasty procedures on both the right knee and the left knee.

K. Tibia Size Templates

Referring to FIGS. 57-60, shown therein is a tibia size template 1000 according to one form of the present invention. Unlike the tibia insert trial 900 illustrated and described above which is used to evaluate the medial resection $R_M$ or the medial and lateral tibial resections $R_M$, $R_L$ in relation to a femoral trial 18 attached to the distal femur 10 (i.e., to evaluate articulation, balance, tightness, and/or laxity of the knee joint in flexion and extension), use of the tibia size template 1000 is limited to evaluation of the peripheral size and shape of the medial resection $R_M$ individually, or the medial and lateral tibial resections $R_M$, $R_L$ simultaneously. Accordingly, the primary evaluation feature associated with the tibia size template 1000 is the peripheral outer cross-sectional profile of the lobed regions. Due to the simple design associated with the tibia size template 1000, manufacturing costs may be significantly reduced compared to the tibia insert trial 900.

The tibia size template 1000 is configured as a single-piece structure including an elongate connector portion or handle 1010, a single-lobe template portion 1012 located at a first end of the handle 1010 and including a medial tibia template lobe 1012a, and a dual-lobe template portion 1014 located at an opposite second end of the handle 1010 and including both a medial tibia template lobe 1014a and a lateral tibia template lobe 1014b. The medial tibia template lobes 1012a, 1014a each have a hemi-elliptical or hemi-ovular configuration sized and shaped to generally match the size and shape of the corresponding medial portion of the tibia implant to be installed on the medial resection $R_M$ of the proximal tibia 12. Similarly, the lateral tibia template lobe 1014b has a hemi-elliptical or hemi-ovular configuration sized and shaped to generally match the size and shape of the corresponding lateral portion of the tibia implant to be installed on the lateral resection $R_L$ of the proximal tibia 12. Additionally, each of the tibia template lobes 1012a, 1014a and 1014b includes a substantially flat/planar inferior surface 1016 and a substantially flat/planar superior surface 1018 (FIGS. 58A/58B and 59A/59B) so that the template lobes rest steadily on the planar horizontal resected surfaces of the medial and lateral tibial resections $R_M$, $R_L$.

Figures 59A, 59B:
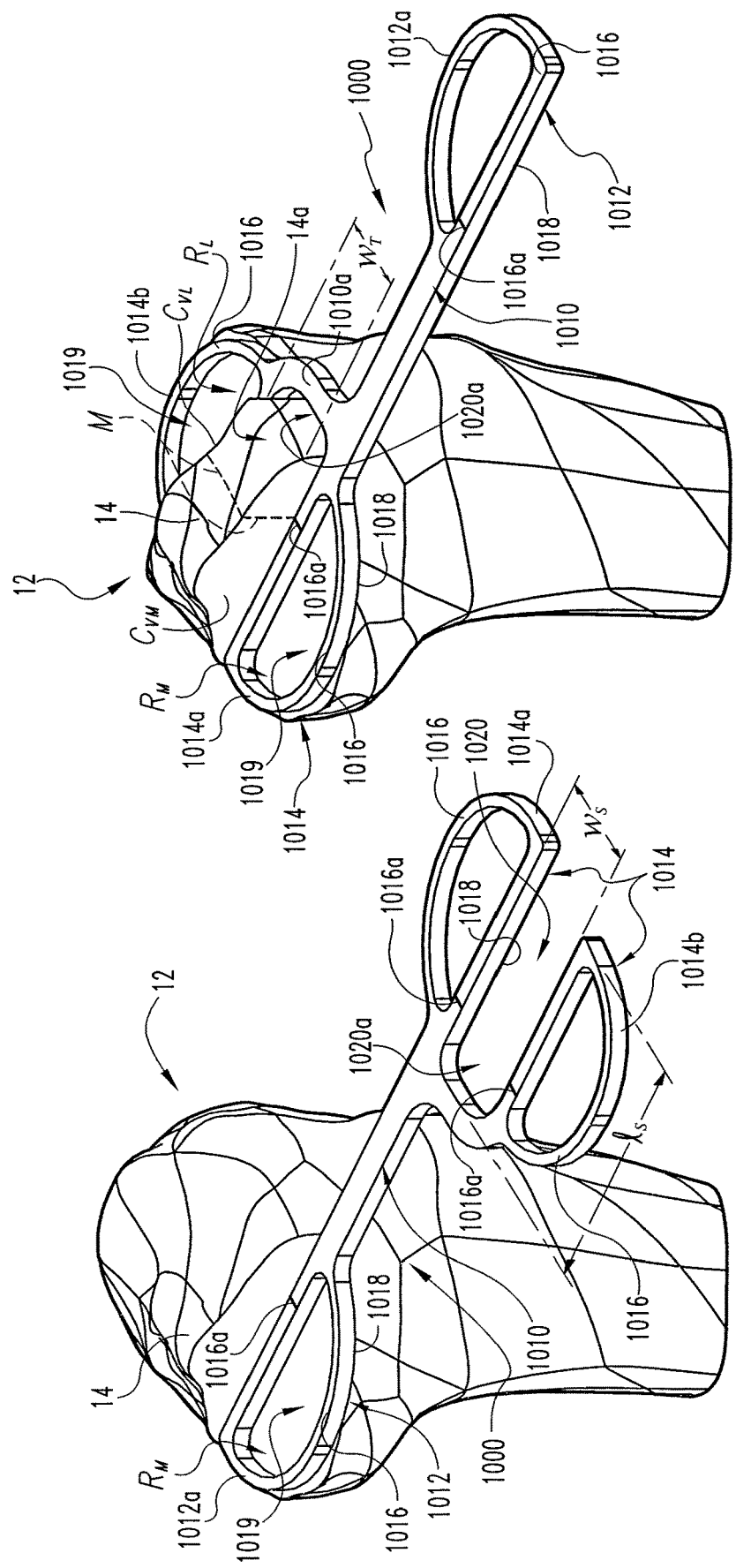
FIG. 59A illustrates a first operational position of the tibia size template of FIG. 57, as shown in relation to the medially resected proximal tibia.
FIG. 59B illustrates a second operational position of the tibia size template of FIG. 57, as shown in relation to the medially and laterally resected proximal tibia.

In a further embodiment, the inferior and superior surfaces 1016, 1018 of the tibia size template 1000 each define reference marks or lines 1016a, 1018a, respectively, along the mesial linear portion of each of the template lobes 1012a, 1014a and 1014b. These reference marks 1016a, 1018a are each located at the same offset position relative to the end of the handle 1010 (i.e., relative to the inward end of each of the lobes 1012a, 1014a and 1014b). As shown in FIGS. 59B and 60B, the reference marks 1016a, 1018a are used as a template to form a reference mark/line M vertically along the vertical medial and lateral resection cuts $C_{VM}$, $C_{VL}$ and across the superior surface of the anterior tibial eminence $14_A$. These reference marks M serve as cut reference lines during removal of the anterior tibial eminence $14_A$ using the anterior chisel 1100 illustrated and described below, and represent the ideal location of the vertical cut along the anterior tibial eminence $14_A$. Although the reference marks M are illustrated as being formed using the dual-lobe template portion 1014 of the tibia size template 1000, it should be understood that the reference marks M can also be made using the single-lobe template portion 1012. Additionally, the reference marks M can be formed on the surface of the bone by scribing, burning, or by any other suitable method for marking bone tissue. Further, each of the tibia template lobes 1012a, 1014a and 1014b includes a hollow interior region 1019 (i.e., the template lobes 1012a, 1014a and 1014b are formed by relatively thin frame-like sections of material) to permit visualization through the template lobes 1012a, 1014a and 1014b when placed on the horizontal resected surfaces of the medial and lateral tibial resections $R_M$, $R_L$, to aid in identifying any misfit or misaligned regions.

The dual-lobe template portion 1014 includes a slot or spacing 1020 separating the medial and lateral tibia template lobes 1014a, 1014b having a width $w_S$ (FIG. 59A) that is slightly larger than the width $w_T$ (FIG. 59B) of the anterior tibial eminence $14_A$ so as to allow the medial and lateral tibia template lobes 1014a, 1014b to be simultaneously positioned on the medial and lateral tibial resections $R_M$, $R_L$, (FIGS. 59B and 60B). Additionally, in some embodiments, the dual-lobe template portion 1014 is used to evaluate the medial and lateral tibial resections $R_M$, $R_L$, prior to resection of the anterior tibial eminence $14_A$ (discussed below). Thus, the overall length $l_S$ of the slot 1020 (FIG. 59A) must be sized to accommodate the full anterior-posterior length of the tibial eminence 14 prior to prior to resection of the anterior tibial eminence $14_A$. Accordingly, the slot 1020 includes an extended portion 1020a that extends beyond the anterior ends of the medial and lateral tibia template lobes 1014a, 1014b adjacent the handle 1010 for receipt of the unresected anterior tibial eminence $14_A$. Stated another way, the handle portion 1010 includes a notched bridge region 1010a that interconnects the medial and lateral tibia template lobes 1014a, 1014b and which is sized to receive the unresected anterior tibial eminence $14_A$ therein.

As should be appreciated, the medial tibia template lobe 1012a of the single-lobe template portion 1012 is configured for positioning on the medial tibial resection $R_M$ (FIGS. 59A and 60A) for evaluation of the peripheral size and shape of the medial tibial resection $R_M$. As should also be appreciated, the medial and lateral tibia template lobes 1014a, 1014b of the dual-lobe template portion 1014 are configured for simultaneous positioning on the medial and lateral tibial resection $R_M$, $R_L$ (FIGS. 59B and 60B) for simultaneous evaluation of the peripheral size and shape of the medial and lateral tibial resection $R_M$, $R_L$. As should be further appreciated, due to the unique configuration of the tibia size template 1000, each of these evaluations can be performed using a single instrument as opposed to two separate instruments. It should also be appreciated that the tibia size template 1000 is ambidextrous, meaning the tibia size template 1000 can be flipped over and used in association with the other knee. Accordingly, a single tibia size template 1000 can be used to perform knee arthroplasty procedures on both the right knee and the left knee. Additionally, although not specifically illustrated in FIGS. 57-60, it should be understood that in an alternative embodiment, another single-lobe template portion may extend from a central portion of the handle 1010 which includes a lateral tibia template lobe configured for positioning on the lateral tibial resection $R_L$ for evaluation of the peripheral size and shape of the lateral tibial resection $R_L$.

L. Anterior Chisel

Figure 61B:
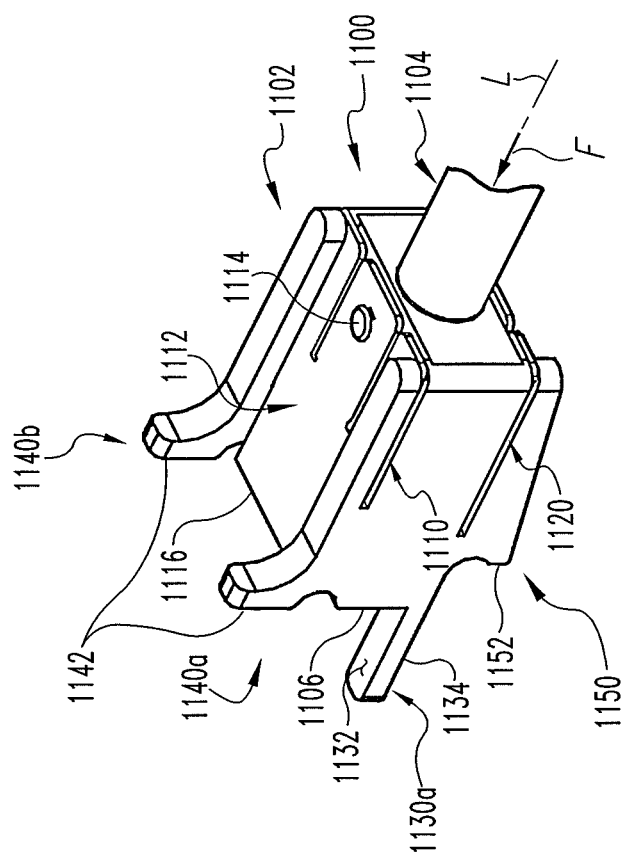
FIG. 61B illustrates another perspective view of the anterior chisel of FIG. 61A.
Figure 61A:
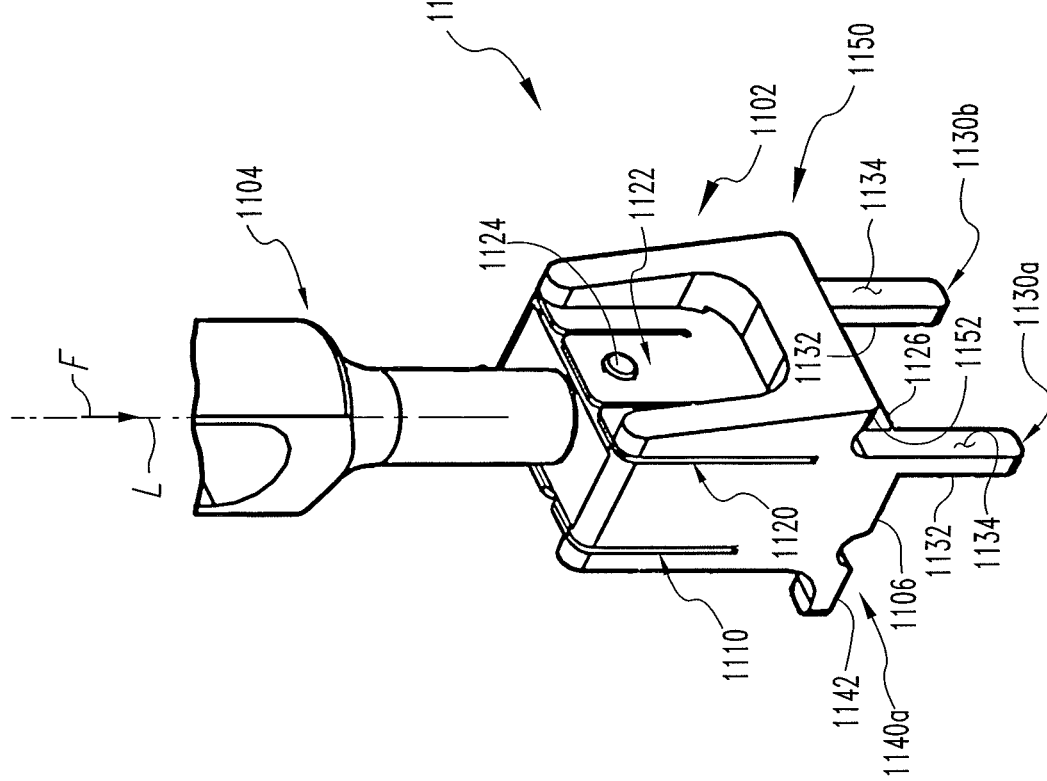
FIG. 61A illustrates a perspective view of an anterior chisel according to one form of the invention.

Referring to FIGS. 61A and 61B, shown therein is an anterior chisel 1100 according to one form of the present invention. As will be discussed in greater detail below, the anterior chisel 1100 is designed and configured to form both vertical and horizontal cuts along the anterior portion $14_A$ of the tibial eminence 14 (FIGS. 64A and 64B) for resection/removal of the anterior tibial eminence portion $14_A$ (FIG. 64C) to provide sufficient clearance for receipt of a tibial implant.

Figure 68:
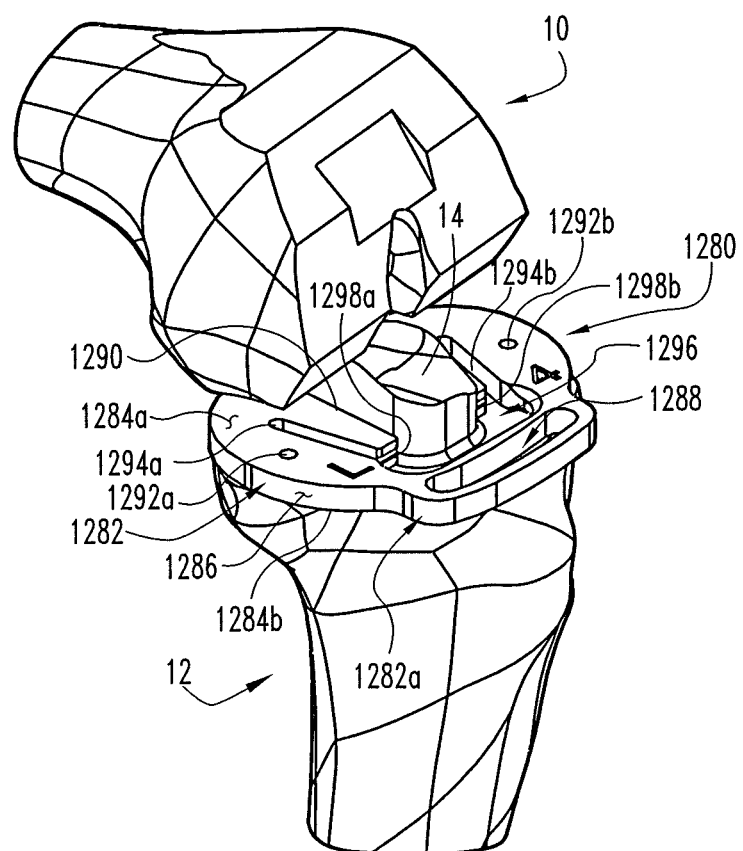
Figure 69:
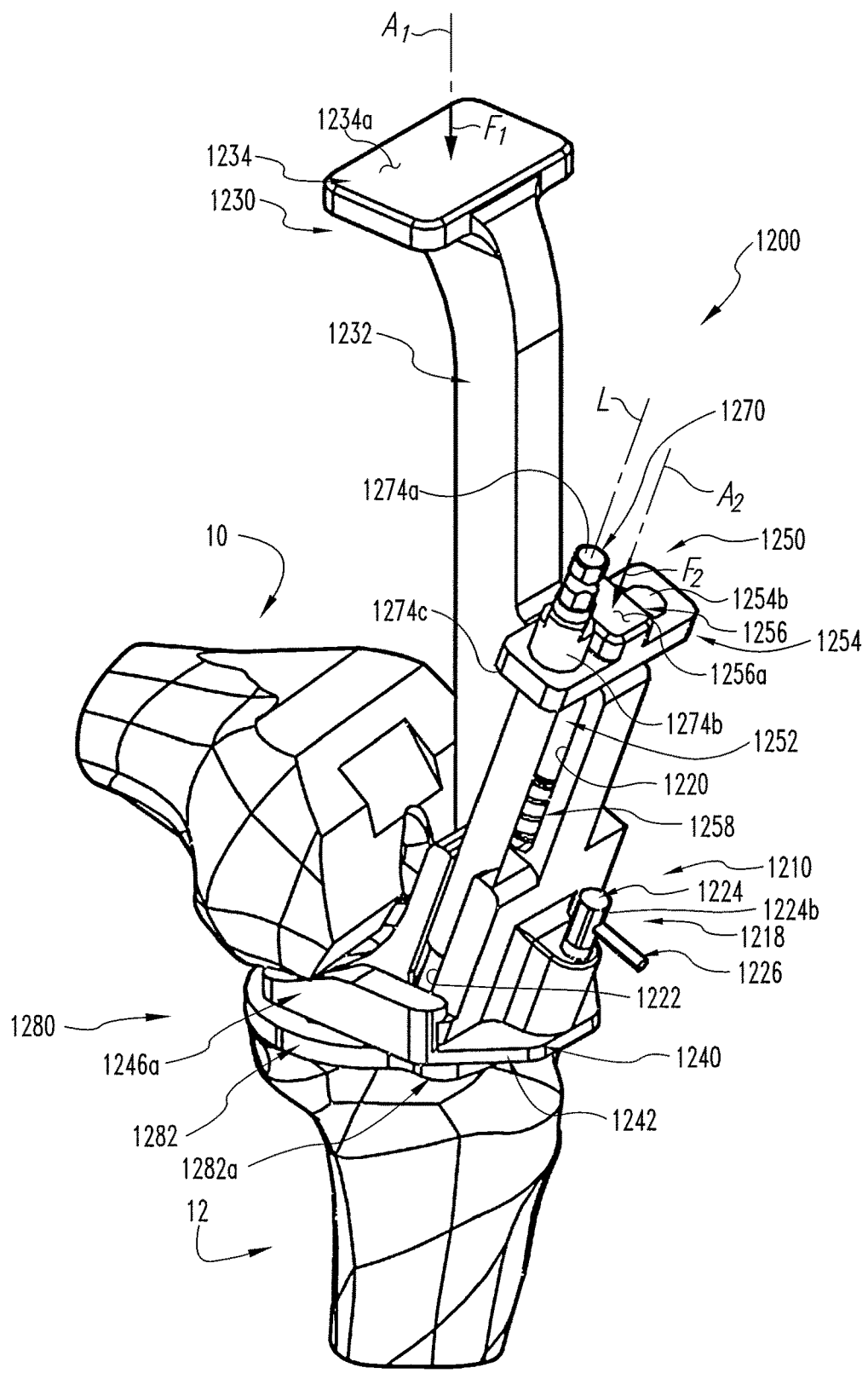

In one embodiment, the anterior portion of the tibial eminence $14_A$ is removed prior to forming keel slots/openings in the resected region of the proximal tibia 12 using the keel formation instrument 1200 illustrated and described below. It should be appreciated that prior removal of the anterior tibial eminence $14_A$ may make formation of the anterior keel slot somewhat easier (i.e., requiring less axial cutting force) because of not having to penetrate through the thickness of the anterior tibial eminence $14_A$. Additionally, removal of the anterior tibial eminence $14_A$ prior to forming the keel slots/openings allows for the use of a tibial baseplate trial having a shape/profile that generally matches that of the tibial implant to be installed on the fully resected proximal tibia 12 to aid in gauging/trialing and/or formation of the keel slots/openings (FIGS. 68 and 69). However, in other embodiments, the anterior tibial eminence $14_A$ may be removed subsequent to forming the keel slots/openings in the resected region of the proximal tibia 12.

In the illustrated embodiment, the anterior chisel 1100 generally includes a cutting block 1102 and an elongate shaft 1104 connected to the cutting block 1102 and extending along a longitudinal axis L. A proximal handle or gripping portion (not shown) may be attached to the proximal end of the elongate shaft 1104 to facilitate manipulation and handling of the anterior chisel 1100 by the user, and to aid in the application of an axial cutting force F onto the elongate shaft 1104 generally along the longitudinal axis L. The axial cutting force F is transmitted along the elongate shaft 1104 and is transferred to the cutting block 1102 to form the vertical and horizontal cuts along the anterior tibial eminence portion $14_A$. The cutting block 1102 includes a substantially flat/planar axially-facing end surface 1106 that is arranged generally perpendicular to the longitudinal axis L.

Figures 63A, 63B:
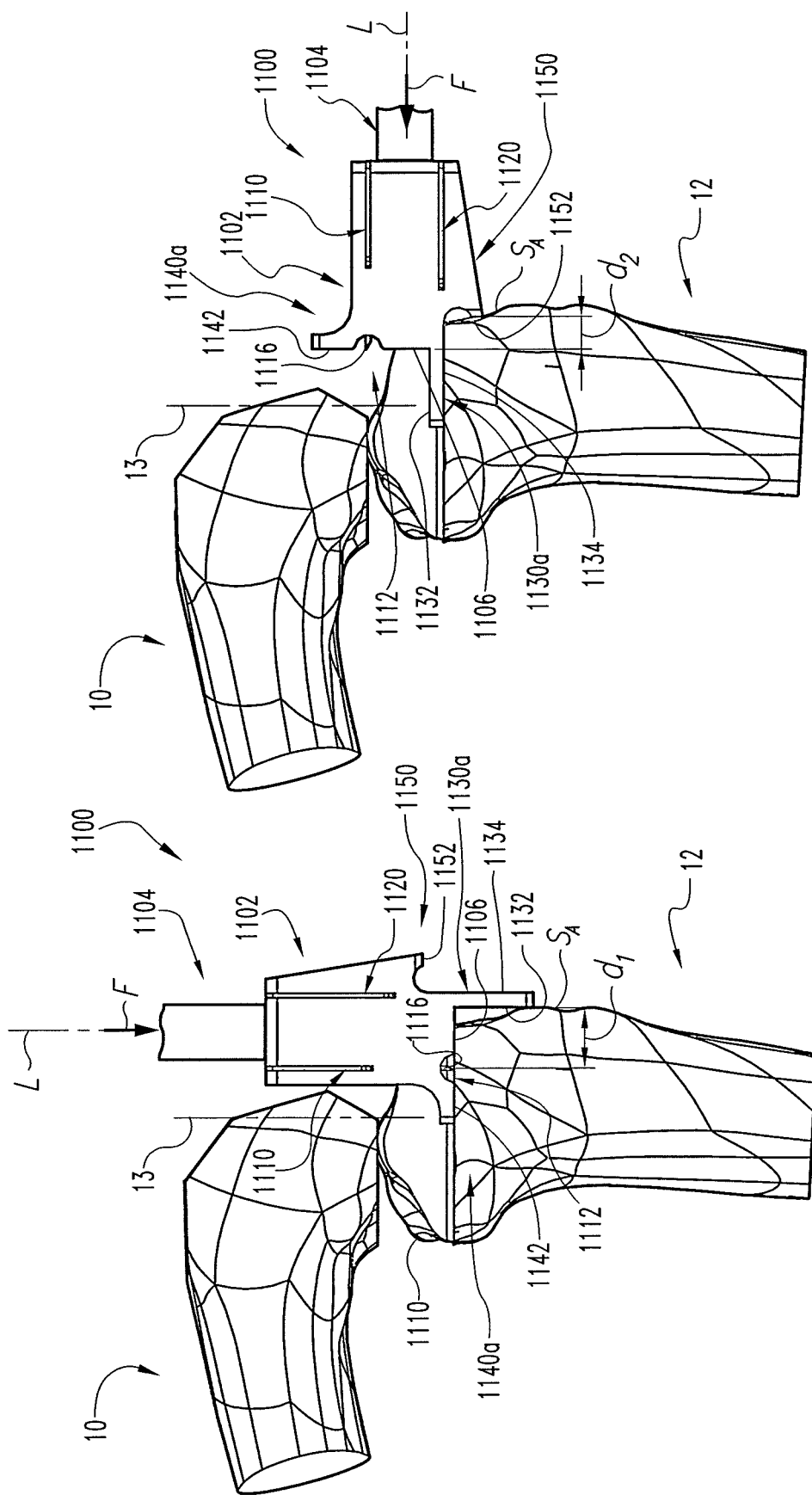
FIG. 63A illustrates a left side view of FIG. 62A.
FIG. 63B illustrates a left side view of FIG. 62B.

In one embodiment, the cutting block 1102 is a single-piece monolithic block defining a hollow interior surrounded by outer walls that define a first slot 1110 sized and configured for receipt of a first cutting blade 1112 extending along a first cutting plane arranged generally parallel with the longitudinal axis L. The first cutting blade 1112 is attached to the cutting block 1102 via a fastener 1114 and includes a distal cutting edge 1116 positioned in general alignment with the planar end surface 1106 of the cutting block 1102 (FIGS. 63A/63B). The outer walls of the cutting block 1102 further define a second slot 1120 sized and configured for receipt of a second cutting blade 1122 extending along a second cutting plane arranged generally parallel with the longitudinal axis L. The second cutting blade 1122 is attached to the cutting block 1102 via a fastener 1124 and includes a distal cutting edge 1126 that is also positioned in general alignment with the planar end surface 1106 of the cutting block

Figure 62B:
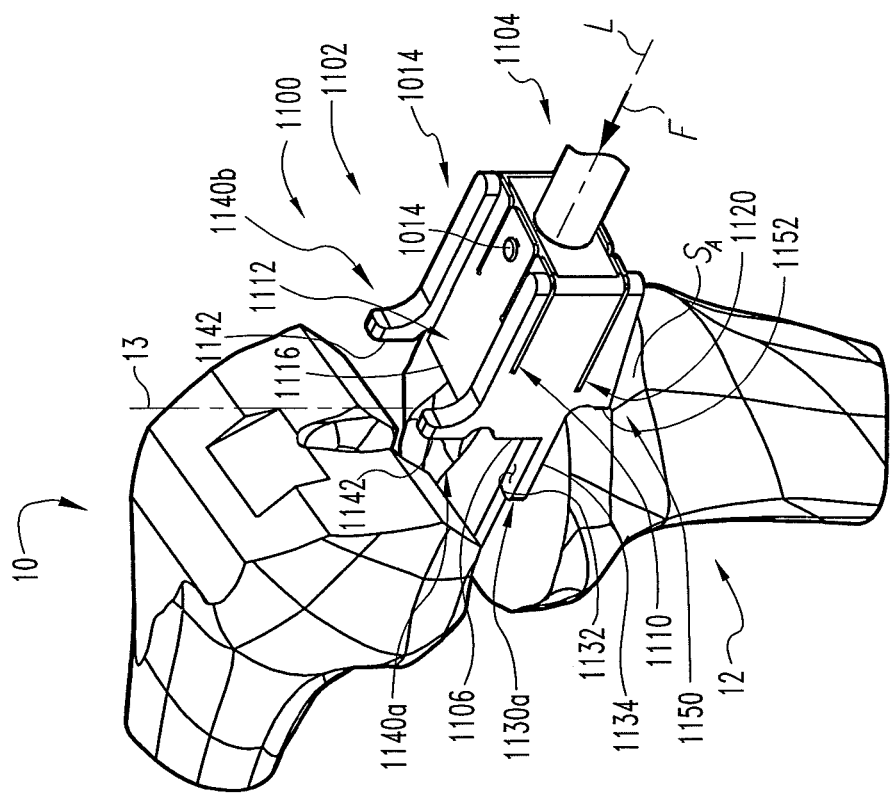
FIG. 62B illustrates the anterior chisel shown in FIG. 61B in relation to the medially and laterally resected proximal tibia.

1102. In the illustrated embodiment, the first cutting plane defined by the first cutting blade 1112 extends substantially parallel with the second cutting plane defined by the second cutting blade 1122. However, other embodiments are also contemplated wherein the first and second cutting planes are not arranged parallel with one another. As will be discussed in greater detail below, the first cutting blade 1112 is arranged to form the vertical cut $C_{VA}$ along the anterior tibial eminence $14_A$ (FIGS. 62A, 63A and 64A), and the second cutting blade 1122 is arranged to form the horizontal cut $C_{HA}$ along the anterior tibial eminence $14_A$ (FIGS. 62B, 63B and 64B).

In the illustrated embodiment, the anterior chisel 1100 also includes alignment and guide features that serve to properly align and guide the cutting blades 1112, 1122 relative to the proximal tibia 12 to form the vertical and horizontal cuts $C_{VA}$, $C_{HA}$ along the anterior tibial eminence $14_A$. The anterior chisel 1100 further includes stop features that limit the bone penetration depth of the vertical and horizontal cuts $C_{VA}$, $C_{HA}$ to prevent the cutting blades 1112, 1122 from cutting too deep into the anterior tibial eminence $14_A$.

In one embodiment, the anterior chisel 1100 includes a pair of elongate legs or axial projections 1130*a*, 1130*b* that extend from the cutting block 1102 in a direction substantially parallel with the longitudinal axis L and which are positioned on opposite sides of the longitudinal axis L. The axial projections 1130*a*, 1130*b* define substantially flat/planar surfaces 1132 along a first side that are arranged generally co-planar with one another, and substantially flat/planar surfaces 1134 along an opposite second side that are arranged co-planar with one another. The planar surfaces 1132 extend along a guide/alignment plane arranged substantially parallel with and offset from the cutting plane of the first cutting blade 1112, and the planar surfaces 1134 extend along a guide/alignment plane arranged substantially parallel and co-planar with the cutting plane of the second cutting blade 1122. As will be discussed below, the flat/planar surfaces 1132, 1134 serve to properly align and guide the cutting blades 1112, 1122 relative to the proximal tibia 12 to form the vertical and horizontal cuts $C_{VA}$, $C_{HA}$ along the anterior tibial eminence $14_A$. Although the axial projections 1130*a*, 1130*b* have been illustrated and described as having a particular configuration, it should be understood that other structures and means for aligning and guiding the anterior chisel 1100 and the cutting blades 1112, 1122 relative to the proximal tibia 12 are also contemplated including, for example, shoulder portions, flange portions, plate portions, lip portions, step portions, or any other structure suitable to align and guide the anterior chisel 1100 and the cutting blades 1112, 1122 relative to the proximal tibia 12.

In another embodiment, the anterior chisel 1100 includes a pair of stop members or feet 1140*a*, 1140*b* that extend from the cutting block 1102 in a direction substantially perpendicular to the longitudinal axis L and which are positioned on opposite sides of the longitudinal axis L. The stop members 1140*a*, 1140*b* define substantially flat/planar axially-facing surfaces 1142 that are arranged substantially co-planar with one another and with the planar end surface 1106 of the cutting block 1102, and which are also arranged substantially perpendicular to the cutting plane of the first cutting blade 1112. As will be discussed below, the flat/planar surfaces 1142 of the stop members 1140*a*, 1140*b* and the planar end surface 1106 of the cutting block 1102 serve to limit the penetration depth of the vertical cut $C_{VA}$ to prevent the cutting blade 1112 from cutting too deep into the anterior tibial eminence $14_A$. Although the stop members 1140*a*, 1140*b* have been illustrated and described as having a particular configuration, it should be understood that other structures and means for limiting travel of the anterior chisel 1100 and the bone penetration depth of the cutting blade 1112 are also contemplated including, for example, shoulder portions, flange portions, lip portions, step portions, interference portions, or any other structure suitable to limit the travel of the anterior chisel 1100 and the bone penetration depth of the cutting blade 1112 into proximal tibia 12.

In a further embodiment, the anterior chisel 1100 includes a stop member or shoulder 1150 defining an axially-facing edge or end surface 1152 (i.e., facing a direction generally along longitudinal axis L). The axially-facing edge or end surface 1152 may be curved or contoured for abutment against a corresponding curved/contoured/irregular anterior surface of the proximal tibia 12, or may alternatively define a substantially flat/planar axially-facing edge or end surface. Additionally, although the shoulder 1150 has been illustrated as extending continuously across the entire width of the cutting block 1102, it should be understood that the shoulder 1150 may alternatively extend across less than the entire width of the cutting block 1102 and/or my extending discontinuously across the width of the cutting block 1102. As will be discussed below, the axially-facing edge or end surface 1152 of the shoulder 1150 serves to limit the bone penetration depth of the horizontal cut $C_{HA}$ to prevent the cutting blade 1122 from cutting too deep into the anterior tibial eminence $14_A$. Although the or shoulder 1150 has been illustrated and described as having a particular configuration, it should be understood that other structures and means for limiting travel of the anterior chisel 1100 and the bone penetration depth of the cutting blade 1122 are also contemplated including, for example, flange portions, lip portions, step portions, interference portions, or any other stop structure suitable to limit the travel of the anterior chisel 1100 and the bone penetration depth of the cutting blade 1122 into proximal tibia 12.

Referring to FIGS. 62-64, reference will now be made to techniques for using the anterior chisel 1100 to form both vertical and horizontal cuts $C_{VA}$, $C_{HA}$ along the anterior portion $14_A$ of the tibial eminence 14 for ultimate removal of the anterior portion $14_A$ to provide sufficient clearance for receipt of a tibial implant. However, it should be understood that other techniques for using the anterior chisel 1100 other than those specifically described herein are also contemplated.

Figure 62A:
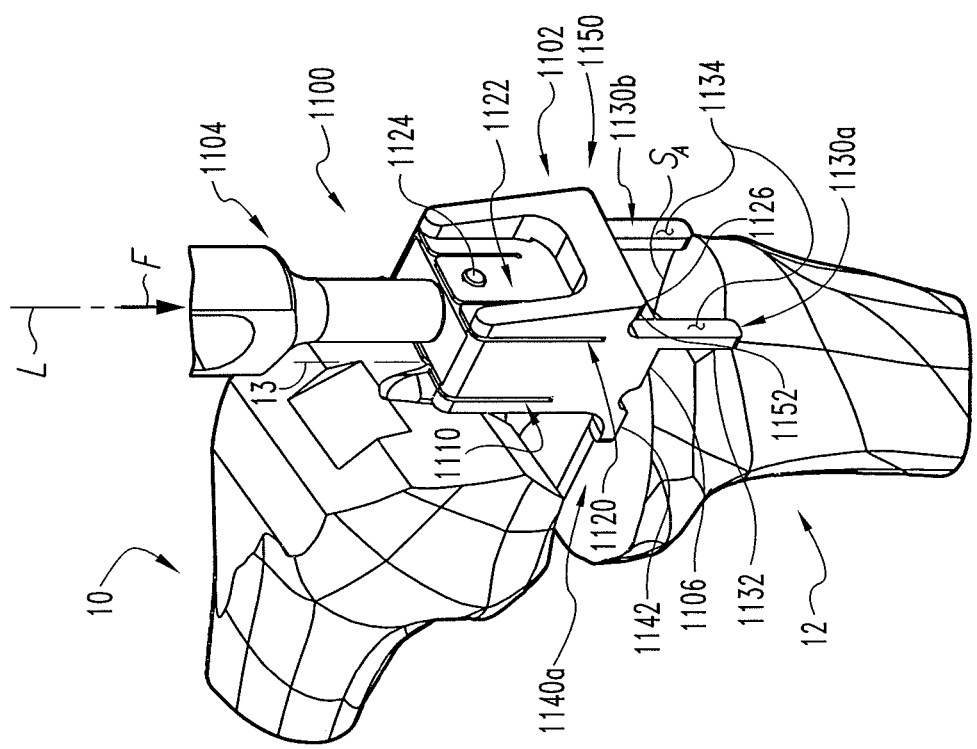
FIG. 62A illustrates the anterior chisel shown in FIG. 61A in relation to the medially and laterally resected proximal tibia.
Figure 64C:
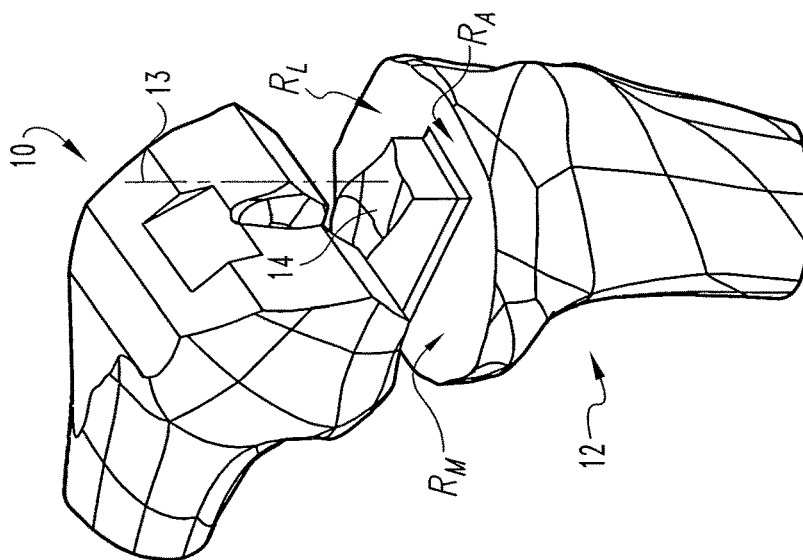
FIG. 64C illustrates a perspective view of the proximal tibia following formation of the vertical and horizontal cuts into the tibial eminence and removal of the superior/anterior portion of the tibial eminence.
Figure 64B:
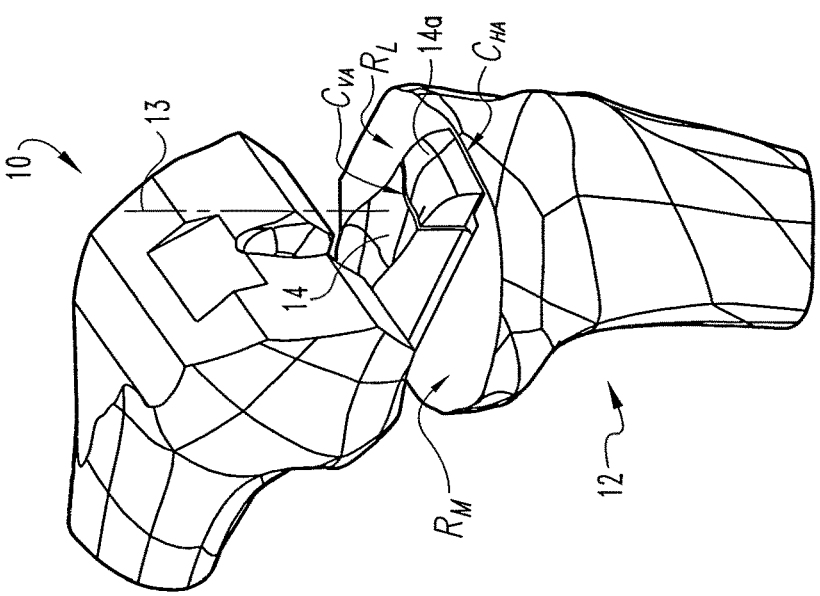
FIG. 64B illustrates a perspective view of the proximal tibia following formation of a horizontal cut into the tibial eminence resulting from the cutting step shown in FIGS. 62B and 63B.
Figure 64A:
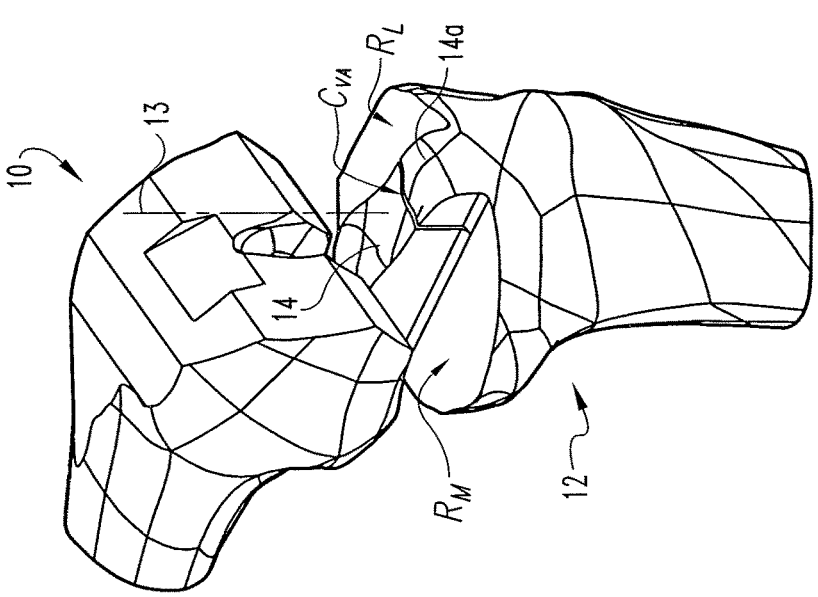
FIG. 64A illustrates a perspective view of the proximal tibia following formation of a vertical cut into the tibial eminence resulting from the cutting step shown in FIGS. 62A and 63A.

Referring specifically to FIGS. 62A, 63A and 64A, shown therein is the step of forming a vertical anterior cut $C_{VA}$ along the anterior tibial eminence $14_A$ using the anterior chisel 1100. The anterior chisel 1100 is initially positioned above and generally aligned with the anterior tibial eminence $14_A$, with the longitudinal axis L of the elongate shaft 1104 arranged generally parallel with the anatomic mechanical axis 13 of the proximal tibia 12. The planar guide/alignment surfaces 1132 defined by the axial projections 1130*a*, 1130*b* are then positioned in contact with the anterior surface $S_A$ of the proximal tibia 12, and the cutting edge 1116 of the first cutting blade 1112 is positioned adjacent the superior surface of the anterior tibial eminence $14_A$. Additionally, the cut reference marks/lines M (FIGS. 59B/60B) previously formed along the vertical medial and lateral resection cuts $C_{VM}$, $C_{VL}$ and across the superior surface of the anterior tibial eminence $14_A$ (using the tibia size template 1000) are used as an alignment/verification aid prior to and during formation of the vertical anterior cut $C_{VA}$. As indicated above, the reference marks M represent the ideal location for the vertical anterior cut $C_{VA}$, and are used as a check/verification via alignment of the cutting edge 1116 of the first cutting blade 1112 with the reference marks M.

An axial cutting force F is then applied to the elongate shaft 1104 which is transmitted to the cutting block 1102 and the first cutting blade 1112 to form the vertical anterior cut $C_{VA}$ along the anterior tibial eminence $14_A$ (FIG. 64A). During formation of the vertical anterior cut $C_{VA}$, the planar guide/alignment surfaces 1132 defined by the axial projections 1130a, 1130b slide along the anterior surface $S_A$ of the proximal tibia 12 to guide the anterior chisel 1100 along the proper cutting plane and to maintain the anterior chisel 1100 in a generally parallel relationship with the anatomic mechanical axis 13 of the proximal tibia 12. Furthermore, displacement of the anterior chisel 1100 is limited by abutment of the flat/planar stop surfaces 1142 defined by the feet 1140a, 1140b and the planar end surface 1106 of the cutting block 1102 against the horizontal planar surfaces of the medial and lateral resections $R_M$, $R_L$ on either side of the tibial eminence 14. Notably, the penetration depth of the first cutting blade 1112 is limited by such abutment so as to prevent the first cutting blade 1112 from cutting too deep into the anterior tibial eminence $14_A$ and potentially weakening the remaining portion of the tibial eminence 14. The penetration depth of the first cutting blade 1112 is preferably limited to the plane defined by the flat/planar stop surfaces 1142 of the feet 1140a, 1140b and the planar end surface 1106 of the cutting block 1102 (which corresponds to the resection plane defined by the planar horizontal surfaces of the medial and lateral resections $R_M$, $R_L$ on either side of the tibial eminence 14).

As should be appreciated, the location of the vertical anterior cut $C_{VA}$ along the anterior tibial eminence $14_A$ in the anterior-posterior direction is determined by the cut reference marks/lines M (FIGS. 59B/60B) previously formed along the vertical medial and lateral resection cuts $C_{VM}$, $C_{VL}$ and across the superior surface of the anterior tibial eminence $14_A$ using the tibia size template 1000, and are used as an alignment/verification aid prior to and during formation of the vertical anterior cut $C_{VA}$. In an alternative embodiment, the location of the vertical anterior cut $C_{VA}$ along the anterior tibial eminence 14a is determined by the offset distance $d_1$ between the planar guide/alignment surfaces 1132 defined by the axial projections 1130a, 1130b and the cutting plane defined by the first cutting blade 1112. As should also be appreciated, the anterior chisel 1100 may be designed with the appropriate offset distance $d_1$ to accommodate for a desired anterior-posterior location of the vertical anterior cut $C_{VA}$. Additionally, a set of anterior chisels 1100 may be provide having different offset distances $d_1$ to accommodate for varying anterior-posterior locations of the vertical anterior cut $C_{VA}$. In the illustrated embodiment, the anterior chisel 1100 is configured to provide a vertical anterior cut $C_{VA}$ along the anterior tibial eminence $14_A$ that is substantially vertical and parallel with the anatomic mechanical axis 13 of the tibia, and substantially perpendicular to the vertical surfaces of the medial and lateral resections $R_M$, $R_L$. However, other embodiments are also contemplated where the vertical anterior cut $C_{VA}$ may be tapered relative to a true vertical orientation, angled either in a superior-inferior direction or a medial-lateral direction (i.e., internal/external rotation).

Referring to FIGS. 62B, 63B and 64B, shown therein is the step of forming a horizontal anterior cut $C_{HA}$ along the anterior tibial eminence $14_A$ using the anterior chisel 1100. The anterior chisel 1100 is initially positioned anterior to and generally aligned with the anterior tibial eminence $14_A$, with the longitudinal axis L of the elongate shaft 1104 oriented generally perpendicular to the anatomic mechanical axis 13 of the proximal tibia 12. The planar guide/alignment surfaces 1134 defined by the axial projections 1130a, 1130b are then positioned in contact with the horizontal planar surfaces of the medial and lateral resections $R_M$, $R_L$ on either side of the tibial eminence 14, and the cutting edge 1126 of the second cutting blade 1122 is positioned in contact with the anterior surface of the anterior tibial eminence $14_A$.

An axial cutting force F is then applied to the elongate shaft 1104 which is transmitted to the cutting block 1102 and the second cutting blade 1122 to form the horizontal anterior cut $C_{HA}$ along the anterior tibial eminence $14_A$ (FIG. 64A). During formation of the horizontal anterior cut $C_{HA}$, the planar guide/alignment surfaces 1134 defined by the axial projections 1130a, 1130b slide along the horizontal planar surfaces of the medial and lateral resections $R_M$, $R_L$ on either side of the tibial eminence 14 to guide the anterior chisel 1100 along the proper cutting plane and to maintain the anterior chisel 1100 in a generally perpendicular orientation relative to the anatomic mechanical axis 13 of the proximal tibia 12. Furthermore, displacement of the anterior chisel 1100 is limited by abutment of the axially-facing edge or end surface 1152 defined by the shoulder 1150 against the anterior surface $S_A$ of the proximal tibia 12. Notably, the penetration depth of the second cutting blade 1122 is limited by such abutment so as to prevent the second cutting blade 1122 from cutting too deep into the anterior tibial eminence $14_A$ and potentially weakening the remaining portion of the tibial eminence 14. The penetration depth of the second cutting blade 1122 is preferably limited to the plane defined by the planar end surface 1106 of the cutting block 1102.

As should be appreciated, the penetration depth of the horizontal anterior cut $C_{HA}$ in the anterior-posterior direction is determined by the offset distance $d_2$ between the axially-facing edge or end surface 1152 defined by the shoulder 1150 and the distal cutting edge 1126 defined by the second cutting blade 1122 (with the cutting edge 1126 preferably aligned with the planar end surface 1106 of the cutting block 1102). As should also be appreciated, the anterior chisel 1100 may be designed with the appropriate offset distance $d_2$ to accommodate for a desired penetration depth of the second cutting blade 1122 in an anterior-posterior direction to form the horizontal anterior cut $C_{HA}$. The penetration depth of the second cutting blade 1122 is preferably determined such that the horizontal anterior cut $C_{HA}$ just intersects the vertical anterior Cut $C_{VA}$ but does not extend significantly beyond the vertical anterior cut $C_{VA}$. Additionally, a set of anterior chisels 1100 may be provide having different offset distances $d_2$ to accommodate for varying penetration depths of the second cutting blade 1122 in an anterior-posterior direction to form the appropriate horizontal anterior cut $C_{HA}$. In the illustrated embodiment, the anterior chisel 1100 is configured to provide a horizontal anterior cut $C_{HA}$ along the anterior tibial eminence $14_A$ that is substantially parallel and co-planar with the horizontal planar surfaces of the medial and lateral resections $R_M$, $R_L$ on either side of the tibial eminence 14. However, other embodiments are also contemplated where the horizontal anterior cut $C_{HA}$ may be tapered relative to the horizontal planar surfaces of the medial and lateral resections $R_M$, $R_L$.

Referring to FIG. 64C, upon formation of the vertical anterior cut $C_{VA}$ and the horizontal anterior cut $C_{HA}$, the bone fragment defining the anterior tibial eminence $14_A$ may be removed to thereby complete the anterior resection $R_A$, which in combination with the medial and lateral resections $R_M$, $R_L$ provides sufficient clearance for installation of a tibial implant onto the resected proximal tibia 12. Additionally, the antero-medial and antero-lateral corners of the tibial eminence 14 shown in FIG. 64C can be rounded to form eminence radii along the corners (FIG. 68). The eminence radii generally serve to provide additional clearance for receipt of the installed tibial implant, and are made by trimming the sharp antero-medial and antero-lateral eminence corners with a rongeur tool or other bone cutting/contouring instruments. Alternatively, the eminence radii may be formed by cutting die features incorporated into the first cutting blade 1112, the cutting block 1100 or, in other embodiments, the keel cavity formation instrument 1200 illustrated and described below.

As should now be appreciated, the anterior chisel 1100 can be used to form both the vertical anterior cut $C_{VA}$ and the horizontal anterior cut $C_{HA}$ to resect the anterior tibial eminence $14_A$, as opposed to using two separate cutting instruments to form these cuts. Additionally, the anterior chisel 1100 includes built-in alignment and guide features that serve to properly align and guide the cutting blades 1112, 1122 to form the vertical and horizontal cuts $C_{VA}$, $C_{HA}$, and also included built-in stop features that limit the bone penetration depth of the vertical and horizontal cuts $C_{VA}$, $C_{HA}$ to prevent the cutting blades 1112, 1122 from cutting too deep into the anterior tibial eminence $14_A$ which might otherwise weaken the remaining portion of the tibial eminence 14 and risk a tibial eminence fracture. These built-in features significantly reduce the risks normally associated with resection of the anterior tibial eminence $14_A$.

M. Keel Cavity Formation Instrument

Figure 65:
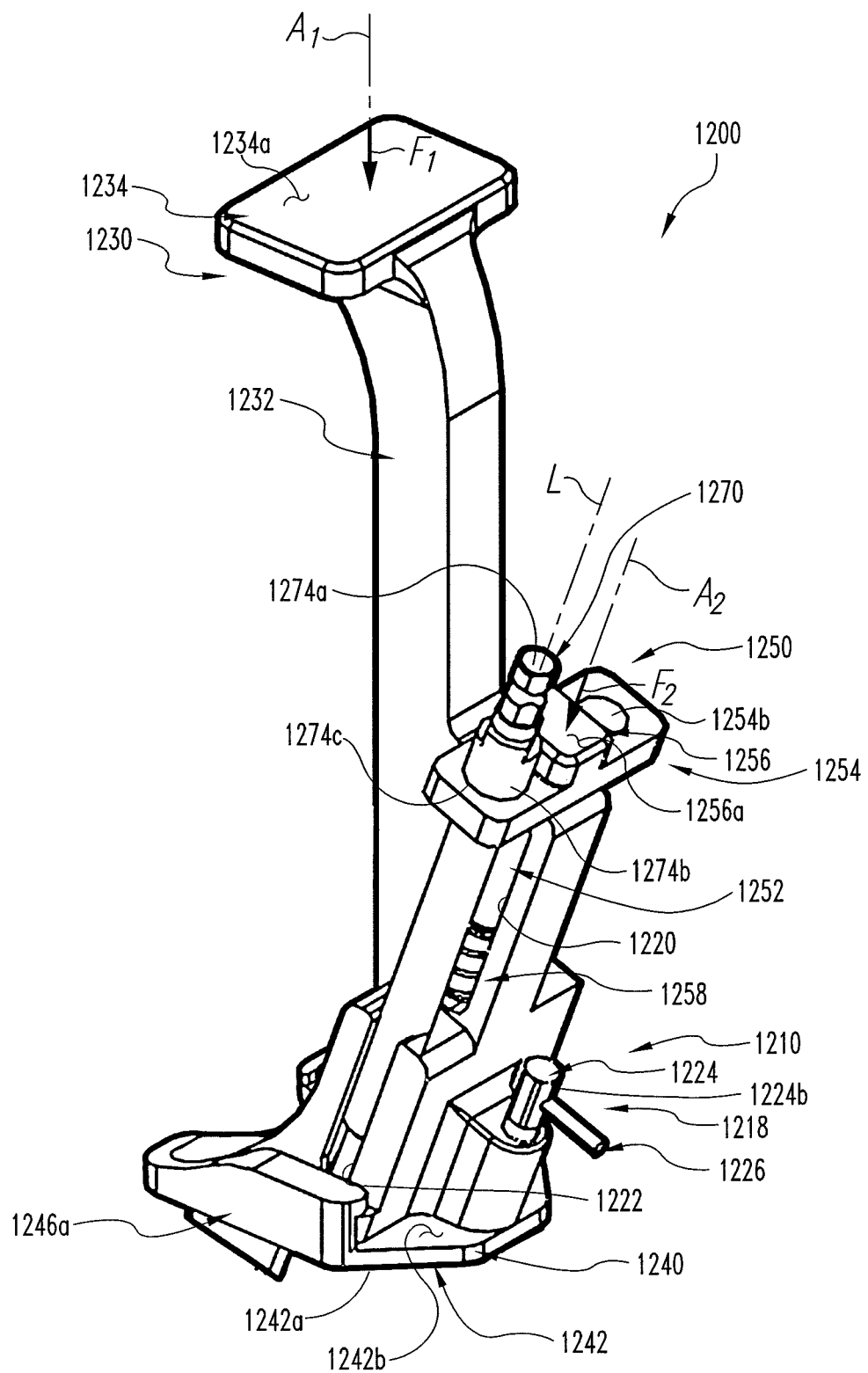
Figure 66:
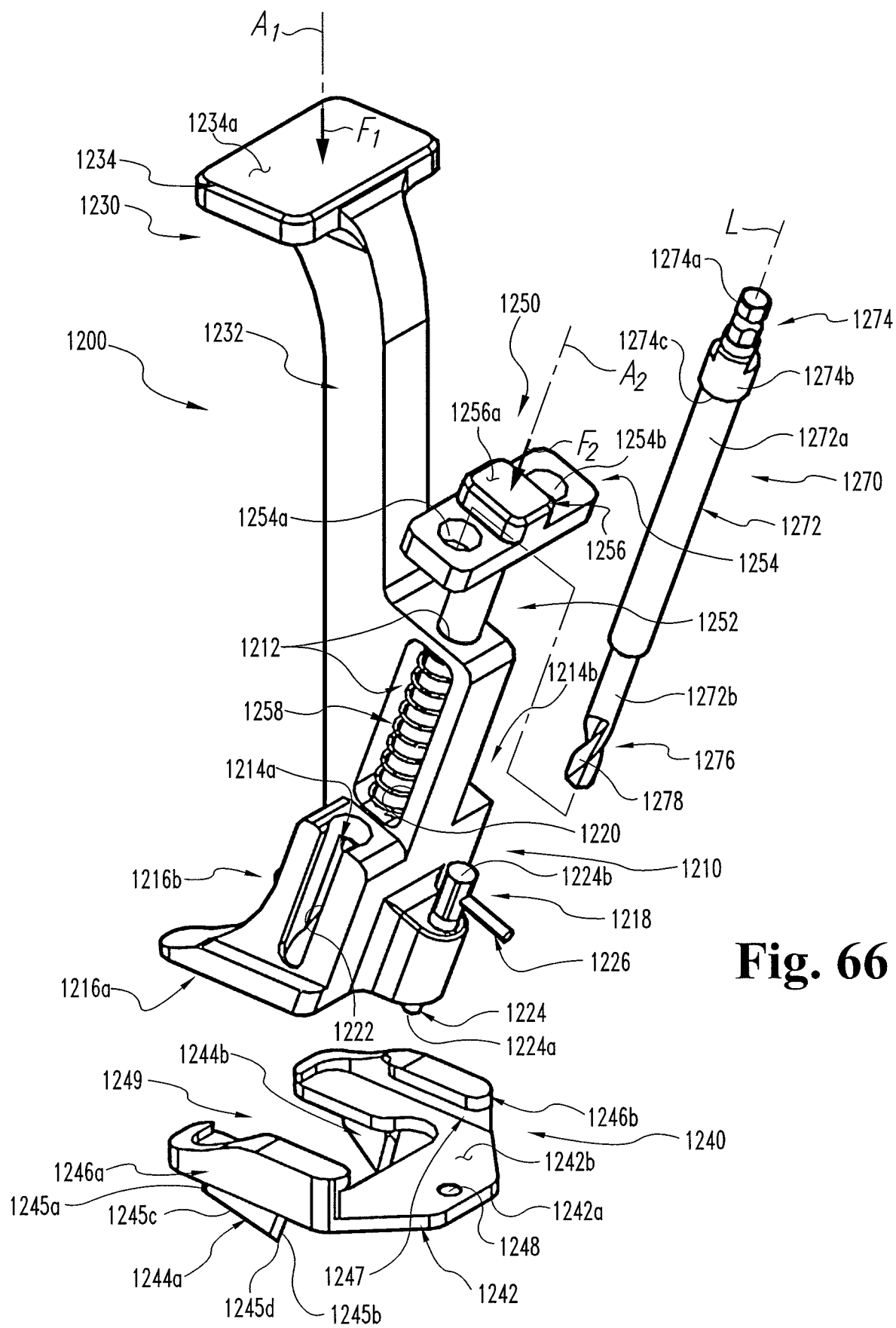
Figure 67:
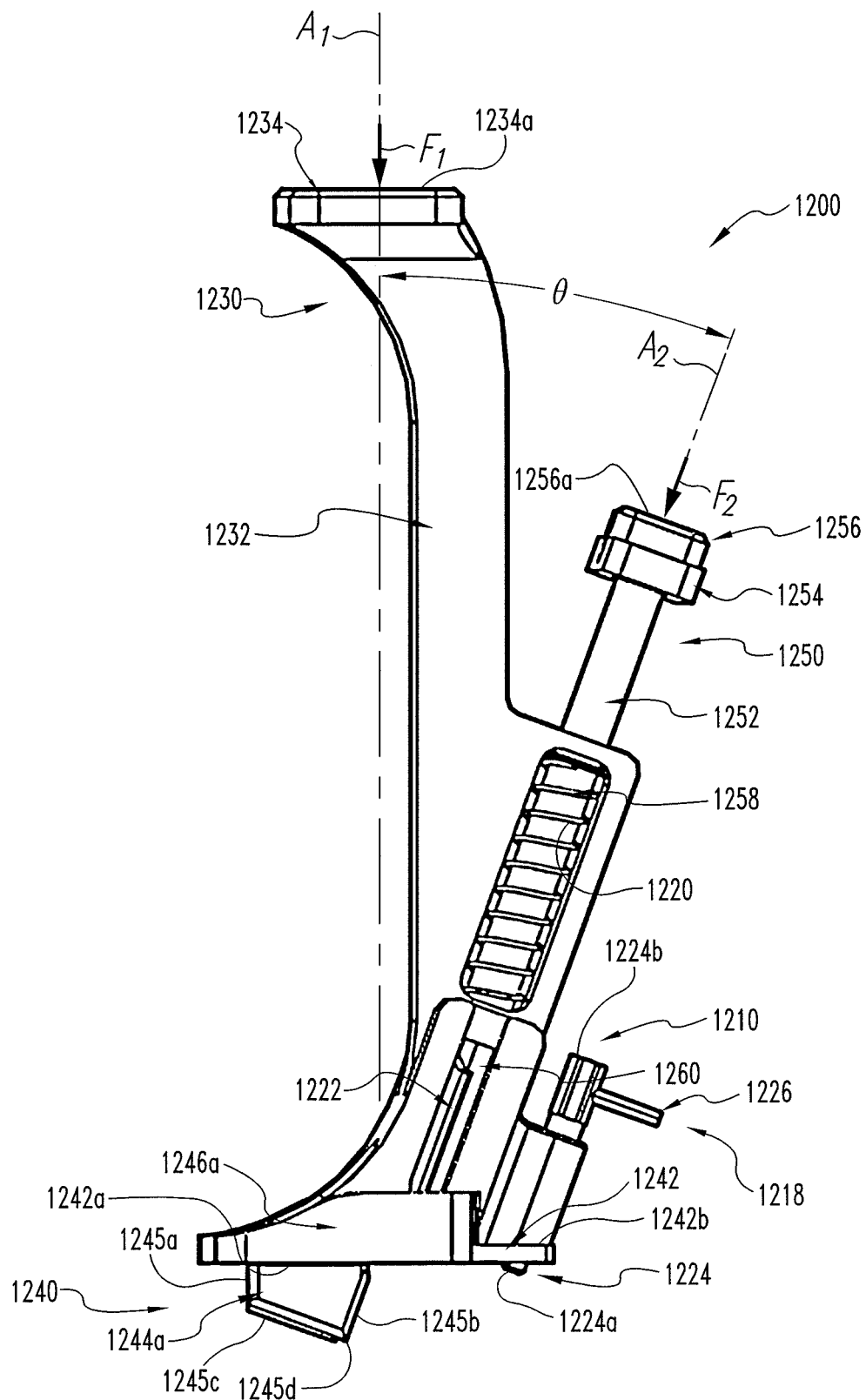

Referring to FIGS. 65-67, shown therein is a keel cavity formation instrument 1200 according to one form of the present invention. As will be discussed in greater detail below, the keel cavity formation instrument 1200 is used to form a keel cavity including one or more slots/openings in the medial and lateral resected regions $R_M$, $R_L$ and the anterior resected region $R_A$ of the proximal tibia 12 (FIGS. 71A-71C), with the slots/openings sized and shaped to receive keels or other projections extending from the tibial implant to be installed onto the proximal tibia 12.

In the illustrated embodiment, the keel cavity formation instrument 1200 is configured to form various portions of the keel cavity in multiple steps to lower the maximum input or impaction force that would otherwise be necessary if the entire keel cavity were formed simultaneously in a single step. Forming the keel cavity in multiple steps also allows portions of the keel cavity to be formed via an input/impaction force exerted along the anatomic mechanical axis of the tibia (which is the preferred direction of the input/impaction force to minimize potential harmful effects on the tibia such as a tibial fracture), and also allows the portions of the keel cavity that must be formed via an oblique input/impaction force (a force exerted at an angle relative to the anatomic mechanical axis of the tibia) to be formed separately, thereby reducing the extent of the oblique input/impaction force necessary to form the overall keel cavity. Additionally, portions of the keel cavity are formed via drilling or boring, thereby further reducing the input/impaction force necessary to form the overall keel cavity.

The keel cavity formation instrument 1200 generally includes a main body 1210, a vertical punch handle 1230 rigidly connected to the main body 1210 and extending along a vertical punch axis $A_1$ (FIG. 67), a keel punch plate 1240 removably attached to the main body 1210, an angled punch handle 1250 movably connected to the main body 1210 and extending along an angled punch axis $A_2$ (FIG. 67), an angled keel punch blade 1260 (FIG. 70B) extending from the angled punch handle 1250 and also arranged along the angled punch axis $A_2$, and a drill bit 1270 displaceable along drill guide passages formed in the angled punch handle 1250 and the main body 1210. Additionally, the keel cavity formation instrument 1200 is used in association with a tibial baseplate trial 1280 attached to the resected proximal tibia 12 which serves as both a gauge and a foundation/guide for the keel cavity formation instrument 1200. Details regarding each of these elements will be set forth below.

In the illustrated embodiment, the main body 1210 generally includes an angled passage 1212 (FIG. 66) extending therethrough along the angled punch axis $A_2$, and a pair of drill guide passages or barrels 1214a, 1214b (FIG. 66) extending along guide axes arranged generally parallel with the angled punch axis $A_2$ and arranged symmetrically on opposites sides of the angled punch axis $A_2$ and the angled passage 1212. The drill guide passages or barrels 1214a, 1214b are sized and configured to guidingly receive a proximal guide shaft portion 1272a of the drill bit 1270 therethrough for guiding displacement of the drill bit 1270 in a direction generally parallel with the angled punch axis $A_2$. In the illustrated embodiment of keel cavity formation instrument 1200, the angled punch axis $A_2$ is oriented at an offset angle α (FIG. 67) of approximately 20° relative to the vertical punch axis $A_1$. However, it should be understood that other offset angles α between the angled punch axis $A_2$ and the vertical punch axis $A_1$ are also contemplated, including offset angles α greater than 20° or offset angles α less than 20°.

The main body 1210 further includes a pair of transverse flanges or tongues 1216a, 1216b (FIG. 66) extending from opposite sides of an inferior portion of the main body 1210 in a medial-lateral direction, and a fastener or lock member 1218 extending through an opening (not shown) in an anterior portion of the main body 1210 and arranged along an axis generally parallel with the angled punch axis A and configured to releasably attach the keel punch plate 1240 to the main body 1210. The main body 1210 also defines a visualization window 1220 extending transversely therethrough and positioned in communication with the angled passage 1212 to provide visualization of the angled punch handle 1250 positioned in the angled passage 1212, and a visualization window 1222 extending transversely therethrough and positioned in communication with the drill guide passages 1214a, 1214b and the angled passage 1212 to provide visualization of the angled keel punch blade 1260 positioned in the angled passage 1212 and the drill bit 1270 positioned in either of the drill guide passages 1214a, 1214b. The fastener or lock member 1218 includes a shaft 1224 having a distal end portion 1224a configured for engagement/disengagement within an opening 1248 in the keel punch plate 1240, and also having a proximal head portion 1224b extending from a superior surface of the main body 1210. The fastener or lock member 1218 further includes a lever or handle 1228 extending transversely from the proximal head portion 1224b and configured to facilitate rotation of the lock member 1218 and engagement/disengagement of the distal end portion 1224a within the opening 1248.

In the illustrated embodiment, the vertical punch handle 1230 generally includes an axial shaft portion 1232 extending generally along the vertical punch axis $A_1$ and having a distal end connected to the main body 1210 and a proximal end connected to a proximal handle portion or impaction plate 1234 which defines a substantially flat/planar superior impaction surface 1234a. As indicated above, the vertical punch handle 1230 is rigidly connected to the main body 1210. However, in alternative embodiments, the vertical punch handle 1230 may be removably and/or movably attached to the main body 1210. As should be appreciated, the flat/planar superior impaction surface 1234*a* of the impaction plate 1234 is configured for receipt of an axial force $F_1$, such as an impaction force, applied to the impaction plate 1234 in a direction generally along the vertical punch axis $A_1$. The impaction force $F_1$ is transmitted along the axial shaft portion 1232, through the main body 1210, and transmitted to the keel punch plate 1240 to drive a pair of keel formation wings or fins 1244*a*, 1244*b* of the keel punch plate 1240 into the medial and lateral resected regions $R_M$, $R_L$, of the proximal tibia 12. Although the axial force $F_1$ is illustrated and described as being applied to the impaction plate 1234 (e.g., via a mallet), other structures and techniques for applying the axial force $F_1$ to the keel formation instrument 1200 are also contemplated including, for example, via a slap hammer coupled to the main body portion 1210 or connected directly to the keel punch plate 1240.

In the illustrated embodiment, the keel punch plate 1240 generally includes a generally flat plate portion 1242 including a pair of keel formation wings or fins 1244*a*, 1244*b* extending from an inferior surface 1242*a* of the plate portion 1242. When the keel punch plate 1240 is attached to the main body 1210 and the keel formation instrument 1200 is properly positioned relative to the proximal tibia 12, the keel formation fins 1244*a*, 1244*b* are arranged on opposite sides of the vertical punch axis $A_1$ and include fin lengths that are outwardly tapered relative to one another in an anterior-posterior direction (FIG. 71A). Additionally, as illustrated in FIG. 67, the keel formation fins 1244*a*, 1244*b* each include a posterior surface 1245*a* extending generally along the vertical punch axis $A_1$, an anterior surface 1245*b* extending generally along the angled punch axis $A_2$, and an inferior surface 1245*c* extending from the posterior surface 1245*a* to the anterior surface 1245*b* and arranged generally perpendicular to the anterior surface 1245*b*. In this arrangement, the keel formation fins 1244*a*, 1244*b* each defines a generally pointed distal-most corner or edge 1245*d* that facilitates penetration of the keel formation fins 1244*a*, 1244*b* into tibial bone. As shown in FIG. 71A, the keel formation fins 1244*a*, 1244*b* are sized and shaped to form medial and lateral keel receiving slots $S_M$, $S_L$ in the medial and lateral resected regions $R_M$, $R_L$ of the proximal tibia 12.

The generally flat plate portion 1242 also includes a pair of L-shaped connection flanges 1246*a*, 1246*b* extending from a superior surface 1242*b* of the plate portion 1242 and each defining a transversely extending groove 1247 sized and configured for receipt of the transverse flanges or tongues 1216*a*, 1216*b* of the main body 1210 therein to removably engage the keel punch plate 1240 to the main body 1210. The generally flat plate portion 1242 also defines an opening 1248 configured to receive the distal end portion 1224*a* of the lock member 1218 associated with the main body 1210 to removably lock the keel punch plate 1240 to the main body 1210. Additionally, the generally flat plate portion 1242 of the keel punch plate 1240 also defines an open region 1249 sized and configured to receive the tibial eminence 14 therein when the keel punch plate 1240 is positioned on the resected proximal tibia 12, and which is also sized and configured to receive the angled keel punch blade 1260 and the distal cutting portion of the drill bit 1270 therethrough during formation of the anterior keel slot and openings in the anterior region of the resected proximal tibia 12, further details of which will be set forth below. As should be appreciated, the keel punch plate 1240 is a modular feature of the keel cavity formation instrument 1200 that can be easily removed from the main body 1210 of the instrument and replaced with a different keel punch plate 1240 having a different size and/or different keel formation fins 1244*a*, 1244*b*. It should be further appreciated that multiple keel punch plates 1240 having different sizes and/or fin features can be provided in a kit or set, thereby allowing for the selection of a keel punch plate 1240 having the appropriate size/fin features to accommodate the specific requirements of a particular knee arthroplasty procedure.

In the illustrated embodiment, the angled punch handle 1250 generally includes an axial shaft portion 1252 extending generally along the angled punch axis $A_2$ and movably positioned in the angled passage 1212 in the main body 1210 for guided axial movement or displacement generally along the angled punch axis $A_2$ relative to the main body 1210. The axial shaft portion 1252 includes a distal end connected to the angled keel punch blade 1260 and a proximal end connected to a proximal drill guide plate 1254, which in turn defines a pair of drill guide passages 1254*a*, 1254*b* extending along axes positioned on opposite sides of the angled punch axis $A_2$ and arranged generally parallel with the angled punch axis $A_2$. The drill guide passages 1254*a*, 1254*b* are sized and configured to guidingly receive a proximal guide shaft portion 1272*a* of the drill bit 1270 therethrough for guiding displacement of the drill bit 1270 in a direction generally parallel with the angled punch axis $A_2$. An impaction plate 1256 extends from a superior surface of the drill guide plate 1254 and defines a substantially flat/planar superior impaction surface 1256*a*. As should be appreciated, the flat/planar superior impaction surface 1256*a* of the impaction plate 1256 is configured for receipt of an axial force $F_2$, such as an impaction force, applied to the impaction plate 1256 in a direction generally along the angled punch axis $A_2$. The impaction force $F_2$ is transmitted along the axial shaft portion 1252 and is transmitted to the angled keel punch blade 1260 to drive the angled keel punch blade 1260 into the anterior resected region $R_A$ of the proximal tibia 12. Although the axial force $F_2$ is illustrated and described as being applied to the impaction plate 1256 (e.g., via a mallet), other structures and techniques for applying the axial force $F_2$ to the angled punch handle 1250 are also contemplated including, for example, via a slap hammer coupled to the axial shaft portion 1252 or connected directly to the angled keel punch blade 1260. The angled punch handle 1250 further includes a biasing member or spring 1258 extending about the axial shaft portion 1252 and positioned within the angled passage 1212 in the main body 1210 to bias the angled punch handle 1250 (and the angled keel punch blade 1260) in an axial direction generally along the angled punch axis $A_2$ toward a superior or retracted position for protection of the cutting edges of the angled keel punch blade 1260 during periods of non-use.

In the illustrated embodiment, the angled keel punch blade 1260 generally includes a distal keel formation blade 1262 arranged generally along the angled punch axis $A_2$. When the keel formation instrument 1200 is properly positioned relative to the proximal tibia 12, the distal keel formation blade 1262 includes a blade length that generally extends in a medial-lateral direction and transverse to the lengths of the keel formation fins 1244*a*, 1244*b* on the keel punch plate 1240. The distal keel formation blade 1262 also defines a generally pointed distal-most corner or edge 1262*a* that facilitates penetration of the keel formation blade 1262 into tibial bone. As shown in FIG. 71B, the distal keel formation blade 1262 is sized and shaped to form an anterior keel receiving slot $S_A$ in the anterior resected region $R_A$ of the proximal tibia 12 positioned anterior to the tibial eminence 14 and extending generally along the angled punch axis $A_2$. As indicated above, the angled keel punch blade 1260 is connected to the distal end of the angled punch handle 1250. Alternatively, the angled keel punch blade 1260 and the angled punch handle 1250 may be formed as a unitary, single-piece element. Additionally, when the angled punch handle 1250 is positioned in a retracted or non-actuated position (FIG. 70A), the distal keel formation blade 1262 is retracted into the angled passage 1212 in the main body 1210 and is fully retracted inwardly beyond the inferior surface of the tibial baseplate trial 1280. However, when the angled punch handle 1250 is positioned in an extended or actuated position (FIG. 70B), the distal keel formation blade 1262 extends out of the angled passage 1212 in the main body 1210 and projects outwardly beyond the inferior surface of the tibial baseplate trial 1280 to form the anterior keel receiving slot $S_A$ in the anterior resected region $R_A$ of the proximal tibia 12.

In the illustrated embodiment, the drill bit 1270 extends along a longitudinal axis L and generally includes a drill shaft 1272 having a proximal guide shaft portion 1272a and distal shaft portion 1272b. The proximal guide shaft portion 1272a is sized and configured for guided displacement in a direction generally parallel with the angled punch axis $A_2$ along the drill guide passages 1254a, 1254b in the proximal drill guide plate 1254 of the angled punch handle 1250, and along the drill guide barrels 1214a, 1214b defined through the main body 1210 of the keel cavity formation instrument 1200. The drill bit 1270 also includes a proximal head 1274 including connection portion 1274a configured for rotational coupling with a rotary driver (e.g., a rotary motor or a torque application handle) to facilitate the application of a rotational force or torque onto the drill bit 1270, and an enlarged stop portion or ring 1274b defining a shoulder 1274c configured to abut the superior surface defined by the drill guide plate 1254 of the angled punch handle 1250 to limit penetration of the distal cutting portion 1276 of the drill bit 1270 into tibial bone. The distal cutting portion 1276 extends axially from the distal shaft portion 1272b and defines one or more cutting flutes 1278 configured for drilling into tibial bone, and may also defined a pointed distal tip to facilitate initial penetration into tibial bone. When the keel cavity formation instrument 1200 is properly positioned relative to the proximal tibia 12, the drill bit 1270 may be inserted through one of the drill guide passages 1254a, 1254b in the proximal drill guide plate 1254 and a corresponding one of the drill guide barrels 1214a, 1214b in the main body 1210, with the distal cutting portion 1276 extending outwardly beyond the inferior surface of the tibial baseplate trial 1280 for drilling into the proximal tibia 12. As indicated above, abutment of the shoulder 1274c defined by the enlarged stop portion or ring 1274b of the drill bit 1270 limits penetration/drill depth of the distal cutting portion 1276 into the proximal tibia 12. In one embodiment, the penetration depth of the drill bit 1270 into the proximal tibia 12 is approximately equal to the penetration depth of the keel formation blade 1262 into the proximal tibia 12.

Figure 71C:
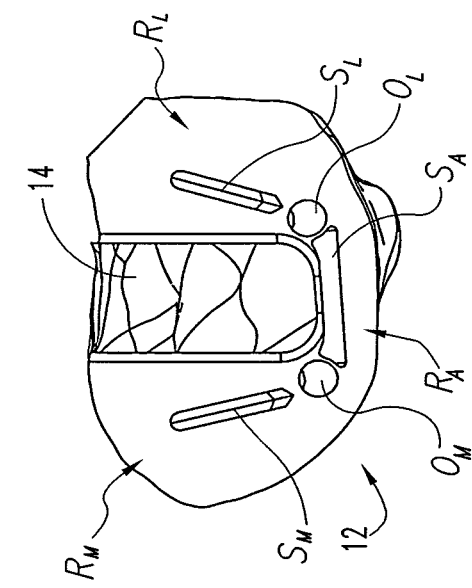
Figure 71B:
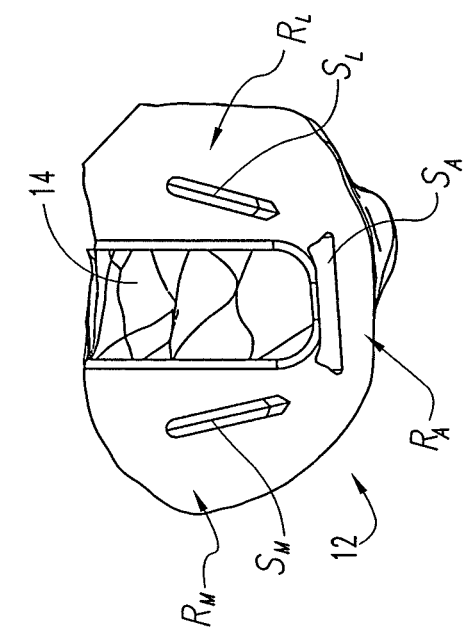
Figure 71A:
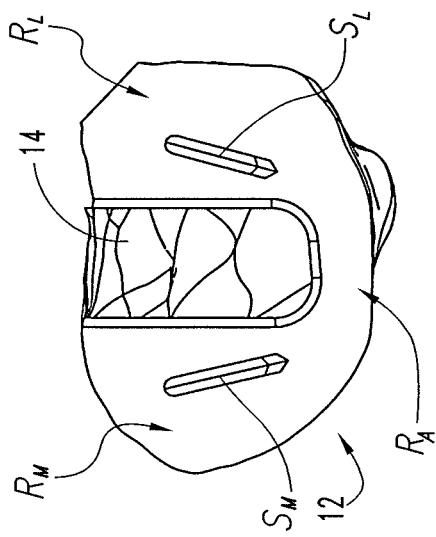

As shown in FIG. 71C, the drill bit 1270 is used to form medial and lateral keel receiving openings $O_M$, $O_L$ in the medial and lateral resected regions $R_M$, $R_L$ of the proximal tibia 12, with each of the openings arranged on opposite sides of the tibial eminence 14 and extending generally along the angled punch axis $A_2$. In the illustrated embodiment, the drill bit 1270 is used to form the medial and lateral keel receiving openings $O_M$, $O_L$ when the angled punch handle 1250 and the distal keel formation blade 1262 are positioned in an extended or actuated position (FIG. 70C) to provide additional stability and support to the keel cavity formation instrument 1200 during the drilling operations. In one embodiment, the angled punch handle 1250 and the distal keel formation blade 1262 are maintained in the extended or actuated position via friction forces exerted onto the distal keel formation blade 1262 by the surrounding bone. However, other embodiments are also contemplated wherein the angled punch handle 1250 and the distal keel formation blade 1262 may be maintained in the extended or actuated position via a positive catch or lock mechanism. Additionally, in other embodiments, the drilling operations may be performed when the angled punch handle 1250 and the distal keel formation blade 1262 are positioned in the retracted or non-actuated position.

Referring to FIG. 68, in the illustrated embodiment, the tibial baseplate trial 1280 acts as both a datum reference for the formation of portions of a keel cavity in the proximal tibia 12 and as a tibial gauge, the details of which will become apparent below. The tibial baseplate trial 1280 generally comprises a plate 1282 defining substantially flat/planar superior and inferior surfaces 1284a, 1284b and an outer peripheral surface or edge 1286 defining an outer perimeter or profile that generally matches/corresponds to the outer profile of the resected proximal tibia 12 (i.e., the outer peripheral surface or edge 1286 is generally alignable with the outer peripheral edge of the resected proximal tibia 12). The plate 1282 may also be provided with an anterior plate extension portion 1282a defining a visualization window 1288 extending therethrough to allow visual inspection/alignment of the anterior region 1286a of the outer peripheral surface 1286 with the anterior peripheral edge of the resected proximal tibia 12. The anterior plate extension portion 1282a provides additional stability and support to the keel cavity formation instrument 1200 during formation of the keel slots/openings in the proximal tibia 12 to aid in counteracting the impaction forces $F_1$ and $F_2$ applied to the keel cavity formation instrument 1200, and may also provide other benefits and advantages.

Additionally, in the illustrated embodiment, the plate 1282 defines a centrally positioned U-shaped slot 1290 extending therethrough between the superior and inferior surfaces 1284a, 1284b and having an open end at the posterior peripheral surface 1286 and extending in a posterior-anterior direction. The slot 1290 defines an open inner region of the plate 1282 that is sized and shaped to receive the tibial eminence 14 therein when the tibial baseplate trial 1280 is positioned on the resected proximal tibia 12. The plate 1282 also defines a pair of passages 1292a, 1292b extending therethrough between the superior and inferior surfaces 1284a, 1284b and positioned along medial and lateral portions of the plate 1282, respectively. The passages 1292a, 1292b are sized to receive fasteners or pins (not shown) to attach the tibial baseplate trial 1280 to the resected proximal tibia 12. The plate 1282 further defines a pair of slots or slits 1294a, 1294b extending therethrough between the superior and inferior surfaces 1284a, 1284b and positioned along medial and lateral portions of the plate 1282, respectively. The slots 1294a, 1294b inwardly taper toward one another in a posterior-anterior direction and are sized and positioned to receive the keel formation fins 1244a, 1244b of the keel punch plate 1240 during formation of the medial and lateral keel receiving slots $S_M$, $S_L$ in the resected proximal tibia 12. The slots 1294a, 1294b are preferably sized and shaped for relatively close tolerance with the keel formation fins 1244a, 1244b so as to guide the keel punch plate 1240 generally along the vertical punch axis $A_1$ during the medial/lateral keel slot formation process. Additionally, the plate 1282 defines an elongate opening 1296 extending therethrough between the superior and inferior surfaces 1284a, 1284b and positioned along an anterior portion of the plate 1282, and including a length extending in a medial-lateral direction and communicating with each of the slots 1294a, 1294b. The elongate opening 1296 is sized and positioned to receive the distal keel formation blade 1262 of the angled keel punch blade 1260 and the distal cutting portion 1276 of the drill bit 1270 during formation of the anterior keel receiving slot $S_A$ and the medial and lateral keel receiving openings $O_M$, $O_L$ in the resected proximal tibia 12. The elongate opening 1296 need not be configured to guide the angled keel punch blade 1260 and the drill bit 1270 during the during the anterior keel slot and medial and lateral opening formation process since these elements are guided by other features associated with the keel cavity formation instrument 1200. Further, interior medial and lateral surfaces of the plate 1282 extending between the central slot 1290 and the medial/lateral slots 1294a, 1294b define recesses or grooves 1298a, 1298b, the purpose of which will be set forth below with regard to the anterior gauge 1300. As should be appreciated, the tibial baseplate trial 1280 is ambidextrous, which means that the tibial baseplate trial 1280 can be flipped over and used in association with the other knee. Accordingly, a single tibial baseplate trial 1280 can be used to perform knee arthroplasty procedures on both the right knee and the left knee.

Referring collectively to FIGS. 68-71, having described the components, elements and features associated with the keel cavity formation instrument 1200, reference will now be made to methods and techniques for forming a keel cavity (including slots and openings) in the resected proximal tibia 12. However, it should be understood that other methods and techniques regarding the use of the keel cavity formation instrument 1200 are also contemplated.

Referring first to FIG. 68, the tibial baseplate trial 1280 is initially positioned atop the resected proximal tibia 12 with the tibial eminence 14 positioned within the central U-shaped slot 1290, and with the planar inferior surface 1284b resting on the substantially flat/planar resected surfaces of the proximal tibia 12. The position and orientation of the tibial baseplate trial 1280 on the resected proximal tibia 12 can then be adjusted to generally align the outer peripheral surface or edge 1286 of the plate 1282 with the outer peripheral edge of the resected proximal tibia 12. As indicated above, the anterior peripheral edge of the resected proximal tibia 12 can be viewed through the visualization window 1288 defined by the anterior plate extension portion 1282a to aid in the alignment of the anterior surface or edge of the plate 1282 with the anterior edge of the resected proximal tibia 12. If the outer peripheral surface or edge 1286 of the tibial baseplate trial 1280 does not properly align with the outer peripheral edge of the resected proximal tibia 12, a tibial baseplate trial 1280 having a different size can be chosen for positioning and alignment on the resected proximal tibia 12. It should be understood that a kit or set of multiple tibial baseplate trials 1280 having different sizes can be provided to aid in the selection of an appropriately sized tibial baseplate trial 1280. Once a tibial baseplate trial 1280 having the correct size is found and is properly aligned on the resected proximal tibia 12 (e.g., properly positioned and oriented), the plate 1282 can be connected/anchored to the resected proximal tibia 12 by passing a pair of fasteners or pins (not shown) through the medial and lateral passages 1292a, 1292b and into engagement with tibial bone.

Referring to FIGS. 69, 70A and 71A, the keel cavity formation instrument 1200 is then positioned in a superior position above the tibial baseplate trial 1280 and the keel formation fins 1244a, 1244b of the keel punch plate 1240 are positioned in the corresponding slots 1294a, 1294b in the plate 1282. With the vertical punch axis $A_1$ generally aligned with the anatomic axis 13 of the tibia, an axial impaction force $F_1$ is applied to the superior impaction surface 1234a of the impaction plate 1234 to drive the keel formation fins 1244a, 1244b of the keel punch plate 1240 into the medial and lateral resected regions $R_M$, $R_L$ of the proximal tibia 12, which in turn forms the medial and lateral keel receiving slots $S_M$, $S_L$ in the resected proximal tibia 12 (FIG. 71A).

Referring to FIGS. 70B and 71B, an axial impaction force $F_2$ is then applied to the superior impaction surface 1256a of the impaction plate 1256 on the angled punch handle 1250 in a direction generally along the angled punch axis $A_2$ to drive the distal keel formation blade 1262 of the keel punch blade 1260 into the anterior resected region $R_A$ of the proximal tibia 12, which in turn forms the anterior keel receiving slot $S_A$ in the anterior resected region $R_A$ of the proximal tibia 12 (FIG. 71B).

Referring to FIGS. 70C and 71C, with the angled punch handle 1250 and the distal keel formation blade 1262 remaining in the extended or actuated position (i.e., to provide additional stability and support to the keel cavity formation instrument 1200), the drill bit 1270 is inserted through one of the drill guide passages 1254a, 1254b and a corresponding one of the drill guide barrels 1214a, 1214b and is drilled into the proximal tibia 12 in a direction generally parallel with the angled punch axis $A_2$ to form one of the medial and lateral keel receiving openings $O_M$, $O_L$ in the medial and lateral resected regions $R_M$, $R_L$ of the proximal tibia 12. The drill bit 1270 is then inserted through the other of the drill guide passages 1254a, 1254b and the corresponding drill guide barrel 1214a, 1214b and drilled into the proximal tibia 12 in a direction generally parallel with the angled punch axis $A_2$ to form the other of the medial and lateral keel receiving openings $O_M$, $O_L$ in the medial and lateral resected regions $R_M$, $R_L$ of the proximal tibia 12 (FIG. 71C).

Following the formation of the medial and lateral keel receiving slots $S_M$, $S_L$, the anterior keel receiving slot $S_A$ and the medial and lateral keel receiving openings $O_M$, $O_L$, the keel cavity formation instrument 1200 may be disengaged and removed from the tibial baseplate trial 1280. However, the tibial baseplate trial 1280 is preferably left anchored to the resected proximal tibia 12 to perform an anterior gauging technique using the anterior gauge 1300 illustrated and described below.

As should be appreciated, the medial and lateral keel receiving slots $S_M$, $S_L$, the anterior keel receiving slot $S_A$ and the medial and lateral keel receiving openings $O_M$, $O_L$ form an overall keel cavity in the resected proximal tibia 12 having a U-shaped configuration, and with the keel receiving slots/openings sized, positioned and oriented to receive or provide clearance for corresponding keels or other projections extending from a tibial implant (not shown) upon installation of the tibial implant onto the resected proximal tibia 12. As should also be appreciated, the keel cavity formation instrument 1200 can be used in association with multiple sizes of proximal tibias and tibial implants, as well as both left and right hand proximal tibias and tibial implants, thereby reducing the need to provide multiple keel cavity formation instruments 1200 to accommodate various knee arthroplasty procedures. Additionally, the precision and accuracy offered by the tibial baseplate trial 1280 when used as a controlled datum reference and/or guide is desirable as it can help ensure that there is no mismatch conflict between the tibial eminence 14 and the portions of the U-shaped keel cavity when the tibial implant is installed onto the resected proximal tibia 12. Since the tibial implant will mate or at least correspond/relate to both the tibial eminence 14 and the portions of the U-shaped keel cavity, it can be important that these two features are positioned/oriented correctly relative to one another so that the tibial implant does not bind, become tilted, sit too proud after installation onto the resected proximal tibia 12, or compromise the remaining portion of the preserved tibial eminence 14.

As should be further appreciated, the keel cavity formation instrument 1200 is configured to form various portions/sections of the overall keel cavity in multiple steps to thereby lower the maximum input or impaction forces that would otherwise be necessary if the entire keel cavity were formed simultaneously in a single step, thereby lowering the risks associated with tibial fractures via application of reduced input or impaction forces. Additionally, forming the keel cavity in multiple steps also allows various portions of the keel cavity (i.e., the medial and lateral keel receiving slots $S_M$, $S_L$) to be formed via an input/impaction force exerted generally along the anatomic mechanical axis of the tibia (i.e., generally along the vertical punch axis $A_1$), which is a preferred direction for application of the input/impaction force, and also allows portions of the keel cavity (i.e., the anterior keel receiving slot $S_A$) that must be formed via an oblique input/impaction force (i.e., generally along the angled punch axis $A_2$) to be formed separately, thereby reducing the extent of the oblique input/impaction force necessary to form the overall keel cavity. Further, still other portions of the keel cavity are formed via drilling (i.e., the medial and lateral keel receiving openings $O_M$, $O_L$), thereby further reducing the input/impaction force necessary to form the overall keel cavity. Therefore, it should be apparent that the design of the keel cavity formation instrument 1200 provides several benefits and advantages over conventional instruments and techniques.

N. Anterior Gauge

Referring to FIGS. 72A/72B, shown therein is an anterior gauge 1300 according to one form of the present invention. As will be discussed below, in one embodiment, the anterior gauge 1300 is used in combination with the tibial baseplate trial 1280 to gauge/inspect various features and aspects associated with the resected anterior portion of the tibial eminence 14 (i.e., position, orientation, size and shape) relative to the tibial baseplate trial 1280 after formation of the keel receiving slots/openings associated with the keel cavity in the resected proximal tibia 12. The anterior gauge 1300 is designed to check and verify the accuracy of these features and aspects to ensure compatibility of the resected proximal tibia 12 with the selected tibial implant prior to installation of the tibial implant. However, it should be appreciated that in other embodiments, the anterior gauge 1300 may be used in combination with the tibial baseplate trial 1280 to gauge/inspect various features and aspects associated with the resected anterior portion of the tibial eminence 14 (i.e., position, orientation, size and shape) to check and verify the accuracy of these features and aspects prior to formation of the keel receiving slots/openings associated with the keel cavity in the resected proximal tibia 12. Other embodiments directed to further uses of the anterior gauge 1300 with or without the tibial baseplate trial 1280 are also contemplated as falling within the scope of the present invention.

In the illustrated embodiment, the anterior gauge 1300 generally includes a connection portion 1302 and a handle portion 1304 extending axially from the connection portion 1302 along a longitudinal axis L. The connection portion 1302 is generally configured for removable connection with the tibial baseplate trial 1280 and for abutment/engagement with the resected anterior portion of the tibial eminence 14. The handle portion 1304 is generally configured to aid in the manipulation and handling of the anterior gauge 1300 and the tibial baseplate trial 1280, and/or for attachment to an alignment rod or "up rod" (not shown), or potentially to other alignment devices or support structures.

In one embodiment, the connection portion 1302 is ambidextrous in that it is configured for removable attachment to both a left hand configuration of the tibial baseplate trial 1280 (FIGS. 73 and 74) and a right hand configuration of the tibial baseplate trial 1280 (formed by flipping the tibial baseplate trial 1280 over). To provide this ambidextrous capability, the connection portion 1302 includes a left hand region 1310 configured for removable attachment to the left hand configuration of the tibial baseplate trial 1280, and a right hand region 1312 configured for removable attachment to the right hand configuration of the tibial baseplate trial 1280. In the illustrated embodiment, the left hand and right hand regions 1310, 1312 are positioned on opposite superior/inferior portions of the connection portion 1302, arranged general symmetric to one another relative to the longitudinal axis L. As should be appreciated, the left hand and right hand regions 1310, 1312 of the connection portion 1302 that are removably connectable with a corresponding left/right hand configuration of the baseplate trial 1280 are appropriately marked with "L" and "R" designations (FIGS. 74A and 74B) along a superior surface of the connection portion 1302, and are also marked with a numeric range which indicates the size of the tibial baseplate trial 1280 (i.e., "1-4" which corresponds to the size of the tibia implant) for which the connection portion 1302 may be attached to. As should also be appreciated, the tibial baseplate trials 1280 are also appropriately marked with "L" and "R" designations along a superior surface of the plate 1282, as well as being marked with a numeric size number which indicates the size of the tibial baseplate trial 1280 and the corresponding size of the tibia implant.

The left hand and right hand regions 1310, 1312 of the connection portion 1302 each include a pair of medial and lateral sections 1310a, 1310b and 1312a, 1312b, respectively, which each include an axially-facing posterior surface defining a detent mechanism or ball 1314 extending therefrom. The detent mechanisms or balls 1314 are sized and shaped for receipt within corresponding ones of the recesses/grooves 1298a, 1298b formed along the interior medial and lateral surfaces of the tibial baseplate trial 1280 for removable attachment of the connection portion 1302 with the tibial baseplate trial 1280. Additionally, the connection portion 1302 includes a pair of central alignment members 1311a, 1311b positioned on opposite sides of the longitudinal axis L and between the left hand and right hand regions 1310, 1312 of the connection portion 1302. The central alignment members 1311a, 1311b define opposite substantially flat/planar abutment surfaces configured for abutment against a corresponding superior surface of the tibial baseplate trial 1280. The connection portion 1302 also defines a curved or contoured posterior-facing gauge surface 1316 extending between the medial and lateral sections 1310a, 1310b, 1312a, 1312b. The curved or contoured posterior-facing gauge surface 1316 of the connection portion 1302 is sized and shaped for close-fitting abutment against the resected anterior portion of the tibial eminence 14 (FIG. 74B).

In one embodiment, the handle portion 1304 includes a shaft portion 1320 extending axially from an anterior surface of the connection portion 1302, and a proximal gripping portion 1322 extending axially from the shaft portion 1320 and configured to be grasped and manipulated by a user. The proximal gripping portion 1322 further defines a series of openings 1324 sized and configured for optional receipt of an alignment rod or "up rod" (not shown) or to other alignment devices or support structures.

Referring to FIGS. 73A and 73B, shown therein is the tibial baseplate trial 1280 attached to the resected proximal tibia 12, with the tibial eminence 14 positioned within the central U-shaped slot 1290 of the baseplate trial 1280, and with the planar inferior surface 1284b resting on the substantially flat/planar resected surfaces of the proximal tibia 12. As should be appreciated, the anterior gauge 1300 may be removably attached to the tibial baseplate trial 1280 to aid in the manipulation and handling of the baseplate trial 1280 relative to the resected proximal tibia 12 by positioning the appropriate left or right hand region 1310, 1312 of the connection portion 1302 into the anterior elongate opening 1296 in the baseplate trial 1280 until the detent mechanisms or balls 1314 snap or click into the recesses/grooves 1298a, 1298b formed along the interior medial and lateral surfaces of the baseplate trial 1280. The position and orientation of the tibial baseplate trial 1280 relative to the resected proximal tibia 12 can be adjusted to generally align the outer peripheral surface or edge 1286 of the plate 1282 with the outer peripheral edge of the resected proximal tibia 12 prior to anchoring of the baseplate trial 1280 to the proximal tibia. Additionally, the anterior gauge 1300 is used to check/verify the accuracy and precision of various aspects and features associated with the tibial eminence 14 (i.e., position, orientation, size and shape) via a close-fitting arrangement between the curved or contoured posterior-facing gauge surface 1316 of the anterior gauge 1300 and the resected anterior portion of the tibial eminence 14. Notably, this check/verification can be conducted either before and/or after formation of the keel cavity in the resected horizontal surfaces of the proximal tibia 12. Additionally, the anterior gauge 1300 can be easily removed from the tibial baseplate trial 1280 to avoid interference with formation of the slots/opening associated with the keel cavity by simply pulling up on the handle portion 1304 in a generally vertical direction until the detent mechanisms or balls 1314 become disengaged from the recesses/grooves 1298a, 1298b in the tibial baseplate trial 1280.

Referring to FIGS. 74A and 74B, shown there is the anterior gauge 1300 removably attached to the tibial baseplate trial 1280. As indicated above, the anterior gauge 1300 is removably attached to the tibial baseplate trial 1280 by positioning the appropriate left or right hand region 1310, 1312 of the connection portion 1302 into the anterior elongate opening 1296 in the tibial baseplate trial 1280 until the detent mechanisms or balls 1314 snap or click into the recesses/grooves 1298a, 1298b formed along the interior medial and lateral surfaces of the tibial baseplate trial 1280. At this point, the substantially flat planar abutment surfaces defined by the central alignment members 1311a, 1311b should abut against the superior surface of the tibial baseplate trial 1280, and the curved or contoured posterior-facing gauge surface 1316 of the connection portion 1302 should abut the resected anterior portion of the tibial eminence 14 in a close-fitting arrangement (FIG. 74B). If these abutting surfaces appropriately mate with one another in a close fitting arrangement, the accuracy and precision of the aspects and features of the tibial eminence 14 (i.e., position, orientation, size and shape) in relation to tibia implant fit have been confirmed, and the baseplate trial 1280 can be removed from the proximal tibia 12 followed by final installation of the tibial implant onto the prepared proximal tibia 12 in a conventional manner. However, if these abutting surfaces do not appropriately mate with one another, additional modifications to the tibial eminence 14 and/or other portions of the resected proximal tibia 12 may be necessary prior to accommodate for the installation of the tibial implant.

It should be understood that method steps disclosed herein may be performed in any order regardless of the order in which they are presented, discussed or illustrated, and that while a medial cut first method may be preferable in some embodiments, the surgical techniques provided herein may be adapted for a lateral cut first method. It should also be understood that any experiments, experimental examples, or experimental results provided herein are intended to be illustrative of the present invention, and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding.

In reading the claims, words such as "a", "an", "at least one", and "at least a portion" are not intended to limit the claims to only one item unless specifically stated to the contrary. Additionally, when the language "at least a portion" and/or "a portion" is used, the claims may include a portion and/or the entire item unless specifically stated to the contrary. Furthermore, when the term "distal" is used with respect to a structure, the term refers to the far end of the structure, and when the term "proximal" is used with respect to a structure, the term refers to the near end of the structure. Moreover, the terms "superior", "inferior", "medial", "lateral", "anterior", "posterior", "up", down", "left", "right", "front", "rear", "horizontal" and "vertical" refer to general directions defined from a normal/upright view point looking toward the anterior region of the proximal tibia.

Various changes and modifications to the described embodiments described herein will be apparent to those skilled in the art, and such changes and modifications can be made without departing from the spirit and scope of the invention and without diminishing its intended advantages. Additionally, while the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

The invention claimed is:

1. A method for forming one or more keel cavities in a resected proximal tibia, the method comprising:
   positioning a tibial baseplate trial atop the resected proximal tibia;
   drilling one or more openings into the resected proximal tibia;
   forming a first keel cavity in the resected proximal tibial via a first keel cavity formation instrument, at least a portion the first keel cavity formation instrument passes through a slot formed in the tibial baseplate trial, the first keel cavity includes a medial keel cavity and a lateral keel cavity; and forming a second keel cavity in the resected proximal tibial via a second keel cavity formation instrument, the second keel cavity formation instrument being inserted through a passage formed in the first keel cavity formation instrument, the second keel cavity includes an anterior keel cavity;

wherein drilling one or more openings, forming the first keel cavity, and forming the second keel cavity are performed in multiple separate steps to thereby reduce an overall amount of required input force.

2. The method of claim 1, wherein the first keel cavity formation instrument is positioned such that a vertical punch axis of the first keel cavity formation instrument is aligned with an anatomic axis of the resected proximal tibia.

3. The method of claim 2, wherein the second keel cavity formation instrument is positioned such that a punch axis of the second keel cavity formation instrument is angled relative to the vertical punch axis of the first keel cavity formation instrument.

4. A method for forming one or more keel cavities in a resected proximal tibia, the method comprising:

positioning a tibial baseplate trial atop the resected proximal tibia;

forming a first keel cavity in the resected proximal tibial via a first keel cavity formation instrument, at least a portion the first keel cavity formation instrument passes through a slot formed in the tibial baseplate trial, the first keel cavity includes a medial keel cavity and a lateral keel cavity; and forming a second keel cavity in the resected proximal tibial via a second keel cavity formation instrument, the second keel cavity formation instrument being inserted through a passage formed in the first keel cavity formation instrument, the second keel cavity includes an anterior keel cavity;

wherein:
  the first keel cavity formation instrument is positioned such that a vertical punch axis of the first keel cavity formation instrument is aligned with an anatomic axis of the resected proximal tibia; and
  the second keel cavity formation instrument is positioned such that a punch axis of the second keel cavity formation instrument is angled relative to the vertical punch axis of the first keel cavity formation instrument.

* * * * *